United States Patent
Crane et al.

(10) Patent No.: US 12,264,155 B2
(45) Date of Patent: Apr. 1, 2025

(54) COMPOUNDS, PHARMACEUTICAL COMPOSITIONS, AND METHODS OF PREPARING COMPOUNDS AND OF THEIR USE AS ATR KINASE INHIBITORS

(71) Applicant: Repare Therapeutics Inc., St-Laurent (CA)

(72) Inventors: Sheldon N. Crane, Pincourt (CA); Vouy Linh Truong, Pierrefonds (CA); Abbas Abdoli, Montreal (CA); Jean-François Truchon, Saint-Laurent (CA); Cameron Black, St-Laurent (CA); Stéphane Dorich, Pointe-Claire (CA); Lee Fader, Hawkesbury (CA); Stéphanie Lanoix, Mansfield (CA); Paul Jones, Verdun (CA); Miguel St-Onge, Vaudreuil-Dorion (CA); Audrey Picard, Mirabel (CA); Cyrus M. Lacbay, Montreal (CA)

(73) Assignee: Repare Therapeutics Inc., St-Laurent (CA)

( * ) Notice: Subject to any disclaimer, the term of this patent is extended or adjusted under 35 U.S.C. 154(b) by 937 days.

(21) Appl. No.: 17/245,574

(22) Filed: Apr. 30, 2021

(65) Prior Publication Data
US 2021/0277002 A1 Sep. 9, 2021

Related U.S. Application Data

(63) Continuation of application No. PCT/CA2019/051539, filed on Oct. 30, 2019.

(60) Provisional application No. 62/877,177, filed on Jul. 22, 2019, provisional application No. 62/752,873, filed on Oct. 30, 2018.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01); *C07B 2200/05* (2013.01)

(58) Field of Classification Search
CPC .................................................. C07D 471/04
See application file for complete search history.

(56) References Cited

U.S. PATENT DOCUMENTS

| | | |
|---|---|---|
| 6,495,541 B1 | 12/2002 | Webber et al. |
| 7,151,102 B2 | 12/2006 | Martin et al. |
| 7,351,701 B2 | 4/2008 | Helleday et al. |
| 7,531,530 B2 | 5/2009 | Helleday et al. |
| 7,550,603 B2 | 6/2009 | Zhu et al. |
| 7,732,491 B2 | 6/2010 | Sherman et al. |
| 8,012,976 B2 | 9/2011 | Wang et al. |
| 8,071,579 B2 | 12/2011 | Ashworth et al. |
| 8,071,623 B2 | 12/2011 | Jones et al. |
| 8,143,241 B2 | 3/2012 | Ashworth et al. |
| 8,236,802 B2 | 8/2012 | Xu et al. |
| 8,552,004 B2 | 10/2013 | Foote et al. |
| 8,716,493 B2 | 5/2014 | Chatterjee et al. |
| 8,841,308 B2 | 9/2014 | Charrier et al. |
| 8,859,562 B2 | 10/2014 | Helleday |
| 8,912,187 B2 | 12/2014 | Martin et al. |
| 9,045,477 B2 | 6/2015 | Campbell et al. |
| 9,549,932 B2 | 1/2017 | Wortmann et al. |
| 9,624,205 B2 | 4/2017 | Campbell |
| 9,637,472 B2 | 5/2017 | Kuntz et al. |
| 9,663,535 B2 | 5/2017 | Breslin et al. |
| 9,820,985 B2 | 11/2017 | Wang et al. |
| 9,861,638 B2 | 1/2018 | Basford et al. |
| 2004/0048866 A1* | 3/2004 | Kolasa ................. C07D 231/56 548/361.1 |
| 2006/0142231 A1 | 6/2006 | Ashworth et al. |
| 2010/0227858 A1 | 9/2010 | Finlay et al. |
| 2011/0053923 A1 | 3/2011 | Foote et al. |
| 2017/0190704 A1 | 7/2017 | Roulet et al. |
| 2018/0118740 A1 | 5/2018 | Ameriks et al. |
| 2018/0127421 A1 | 5/2018 | Larsen |
| 2019/0055240 A1 | 2/2019 | Di Francesco et al. |
| 2021/0177856 A1 | 6/2021 | Zimmermann et al. |
| 2022/0185809 A1 | 6/2022 | Crane et al. |
| 2024/0173330 A1 | 5/2024 | Black et al. |

FOREIGN PATENT DOCUMENTS

| | | |
|---|---|---|
| CN | 106117248 A | 11/2016 |
| CN | 106795156 A | 5/2017 |
| CN | 106795156 B | 5/2017 |
| CN | 107835814 A | 3/2018 |
| CN | 108699057 A | 10/2018 |

(Continued)

OTHER PUBLICATIONS

International Search Report And Written Opinion For Patent Application No. PCT/CA2020/051014 mailed on Oct. 13, 2020, 11 pages.
Lecona et al. (Sep. 2018) "Targeting ATR in Cancer", Nature Reviews Cancer, 18(9):586-595.
Llona-Minguez et al. (May 2014) "Chemical Strategies for Development of ATR Inhibitors", Expert Reviews in Molecular Medicine, 16(10):17 Pages.
Neres et al. (Feb. 26, 2013) "Non-Nucleoside Inhibitors of BasE, an Adenylating Enzyme in the Siderophore Biosynthetic Pathway of the Opportunistic Pathogen Acinetobacter baumannii", Journal of Medicinal Chemistry, 56 (6):2385-2405.
Thomas et al. (Jun. 1, 2018) "Phase I Study of ATR Inhibitor M6620 in Combination With Topotecan in Patients With Advanced Solid Tumors", Journal of Clinical Oncology, 36(16):1594-1602(11 Pages).
Buisson et al., "APOBEC3A and APOBEC3B Activities Render Cancer Cells Susceptible to ATR Inhibition," Cancer Res. 77(17):4567-78 (2017).

(Continued)

*Primary Examiner* — James D. Anderson
(74) *Attorney, Agent, or Firm* — Clark & Elbing LLP

(57) ABSTRACT

Disclosed are compounds and pharmaceutically acceptable salts thereof that may be used in the treatment of subjects in need thereof. The compounds disclosed herein may be inhibitors of Ataxia-telangiectasia and RAD-3-related protein kinase (ATR). Also disclosed are pharmaceutical compositions containing the compounds or pharmaceutically acceptable salts thereof and methods of their preparation and use.

23 Claims, No Drawings

(56) References Cited

FOREIGN PATENT DOCUMENTS

| | | |
|---|---|---|
| CN | 112142744 A | 12/2020 |
| EA | 201200951 A1 | 9/2013 |
| JP | 2017523987 A | 8/2017 |
| WO | WO-2011/005119 A1 | 1/2011 |
| WO | WO-2011/079804 A1 | 7/2011 |
| WO | WO-2012/005805 A1 | 1/2012 |
| WO | WO-2012/118812 A2 | 9/2012 |
| WO | WO-2012/138938 A1 | 10/2012 |
| WO | WO-2013/039988 A1 | 3/2013 |
| WO | WO-2013/067302 A1 | 5/2013 |
| WO | WO-2013/095761 A1 | 6/2013 |
| WO | WO-2013/152298 A1 | 10/2013 |
| WO | WO-2016/020320 A1 | 2/2016 |
| WO | WO-2016/176460 A1 | 11/2016 |
| WO | WO-2017/118734 A1 | 7/2017 |
| WO | WO-2017/121684 A1 | 7/2017 |
| WO | WO-2017/133657 A1 | 8/2017 |
| WO | WO-2017/202748 A1 | 11/2017 |
| WO | WO-2018/153968 A1 | 8/2018 |
| WO | WO-2018/153973 A1 | 8/2018 |
| WO | WO-2020/049017 A1 | 3/2020 |
| WO | WO-2020/087170 A1 | 5/2020 |
| WO | WO-2020/259601 A1 | 12/2020 |
| WO | 2021012049 A1 | 1/2021 |
| WO | WO-2021/119523 A1 | 6/2021 |
| WO | WO-2022/226655 A1 | 11/2022 |
| WO | WO-2022/251971 A1 | 12/2022 |
| WO | WO-2022/261777 A1 | 12/2022 |
| WO | WO-2023/193110 A1 | 10/2023 |
| WO | WO-2023/193114 A1 | 10/2023 |
| WO | WO-2024/123932 A1 | 6/2024 |

OTHER PUBLICATIONS

Hocke et al., "A synthetic lethal screen identifies ATR-inhibition as a novel therapeutic approach for POLD1-deficient cancers," Oncotarget. 7(6):7080-95 (2016).

International Search Report and Written Opinion for International Patent Application No. PCT/CA2019/051539, mailed Jan. 23, 2020 (11 pages).

Barsanti et al., "Structure-Based Drug Design of Novel, Potent, and Selective Azabenzimidazoles (ABI) as ATR Inhibitors," ACS Medicinal Chemistry Letters. 6(1): 42-46 (2015) (5 pages).

Demeulemeester et al., "Biallelic mutations in cancer genomes reveal local mutational determinants," Nat Genet. 54(2):128-133 (Feb. 2022) (22 pages).

Fang et al., "Sequential Therapy with PARP and WEE1 Inhibitors Minimizes Toxicity while Maintaining Efficacy," Cancer Cell. 35(6): 851-867 (Jun. 2019) (25 pages).

Ianevski et al., "SynergyFinder: a web application for analyzing drug combination dose-response matrix data," Bioinformatics. 33(15): 2413-2415 (2017) (3 pages).

Kim et al., "Targeting the ATR/CHK1 Axis with PARP Inhibition Results in Tumor Regression in BRCA-Mutant Ovarian Cancer Models," Clin Cancer Res. 23(12):3097-3108 (2017) (12 pages).

Lai et al., "VarDict: a novel and versatile variant caller for next-generation sequencing in cancer research," Nucleic Acids Res. 44(11):e108 (Jun. 2016) (11 pages).

Mei et al., "Ataxia telangiectasia and Rad3-related inhibitors and cancer therapy: where we stand." J Hematol Oncol. 12(43):1-8 (Apr. 2019) (8 pages).

Mondal et al., "A requirement for STAG2 in replication fork progression creates a targetable synthetic lethality in cohesin-mutant cancers," Nat Commun. 10(1):1686 (Apr. 2019) (57 pages).

Roulston et al., "RP-3500: a Novel, Potent, and Selective ATR Inhibitor that is Effective in Preclinical Models as a Monotherapy and in Combination with PARP Inhibitors," Mol Cancer Ther. 21(2):245-256 (Feb. 2022) (12 pages).

Sachdev et al., "PARP Inhibition in Cancer: an Update on Clinical Development," Targeted Oncology. 14(6):657-679 (Oct. 2019) (23 pages).

Shen et al., "FACETS: allele-specific copy number and clonal heterogeneity analysis tool for high-throughput DNA sequencing," Nucleic Acids Res. 44(16):e131 (Sep. 2016) (9 pages).

Wang et al., "Genome-wide CRISPR screens reveal synthetic lethality of RNASEH2 deficiency and ATR inhibition," Oncogene. 38(14):2451-2463 (Apr. 2019) (24 pages).

Yadav et al., "Searching for Drug Synergy in Complex Dose-Response Landscapes Using an Interaction Potency Model," Comput Struct Biotechnol J. 13:504-513 (2015) (10 pages).

Yap et al., "Phase I modular study of AZD6738, a novel oral, potent and selective ataxia telangiectasia Rad3-related (ATR) inhibitor in combination (combo) with carboplatin, olaparib or durvalumab in patients (pts) with advanced cancers," Eur J Cancer. 69(1):S2 (2016) (Abstract).

Yazinski et al., "ATR inhibition disrupts rewired homologous recombination and fork protection pathways in PARP inhibitor-resistant BRCA-deficient cancer cells," Genes Dev. 31(3):318-332 (2017) (15 pages).

Zhang et al., "Alternative lengthening of telomeres: from molecular mechanisms to therapeutic outlooks," Cell Biosci. 10(30):1-9 (2020) (9 pages).

\* cited by examiner

COMPOUNDS, PHARMACEUTICAL COMPOSITIONS, AND METHODS OF PREPARING COMPOUNDS AND OF THEIR USE AS ATR KINASE INHIBITORS

FIELD OF THE INVENTION

The invention relates to compounds and pharmaceutical compositions, their preparation and their use in the treatment of a disease or condition, e.g., cancer, and, in particular, those diseases or conditions (e.g., cancers) which are dependent on the activity of Ataxia-telangiectasia and RAD-3-related protein (ATR) kinase.

BACKGROUND

DNA damage occurs continually in cells as a result of environmental insults including ultraviolet radiation, X-rays and endogenous stress factors, such as reactive oxygen and hydrolysis of bases. Cancer cells are subject to a higher rate of DNA damage inherently induced by higher rates of DNA replication in these cells. Several DNA damage response (DDR) pathways have evolved in a highly coordinated manner to help repair DNA damage and to act as a cellular checkpoint to stop the replication of cells with damaged DNA, allowing for repair functions to occur before the damaged DNA is passed on to daughter cells. Each of the identified DNA repair pathways sense and repair distinct but overlapping types of DNA damage.

One major DDR protein that acts as a key cell cycle checkpoint is the ataxia telangiectasia mutated and rad3-related (ATR) kinase, related to the family of phosphoinositide 3-kinase-related protein kinases (PIKKs). ATR is activated by single stranded (ss) DNA lesions caused by stalled replication forks or during nucleotide excision repair but is also activated by double strand breaks following DNA end resection during homologous recombination. ATR is recruited to sites of DNA damage by binding to the RPA protein that coats ssDNA along with an accessory factor called ATR-interacting protein (ATRIP). The ATR/ATRIP complex is then activated by recruitment of additional factors in the 9-1-1 complex (RAD 9, RAD1 and HUS1) which subsequently recruits the TOPBP1 protein and represents critical steps for activation of the downstream phosphorylation cascade that results in cell cycle arrest. The primary target for ATR kinase is CHK1, which when phosphorylated, targets both cdc25 proteins and Wee1 resulting in inhibition of cyclin-dependent kinase activity and cell cycle arrest in S-phase or in G2/M.

ATR has been identified as an important cancer target since it is essential for dividing cells. ATR deficient mice are embryonic lethal, however, adult mice with conditional ATR knocked out are viable with effects on rapidly proliferating tissues and stem cell populations. Mouse embryonic stem cells lacking ATR will only divide for 1-2 doublings and then die, suggesting that ATR is required for the maintenance of dividing cells. Interestingly, mice harboring hypomorphic ATR mutations that reduce expression of ATR to 10% of normal levels showed reduced H-rasG12D-induced tumor growth with minimal effects on proliferating normal cells, e.g., the bone marrow or intestinal epithelial cells. Cancer cells that have high levels of replication stress due to oncogenic mutations, dysfunctional G1/S checkpoint control (e.g., loss of p53 function), defects in other DNA repair pathways (e.g., ATM) or that are subject to the effects of DNA damaging agents, e.g., radiation therapy or chemotherapeutic agents, are therefore more dependent on ATR for DNA repair and survival. Together, these results highlight a rationale for the selective sensitivity of proliferating tumor cells to ATR inhibition and the potential for a therapeutic window over healthy proliferating cells.

There is a need for new anti-cancer therapies and, in particular, for ATR inhibitor-based anti-cancer therapies.

SUMMARY OF THE INVENTION

In one aspect, the invention provides a compound of formula (I):

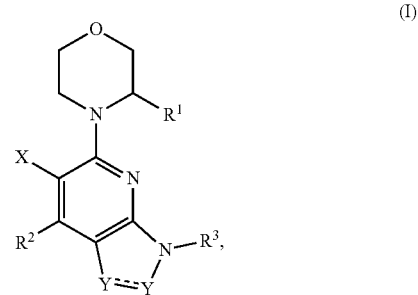

or a pharmaceutically acceptable salt thereof,
where
- ----- is a double bond, and each Y is independently N or $CR^4$; or ----- is a single bond, and each Y is independently $NR^Y$, carbonyl, or $C(R^Y)_2$; where each $R^Y$ is independently H or optionally substituted $C_{1-6}$ alkyl;
- $R^1$ is optionally substituted $C_{1-6}$ alkyl or H;
- $R^2$ is optionally substituted $C_{2-9}$ heterocyclyl, optionally substituted $C_{1-6}$ alkyl, optionally substituted $C_{3-8}$ cycloalkyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, $-N(R^5)_2$, $-OR^5$, $-CON(R^6)_2$, $-SO_2N(R^6)_2$, $-SO_2R^{5A}$, or $-Q-R^{5B}$;
- $R^3$ is optionally substituted $C_{1-9}$ heteroaryl or optionally substituted $C_{1-9}$ heteroaryl $C_{1-6}$ alkyl;
- each $R^4$ is independently hydrogen, halogen, optionally substituted $C_{1-6}$ alkyl, optionally substituted $C_{2-6}$ alkenyl, or optionally substituted $C_{2-6}$ alkynyl;
- each $R^5$ is independently hydrogen, optionally substituted $C_{1-6}$ alkyl, optionally substituted $C_{6-10}$ aryl $C_{1-6}$ alkyl, optionally substituted $C_{6-10}$ aryl, optionally substituted $C_{1-9}$ heteroaryl, or $-SO_2R^{5A}$; or both $R^5$, together with the atom to which they are attached, combine to form an optionally substituted $C_{2-9}$ heterocyclyl;
- each $R^{5A}$ is independently optionally substituted $C_{1-6}$ alkyl, optionally substituted $C_{3-8}$ cycloalkyl, or optionally substituted $C_{6-10}$ aryl;
- $R^{5B}$ is hydroxyl, optionally substituted $C_{1-6}$ alkyl, optionally substituted $C_{6-10}$ aryl, optionally substituted $C_{1-9}$ heteroaryl, $-N(R^5)_2$, $-CON(R^6)_2$, $-SO_2N(R^6)_2$, $-SO_2R^{5A}$, or optionally substituted alkoxy;
- each $R^6$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or both $R^6$, together with the atom to which they are attached, combine to form an optionally substituted $C_{2-9}$ heterocyclyl;

Q is optionally substituted $C_{2-9}$ heterocyclylene, optionally substituted $C_{3-8}$ cycloalkylene, optionally substituted $C_{1-9}$ heteroarylene, or optionally substituted $C_{6-10}$ arylene; and X is hydrogen or halogen.

In some embodiments, ===== is a double bond. In some embodiments, ===== is a single bond.

In some embodiments, the compound is a compound of formula (II):

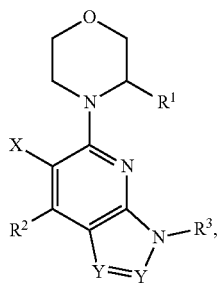
(II)

or a pharmaceutically acceptable salt thereof, where each Y is independently N or $CR^4$; and the remaining variables are as described for formula (I).

In some embodiments, in the compound of formula (I) or (II):

each Y is independently N or $CR^4$;

$R^1$ is H or optionally substituted $C_{1-6}$ alkyl;

$R^2$ is optionally substituted $C_{1-6}$ alkyl, optionally substituted $C_{3-8}$ cycloalkyl, optionally substituted $C_{2-9}$ heterocyclyl, optionally substituted $C_{6-10}$ aryl, optionally substituted $C_{1-9}$ heteroaryl, optionally substituted $C_{1-9}$ heteroaryl $C_{1-6}$ alkyl, $-N(R^5)_2$, $-CON(R^6)_2$, $-SO_2N(R^6)_2$, or $-SO_2R^{5A}$;

$R^3$ is optionally substituted $C_{1-9}$ heteroaryl;

each $R^4$ is independently hydrogen or optionally substituted $C_{1-6}$ alkyl;

each $R^5$ is independently hydrogen, optionally substituted $C_{1-6}$ alkyl, optionally substituted $C_{6-10}$ aryl $C_{1-6}$ alkyl, optionally substituted $C_{6-10}$ aryl, optionally substituted $C_{1-9}$ heteroaryl, or $-SO_2R^{5A}$; or both $R^5$, together with the atom to which they are attached, combine to form an optionally substituted $C_{2-9}$ heterocyclyl;

each $R^{5A}$ is independently optionally substituted $C_{1-6}$ alkyl or optionally substituted $C_{3-8}$ cycloalkyl; and each $R^6$ is independently hydrogen, optionally substituted $C_{1-6}$ alkyl, optionally substituted $C_{6-10}$ aryl $C_{1-6}$ alkyl, optionally substituted $C_{6-10}$ aryl, or optionally substituted $C_{1-9}$ heteroaryl; or both $R^6$, together with the atom to which they are attached, combine to form an optionally substituted $C_{2-9}$ heterocyclyl.

In some embodiments, the compound is a compound of formula (I-a):

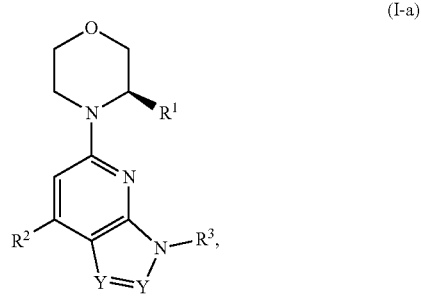
(I-a)

or a pharmaceutically acceptable salt thereof, where all variables are as described herein.

In some embodiments, the compound is a compound of formula (I-b):

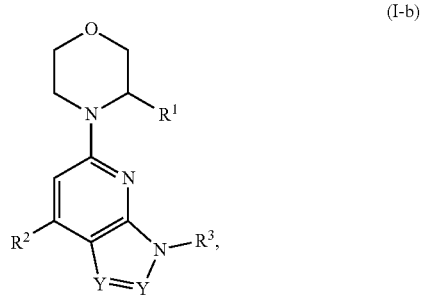
(I-b)

or a pharmaceutically acceptable salt thereof, where all variables are as described herein.

In some embodiments, the compound is a compound of formula (IA):

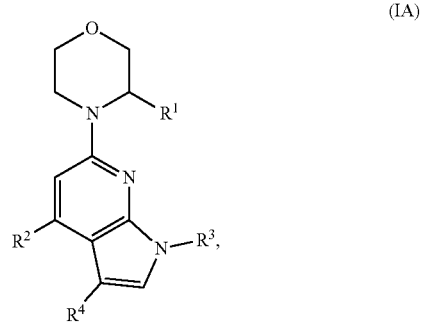
(IA)

or a pharmaceutically acceptable salt thereof, where all variables are as described herein.

In some embodiments, the compound is a compound of formula (IA-a):

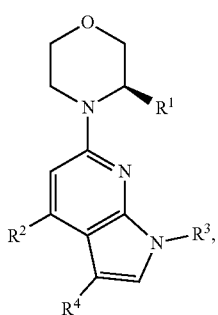

(IA-a)

or a pharmaceutically acceptable salt thereof, where all variables are as described herein.

In some embodiments, the compound is a compound of formula (IB):

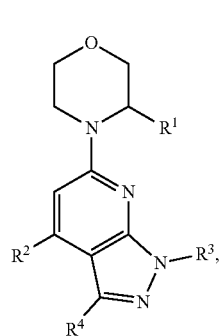

(IB)

or a pharmaceutically acceptable salt thereof, where all variables are as described herein.

In some embodiments, the compound is a compound of formula (IB-a):

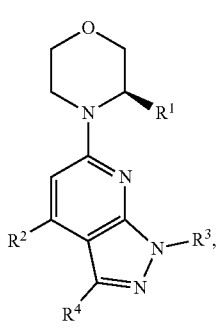

(IB-a)

or a pharmaceutically acceptable salt thereof, where all variables are as described herein.

In some embodiments, the compound is a compound of formula (IC):

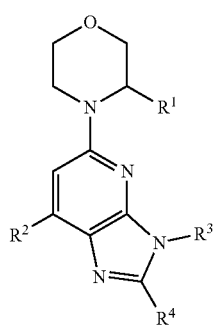

(IC)

or a pharmaceutically acceptable salt thereof, where all variables are as described herein.

In some embodiments, the compound is a compound of formula (IC-a):

(IC-a)

or a pharmaceutically acceptable salt thereof, where all variables are as described herein.

In some embodiments, the compound is a compound of formula (ID):

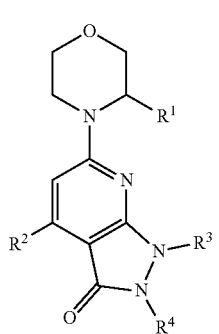

(ID)

or a pharmaceutically acceptable salt thereof, where all variables are as described herein.

In some embodiments, the compound is a compound of formula (ID-a):

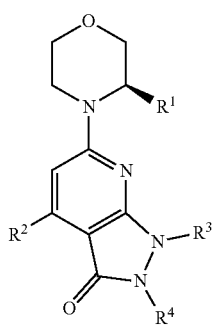

(ID-a)

or a pharmaceutically acceptable salt thereof, where all variables are as described herein.

In some embodiments of any of formulas (I), (II), (IA), (IA-a), (IB), (IB-a), (IC), (IC-a), (ID), and (ID-a), $R^1$ is methyl.

In some embodiments of any of formulas (I), (II), (IA), (IA-a), (IB), (IB-a), (IC), (IC-a), (ID), and (ID-a), $R^2$ is optionally substituted $C_{1-6}$ alkyl, optionally substituted $C_{3-8}$ cycloalkyl, optionally substituted $C_{2-9}$ heterocyclyl, optionally substituted $C_{6-10}$ aryl, optionally substituted $C_{1-9}$ heteroaryl, optionally substituted $C_{1-9}$ heteroaryl $C_{1-6}$ alkyl, —N($R^5$)$_2$, —CON($R^6$)$_2$, —SO$_2$N($R^6$)$_2$, or —SO$_2$R$^{5A}$.

In some embodiments of any of formulas (I), (II), (IA), (IA-a), (IB), (IB-a), (IC), (IC-a), (ID), and (ID-a), $R^2$ is optionally substituted $C_{3-8}$ cycloalkyl. In some embodiments, $R^2$ is a group of formula (A):

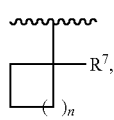

(A)

where
n is 0, 1, 2, or 3; and
$R^7$ is hydrogen, alkylsulfonyl, cyano, —CON($R^A$)$_2$, —SON($R^A$)$_2$, optionally substituted $C_{1-9}$ heteroaryl, hydroxy, or alkoxy, where each $R^A$ is independently H or alkyl; or both $R^A$, together with the atom to which they are attached, combine to form $C_{2-9}$ heterocyclyl.

In some embodiments of any of formulas (I), (II), (IA), (IA-a), (IB), (IB-a), (IC), (IC-a), (ID), and (ID-a), $R^2$ is a group of formula (B):

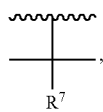

(B)

where $R^7$ is hydrogen, alkylsulfonyl, cyano, —CON($R^A$)$_2$, —SON($R^A$)$_2$, optionally substituted $C_{1-9}$ heteroaryl, hydroxy, or alkoxy, where each $R^A$ is independently H or alkyl; or both $R^A$, together with the atom to which they are attached, combine to form $C_{2-9}$ heterocyclyl.

In some embodiments of any of formulas (I), (II), (IA), (IA-a), (IB), (IB-a), (IC), (IC-a), (ID), and (ID-a), $R^2$ is optionally substituted non-aromatic $C_{2-9}$ heterocyclyl. In some embodiments of any of formulas (I), (II), (IA), (IA-a), (IB), (IB-a), (IC), (IC-a), (ID), and (ID-a), $R^2$ is optionally substituted, non-aromatic, bridged $C_{2-9}$ heterocyclyl. In some embodiments of any of formulas (I), (II), (IA), (IA-a), (IB), (IB-a), (IC), (IC-a), (ID), and (ID-a), $R^2$ is optionally substituted, non-aromatic, spiro $C_{2-9}$ heterocyclyl.

In some embodiments of any of formulas (I), (II), (IA), (IA-a), (IB), (IB-a), (IC), (IC-a), (ID), and (ID-a), $R^2$ is -Q-R$^{5B}$. In some embodiments of any of formulas (I), (II), (IA), (IA-a), (IB), (IB-a), (IC), (IC-a), (ID), and (ID-a), Q is optionally substituted $C_{2-9}$ heterocyclylene. In some embodiments of any of formulas (I), (II), (IA), (IA-a), (IB), (IB-a), (IC), (IC-a), (ID), and (ID-a), $R^{5B}$ is hydroxyl.

In some embodiments of any of formulas (I), (II), (IA), (IA-a), (IB), (IB-a), (IC), (IC-a), (ID), and (ID-a), $R^2$ is:

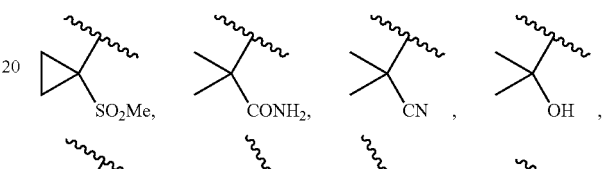

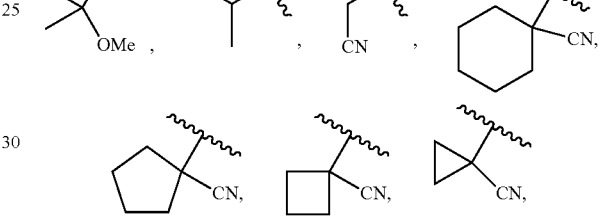

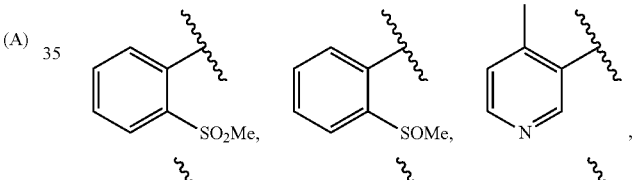

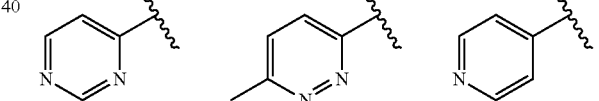

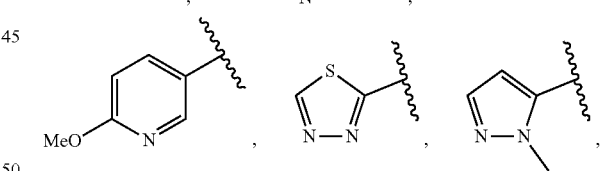

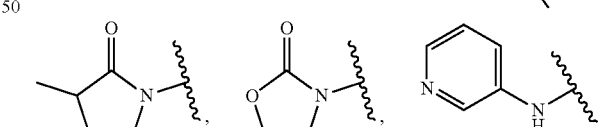

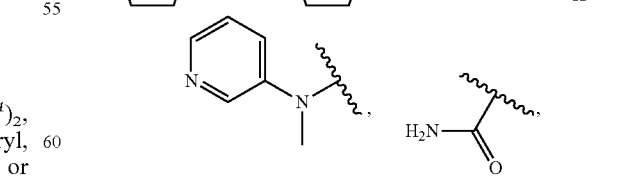

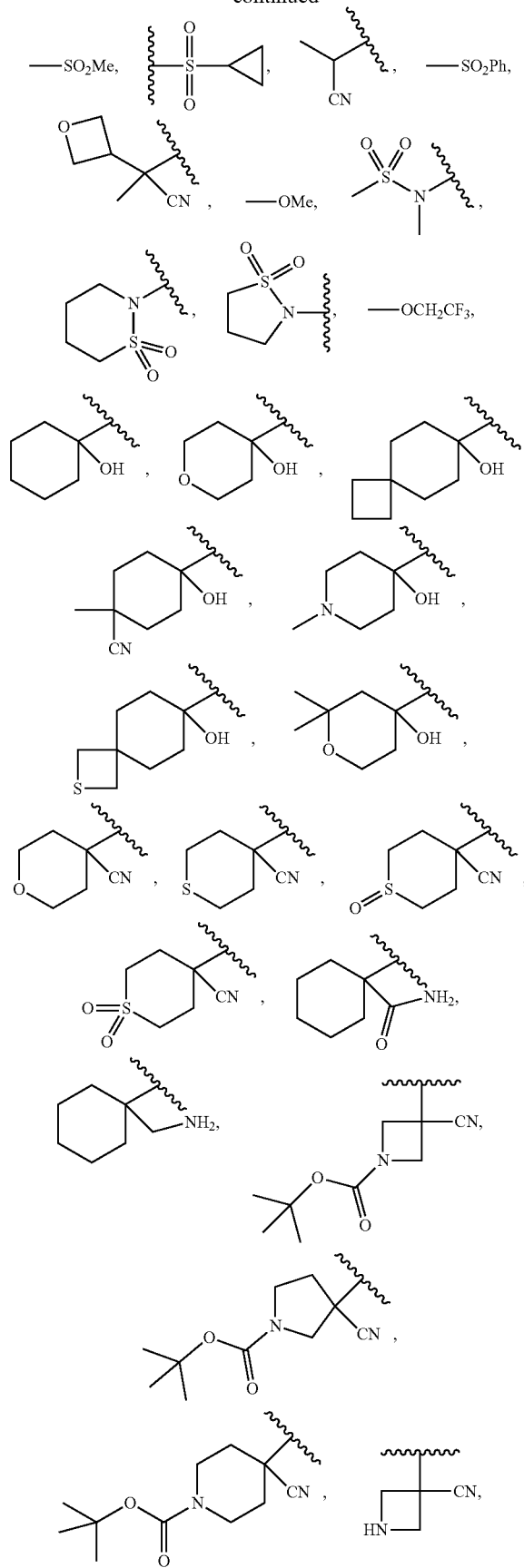
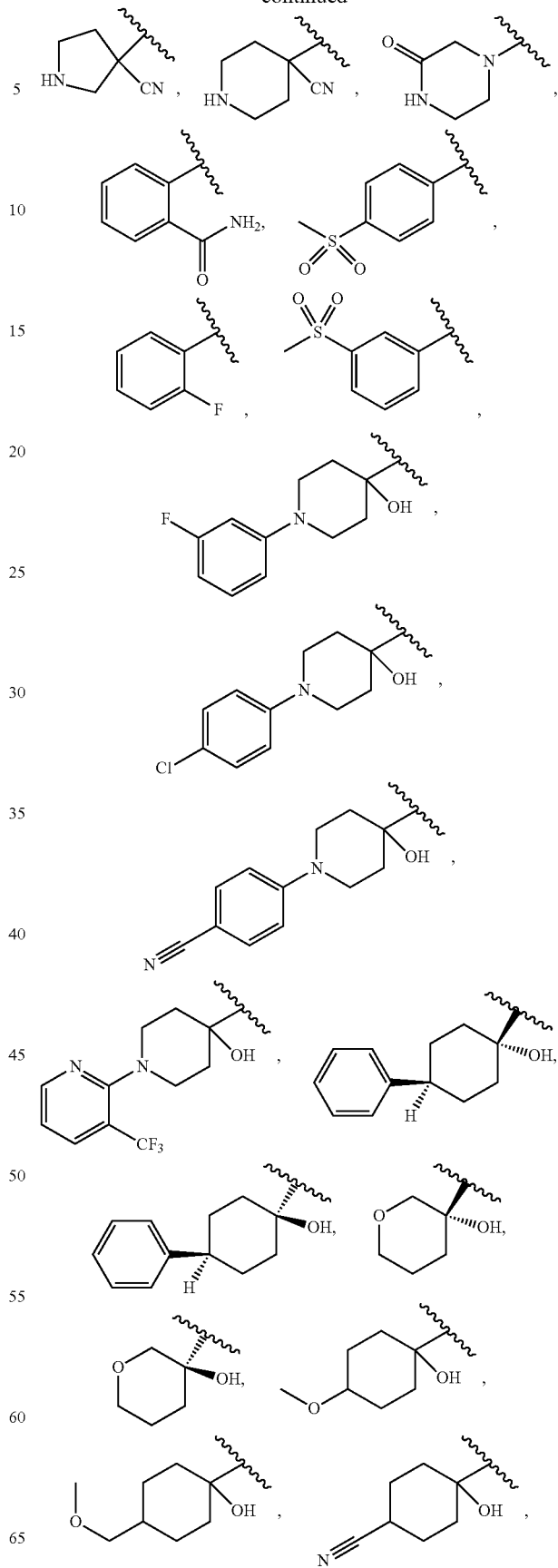

-continued
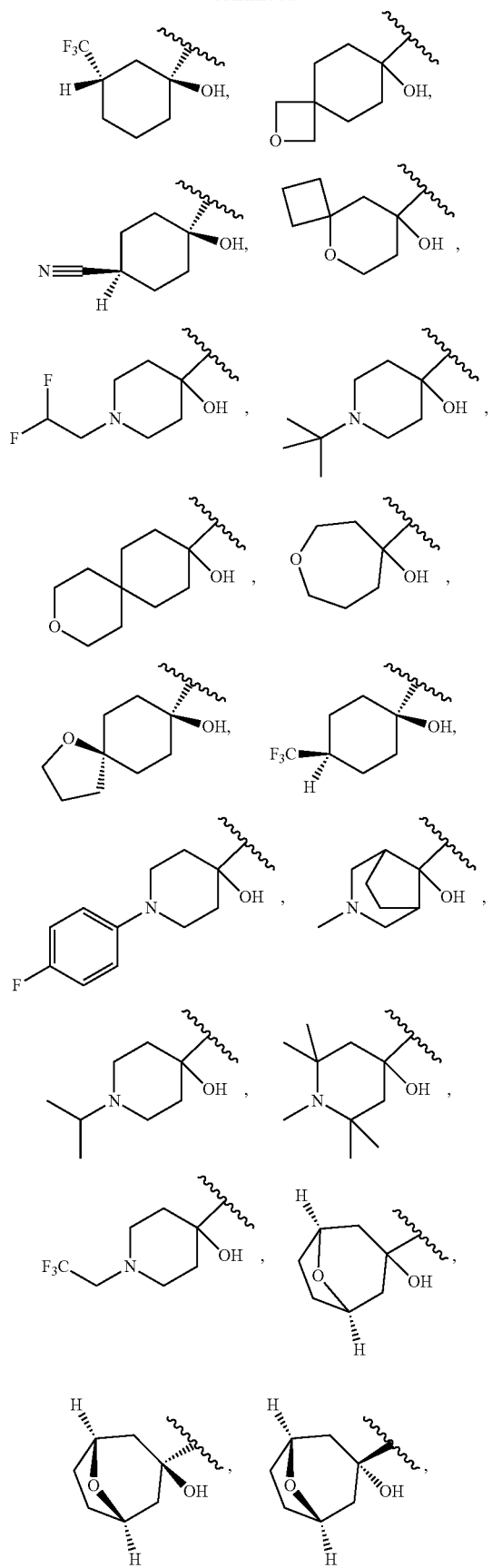
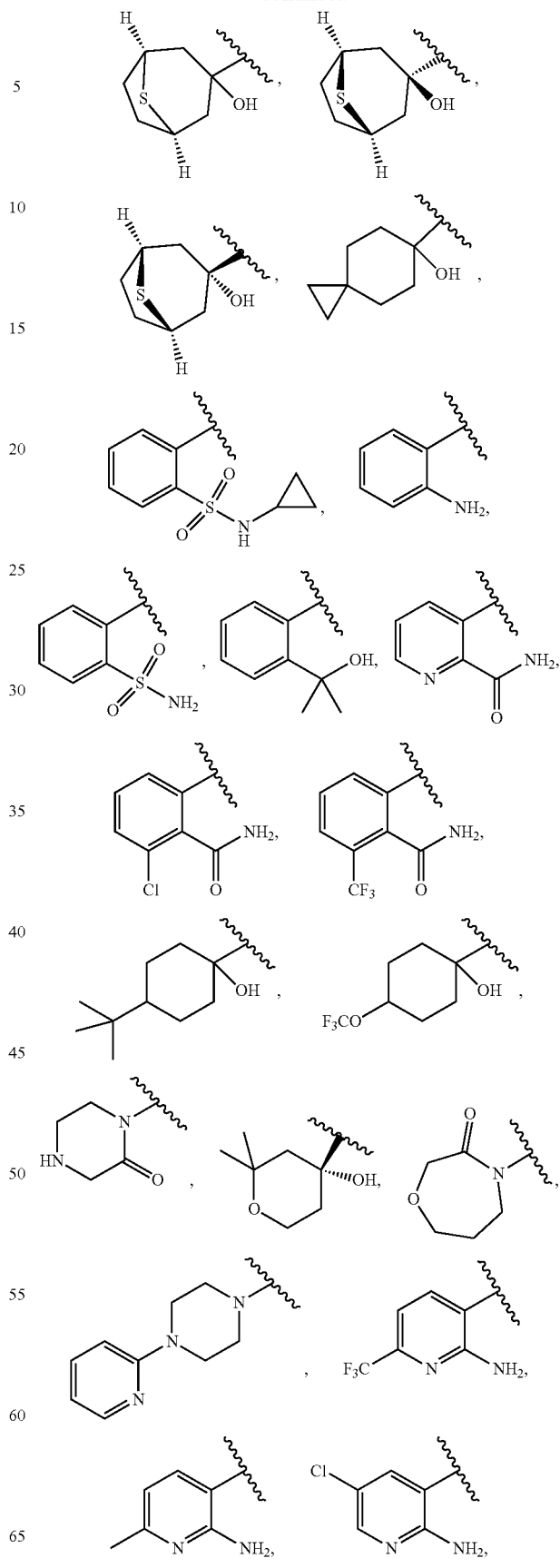

-continued

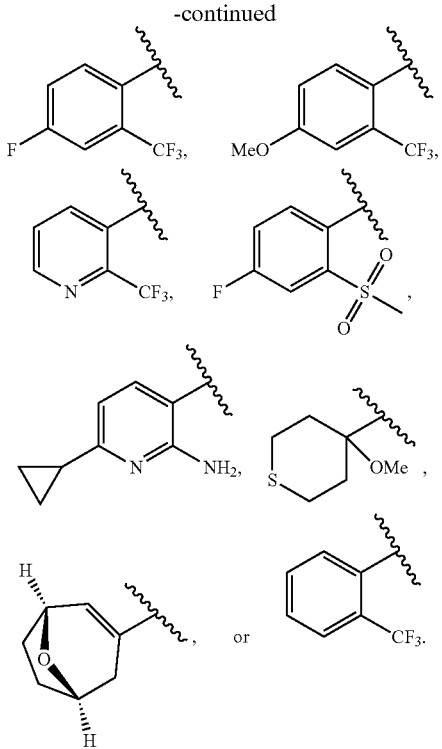

In some embodiments of any of formulas (I), (II), (IA), (IA-a), (IB), (IB-a), (IC), (IC-a), (ID), and (ID-a), R³ is optionally substituted, monocyclic C₁₋₉ heteroaryl including at least one nitrogen atom. In some embodiments of any of formulas (I), (II), (IA), (IA-a), (IB), (IB-a), (IC), (IC-a), (ID), and (ID-a), R³ is optionally substituted, monocyclic C₁₋₉ heteroaryl including two nitrogen atoms. In some embodiments of any of formulas (I), (II), (IA), (IA-a), (IB), (IB-a), (IC), (IC-a), (ID), and (ID-a), R³ is a group of formula (C):

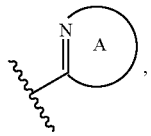

(C)

where A is optionally substituted, monocyclic C₁₋₉ heteroaryl ring.

In some embodiments of any of formulas (I), (II), (IA), (IA-a), (IB), (IB-a), (IC), (IC-a), (ID), and (ID-a), R³ is a group of formula (C1):

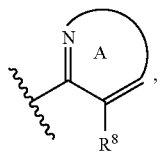

(C1)

where R⁸ is hydrogen, halogen, or optionally substituted C₁₋₆ alkyl.

In some embodiments of any of formulas (I), (II), (IA), (IA-a), (IB), (IB-a), (IC), (IC-a), (ID), and (ID-a), A is optionally substituted, monocyclic C₁₋₉ heteroaryl ring including two nitrogen atoms.

In some embodiments of any of formulas (I), (II), (IA), (IA-a), (IB), (IB-a), (IC), (IC-a), (ID), and (ID-a), R³ is:

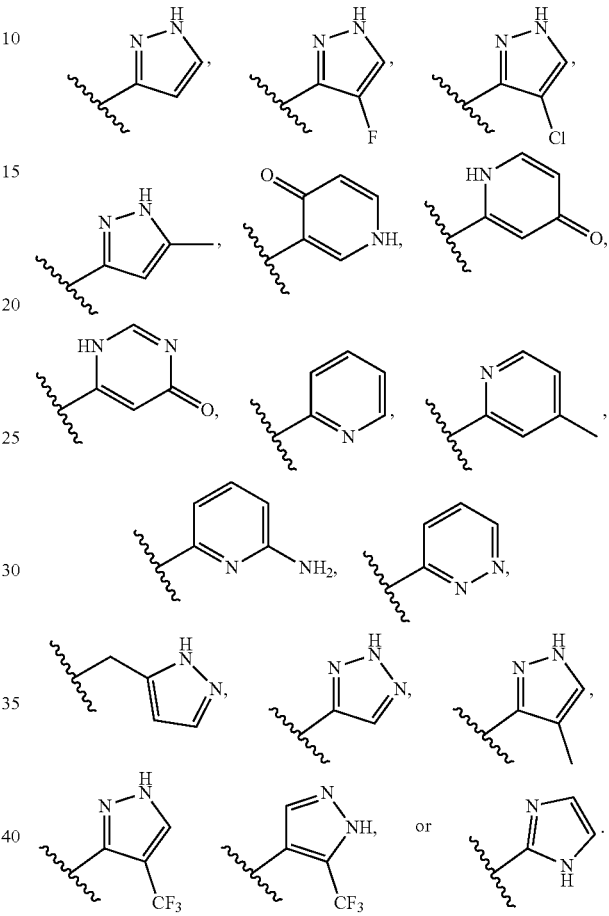

In some embodiments of any of formulas (I), (II), (IA), (IA-a), (IB), (IB-a), (IC), (IC-a), (ID), and (ID-a), R³ is:

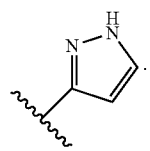

In some embodiments of any of formulas (I), (II), (IA), (IA-a), (IB), (IB-a), (IC), (IC-a), (ID), and (ID-a), R⁴ is hydrogen.

In some embodiments of any of formulas (I), (II), (IA), (IA-a), (IB), (IB-a), (IC), (IC-a), (ID), and (ID-a), X is hydrogen.

In some embodiments, the compound is selected from the group consisting of compounds 1-152 (e.g., compounds 1-140) and pharmaceutically acceptable salts thereof (e.g., the compound is selected from the group consisting of: 1, 2, 3, 4, 5, 6, 7, 8, 43, 45, 47, 48, 49, 52, 53, 55, 57, 58, 59, 61, 62, 63, 73, 74, 77, 80, 81, 82, 84, 86, 87, 92, 93, 94, 95, 97, 98, 99, 100, 101, 102, 103, 104, 105, 106, 107, 108, 109, 110, 111, 112, 113, 114, 115, 116, 118, 119, 120, 121, 122, 123, 125, 126, 127, 128, 129, 130, 131, 132, 133, 135, 137, 138, 139, 140, 141, 142, 143, 144, 145, 146, 147, 148, 150, 151, and pharmaceutically acceptable salts thereof).

In another aspect, the invention provides a pharmaceutical composition including the compound of the invention and a pharmaceutically acceptable excipient. In some embodiments, the compound of the invention is isotopically enriched in deuterium.

In a further aspect, the invention provides a method of inhibiting ATR kinase in a cell expressing ATR kinase by contacting the cell with the compound of the invention. In some embodiments, the cell is in vitro. In some embodiments, the cell is in a subject.

In a yet further aspect, the invention provides a method of treating a subject in need thereof including administering to the subject an effective amount of the compound of the invention or the pharmaceutical composition of the invention.

In some embodiments, the subject is suffering from, and is in need of a treatment for, a disease or condition having the symptom of cell hyperproliferation (e.g., the disease or condition is a cancer or pre-malignant or pre-cancerous condition). In some embodiments, the cancer is a carcinoma, sarcoma, adenocarcinoma, leukemia, or melanoma.

In some embodiments, the cancer is a carcinoma selected from the group consisting of medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

In some embodiments, the cancer is a sarcoma selected from the group consisting of chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangieotaltic sarcoma.

In some embodiments, the cancer is a leukemia selected from the group consisting of nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Riedercell leukemia, Schilling's leukemia, stem cell leukemia, subleukemic leukemia, and undifferentiated cell leukemia.

In some embodiments, the cancer is a melanoma selected from the group consisting of acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungual melanoma, and superficial spreading melanoma.

In some embodiments, the cancer is prostate cancer, thyroid cancer, endocrine system cancer, brain cancer, breast cancer, cervix cancer, colon cancer, head & neck cancer, liver cancer, kidney cancer, lung cancer, non-small cell lung cancer, melanoma, mesothelioma, ovarian cancer, sarcoma, stomach cancer, uterus cancer, medulloblastoma, ampullary cancer, colorectal cancer, or pancreatic cancer.

In some embodiments, the cancer is Hodgkin's disease, Non-Hodgkin's lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphoma, thyroid cancer, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

In some embodiments, the subject is suffering from, and is in need of a treatment for, a pre-malignant condition.

The invention is also described by the following enumerated items.

1. A compound of formula (I):

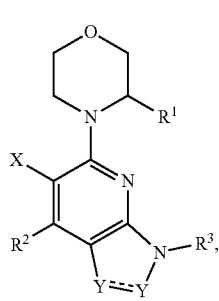

(I)

or a pharmaceutically acceptable salt thereof, where
- - - - - is a double bond, and each Y is independently N or $CR^4$; or - - - - - is a single bond, and each Y is independently $NR^Y$, carbonyl, or $C(R^Y)_2$; where each $R^Y$ is independently H or optionally substituted $C_{1-6}$ alkyl;

$R^1$ is optionally substituted $C_{1-6}$ alkyl or H;

$R^2$ is optionally substituted $C_{2-9}$ heterocyclyl, optionally substituted $C_{1-6}$ alkyl, optionally substituted $C_{3-8}$ cycloalkyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, —$N(R^5)_2$, —$OR^5$, —$CON(R^6)_2$, —$SO_2N(R^6)_2$, —$SO_2R^{5A}$, or -Q-$R^{5B}$;

$R^3$ is optionally substituted $C_{1-9}$ heteroaryl or optionally substituted $C_{1-9}$ heteroaryl $C_{1-6}$ alkyl;

each $R^4$ is independently hydrogen, halogen, optionally substituted $C_{1-6}$ alkyl, optionally substituted $C_{2-6}$ alkenyl, or optionally substituted $C_{2-6}$ alkynyl;

each $R^5$ is independently hydrogen, optionally substituted $C_{1-6}$ alkyl, optionally substituted $C_{6-10}$ aryl $C_{1-6}$ alkyl, optionally substituted $C_{6-10}$ aryl, optionally substituted $C_{1-9}$ heteroaryl, or —$SO_2R^{5A}$; or both $R^5$, together with the atom to which they are attached, combine to form an optionally substituted $C_{2-9}$ heterocyclyl;

each $R^{5A}$ is independently optionally substituted $C_{1-6}$ alkyl, optionally substituted $C_{3-8}$ cycloalkyl, or optionally substituted $C_{6-10}$ aryl;

$R^{5B}$ is hydroxyl, optionally substituted $C_{1-6}$ alkyl, optionally substituted $C_{6-10}$ aryl, optionally substituted $C_{1-9}$ heteroaryl, —$N(R^5)_2$, —$CON(R^6)_2$, —$SO_2N(R^6)_2$, —$SO_2R^{5A}$, or optionally substituted alkoxy;

each $R^6$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or both $R^6$, together with the atom to which they are attached, combine to form an optionally substituted $C_{2-9}$ heterocyclyl;

Q is optionally substituted $C_{2-9}$ heterocyclylene, optionally substituted $C_{3-8}$ cycloalkylene, optionally substituted $C_{1-9}$ heteroarylene, or optionally substituted $C_{6-10}$ arylene; and X is hydrogen or halogen.

2. The compound of item 1, where - - - - - is a double bond.

3. The compound of item 1, where - - - - - is a single bond,

4. The compound of item 1, where the compound is a compound of formula (II):

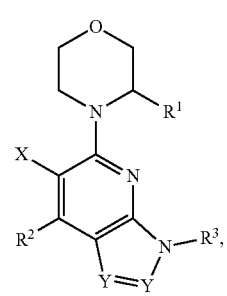

(II)

or a pharmaceutically acceptable salt thereof, where
each Y is independently N or $CR^4$;

$R^1$ is optionally substituted $C_{1-6}$ alkyl or H;

$R^2$ is optionally substituted $C_{2-9}$ heterocyclyl, optionally substituted $C_{1-6}$ alkyl, optionally substituted $C_{3-8}$ cycloalkyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, —$N(R^5)_2$, —$OR^5$, —$CON(R^6)_2$, —$SO_2N(R^6)_2$, —$SO_2R^{5A}$, or -Q-$R^{5B}$;

$R^3$ is optionally substituted $C_{1-9}$ heteroaryl or optionally substituted $C_{1-9}$ heteroaryl $C_{1-6}$ alkyl;

each $R^4$ is independently hydrogen, halogen, optionally substituted $C_{1-6}$ alkyl, optionally substituted $C_{2-6}$ alkenyl, or optionally substituted $C_{2-6}$ alkynyl;

each $R^5$ is independently hydrogen, optionally substituted $C_{1-6}$ alkyl, optionally substituted $C_{6-10}$ aryl $C_{1-6}$ alkyl, optionally substituted $C_{6-10}$ aryl, optionally substituted $C_{1-9}$ heteroaryl, or —$SO_2R^{5A}$; or both $R^5$, together with the atom to which they are attached, combine to form an optionally substituted $C_{2-9}$ heterocyclyl;

each $R^{5A}$ is independently optionally substituted $C_{1-6}$ alkyl, optionally substituted $C_{3-8}$ cycloalkyl, or optionally substituted $C_{6-10}$ aryl;

$R^{5B}$ is hydroxyl, optionally substituted $C_{1-6}$ alkyl, optionally substituted $C_{6-10}$ aryl, optionally substituted $C_{1-9}$ heteroaryl, —$N(R^5)_2$, —$CON(R^6)_2$, —$SO_2N(R^6)_2$, —$SO_2R^{5A}$, or optionally substituted alkoxy;

each $R^6$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or both $R^6$, together with the atom to which they are attached, combine to form an optionally substituted $C_{2-9}$ heterocyclyl;

Q is optionally substituted $C_{2-9}$ heterocyclylene, optionally substituted $C_{3-8}$ cycloalkylene, optionally substituted $C_{1-9}$ heteroarylene, or optionally substituted $C_{6-10}$ arylene; and X is hydrogen or halogen.

5. The compound of item 1, where the compound is a compound of formula (I-a):

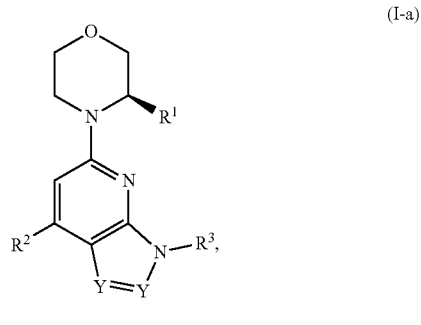
(I-a)

or a pharmaceutically acceptable salt thereof.

6. The compound of item 1, where the compound is a compound of formula (IA):

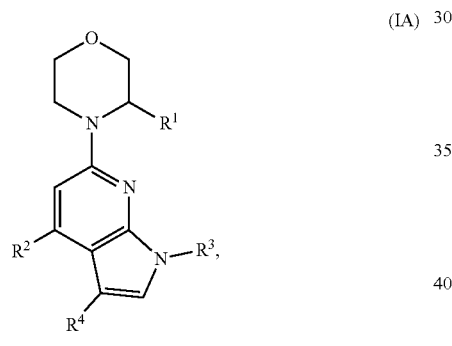
(IA)

or a pharmaceutically acceptable salt thereof.

7. The compound of item 6, where the compound is a compound of formula (IA-a):

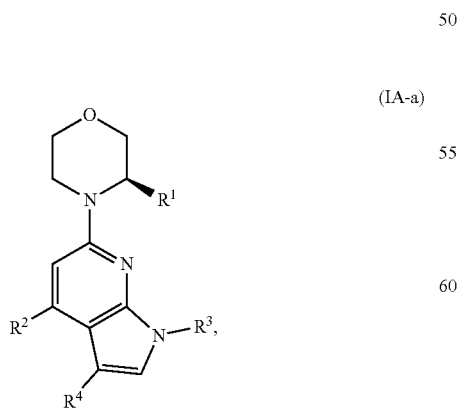
(IA-a)

or a pharmaceutically acceptable salt thereof.

8. The compound of item 1, where the compound is a compound of formula (IB):

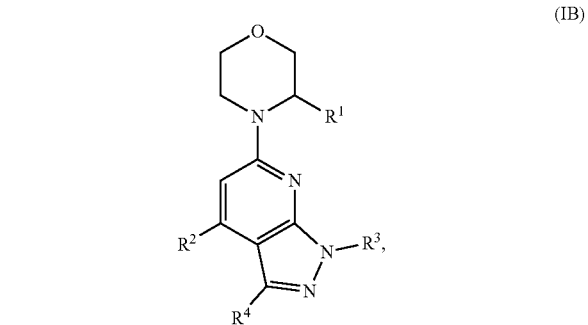
(IB)

or a pharmaceutically acceptable salt thereof.

9. The compound of item 8, where the compound is a compound of formula (IB-a):

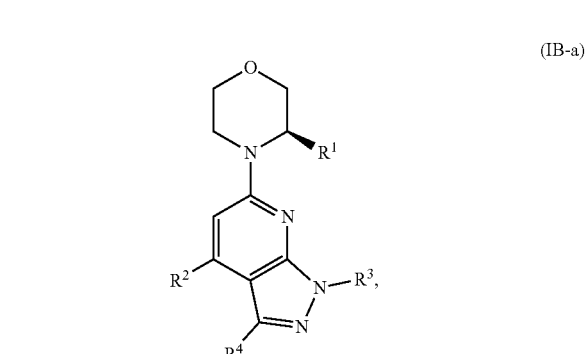
(IB-a)

or a pharmaceutically acceptable salt thereof.

10. The compound of item 1, where the compound is a compound of formula (IC):

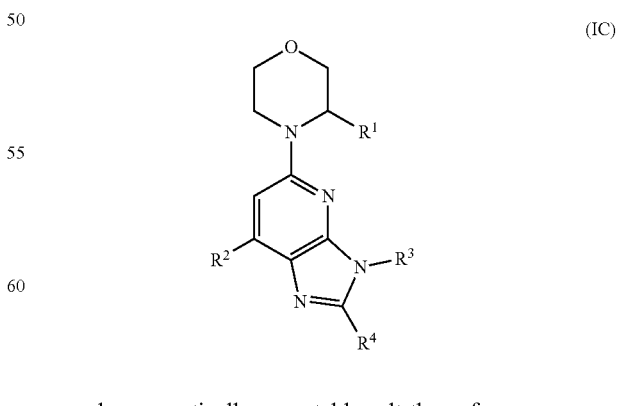
(IC)

or a pharmaceutically acceptable salt thereof.

11. The compound of item 10, where the compound is a compound of formula (IC-a):

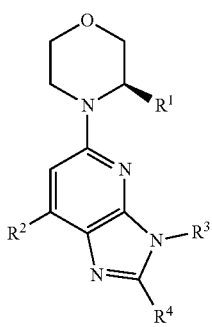

or a pharmaceutically acceptable salt thereof.

12. The compound of any one of items 1 to 11, where $R^1$ is methyl.

13. The compound of any one of items 1 to 12, where $R^2$ is optionally substituted $C_{1-6}$ alkyl, optionally substituted $C_{3-8}$ cycloalkyl, optionally substituted $C_{2-9}$ heterocyclyl, optionally substituted $C_{6-10}$ aryl, optionally substituted $C_{1-9}$ heteroaryl, optionally substituted $C_{1-9}$ heteroaryl $C_{1-6}$ alkyl, —N($R^5$)$_2$, —CON($R^6$)$_2$, —SO$_2$N($R^6$)$_2$, or —SO$_2$R$^{5A}$.

14. The compound of any one of items 1 to 13, where each $R^{5A}$ is independently optionally substituted $C_{1-6}$ alkyl or optionally substituted $C_{3-8}$ cycloalkyl.

15. The compound of any one of items 1 to 13, where each $R^6$ is independently hydrogen, optionally substituted $C_{1-6}$ alkyl, optionally substituted $C_{6-10}$ aryl $C_{1-6}$ alkyl, optionally substituted $C_{6-10}$ aryl, or optionally substituted $C_{1-9}$ heteroaryl; or both $R^6$, together with the atom to which they are attached, combine to form an optionally substituted $C_{2-9}$ heterocyclyl.

16. The compound of any one of items 1 to 15, where $R^2$ is optionally substituted $C_{3-8}$ cycloalkyl.

17. The compound of item 16, where $R^2$ is $C_{3-8}$ cycloalkyl optionally substituted with alkylsulfonyl, cyano, —CON(R$^A$)$_2$, hydroxy, or alkoxy, where each R$^A$ is independently H or alkyl; or both R$^A$, together with the atom to which they are attached, combine to form $C_{2-9}$ heterocyclyl.

18. The compound of item 16, where $R^2$ is a group of formula (A):

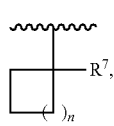

(A)

where
n is 0, 1, 2, or 3; and
R$^7$ is hydrogen, alkylsulfonyl, cyano, —CON(R$^A$)$_2$, —SON(R$^A$)$_2$, optionally substituted $C_{1-9}$ heteroaryl, hydroxy, or alkoxy, where each R$^A$ is independently H or alkyl; or both R$^A$, together with the atom to which they are attached, combine to form $C_{2-9}$ heterocyclyl.

19. The compound of any one of items 1 to 15, where $R^2$ is a group of formula (B):

(B)

where R$^7$ is hydrogen, alkylsulfonyl, cyano, —CON(R$^A$)$_2$, —SON(R$^A$)$_2$, optionally substituted $C_{1-9}$ heteroaryl, hydroxy, or alkoxy, where each R$^A$ is independently H or alkyl; or both R$^A$, together with the atom to which they are attached, combine to form $C_{2-9}$ heterocyclyl.

20. The compound of item 18 or 19, where R$^7$ is alkylsulfonyl, cyano, or —CON(R$^A$)$_2$.

21. The compound of any one of items 1 to 12, where $R^2$ is optionally substituted $C_{1-6}$ alkyl.

22. The compound of item 21, where $R^2$ is optionally substituted tertiary $C_{3-6}$ alkyl.

23. The compound of any one of items 1 to 15, where $R^2$ is optionally substituted non-aromatic $C_{2-9}$ heterocyclyl.

24. The compound of item 23, where $R^2$ is optionally substituted, non-aromatic, bridged $C_{2-9}$ heterocyclyl.

25. The compound of item 23, where $R^2$ is optionally substituted, non-aromatic, spiro $C_{2-9}$ heterocyclyl.

26. The compound of any one of items 1 to 15, where $R^2$ is optionally substituted $C_{3-8}$ cycloalkyl.

27. The compound of item 26, where $R^2$ is optionally substituted, spiro $C_{3-8}$ cycloalkyl.

28. The compound of any one of items 1 to 12, where $R^2$ is -Q-R$^{5B}$.

29. The compound of item 28, where Q is optionally substituted $C_{1-9}$ heteroarylene.

30. The compound of item 28, where Q is optionally substituted $C_{3-8}$ cycloalkylene.

31. The compound of item 28, where Q is optionally substituted $C_{2-9}$ heterocyclylene.

32. The compound of item 28, where Q is optionally substituted $C_{6-10}$ arylene.

33. The compound of any one of items 28 to 32, where R$^{5B}$ is optionally substituted $C_{1-6}$ alkyl.

34. The compound of any one of items 28 to 32, where R$^{5B}$ is hydroxyl.

35. The compound of any one of items 28 to 32, where R$^{5B}$ is optionally substituted $C_{6-10}$ aryl.

36. The compound of any one of items 28 to 32, where R$^{5B}$ is optionally substituted $C_{1-9}$ heteroaryl.

37. The compound of any one of items 28 to 32, where R$^{5B}$ is-N(R$^5$)$_2$.

38. The compound of item 37, where each R$^5$ is hydrogen.

39. The compound of any one of items 28 to 32, where R$^{5B}$ is optionally substituted alkoxy.

38. The compound of any one of items 28 to 32, where R$^{5B}$ is —SO$_2$N(R$^6$)$_2$.

39. The compound of item 38, where each R$^6$ is hydrogen.

40. The compound of any one of items 28 to 32, where R$^{5B}$ is —SO$_2$R$^{5A}$.

41. The compound of item 40, where R$^{5A}$ is optionally substituted $C_{1-6}$ alkyl.

42. The compound of any one of items 1 to 15, where $R^2$ is:

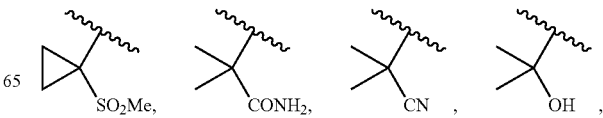

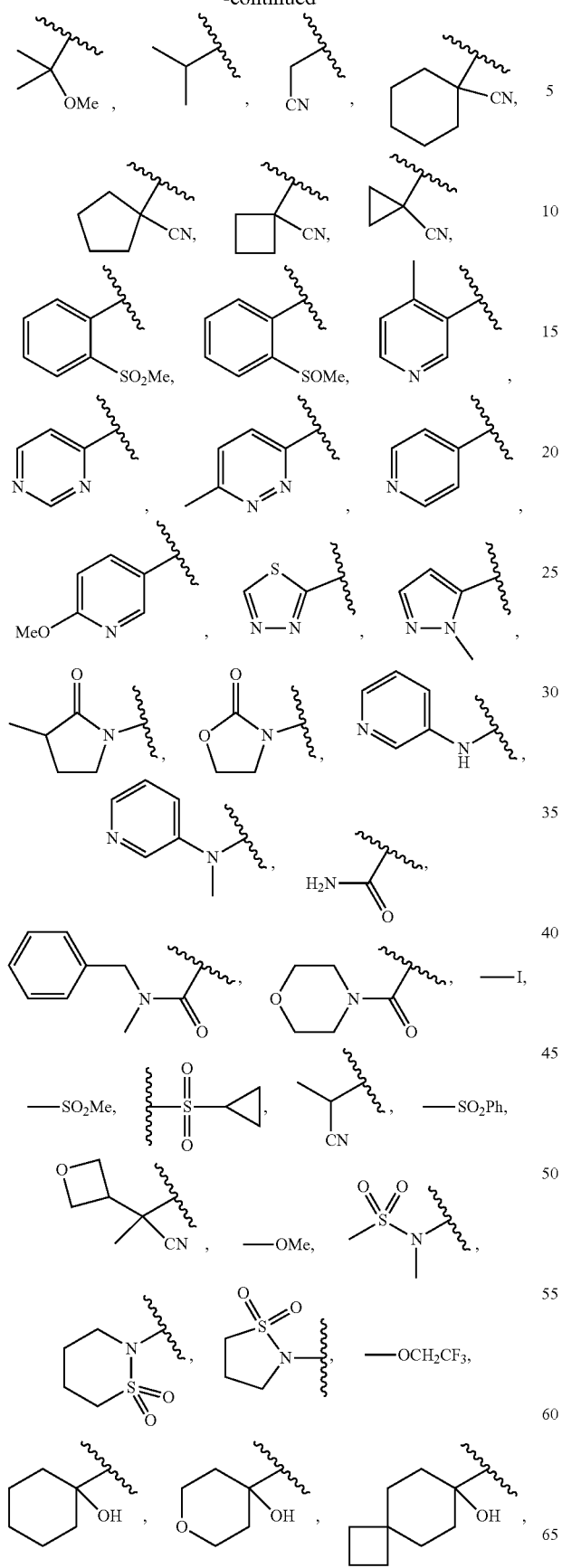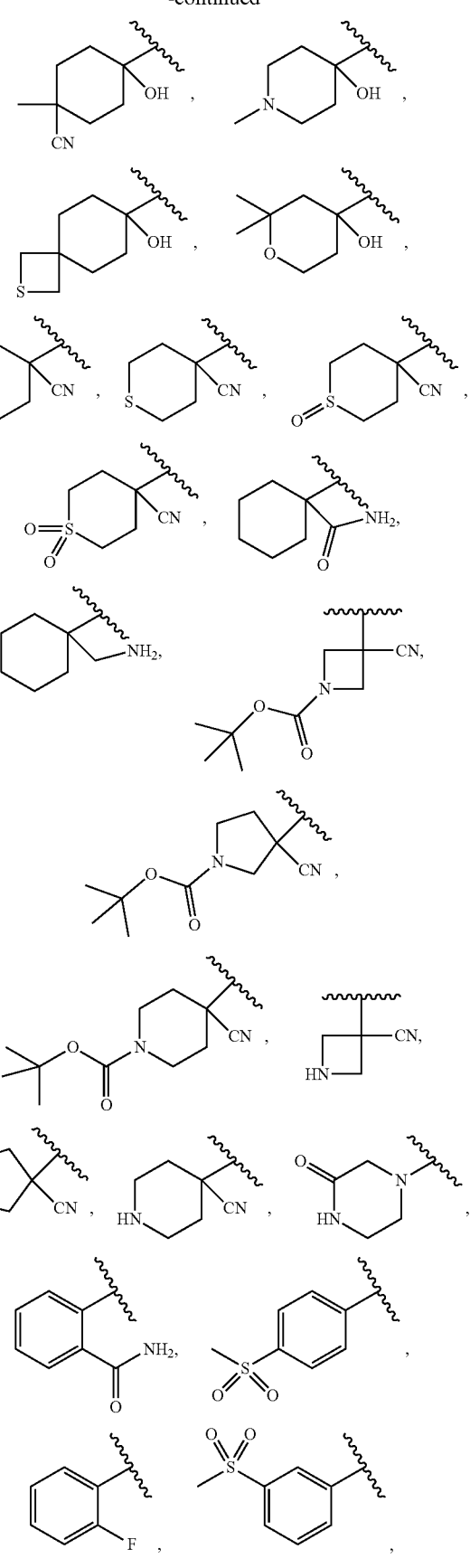

-continued
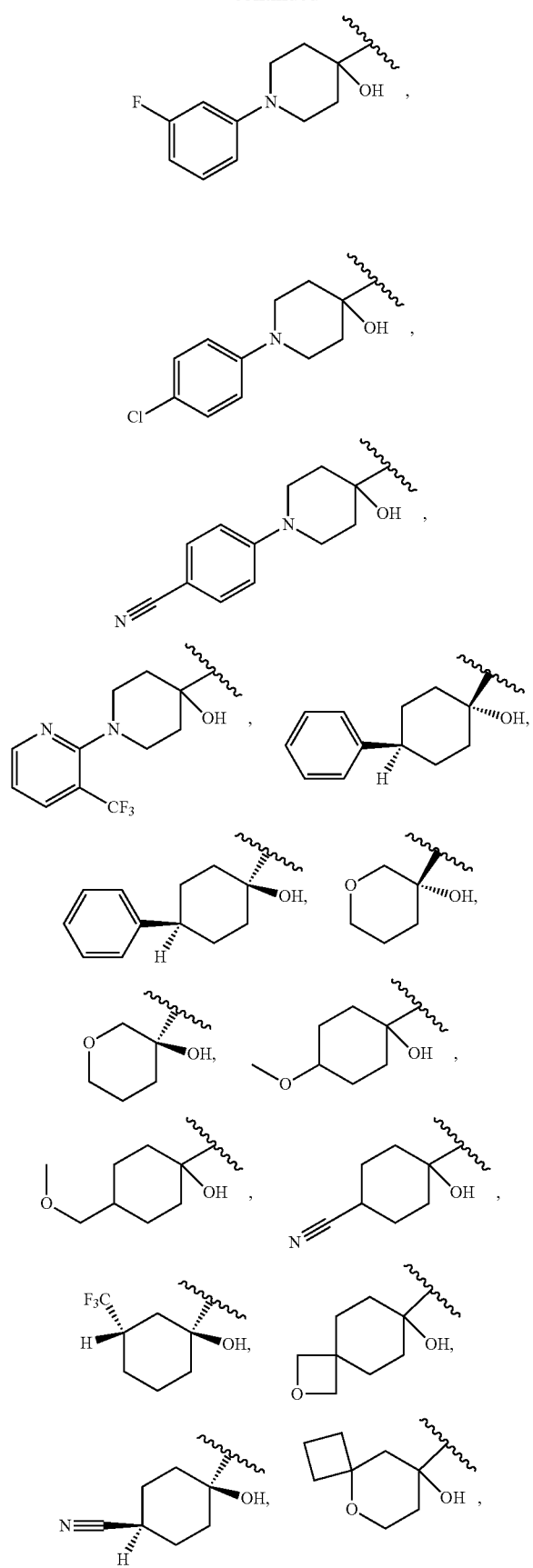
-continued
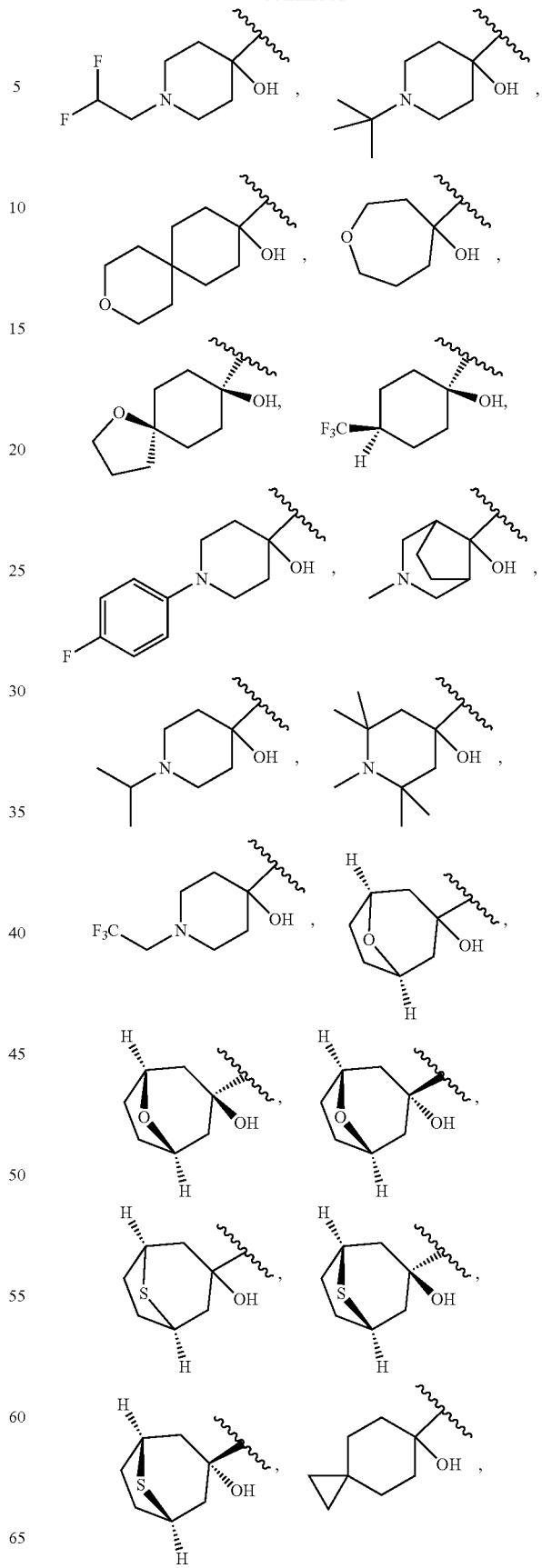

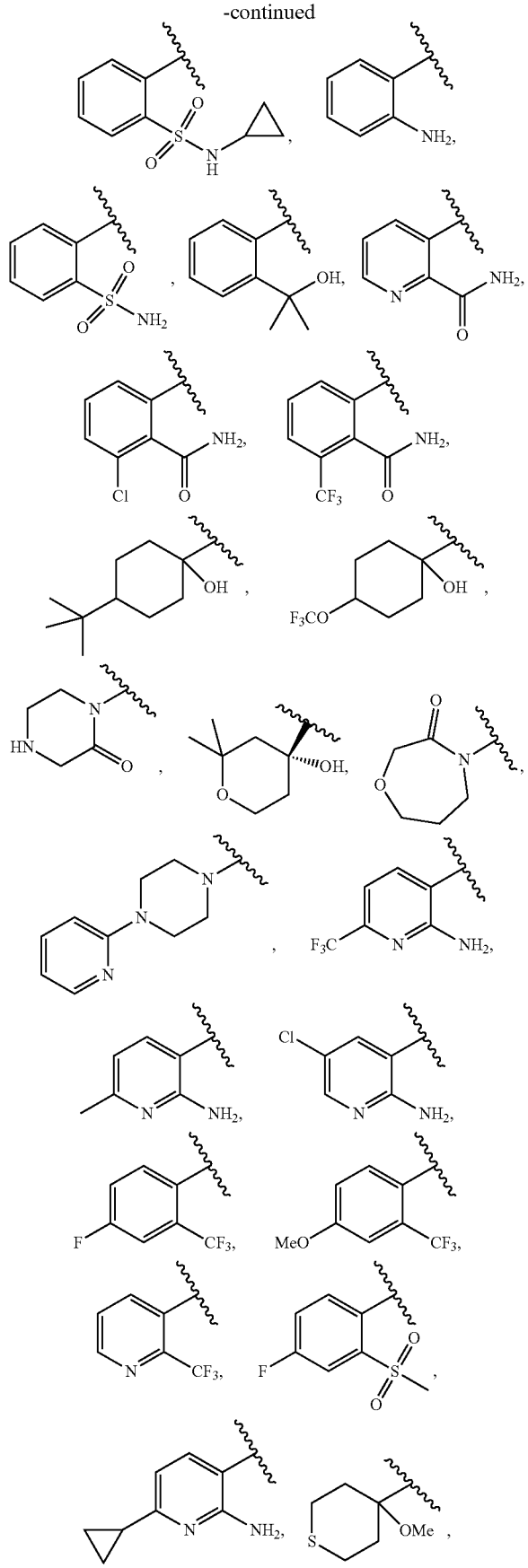
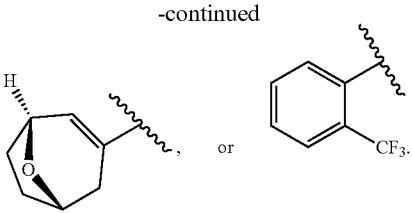
43. The compound of item 42, where R² is:
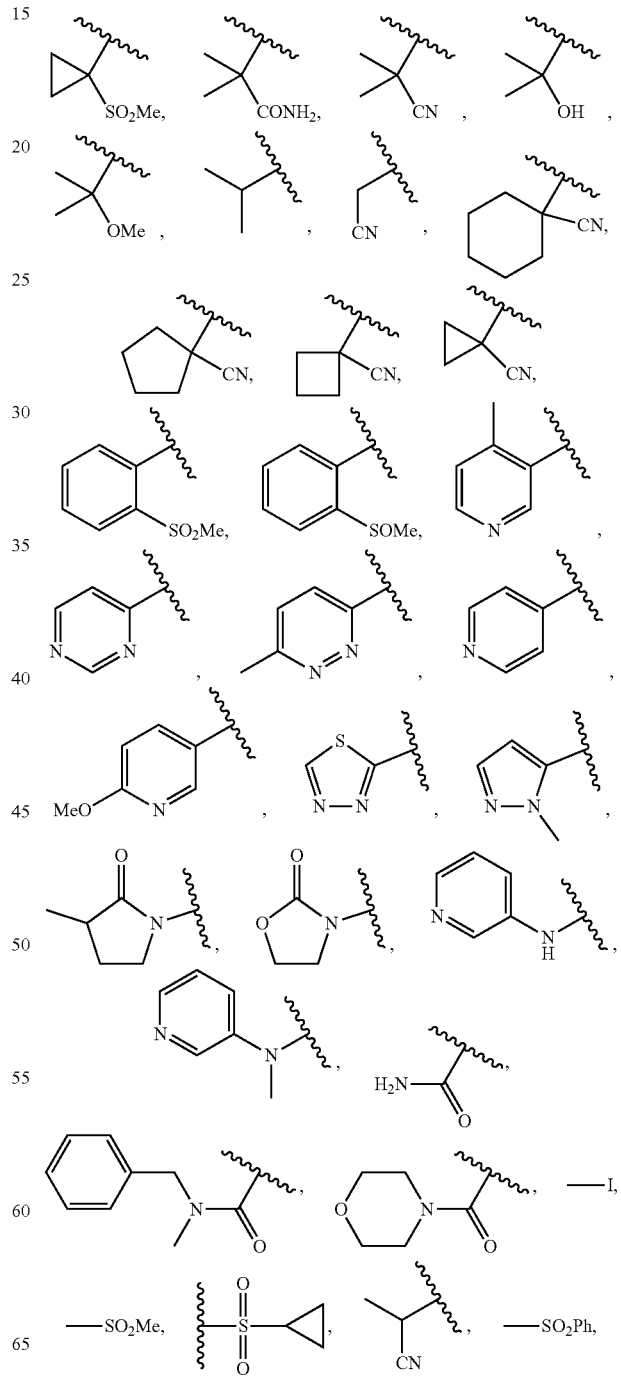

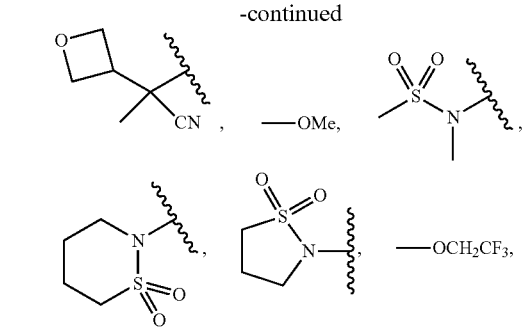
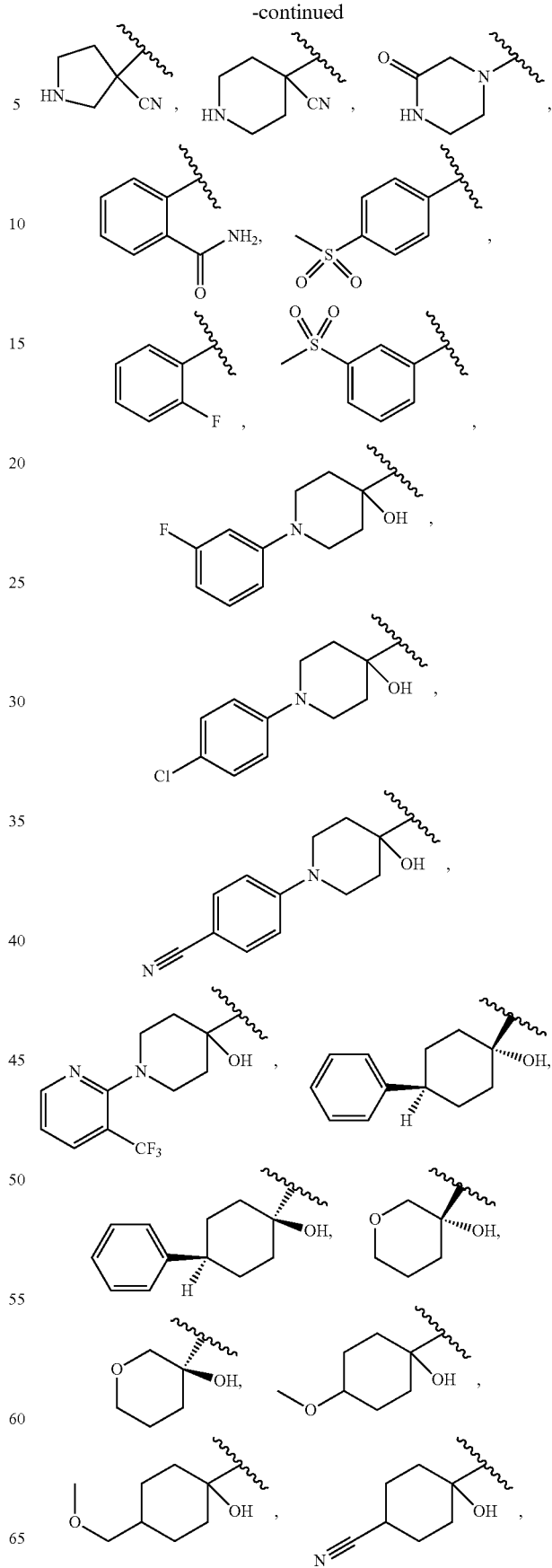

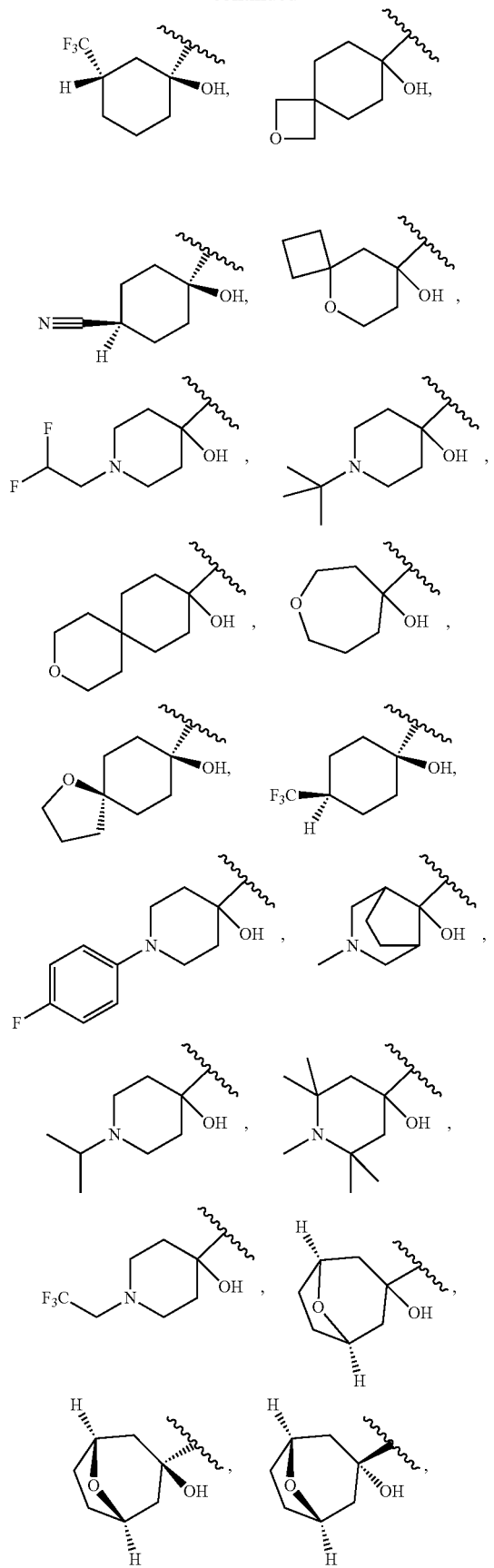
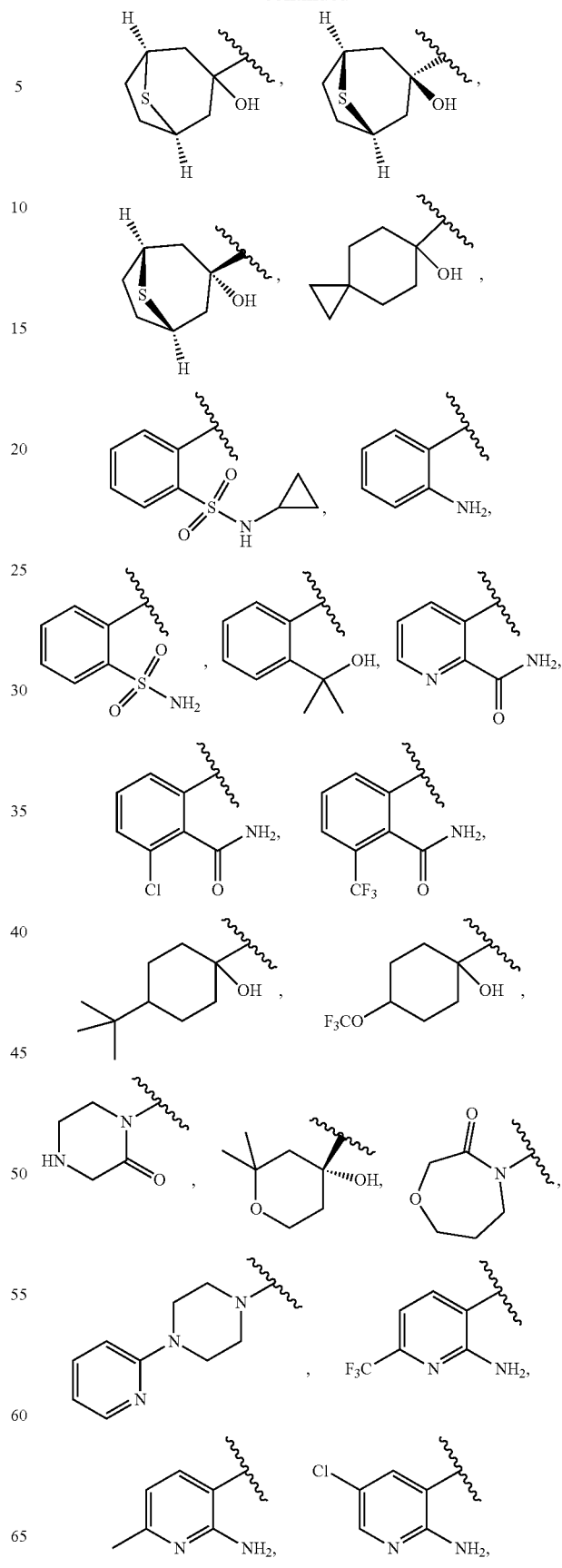

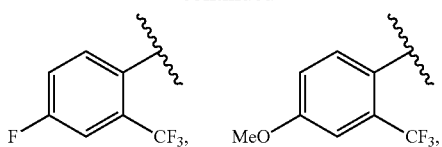
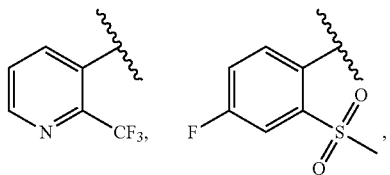
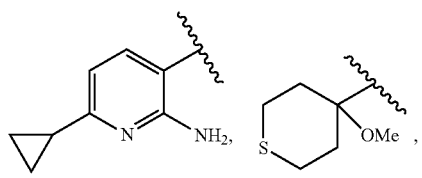
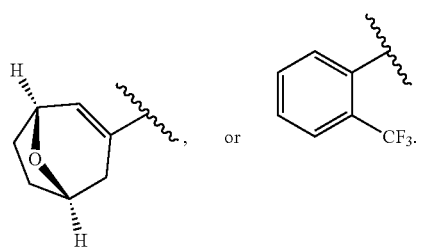
44. The compound of item 42, where R² is:
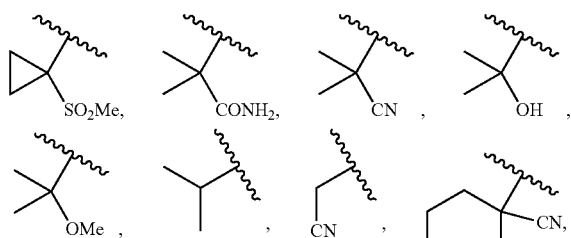
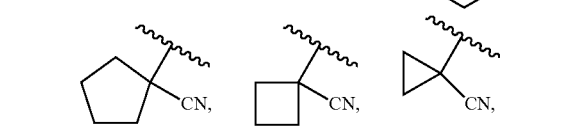
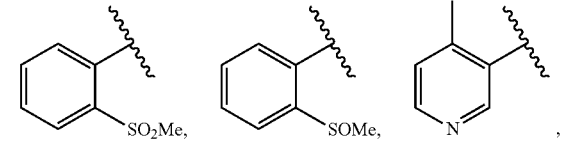
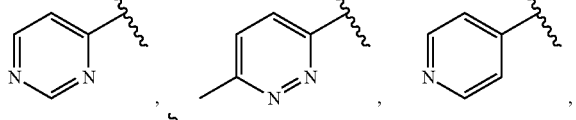
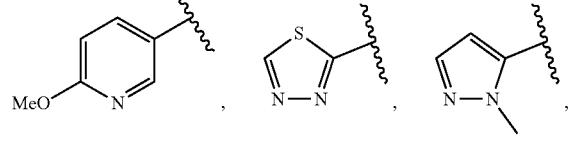
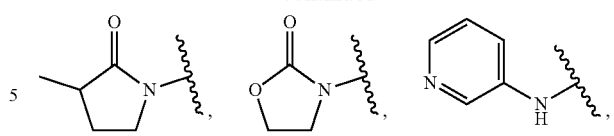
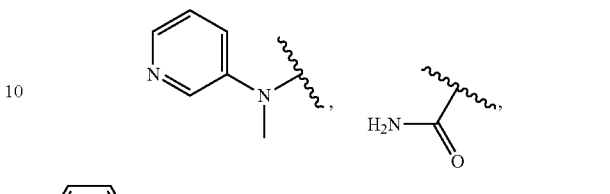
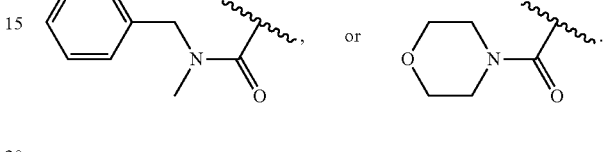
45. The compound of item 42, where R² is:
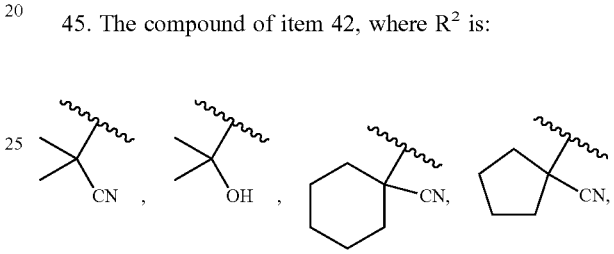
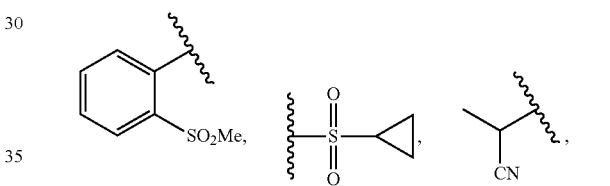
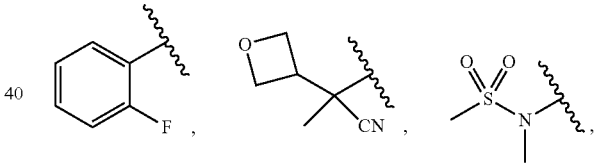
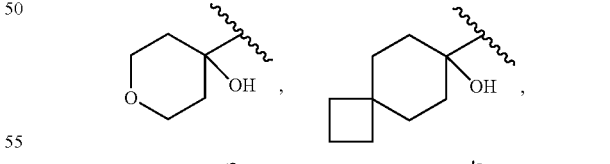
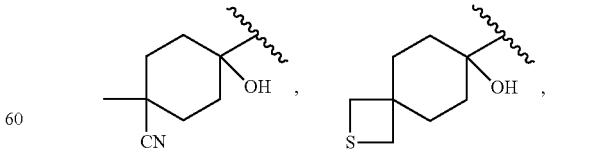
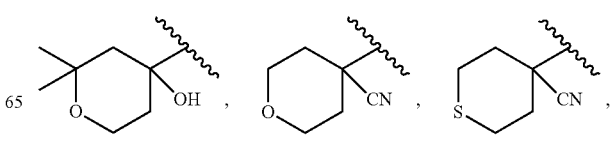

-continued
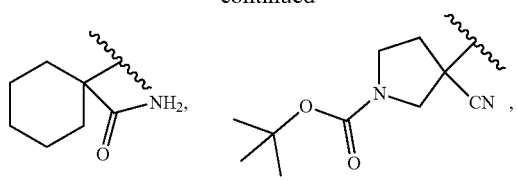
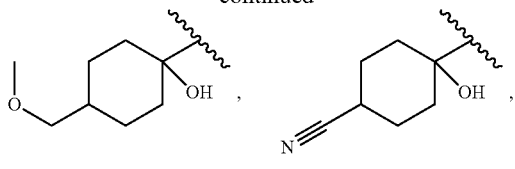
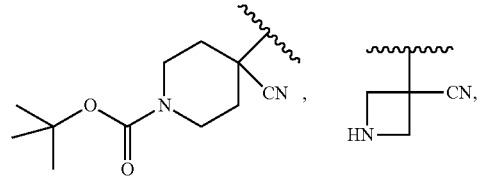
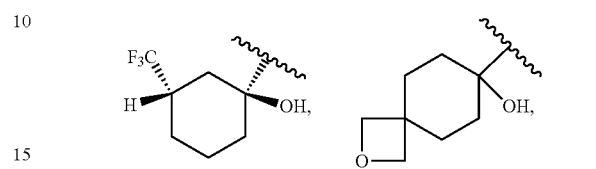
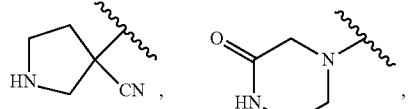
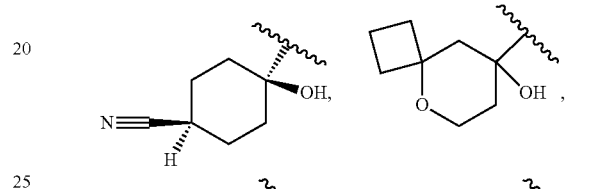
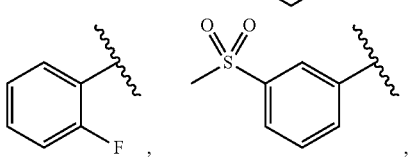
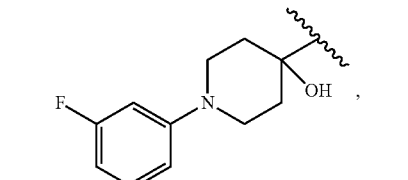
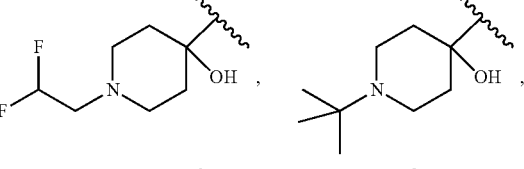
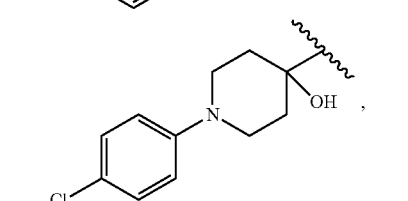
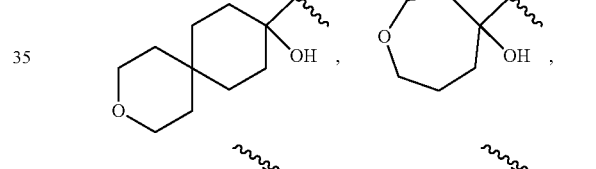
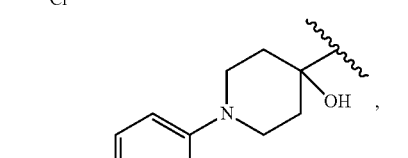
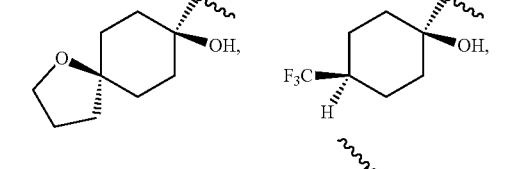
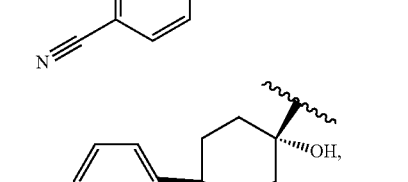
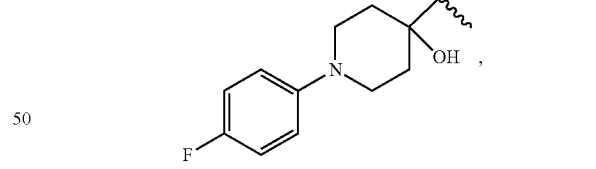
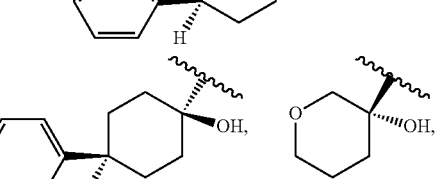
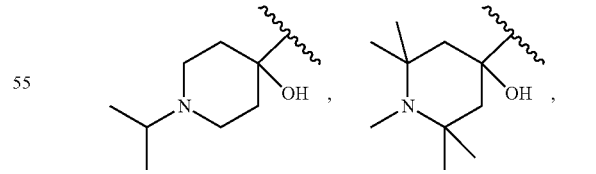
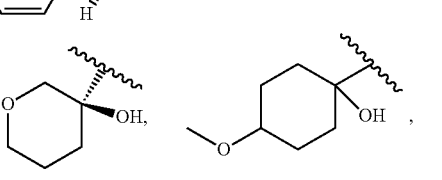
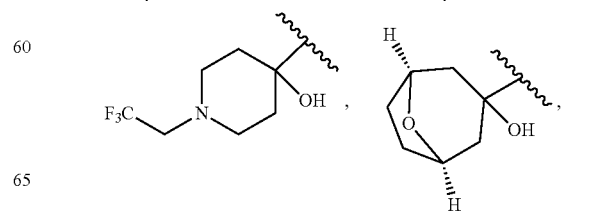

-continued
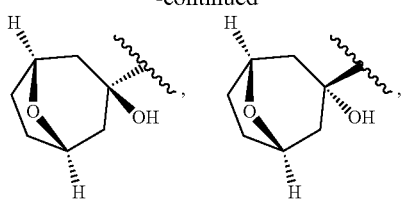
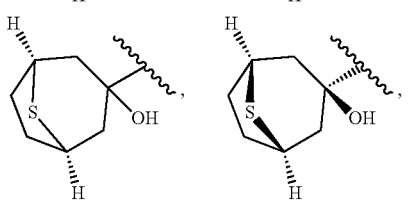
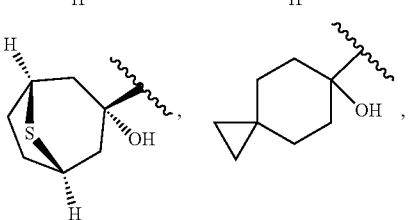
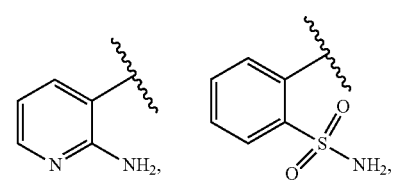
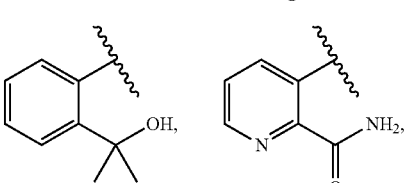
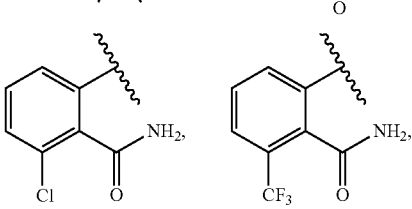
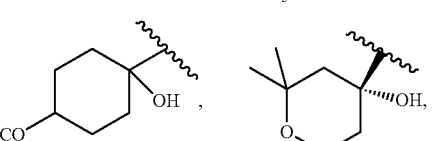
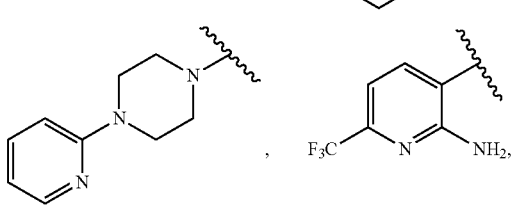
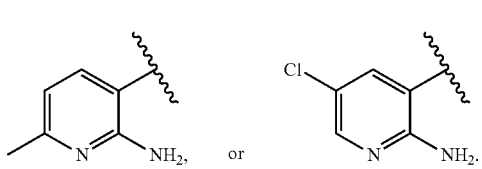
46. The compound of item 42, where $R^2$ is:
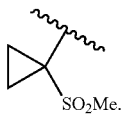
47. The compound of item 42, where $R^2$ is:
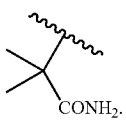
48. The compound of item 42, where $R^2$ is:
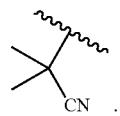
49. The compound of item 42, where $R^2$ is:
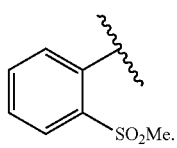
50. The compound of item 42, where $R^2$ is:
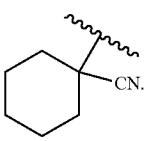 [SMILES: *C1(C#N)CCCCC1]
51. The compound of item 42, where $R^2$ is:
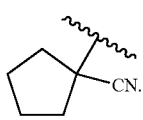
52. The compound of item 42, where $R^2$ is:

53. The compound of item 42, where R² is:

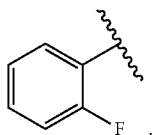 [SMILES: *c1ccccc1F]

54. The compound of item 42, where R² is:

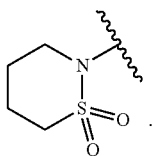 [SMILES: *N1CCCCS1(=O)=O]

55. The compound of item 42, where R² is:

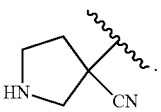

56. The compound of item 42, where R² is:

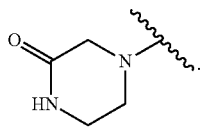 [SMILES: *N1CCNC(=O)C1]

57. The compound of item 42, where R² is:

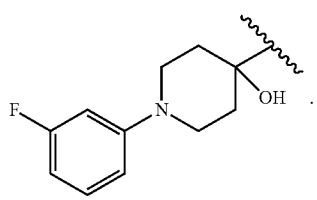 [SMILES: *C1(O)CCN(c2cccc(F)c2)CC1]

58. The compound of item 42, where R² is:

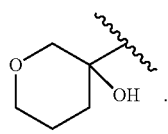

59. The compound of item 42, where R² is:

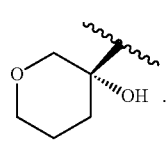 [SMILES: *[C@@]1(O)CCCOC1]

60. The compound of item 42, where R² is:

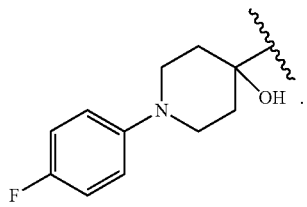

61. The compound of item 42, where R² is:

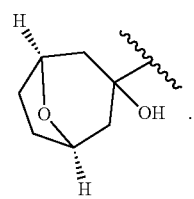

62. The compound of item 61, where R² is:

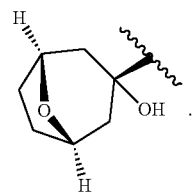 [SMILES: *[C@@]1(O)C[C@H]2CC[C@@H](C1)O2]

63. The compound of item 42, where R² is:

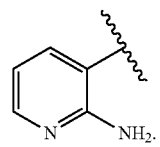 [SMILES: *c1cccnc1N]

64. The compound of item 42, where R² is:

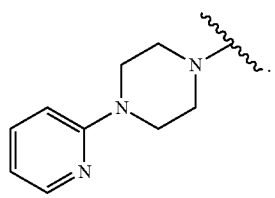 [SMILES: *N1CCN(c2ccccn2)CC1]

65. The compound of item 42, where R² is:

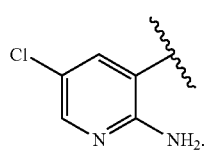 [SMILES: *c1cc(Cl)cnc1N]

66. The compound of item 42, where $R^2$ is:

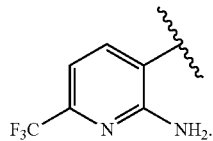

67. The compound of item 42, where $R^2$ is:

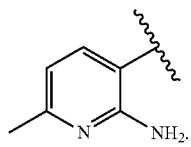

68. The compound of item 42, where $R^2$ is:

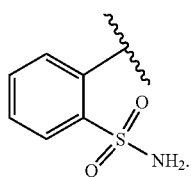 [SMILES: *c1ccccc1S(N)(=O)=O]

69. The compound of item 42, where $R^2$ is:

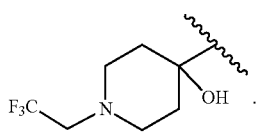

70. The compound of any one of items 1 to 69, where $R^3$ is optionally substituted, monocyclic $C_{1-9}$ heteroaryl including at least one nitrogen atom.

71. The compound of item 70, where $R^3$ is optionally substituted, monocyclic $C_{1-9}$ heteroaryl including two nitrogen atoms.

72. The compound of item 70, where $R^3$ is a group of formula (C):

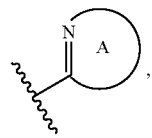

where A is optionally substituted, monocyclic $C_{1-9}$ heteroaryl ring.

73. The compound of item 70, where $R^3$ is a group of formula (C1):

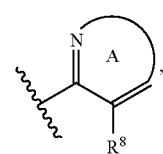

where $R^8$ is hydrogen, halogen, or optionally substituted $C_{1-6}$ alkyl.

74. The compound of item 73, where $R^8$ is hydrogen or halogen.

75. The compound of any one of items 72 to 74, where A is optionally substituted, monocyclic $C_{1-9}$ heteroaryl ring including two nitrogen atoms.

76. The compound of any one of items 1 to 75, where $R^3$ is:

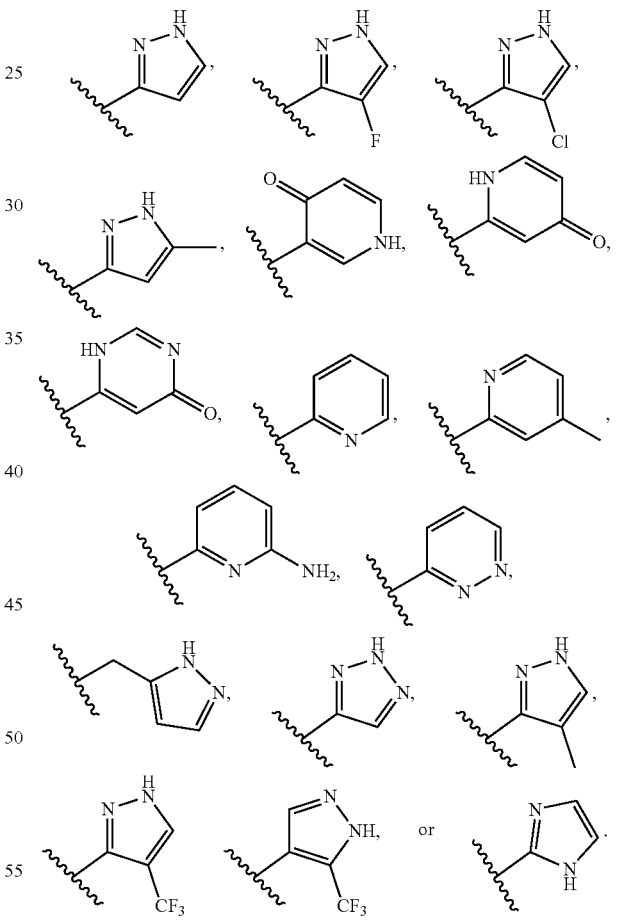

77. The compound of item 76, where $R^3$ is:

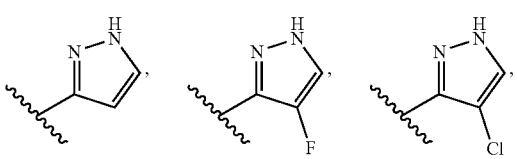

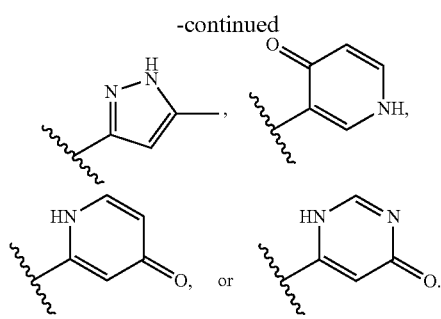

78. The compound of item 76, where R³ is:

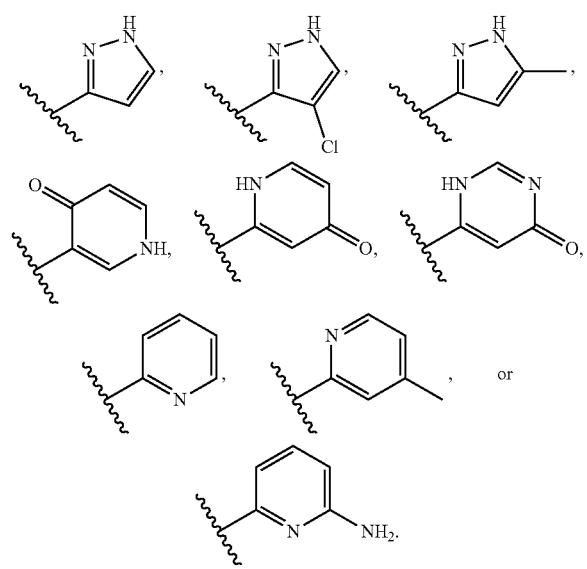

79. The compound of item 76, where R³ is:

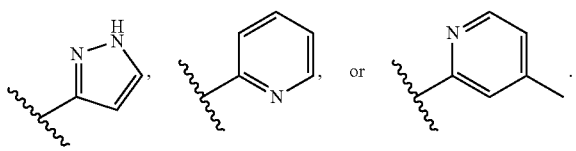

80. The compound of item 76, where R³ is:

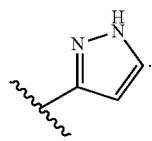

81. The compound of any one of items 1 to 80, where R⁴ is hydrogen.

82. The compound of any one of items 1 to 80, where R⁴ is halogen.

83. The compound of any one of items 1 to 80, where R⁴ is optionally substituted $C_{2-6}$ alkenyl.

84. The compound of any one of items 1 to 80, where X is hydrogen.

85. A compound selected from the group consisting of compounds 1-152 and pharmaceutically acceptable salts thereof.

87. The compound of item 85, where the compound is selected from the group consisting of:
compound 1, 2, 3, 4, 5, 6, 7, 8, 24, 43, 45, 47, 48, 49, 52, 53, 55, 57, 58, 59, 61, 62, 63, 73, 74, 77, 80, 81, 82, 84, 86, 87, 92, 93, 94, 95, 97, 98, 99, 100, 101, 102, 103, 104, 105, 106, 107, 108, 109, 110, 111, 112, 113, 114, 115, 116, 118, 119, 120, 121, 122, 123, 125, 126, 127, 128, 129, 130, 131, 132, 133, 135, 137, 138, 139, 140, 141, 142, 143, 144, 145, 146, 147, 148, 150, 151, and pharmaceutically acceptable salts thereof.

88. The compound of item 85, where the compound is selected from the group consisting of compounds 6, 8, 43, 48, 92, 126, 128, 130, 131, 141, 142, 143, 145, 150, and pharmaceutically acceptable salts thereof.

89. The compound of item 85, where the compound is selected from the group consisting of compounds 2, 4, 7, 47, 49, 63, 86, and pharmaceutically acceptable salts thereof.

90. The compound of item 85, where the compound is selected from the group consisting of compounds 57, 62, 73, 74, 80, 81, 82, 84, 87, 93, 94, 95, 99, 100, 106, 107, 108, 109, 111, 112, 113, 114, 115, 116, 118, 119, 120, 121, 122, 123, 135, 137, 138, 144, 146, 147, 148, 151, and pharmaceutically acceptable salts thereof.

91. The compound of item 85, where the compound is selected from the group consisting of compounds 57, 62, 87, 93, 94, 95, 99, 100, 106, 107, 108, 109, 111, 112, 113, 114, 115, 116, 118, 119, 120, 121, 122, 123, 135, 147, 148, and pharmaceutically acceptable salts thereof.

92. The compound of item 85, where the compound is selected from the group consisting of compounds 61, 105, 107, 110, 112, 113, and pharmaceutically acceptable salts thereof.

93. The compound of item 56, where the compound is selected from the group consisting of compounds 121, 122, and pharmaceutically acceptable salts thereof.

94. The compound of item 85, where the compound is selected from the group consisting of compounds 125, 127, 129, 138, 139, 140, 144, 146, 151, and pharmaceutically acceptable salts thereof.

95. The compound of item 85, where the compound is selected from the group consisting of compounds 58, 123, and pharmaceutically acceptable salts thereof.

96. The compound of item 85, where the compound is selected from the group consisting of compounds 1, 3, 5, 59, 77, 97, 98, 101, 102, 103, 104, 106, 114, 115, 132, 133, and pharmaceutically acceptable salts thereof.

97. The compound of item 85, where the compound is selected from the group consisting of compounds 45, 52, 55, and pharmaceutically acceptable salts thereof.

98. The compound of item 85, where the compound is compound 1 or a pharmaceutically acceptable salt thereof.

99. The compound of item 85, where the compound is compound 2 or a pharmaceutically acceptable salt thereof.

100. The compound of item 85, where the compound is compound 3 or a pharmaceutically acceptable salt thereof.

101. The compound of item 85, where the compound is compound 4 or a pharmaceutically acceptable salt thereof.

102. The compound of item 85, where the compound is compound 5 or a pharmaceutically acceptable salt thereof.

103. The compound of item 85, where the compound is compound 6 or a pharmaceutically acceptable salt thereof.

104. The compound of item 85, where the compound is compound 7 or a pharmaceutically acceptable salt thereof.

105. The compound of item 85, where the compound is compound 8 or a pharmaceutically acceptable salt thereof.

106. The compound of item 85, where the compound is compound 9 or a pharmaceutically acceptable salt thereof.

107. The compound of item 85, where the compound is compound 86 or a pharmaceutically acceptable salt thereof.

108. The compound of item 85, where the compound is compound 99 or a pharmaceutically acceptable salt thereof.

109. The compound of item 85, where the compound is compound 100 or a pharmaceutically acceptable salt thereof.

110. The compound of item 85, where the compound is compound 115 or a pharmaceutically acceptable salt thereof.

111. The compound of item 85, where the compound is compound 120 or a pharmaceutically acceptable salt thereof.

112. The compound of item 85, where the compound is compound 121 or a pharmaceutically acceptable salt thereof.

113. The compound of item 85, where the compound is compound 125 or a pharmaceutically acceptable salt thereof.

114. The compound of item 85, where the compound is compound 126 or a pharmaceutically acceptable salt thereof.

115. The compound of item 85, where the compound is compound 138 or a pharmaceutically acceptable salt thereof.

116. The compound of item 85, where the compound is compound 139 or a pharmaceutically acceptable salt thereof.

117. The compound of item 85, where the compound is compound 140 or a pharmaceutically acceptable salt thereof.

118. The compound of item 85, where the compound is compound 142 or a pharmaceutically acceptable salt thereof.

119. The compound of item 85, where the compound is compound 144 or a pharmaceutically acceptable salt thereof.

120. The compound of item 85, where the compound is compound 147 or a pharmaceutically acceptable salt thereof.

121. The compound of item 85, where the compound is compound 148 or a pharmaceutically acceptable salt thereof.

122. The compound of item 85, where the compound is compound 150 or a pharmaceutically acceptable salt thereof.

123. The compound of item 85, where the compound is compound 151 or a pharmaceutically acceptable salt thereof.

124. A pharmaceutical composition including the compound of any one of items 1 to 123 and a pharmaceutically acceptable excipient.

125. The pharmaceutical composition of item 124, where the compound is isotopically enriched in deuterium.

126. A method of inhibiting ATR kinase in a cell expressing ATR kinase, the method including contacting the cell with the compound of any one of items 1 to 123.

127. The method of item 126, where the cell is in vitro.

128. The method of item 126, where the cell is in a subject.

129. A method of treating a subject in need thereof including administering to the subject the compound of any one of items 1 to 123 or the pharmaceutical composition of item 124 or 125.

130. The method of item 128 or 129, where the subject is suffering from, and is in need of a treatment for, a disease or condition having the symptom of cell hyperproliferation.

131. The method of item 130, where the disease or condition is a cancer.

132. The method of item 131, where the cancer is a solid tumor.

133. The method of item 131, where the cancer is a carcinoma, sarcoma, adenocarcinoma, leukemia, or melanoma.

134. The method of item 131, where the cancer is a carcinoma selected from the group consisting of medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, Schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

135. The method of item 131, where the cancer is a sarcoma selected from the group consisting of chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

136. The method of item 131, where the cancer is a leukemia selected from the group consisting of nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Riedercell leukemia, Schilling's leukemia, stem cell leukemia, subleukemic leukemia, and undifferentiated cell leukemia.

137. The method of item 136, where the cancer is chronic lymphocytic leukemia.

138. The method of item 131, where the cancer is a lymphoma.

139. The method of item 138, where the lymphoma is non-Hodgkin lymphoma, Hodgkin disease, diffuse large B-cell lymphoma, follicular lymphoma, mucosa-associated lymphatic tissue (MALT) lymphoma, small cell lymphocytic lymphoma-chronic lymphocytic leukemia, mantle ceil lymphoma, mediastinal (thymic) large B-cell lymphoma, lymphoplasmacytic lymphoma-Waldenstrom macroglobulinemia, peripheral T-cell lymphoma (PTCL), angioimmunoblastic T-cell lymphoma (AITL)/follicular T-cell lymphoma (FTCL), anaplastic large cell lymphoma (ALCL), enteropathy-associated T-cell lymphoma (EATL), adult T-cell leukaemia/lymphoma (ATLL), or extranodal NK/T-cell lymphoma, nasal type.

140. The method of item 139, where the lymphoma is mantle cell lymphoma.

141. The method of item 131, where the cancer is a melanoma selected from the group consisting of acrallentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungual melanoma, and superficial spreading melanoma.

142. The method of item 131, where the cancer is prostate cancer, thyroid cancer, endocrine system cancer, brain cancer, breast cancer, cervix cancer, colon cancer, head & neck cancer, liver cancer, kidney cancer, lung cancer, non-small cell lung cancer, melanoma, mesothelioma, ovarian cancer, sarcoma, stomach cancer, uterus cancer, medulloblastoma, ampullary cancer, colorectal cancer, or pancreatic cancer.

143. The method of item 131, where the cancer is prostate cancer.

144. The method of item 131, where the cancer is ampullary cancer.

145. The method of item 131, where the cancer is colorectal cancer.

146. The method of item 131, where the cancer is lung cancer.

147. The method of item 131, where the cancer is non-small cell lung cancer.

148. The method of item 131, where the cancer is ovarian cancer.

149. The method of item 131, where the cancer is pancreatic cancer.

150. The method of item 131, where the cancer is Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

151. The method of item 129, where the subject is suffering from, and is in need of a treatment for, a premalignant condition.

Abbreviations

Abbreviations and terms that are commonly used in the fields of organic chemistry, medicinal chemistry, pharmacology, and medicine and are well known to practitioners in these fields are used herein. Representative abbreviations and definitions are provided below:

Ac is acetyl [$CH_3C(O)$—], $Ac_2O$ is acetic anhydride; AcOH is acetic acid; APC is antigen-presenting cell; aq. is aqueous; 9-BBN is 9-borabicyclo[3.3.1]nonane; BINAP is (2,2-bis(diphenylphosphino)-1,1'-binaphthyl); Bn is benzyl; BOC is tert Butyloxycarbonyl; CDI is carbonyldiimidazole; DCM is dichloromethane; DIAD is diisopropylazodicarboxylate; DIBAL is diisobutylaluminum hydride; DIPEA is diisoproplyethyl amine; DMA is dimethylacetamide; DMAP is 4-dimethylaminopyridine; DMF is N,N-dimethylformamide; DMSO is dimethyl sulfoxide; dppf is 1,1'-bis(diphenylphosphino)ferrocene; EDAC (or EDC) is 1-ethyl-3-[3-(dimethylamino)propyl]-carbodiimide HCl; ESI is electrospray ionization mass spectrometry; $Et_2O$ is diethyl ether; $Et_3N$ is triethylamine; Et is ethyl; EtOAc is ethyl acetate; EtOH is ethanol; 3-F-Ph is 3-fluorophenyl, HATU is (1-[bis(dimethylamino)methylene]-1H-1,2,3-triazolo[4,5-b]pyridinium 3-oxide hexafluorophosphate; HCl is hydrochloric acid; HOBt is 1-hydroxybenzotriazole; HPLC is high performance liquid chromatography; LCMS is HPLC with mass spectral detection; LiHMDS is lithium bis(trimethylsilyl)amide; LG is leaving group; M is molar; mCPBA is metachloroperbenzoic acid; mmol is millimole; Me is methyl; MeCN is acetonitrile; MeOH is methanol; Ms is methanesulfonyl; MS is mass spectrometry; N is normal; NaHMDS is sodium hexamethyldisiliazide; NaOAc is sodium acetate; NaOtBu is sodium tert-butoxide; NMO is N-methylmorpholine N-oxide; NMP is N-methyl pyrrolidinone; NMR is nuclear magnetic resonance spectroscopy; $Pd_2(dba)_3$ is tris(dibenzylideneacetone)dipalladium; $PdCl_2(PPh_3)_2$ is dichlorobis-(triphenylphosphene) palladium; PG Denotes an unspecified protecting group; Ph is phenyl; PhMe is toluene; $PPh_3$ is triphenylphosphine; PMB is paramethoxybenzyl; rt is room temperature; RBF is round-bottom flask; RuPhos Pd G1 is chloro-(2-Dicyclohexylphosphino-2',6'-diisopropoxy-1,1'-biphenyl)[2-(2-aminoethyl)phenyl]palladium(II); SEM is [2-(trimethylsilyl)ethoxy]methyl; SFC is supercritical fluid chromatography; SNAr is nucleophilic aromatic substitution; TBAB is tetrabutyl ammonium bromide; TBAF is tetrabutyl ammonium fluoride; TBS is tert-butyldimethylsilyl; tBu is tert-butyl; Tf is triflate; TFA is trifluoroacetic acid; THF is tetrahydrofuran; THP is tetrahydropyran; TLC is thin layer chromatography; TMAD is tetramethylazodicarboxamide; TMS is trimethylsilyl; TPAP is tetrapropylammonium perruthenate; Ts is p-toluenesulfonyl; UPLC is ultra performance liquid chromatography.

Definitions

The term "aberrant," as used herein, refers to different from normal. When used to describe enzymatic activity, aberrant refers to activity that is greater or less than a normal control or the average of normal non-diseased control samples. Aberrant activity may refer to an amount of activity that results in a disease, where returning the aberrant activity to a normal or non-disease-associated amount (e.g. by administering a compound or using a method as described herein), results in reduction of the disease or one or more disease symptoms. The aberrant activity can be measured by measuring the modification of a substrate of the enzyme in question; a difference of greater or equal to a 2-fold change in activity could be considered as aberrant. Aberrant activity could also refer to an increased dependence on a particular signaling pathway as a result of a deficiency in a separate complementary pathway The term "acyl," as used herein, represents a group-C(=O)—R, where R is alkyl, alkenyl, alkynyl, cycloalkyl, cycloalkenyl, cycloalkynyl, aryl, heteroaryl, or heterocyclyl. Acyl may be optionally substituted as described herein for each respective R group.

The term "adenocarcinoma," as used herein, represents a malignancy of the arising from the glandular cells that line organs within an organism. Non-limiting examples of adenocarcinomas include non-small cell lung cancer, prostate cancer, pancreatic cancer, esophageal cancer, and colorectal cancer.

The term "alkanoyl," as used herein, represents a hydrogen or an alkyl group that is attached to the parent molecular group through a carbonyl group and is exemplified by formyl (i.e., a carboxyaldehyde group), acetyl, propionyl, butyryl, and iso-butyryl. Unsubstituted alkanoyl groups contain from 1 to 7 carbons. The alkanoyl group may be unsubstituted of substituted (e.g., optionally substituted $C_{1-7}$ alkanoyl) as described herein for alkyl group. The ending "-oyl" may be added to another group defined herein, e.g., aryl, cycloalkyl, and heterocyclyl, to define "aryloyl," "cycloalkanoyl," and "(heterocyclyl)oyl." These groups represent a carbonyl group substituted by aryl, cycloalkyl, or heterocyclyl, respectively. Each of "aryloyl," "cycloalkanoyl," and "(heterocyclyl)oyl" may be optionally substituted as defined for "aryl," "cycloalkyl," or "heterocyclyl," respectively.

The term "alkenyl," as used herein, represents acyclic monovalent straight or branched chain hydrocarbon groups of containing one, two, or three carbon-carbon double bonds. Non-limiting examples of the alkenyl groups include ethenyl, prop-1-enyl, prop-2-enyl, 1-methylethenyl, but-1-enyl, but-2-enyl, but-3-enyl, 1-methylprop-1-enyl, 2-methylprop-1-enyl, and 1-methylprop-2-enyl. Alkenyl groups may be optionally substituted as defined herein for alkyl.

The term "alkoxy," as used herein, represents a chemical substituent of formula —OR, where R is a $C_{1-6}$ alkyl group, unless otherwise specified. In some embodiments, the alkyl group can be further substituted as defined herein. The term "alkoxy" can be combined with other terms defined herein, e.g., aryl, cycloalkyl, or heterocyclyl, to define an "aryl alkoxy," "cycloalkyl alkoxy," and "(heterocyclyl)alkoxy" groups. These groups represent an alkoxy that is substituted by aryl, cycloalkyl, or heterocyclyl, respectively. Each of "aryl alkoxy," "cycloalkyl alkoxy," and "(heterocyclyl)alkoxy" may optionally substituted as defined herein for each individual portion.

The term "alkoxyalkyl," as used herein, represents a chemical substituent of formula -L-O—R, where L is $C_{1-6}$ alkylene, and R is $C_{1-6}$ alkyl. An optionally substituted alkoxyalkyl is an alkoxyalkyl that is optionally substituted as described herein for alkyl.

The term "alkyl," as used herein, refers to an acyclic straight or branched chain saturated hydrocarbon group, which, when unsubstituted, has from 1 to 12 carbons, unless otherwise specified. In certain preferred embodiments, unsubstituted alkyl has from 1 to 6 carbons. Alkyl groups are exemplified by methyl; ethyl; n- and iso-propyl; n-, sec-, iso- and tert-butyl; neopentyl, and the like, and may be optionally substituted, valency permitting, with one, two, three, or, in the case of alkyl groups of two carbons or more, four or more substituents independently selected from the group consisting of: amino; aryl; aryloxy; azido; cycloalkyl; cycloalkoxy; cycloalkenyl; cycloalkynyl; halo; heterocyclyl; (heterocyclyl)oxy; heteroaryl; hydroxy; nitro; thiol; silyl; cyano; alkylsulfonyl; alkylsulfinyl; alkylsulfenyl; =O; =S; —SO$_2$R, where R is amino or cycloalkyl; =NR', where R' is H, alkyl, aryl, or heterocyclyl. Each of the substituents may itself be unsubstituted or, valency permitting, substituted with unsubstituted substituent(s) defined herein for each respective group.

The term "alkylene," as used herein, refers to a divalent alkyl group. An optionally substituted alkylene is an alkylene that is optionally substituted as described herein for alkyl.

The term "alkylamino," as used herein, refers to a group having the formula —N(R$^{N1}$)$_2$ or —NHR$^{N1}$, in which R$^{N1}$ is alkyl, as defined herein. The alkyl portion of alkylamino can be optionally substituted as defined for alkyl. Each optional substituent on the substituted alkylamino may itself be unsubstituted or, valency permitting, substituted with unsubstituted substituent(s) defined herein for each respective group.

The term "alkylsulfenyl," as used herein, represents a group of formula —S-(alkyl). Alkylsulfenyl may be optionally substituted as defined for alkyl.

The term "alkylsulfinyl," as used herein, represents a group of formula —S(O)-(alkyl). Alkylsulfinyl may be optionally substituted as defined for alkyl.

The term "alkylsulfonyl," as used herein, represents a group of formula —S(O)$_2$-(alkyl). Alkylsulfonyl may be optionally substituted as defined for alkyl.

The term "alkynyl," as used herein, represents monovalent straight or branched chain hydrocarbon groups of from two to six carbon atoms containing at least one carbon-carbon triple bond and is exemplified by ethynyl, 1-propynyl, and the like. The alkynyl groups may be unsubstituted or substituted (e.g., optionally substituted alkynyl) as defined for alkyl.

The term "amino," as used herein, represents —N(R$^{N1}$)$_2$, where, if amino is unsubstituted, both R$^{N1}$ are H; or, if amino is substituted, each R$^{N1}$ is independently H, —OH, —NO$_2$, —N(R$^{N2}$)$_2$, —SO$_2$OR$^{N2}$, —SO$_2$R$^{N2}$, —SOR$^{N2}$, —COOR$^{N2}$, an N-protecting group, alkyl, alkenyl, alkynyl, alkoxy, aryl, arylalkyl, aryloxy, cycloalkyl, cycloalkenyl, heteroalkyl, or heterocyclyl, provided that at least one R$^{N1}$ is not H, and where each R$^{N2}$ is independently H, alkyl, or aryl. Each of the substituents may itself be unsubstituted or substituted with unsubstituted substituent(s) defined herein for each respective group. In some embodiments, amino is unsubstituted amino (i.e., —NH$_2$) or substituted amino (e.g., NHR$^{N1}$), where R$^{N1}$ is independently —OH, SO$_2$OR$^{N2}$, —SO$_2$R$^{N2}$, —SOR$^{N2}$, —COOR$^{N2}$, optionally substituted alkyl, or optionally substituted aryl, and each R$^{N2}$ can be optionally substituted alkyl or optionally substituted aryl. In some embodiments, substituted amino may be alkylamino, in which the alkyl groups are optionally substituted as described herein for alkyl. In some embodiments, an amino group is —NHR$^{N1}$, in which R$^{N1}$ is optionally substituted alkyl.

The term "aryl," as used herein, represents a mono-, bicyclic, or multicyclic carbocyclic ring system having one or two aromatic rings. Aryl group may include from 6 to 10 carbon atoms. All atoms within an unsubstituted carbocyclic aryl group are carbon atoms. Non-limiting examples of carbocyclic aryl groups include phenyl, naphthyl, 1,2-dihydronaphthyl, 1,2,3,4-tetrahydronaphthyl, fluorenyl, indanyl, indenyl, etc. The aryl group may be unsubstituted or substituted with one, two, three, four, or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; hydroxy; nitro; thiol; silyl; and cyano. Each of the substituents may itself be unsubstituted or substituted with unsubstituted substituent(s) defined herein for each respective group.

The term "aryl alkyl," as used herein, represents an alkyl group substituted with an aryl group. The aryl and alkyl portions may be optionally substituted as the individual groups as described herein.

The term "arylene," as used herein, refers to a divalent aryl group. An optionally substituted arylene is an arylene that is optionally substituted as described herein for aryl.

The term "aryloxy," as used herein, represents a chemical substituent of formula —OR, where R is an aryl group, unless otherwise specified. In optionally substituted aryloxy, the aryl group is optionally substituted as described herein for aryl.

The term "ATR inhibitor," as used herein, represents a compound that upon contacting the enzyme ATR kinase, whether in vitro, in cell culture, or in an animal, reduces the activity of ATR kinase, such that the measured ATR kinase $IC_{50}$ is 10 µM or less (e.g., 5 µM or less or 1 µM or less). For certain ATR inhibitors, the ATR kinase $IC_{50}$ may be 100 nM or less (eg 10 nM or less, or 1 nM or less) and could be as low as 100 µM or 10 µM. Preferably, the ATR kinase $IC_{50}$ is 1 nM to 1 µM (e.g., 1 nM to 750 nM, 1 nM to 500 nM, or 1 nM to 250 nM).

The term "ATR kinase," as used herein, refers to Ataxia-telangiectasia and RAD-3-related protein kinase.

The term "azido," as used herein, represents an —$N_3$ group.

The term "cancer," as used herein, refers to all types of cancer, neoplasm or malignant tumors found in mammals (e.g. humans), including leukemia, carcinomas and sarcomas. Non-limiting examples of cancers that may be treated with a compound or method provided herein include prostate cancer, thyroid cancer, endocrine system cancer, brain cancer, breast cancer, cervix cancer, colon cancer, head & neck cancer, liver cancer, kidney cancer, lung cancer, non-small cell lung cancer, melanoma, mesothelioma, ovarian cancer, sarcoma, stomach cancer, uterus cancer, medulloblastoma, ampullary cancer, colorectal cancer, and pancreatic cancer. Additional non-limiting examples may include, Hodgkin's disease, Non-Hodgkin's lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulinoma, malignant carcinoid, urinary bladder cancer, premalignant skin lesions, testicular cancer, lymphoma, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, and prostate cancer.

The term "carbocyclic," as used herein, represents an optionally substituted $C_{3-16}$ monocyclic, bicyclic, or tricyclic structure in which the rings, which may be aromatic or non-aromatic, are formed by carbon atoms. Carbocyclic structures include cycloalkyl, cycloalkenyl, cycloalkynyl, and certain aryl groups.

The term "carbonyl," as used herein, represents a —C(O)— group.

The term "carcinoma," as used herein, refers to a malignant new growth made up of epithelial cells tending to infiltrate the surrounding tissues and give rise to metastases. Non-limiting examples of carcinomas that may be treated with a compound or method provided herein include, e.g., medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, Schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

The term "cyano," as used herein, represents —CN group.

The term "cycloalkenyl," as used herein, refers to a non-aromatic carbocyclic group having at least one double bond in the ring and from three to ten carbons (e.g., a $C_{3-10}$ cycloalkenyl), unless otherwise specified. Non-limiting examples of cycloalkenyl include cycloprop-1-enyl, cycloprop-2-enyl, cyclobut-1-enyl, cyclobut-1-enyl, cyclobut-2-enyl, cyclopent-1-enyl, cyclopent-2-enyl, cyclopent-3-enyl, norbornen-1-yl, norbornen-2-yl, norbornen-5-yl, and norbornen-7-yl. The cycloalkenyl group may be unsubstituted or substituted (e.g., optionally substituted cycloalkenyl) as described for cycloalkyl.

The term "cycloalkenyl alkyl," as used herein, represents an alkyl group substituted with a cycloalkenyl group, each as defined herein. The cycloalkenyl and alkyl portions may be substituted as the individual groups defined herein.

The term "cycloalkoxy," as used herein, represents a chemical substituent of formula —OR, where R is cycloalkyl group, unless otherwise specified. In some embodiments, the cycloalkyl group can be further substituted as defined herein.

The term "cycloalkyl," as used herein, refers to a cyclic alkyl group having from three to ten carbons (e.g., a $C_{3-C10}$ cycloalkyl), unless otherwise specified. Cycloalkyl groups may be monocyclic or bicyclic. Bicyclic cycloalkyl groups may be of bicyclo[p.q.0]alkyl type, in which each of p and q is, independently, 1, 2, 3, 4, 5, 6, or 7, provided that the sum of p and q is 2, 3, 4, 5, 6, 7, or 8. Alternatively, bicyclic cycloalkyl groups may include bridged cycloalkyl structures, e.g., bicyclo[p.q.r]alkyl, in which r is 1, 2, or 3, each of p and q is, independently, 1, 2, 3, 4, 5, or 6, provided that the sum of p, q, and r is 3, 4, 5, 6, 7, or 8. The cycloalkyl group may be a spirocyclic group, e.g., spiro[p.q]alkyl, in which each of p and q is, independently, 2, 3, 4, 5, 6, or 7, provided that the sum of p and q is 4, 5, 6, 7, 8, or 9. Non-limiting examples of cycloalkyl include cyclopropyl, cyclobutyl, cyclopentyl, cyclohexyl, cycloheptyl, 1-bicyclo[2.2.1,]heptyl, 2-bicyclo[2.2.1,]heptyl, 5-bicyclo[2.2.1,]heptyl, 7-bicyclo[2.2.1,]heptyl, and decalinyl. The cycloalkyl group may be unsubstituted or substituted (e.g., optionally substituted cycloalkyl) with one, two, three, four, or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; heteroaryl; hydroxy; nitro; thiol; silyl; cyano; =O; =S; —$SO_2R$, where R is amino or cycloalkyl; =NR', where R' is H, alkyl, aryl, or heterocyclyl; or —$CON(R^A)_2$, where each $R^A$ is independently H or alkyl, or both $R^A$, together with the atom to which they are attached, combine to form heterocyclyl. Each of the substituents may itself be unsubstituted or substituted with unsubstituted substituent(s) defined herein for each respective group.

The term "cycloalkyl alkyl," as used herein, represents an alkyl group substituted with a cycloalkyl group, each as defined herein. The cycloalkyl and alkyl portions may be optionally substituted as the individual groups described herein.

The term "cycloalkylene," as used herein, represents a divalent cycloalkyl group. An optionally substituted cycloalkylene is a cycloalkylene that is optionally substituted as described herein for cycloalkyl.

The term "cycloalkynyl," as used herein, refers to a monovalent carbocyclic group having one or two carbon-carbon triple bonds and having from eight to twelve carbons, unless otherwise specified. Cycloalkynyl may include one transannular bond or bridge. Non-limiting examples of cycloalkynyl include cyclooctynyl, cyclononynyl, cyclodecynyl, and cyclodecadiynyl. The cycloalkynyl group may be unsubstituted or substituted (e.g., optionally substituted cycloalkynyl) as defined for cycloalkyl.

"Disease" or "condition" refer to a state of being or health status of a patient or subject capable of being treated with the compounds or methods provided herein.

The term "halo," as used herein, represents a halogen selected from bromine, chlorine, iodine, and fluorine.

The term "heteroalkyl," as used herein refers to an alkyl, alkenyl, or alkynyl group interrupted once by one or two heteroatoms; twice, each time, independently, by one or two heteroatoms; three times, each time, independently, by one or two heteroatoms; or four times, each time, independently, by one or two heteroatoms. Each heteroatom is, independently, O, N, or S. In some embodiments, the heteroatom is O or N. None of the heteroalkyl groups includes two contiguous oxygen or sulfur atoms. The heteroalkyl group may be unsubstituted or substituted (e.g., optionally substituted heteroalkyl). When heteroalkyl is substituted and the substituent is bonded to the heteroatom, the substituent is selected according to the nature and valency of the heteroatom. Thus, the substituent bonded to the heteroatom, valency permitting, is selected from the group consisting of =O, —$N(R^{N2})_2$, —$SO_2OR^{N3}$, —$SO_2R^{N2}$, —$SOR^{N3}$, —$COOR^{N3}$, an N protecting group, alkyl, alkenyl, alkynyl, aryl, cycloalkyl, cycloalkenyl, cycloalkynyl, heterocyclyl, or cyano, where each $R^{N2}$ is independently H, alkyl, cycloalkyl, cycloalkenyl, cycloalkynyl, aryl, or heterocyclyl, and each $R^{N3}$ is independently alkyl, cycloalkyl, cycloalkenyl, cycloalkynyl, aryl, or heterocyclyl. Each of these substituents may itself be unsubstituted or substituted with unsubstituted substituent(s) defined herein for each respective group. When heteroalkyl is substituted and the substituent is bonded to carbon, the substituent is selected from those described for alkyl, provided that the substituent on the carbon atom bonded to the heteroatom is not Cl, Br, or I. It is understood that carbon atoms are found at the termini of a heteroalkyl group.

The term "heteroaryl alkyl," as used herein, represents an alkyl group substituted with a heteroaryl group, each as defined herein. The heteroaryl and alkyl portions may be optionally substituted as the individual groups described herein.

The term "heteroarylene," as used herein, represents a divalent heteroaryl. An optionally substituted heteroarylene is a heteroarylene that is optionally substituted as described herein for heteroaryl.

The term "heteroaryloxy," as used herein, refers to a structure —OR, in which R is heteroaryl. Heteroaryloxy can be optionally substituted as defined for heterocyclyl.

The term "heterocyclyl," as used herein, represents a monocyclic, bicyclic, tricyclic, or tetracyclic ring system having fused, bridging, and/or spiro 3-, 4-, 5-, 6-, 7-, or 8-membered rings, unless otherwise specified, containing one, two, three, or four heteroatoms independently selected from the group consisting of nitrogen, oxygen, and sulfur. In some embodiments, "heterocyclyl" is a monocyclic, bicyclic, tricyclic, or tetracyclic ring system having fused or bridging 5-, 6-, 7-, or 8-membered rings, unless otherwise specified, containing one, two, three, or four heteroatoms independently selected from the group consisting of nitrogen, oxygen, and sulfur. Heterocyclyl can be aromatic or non-aromatic. Non-aromatic 5-membered heterocyclyl has zero or one double bonds, non-aromatic 6- and 7-membered heterocyclyl groups have zero to two double bonds, and non-aromatic 8-membered heterocyclyl groups have zero to two double bonds and/or zero or one carbon-carbon triple bond. Heterocyclyl groups include from 1 to 16 carbon atoms unless otherwise specified. Certain heterocyclyl groups may include up to 9 carbon atoms. Non-aromatic heterocyclyl groups include pyrrolinyl, pyrrolidinyl, pyrazolinyl, pyrazolidinyl, imidazolinyl, imidazolidinyl, piperidinyl, homopiperidinyl, piperazinyl, pyridazinyl, oxazolidinyl, isoxazolidiniyl, morpholinyl, thiomorpholinyl, thiazolidinyl, isothiazolidinyl, thiazolidinyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, etc. If the heterocyclic ring system has at least one aromatic resonance structure or at least one aromatic tautomer, such structure is an aromatic heterocyclyl (i.e., heteroaryl). Non-limiting examples of heteroaryl groups include benzimidazolyl, benzofuryl, benzothiazolyl, benzothienyl, benzoxazolyl, furyl, imidazolyl, indolyl, isoindazolyl, isoquinolinyl, isothiazolyl, isothiazolyl, isoxazolyl, oxadiazolyl, oxazolyl, purinyl, pyrrolyl, pyridinyl, pyrazinyl, pyrimidinyl, qunazolinyl, quinolinyl, thiadiazolyl (e.g., 1,3,4-thiadiazole), thiazolyl, thienyl, triazolyl, tetrazolyl, etc. The term "heterocyclyl" also represents a heterocyclic compound having a bridged multicyclic structure in which one or more carbons and/or heteroatoms bridges two non-adjacent members of a monocyclic ring, e.g., quinuclidine, tropanes, or diaza-bicyclo[2.2.2]octane. The term "heterocyclyl" includes bicyclic, tricyclic, and tetracyclic groups in which any of the above heterocyclic rings is fused to one, two, or three carbocyclic rings, e.g., an aryl ring, a cyclohexane ring, a cyclohexene ring, a cyclopentane ring, a cyclopentene ring, or another monocyclic heterocyclic ring. Examples of fused heterocyclyls include 1,2,3,5,8,8a-hexahydroindolizine; 2,3-dihydrobenzofuran; 2,3-dihydroindole; and 2,3-dihydrobenzothiophene. The heterocyclyl group may be unsubstituted or substituted with one, two, three, four or five substituents independently selected from the group consisting of: alkyl; alkenyl; alkynyl; alkoxy; alkylsulfinyl; alkylsulfenyl; alkylsulfonyl; amino; aryl; aryloxy; azido; cycloalkyl; cycloalkoxy; cycloalkenyl; cycloalkynyl; halo; heteroalkyl; heterocyclyl; (heterocyclyl)oxy; hydroxy; nitro; thiol; silyl; cyano; =O; =S; =NR', where R' is H, alkyl, aryl, or heterocyclyl. Each of the substituents may itself be unsubstituted or substituted with unsubstituted substituent(s) defined herein for each respective group.

The term "heterocyclyl alkyl," as used herein, represents an alkyl group substituted with a heterocyclyl group, each as defined herein. The heterocyclyl and alkyl portions may be optionally substituted as the individual groups described herein.

The term "heterocyclylene," as used herein, represents a divalent heterocyclyl. An optionally substituted heterocyclylene is a heterocyclylene that is optionally substituted as described herein for heterocyclyl.

The term "(heterocyclyl)oxy," as used herein, represents a chemical substituent of formula —OR, where R is a heterocyclyl group, unless otherwise specified. (Heterocyclyl)oxy can be optionally substituted in a manner described for heterocyclyl.

The terms "hydroxyl" and "hydroxy," as used interchangeably herein, represent an —OH group.

The term "isotopically enriched," as used herein, refers to the pharmaceutically active agent with the isotopic content for one isotope at a predetermined position within a molecule that is at least 100 times greater than the natural abundance of this isotope. For example, a composition that is isotopically enriched for deuterium includes an active agent with at least one hydrogen atom position having at least 100 times greater abundance of deuterium than the natural abundance of deuterium. Preferably, an isotopic enrichment for deuterium is at least 1000 times greater than the natural abundance of deuterium. More preferably, an isotopic enrichment for deuterium is at least 4000 times greater (e.g., at least 4750 times greater, e.g., up to 5000 times greater) than the natural abundance of deuterium.

The term "leukemia," as used herein, refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, e.g., acute non lymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

The term "lymphoma," as used herein, refers to a cancer arising from cells of immune origin. Non-limiting examples of T and B cell lymphomas include non-Hodgkin lymphoma and Hodgkin disease, diffuse large B-ceil lymphoma, follicular lymphoma, mucosa-associated lymphatic tissue (MALT) lymphoma, small cell lymphocytic lymphoma-chronic lymphocytic leukemia, Mantle cell lymphoma, mediastinal (thymic) large B-cell lymphoma, lymphoplasmacytic lymphoma-Waldenstrom macroglobulinemia, peripheral T-cell lymphoma (PTCL), angioimmunoblastic T-ceil lymphoma (AITL)/follicular T-cell lymphoma (FTCL), anaplastic large cell lymphoma (ALCL), enteropathy-associated T-cell lymphoma (EATL), adult T-cell leukaemia/lymphoma (ATLL), or extranodal NK/T-cell lymphoma, nasal type.

The term "melanoma," as used herein, is taken to mean a tumor arising from the melanocytic system of the skin and other organs. Melanomas that may be treated with a compound or method provided herein include, e.g., acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungual melanoma, and superficial spreading melanoma.

The term "nitro," as used herein, represents an —NO$_2$ group.

The term "oxo," as used herein, represents a divalent oxygen atom (e.g., the structure of oxo may be shown as =O).

The term "Ph," as used herein, represents phenyl.

The term "pharmaceutical composition," as used herein, represents a composition containing a compound described herein, formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other formulation described herein.

The term "pharmaceutically acceptable excipient" or "pharmaceutically acceptable carrier," as used interchangeably herein, refers to any ingredient other than the compounds described herein (e.g., a vehicle capable of suspending or dissolving the active compound) and having the properties of being nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, or waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethyleneglycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, stearic acid, sucrose, talc, titanium dioxide, vitamin A, vitamin E, vitamin C, and xylitol.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in Pharmaceutical Salts: Properties, Selection, and Use, (Eds. P. H. Stahl and C. G. Wermuth), Wiley-VCH, 2008. The salts can be prepared in situ during the final isolation and purification of the compounds described herein or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like.

The term "pre-malignant" or "pre-cancerous," as used herein, refers to a condition that is not malignant but is poised to become malignant. Non-limiting examples of pre-malignant conditions include myelodysplastic syndrome, polyps in the colon, actinic keratosis of the skin, dysplasia of the cervix, metaplasia of the lung, and leukoplakia.

The term "protecting group," as used herein, represents a group intended to protect a hydroxy, an amino, or a carbonyl from participating in one or more undesirable reactions during chemical synthesis. The term "O-protecting group," as used herein, represents a group intended to protect a hydroxy or carbonyl group from participating in one or more undesirable reactions during chemical synthesis. The term "N-protecting group," as used herein, represents a group intended to protect a nitrogen containing (e.g., an amino, amido, heterocyclic N—H, or hydrazine) group from participating in one or more undesirable reactions during chemical synthesis. Commonly used O- and N-protecting groups are disclosed in Greene, "Protective Groups in Organic Synthesis," 3rd Edition (John Wiley & Sons, New York, 1999), which is incorporated herein by reference. Exemplary O- and N-protecting groups include alkanoyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, t-butyldimethylsilyl, tri-iso-propylsilyloxymethyl, 4,4'-dimethoxytrityl, isobutyryl, phenoxyacetyl, 4-isopropylpehenoxyacetyl, dimethylformamidino, and 4-nitrobenzoyl.

Exemplary O-protecting groups for protecting carbonyl containing groups include, but are not limited to: acetals, acylals, 1,3-dithianes, 1,3-dioxanes, 1,3-dioxolanes, and 1,3-dithiolanes.

Other O-protecting groups include, but are not limited to: substituted alkyl, aryl, and aryl-alkyl ethers (e.g., trityl; methylthiomethyl; methoxymethyl; benzyloxymethyl; siloxymethyl; 2,2,2,-trichloroethoxymethyl; tetrahydropyranyl; tetrahydrofuranyl; ethoxyethyl; 1-[2-(trimethylsilyl) ethoxy]ethyl; 2-trimethylsilylethyl; t-butyl ether; p-chlorophenyl, p-methoxyphenyl, p-nitrophenyl, benzyl, p-methoxybenzyl, and nitrobenzyl); silyl ethers (e.g., trimethylsilyl; triethylsilyl; triisopropylsilyl; dimethylisopropylsilyl; t-butyldimethylsilyl; t-butyldiphenylsilyl; tribenzylsilyl; triphenylsilyl; and diphenymethylsilyl); carbonates (e.g., methyl, methoxymethyl, 9-fluorenylmethyl; ethyl; 2,2, 2-trichloroethyl; 2-(trimethylsilyl)ethyl; vinyl, allyl, nitrophenyl; benzyl; methoxybenzyl; 3,4-dimethoxybenzyl; and nitrobenzyl).

Other N-protecting groups include, but are not limited to, chiral auxiliaries such as protected or unprotected D, L or D, L-amino acids such as alanine, leucine, phenylalanine, and the like; sulfonyl-containing groups such as benzenesulfonyl, p-toluenesulfonyl, and the like; carbamate forming groups such as benzyloxycarbonyl, p-chlorobenzyloxycarbonyl, p methoxybenzyloxycarbonyl, p-nitrobenzyloxycarbonyl, 2-nitrobenzyloxycarbonyl, p bromobenzyloxycarbonyl, 3,4-dimethoxybenzyloxycarbonyl, 3,5 dimethoxybenzyl oxycarbonyl, 2,4-dimethoxybenzyloxycarbonyl, 4 methoxybenzyloxycarbonyl, 2-nitro-4,5-dimethoxybenzyloxycarbonyl, 3,4,5 trimethoxybenzyloxycarbonyl, 1-(p-biphenylyl)-1-methylethoxycarbonyl, α,α-dimethyl-3,5 dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, aryl-alkyl groups such as benzyl, p-methoxybenzyl, 2,4-dimethoxybenzyl, triphenylmethyl, benzyloxymethyl, and the like, silylalkylacetal groups such as [2-(trimethylsilyl)ethoxy]methyl and silyl groups such as trimethylsilyl, and the like. Useful N-protecting groups are formyl, acetyl, benzoyl, pivaloyl, t-butylacetyl, alanyl, phenylsulfonyl, benzyl, dimethoxybenzyl, [2-(trimethylsilyl)ethoxy]methyl (SEM), tetrahydropyranyl (THP), t-butyloxycarbonyl (Boc), and benzyloxycarbonyl (Cbz).

The term "tautomer" refers to structural isomers that readily interconvert, often by relocation of a proton. Tautomers are distinct chemical species that can be identified by differing spectroscopic characteristics, but generally cannot be isolated individually. Non-limiting examples of tautomers include ketone-enol, enamine-imine, amide-imidic acid, nitroso-oxime, ketene-ynol, and amino acid-ammonium carboxylate.

The term "sarcoma" generally refers to a tumor which is made up of a substance like the embryonic connective tissue and is generally composed of closely packed cells embedded in a fibrillar or homogeneous substance. Non-limiting examples of sarcomas that may be treated with a compound or method provided herein include, e.g., a chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "subject," as used herein, represents a human or non-human animal (e.g., a mammal) that is suffering from, or is at risk of, disease or condition, as determined by a qualified professional (e.g., a doctor or a nurse practitioner) with or without known in the art laboratory test(s) of sample(s) from the subject. Preferably, the subject is a human. Non-limiting examples of diseases and conditions include diseases having the symptom of cell hyperproliferation, e.g., a cancer.

"Treatment" and "treating," as used herein, refer to the medical management of a subject with the intent to improve, ameliorate, stabilize, prevent or cure a disease or condition. This term includes active treatment (treatment directed to improve the disease or condition); causal treatment (treatment directed to the cause of the associated disease or condition); palliative treatment (treatment designed for the relief of symptoms of the disease or condition); preventative treatment (treatment directed to minimizing or partially or completely inhibiting the development of the associated disease or condition); and supportive treatment (treatment employed to supplement another therapy).

DETAILED DESCRIPTION OF THE INVENTION

In general, the invention provides compounds, pharmaceutical compositions containing the same, methods of preparing the compounds, and methods of use. Compounds of the invention may be ATR kinase inhibitors. These compounds may be used to inhibit ATR kinase in a cell, e.g., a cell in a subject. The subject may be in need of a treatment for a disease or condition, e.g., a disease or condition having a symptom of cell hyperproliferation, e.g., a cancer. The ATR kinase inhibitory activity of the compounds disclosed herein is useful for treating a subject in need of a treatment for cancer. Non-limiting examples of cancers that may be treated using compounds disclosed herein are provided in Foote et al., *J. Med. Chem.*, 61:9889-9907, 2018; Wengner et al., *Mol. Cancer Ther.*, doi: 10.1158/1535-7163.MCT-19-0019; and Dillon and Harrington, "Targeting ATR for Cancer Therapy: ATR-Targeted Drug Candidates" in Targeting the DNA Damage Response for Anti-Cancer Therapy, Eds.: Pollard and Curtin; Humana Press, Cham (2018), pp. 99-127.

The invention provides a compound of formula (I):

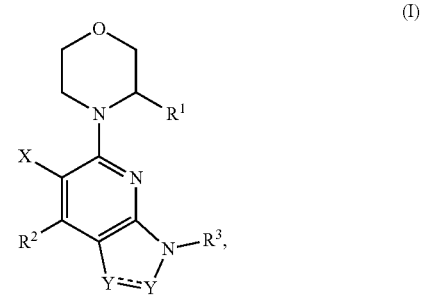

or a pharmaceutically acceptable salt thereof, where

===== is a double bond, and each Y is independently N or $CR^4$; or ===== is a single bond, and each Y is independently $NR^Y$, carbonyl, or $C(R^Y)_2$; where each $R^Y$ is independently H or optionally substituted $C_{1-6}$ alkyl;

$R^1$ is optionally substituted $C_{1-6}$ alkyl or H;

$R^2$ is optionally substituted $C_{2-9}$ heterocyclyl, optionally substituted $C_{1-6}$ alkyl, optionally substituted $C_{3-8}$ cycloalkyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, —$N(R^5)_2$, —$OR^5$, —$CON(R^6)_2$, —$SO_2N(R^6)_2$, —$SO_2R^{5A}$, or -Q-$R^{5B}$;

$R^3$ is optionally substituted $C_{1-9}$ heteroaryl or optionally substituted $C_{1-9}$ heteroaryl $C_{1-6}$ alkyl;

each $R^4$ is independently hydrogen, halogen, optionally substituted $C_{1-6}$ alkyl, optionally substituted $C_{2-6}$ alkenyl, or optionally substituted $C_{2-6}$ alkynyl;

each $R^5$ is independently hydrogen, optionally substituted $C_{1-6}$ alkyl, optionally substituted $C_{6-10}$ aryl $C_{1-6}$ alkyl, optionally substituted $C_{6-10}$ aryl, optionally substituted $C_{1-9}$ heteroaryl, or —$SO_2R^{5A}$; or both $R^5$, together with the atom to which they are attached, combine to form an optionally substituted $C_{2-9}$ heterocyclyl;

each $R^{5A}$ is independently optionally substituted $C_{1-6}$ alkyl, optionally substituted $C_{3-8}$ cycloalkyl, or optionally substituted $C_{6-10}$ aryl;

$R^{5B}$ is hydroxyl, optionally substituted $C_{1-6}$ alkyl, optionally substituted $C_{6-10}$ aryl, optionally substituted $C_{1-9}$ heteroaryl, $-N(R^5)_2$, $-CON(R^6)_2$, $-SO_2N(R^6)_2$, $-SO_2R^{5A}$, or optionally substituted alkoxy;

each $R^6$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or both $R^6$, together with the atom to which they are attached, combine to form an optionally substituted $C_{2-9}$ heterocyclyl;

Q is optionally substituted $C_{2-9}$ heterocyclylene, optionally substituted $C_{3-8}$ cycloalkylene, optionally substituted $C_{1-9}$ heteroarylene, or optionally substituted $C_{6-10}$ arylene; and X is hydrogen or halogen.

The compound of the invention may be, e.g., a compound of formula (II):

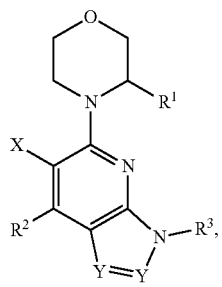

(II)

or a pharmaceutically acceptable salt thereof,
where each Y is independently N or $CR^4$;

$R^1$ is optionally substituted $C_{1-6}$ alkyl or H;

$R^2$ is optionally substituted $C_{2-9}$ heterocyclyl, optionally substituted $C_{1-6}$ alkyl, optionally substituted $C_{3-8}$ cycloalkyl, optionally substituted $C_{2-9}$ heterocyclyl $C_{1-6}$ alkyl, optionally substituted $C_{6-10}$ aryl, optionally substituted $C_{1-9}$ heteroaryl, optionally substituted $C_{1-9}$ heteroaryl $C_{1-6}$ alkyl, halogen, $-N(R^5)_2$, $-OR^5$, $-CON(R^6)_2$, $-SO_2N(R^6)_2$, $-SO_2R^{5A}$, or $-Q-R^{5B}$;

$R^3$ is optionally substituted $C_{1-9}$ heteroaryl or optionally substituted $C_{1-9}$ heteroaryl $C_{1-6}$ alkyl;

each $R^4$ is independently hydrogen, halogen, optionally substituted $C_{1-6}$ alkyl, optionally substituted $C_{2-6}$ alkenyl, or optionally substituted $C_{2-6}$ alkynyl;

each $R^5$ is independently hydrogen, optionally substituted $C_{1-6}$ alkyl, optionally substituted $C_{6-10}$ aryl $C_{1-6}$ alkyl, optionally substituted $C_{6-10}$ aryl, optionally substituted $C_{1-9}$ heteroaryl, or $-SO_2R^{5A}$; or both $R^5$, together with the atom to which they are attached, combine to form an optionally substituted $C_{2-9}$ heterocyclyl;

each $R^{5A}$ is independently optionally substituted $C_{1-6}$ alkyl, optionally substituted $C_{3-8}$ cycloalkyl, or optionally substituted $C_{6-10}$ aryl;

$R^{5B}$ is hydroxyl, optionally substituted $C_{1-6}$ alkyl, optionally substituted $C_{6-10}$ aryl, optionally substituted $C_{1-9}$ heteroaryl, $-N(R^5)_2$, $-CON(R^6)_2$, $-SO_2N(R^6)_2$, $-SO_2R^{5A}$, or optionally substituted alkoxy;

each $R^6$ is independently hydrogen, optionally substituted $C_{1-6}$ alkyl, optionally substituted $C_{2-6}$ alkoxyalkyl, optionally substituted $C_{6-10}$ aryl $C_{1-6}$ alkyl, optionally substituted $C_{6-10}$ aryl, optionally substituted $C_{3-8}$ cycloalkyl, or optionally substituted $C_{1-9}$ heteroaryl; or both $R^6$, together with the atom to which they are attached, combine to form an optionally substituted $C_{2-9}$ heterocyclyl;

Q is optionally substituted $C_{2-9}$ heterocyclylene, optionally substituted $C_{3-8}$ cycloalkylene, optionally substituted $C_{1-9}$ heteroarylene, or optionally substituted $C_{6-10}$ arylene; and X is hydrogen or halogen.

In some embodiments, in the compound of formula (II), (I), or (I-b):

each Y is independently N or $CR^4$;

$R^1$ is H or optionally substituted $C_{1-6}$ alkyl;

$R^2$ is optionally substituted $C_{1-6}$ alkyl, optionally substituted $C_{3-8}$ cycloalkyl, optionally substituted $C_{2-9}$ heterocyclyl, optionally substituted $C_{6-10}$ aryl, optionally substituted $C_{1-9}$ heteroaryl, optionally substituted $C_{1-9}$ heteroaryl $C_{1-6}$ alkyl, $-N(R^5)_2$, $-CON(R^6)_2$, $-SO_2N(R^6)_2$, or $-SO_2R^{5A}$;

$R^3$ is optionally substituted $C_{1-9}$ heteroaryl;

each $R^4$ is independently H or optionally substituted $C_{1-6}$ alkyl;

each $R^5$ is independently hydrogen, optionally substituted $C_{1-6}$ alkyl, optionally substituted $C_{6-10}$ aryl $C_{1-6}$ alkyl, optionally substituted $C_{6-10}$ aryl, optionally substituted $C_{1-9}$ heteroaryl, or $-SO_2R^{5A}$, where each $R^{5A}$ is independently optionally substituted $C_{1-6}$ alkyl or optionally substituted $C_{3-8}$ cycloalkyl; or both $R^5$, together with the atom to which they are attached, combine to form an optionally substituted $C_{2-9}$ heterocyclyl;

each $R^{5A}$ is independently optionally substituted $C_{1-6}$ alkyl or optionally substituted $C_{3-8}$ cycloalkyl; and each $R^6$ is independently hydrogen, optionally substituted $C_{1-6}$ alkyl, optionally substituted $C_{6-10}$ aryl $C_{1-6}$ alkyl, optionally substituted $C_{6-10}$ aryl, or optionally substituted $C_{1-9}$ heteroaryl; or both $R^6$, together with the atom to which they are attached, combine to form an optionally substituted $C_{2-9}$ heterocyclyl.

The compound of the invention may be, e.g., a compound of formula (I-a):

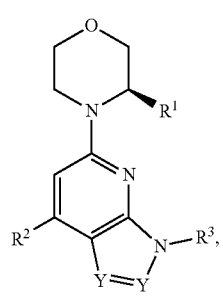

(I-a)

or a pharmaceutically acceptable salt thereof, where Y, $R^1$, $R^2$, $R^3$, and $R^4$ are as described for formula (I).

The compound of the invention may be, e.g., a compound of formula (I-b):

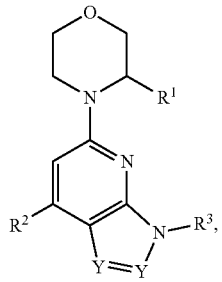
(I-b)

or a pharmaceutically acceptable salt thereof, where Y, R¹, R², R³, and R⁴ are as described for formula (I).

The compound of the invention may be, e.g., a compound of formula (IA):

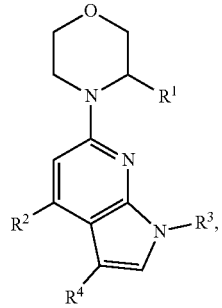
(IA)

or a pharmaceutically acceptable salt thereof, where R¹, R², R³, and R⁴ are as described for formula (I).

The compound of formula (IA) may be, e.g., a compound of formula (IA-a):

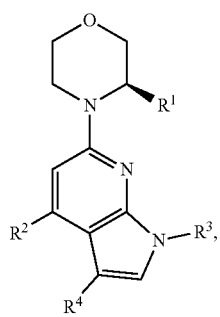
(IA-a)

or a pharmaceutically acceptable salt thereof, where R¹, R², R³, and R⁴ are as described for formula (I).

The compound of the invention may be, e.g., a compound of Formula (IB):

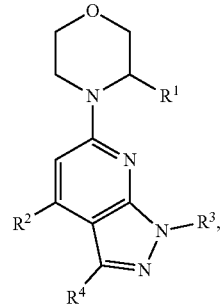
(IB)

or a pharmaceutically acceptable salt thereof, where R¹, R², R³, and R⁴ are as described for formula (I).

The compound of formula (IB) may be, e.g., a compound of formula (IB-a):

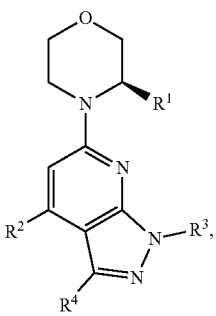
(IB-a)

or a pharmaceutically acceptable salt thereof, where R¹, R², R³, and R⁴ are as described for formula (I).

The compound of the invention may be, e.g., a compound of Formula (IC):

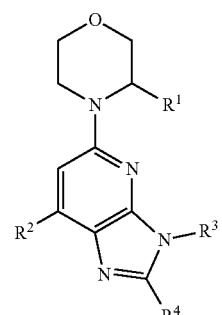
(IC)

or a pharmaceutically acceptable salt thereof, where R¹, R², R³, and R⁴ are as described for formula (I).

The compound of formula (IC) may be, e.g., a compound of formula (IC-a):

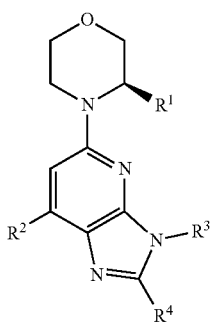
(IC-a)

or a pharmaceutically acceptable salt thereof, where R¹, R², R³, and R⁴ are as described for formula (I).

The compound of the invention may be, e.g., a compound of formula (ID):

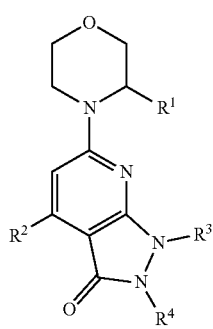
(ID)

or a pharmaceutically acceptable salt thereof, where R¹, R², R³, and R⁴ are as described for formula (I).

The compound of formula (ID) may be, e.g., a compound of formula (ID-a):

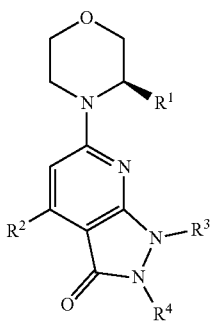
(ID-a)

or a pharmaceutically acceptable salt thereof, where R¹, R², R³, and R⁴ are as described for formula (I).

Preferably, R¹ is methyl.

In the compounds of the invention, R² may be, e.g., optionally substituted $C_{3-8}$ cycloalkyl. For example, R² may be a group of formula (A):

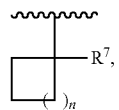
(A)

where n is 0, 1, 2, or 3; and

R⁷ is hydrogen, alkylsulfonyl, cyano, —CON($R^A$)₂, —SON($R^A$)₂, optionally substituted $C_{1-9}$ heteroaryl, hydroxy, or alkoxy, where each $R^A$ is independently H or alkyl; or both $R^A$, together with the atom to which they are attached, combine to form $C_{2-9}$ heterocyclyl.

In the compounds of the invention, R² may be, e.g., optionally substituted $C_{1-6}$ alkyl (e.g., optionally substituted tertiary $C_{3-6}$ alkyl. For example, R² may be a group of formula (B):

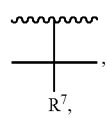
(B)

where R⁷ is hydrogen, alkylsulfonyl, cyano, —CON($R^A$)₂, —SON($R^A$)₂, optionally substituted $C_{1-9}$ heteroaryl, hydroxy, or alkoxy, where each $R^A$ is independently H or alkyl; or both $R^A$, together with the atom to which they are attached, combine to form $C_{2-9}$ heterocyclyl.

In the compounds of the invention, R² may be, e.g., optionally substituted non-aromatic $C_{2-9}$ heterocyclyl.

In the compounds of the invention, R² may be, e.g.:

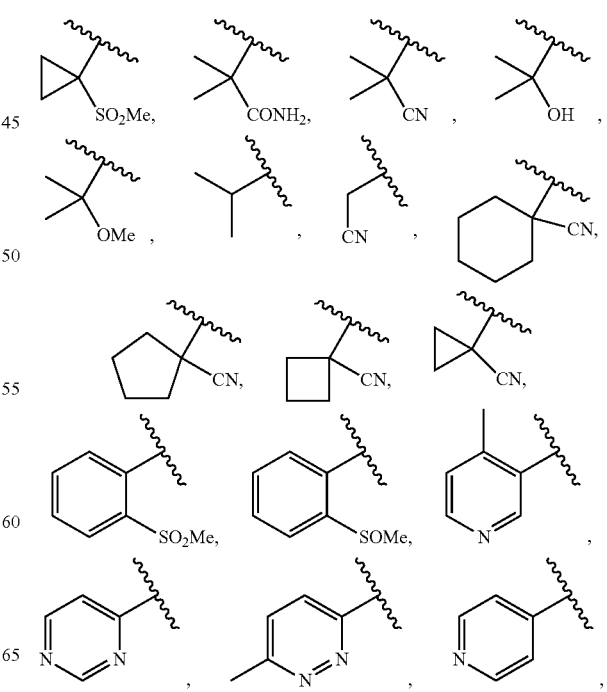

-continued
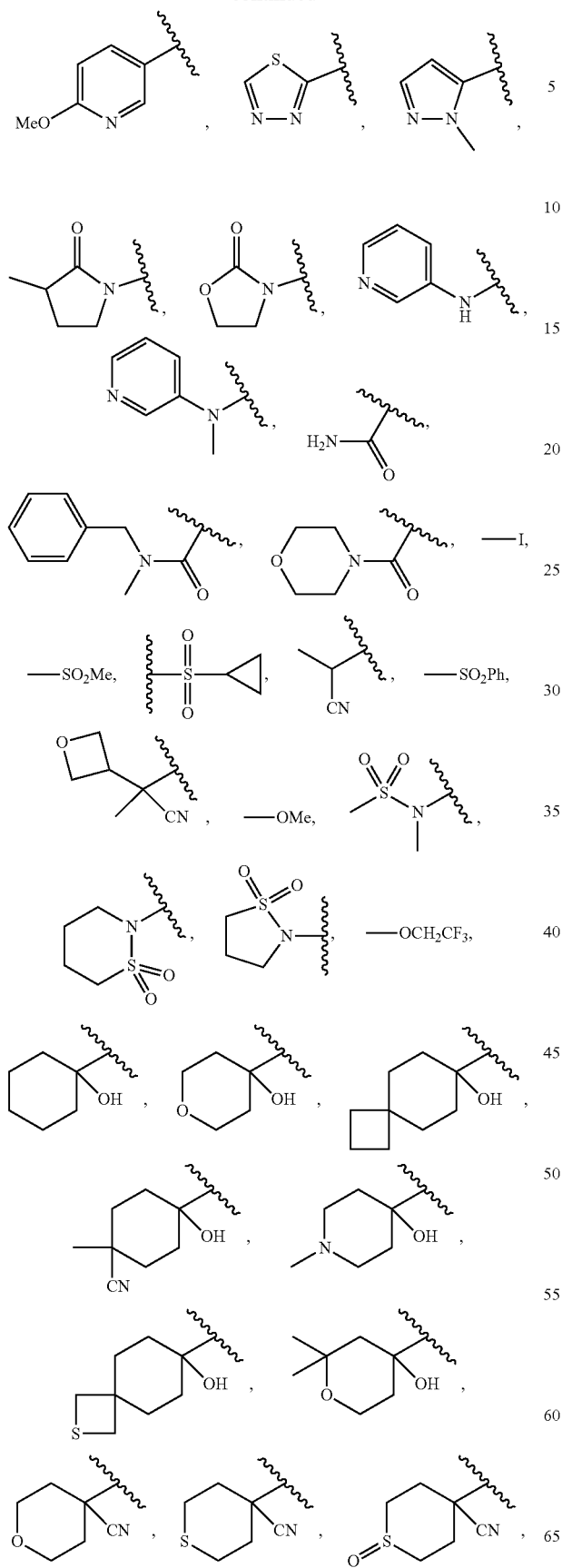
-continued
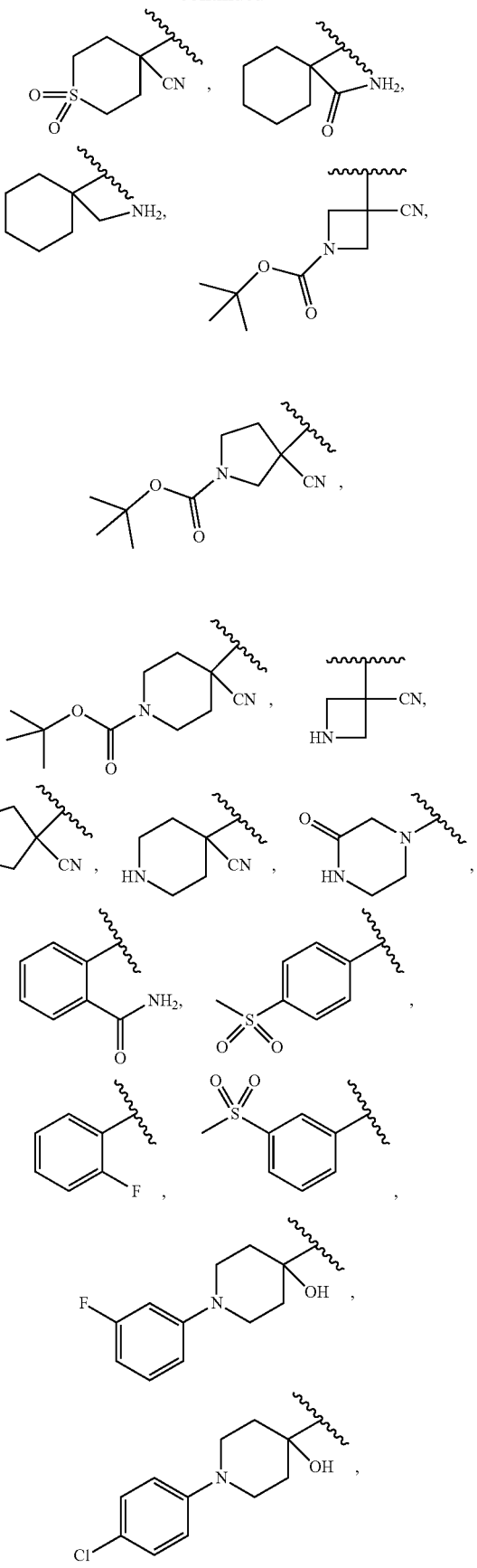

-continued
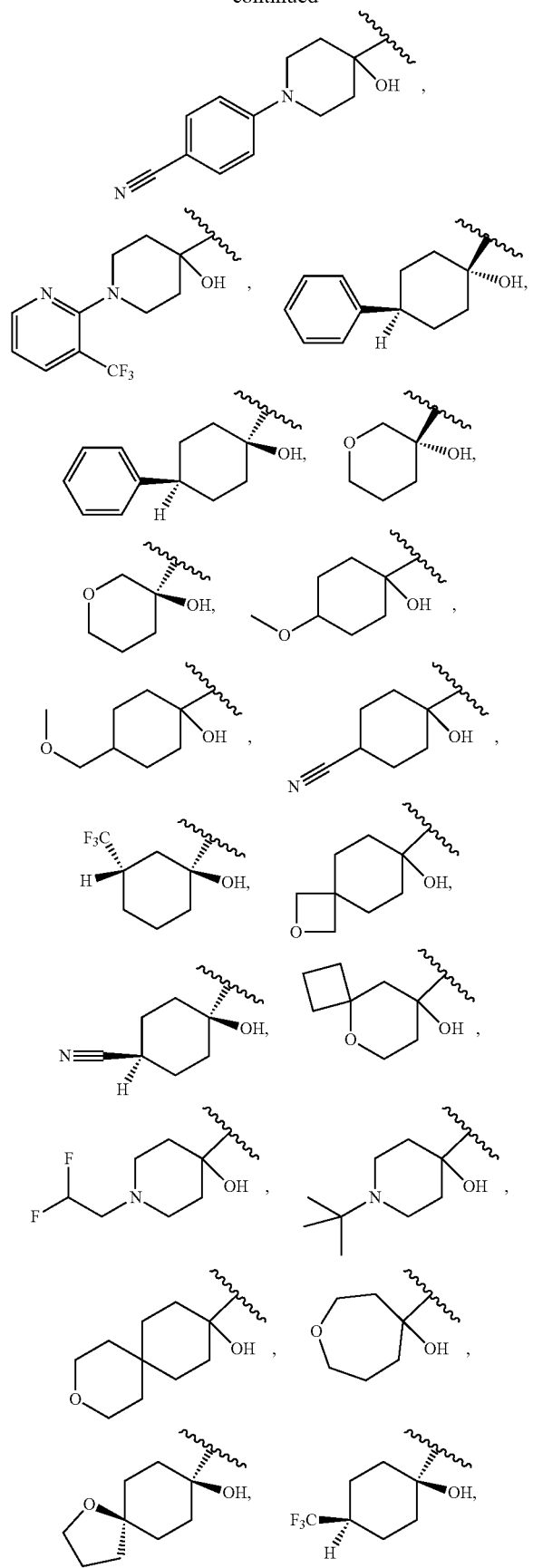
-continued
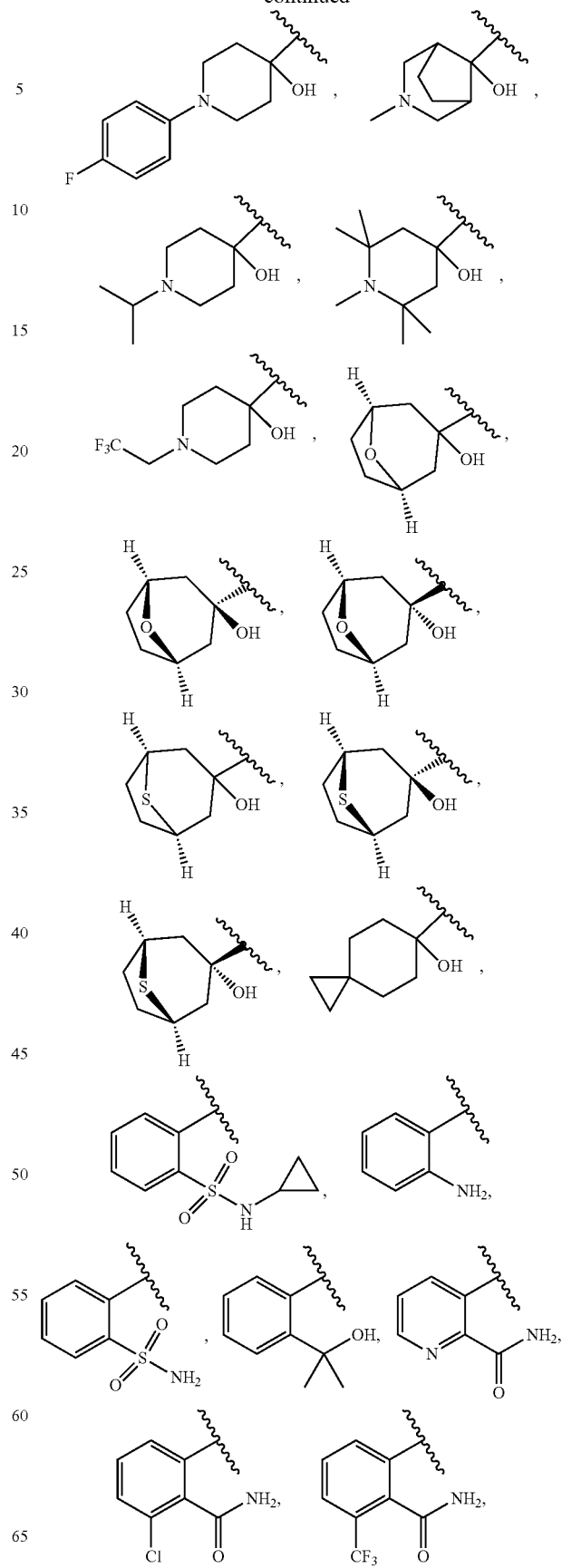

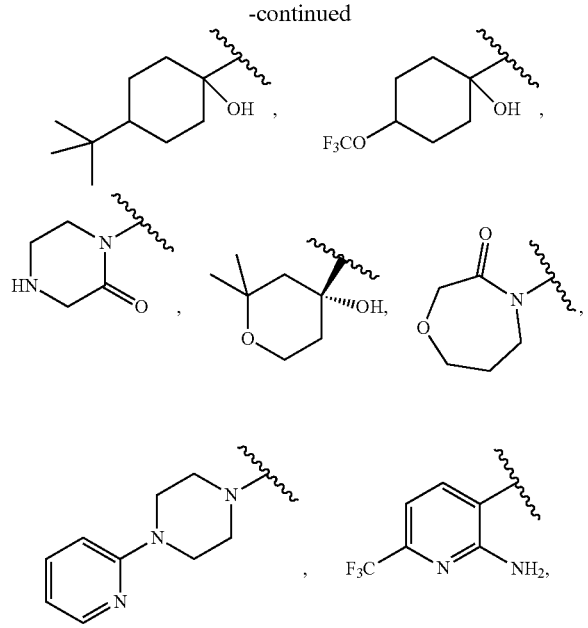

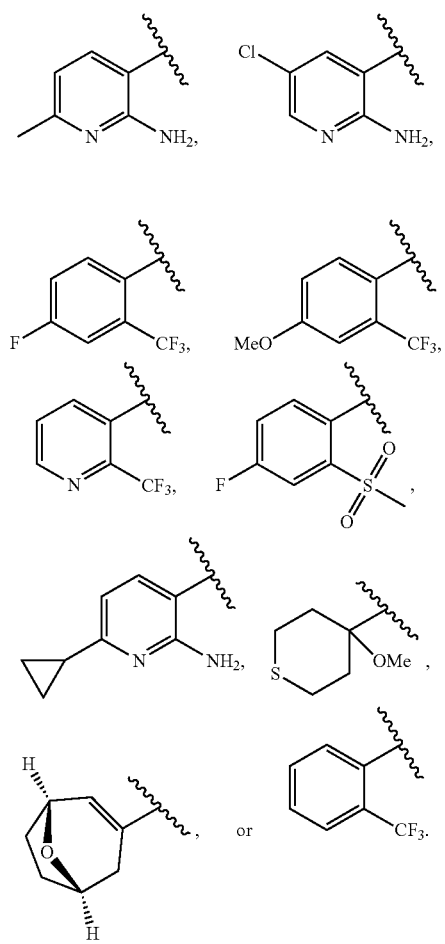

In the compounds of the invention, R³ may be, e.g., optionally substituted, monocyclic $C_{1-9}$ heteroaryl including at least one nitrogen atom (e.g., two nitrogen atoms). For example, R³ may be a group of formula (C):

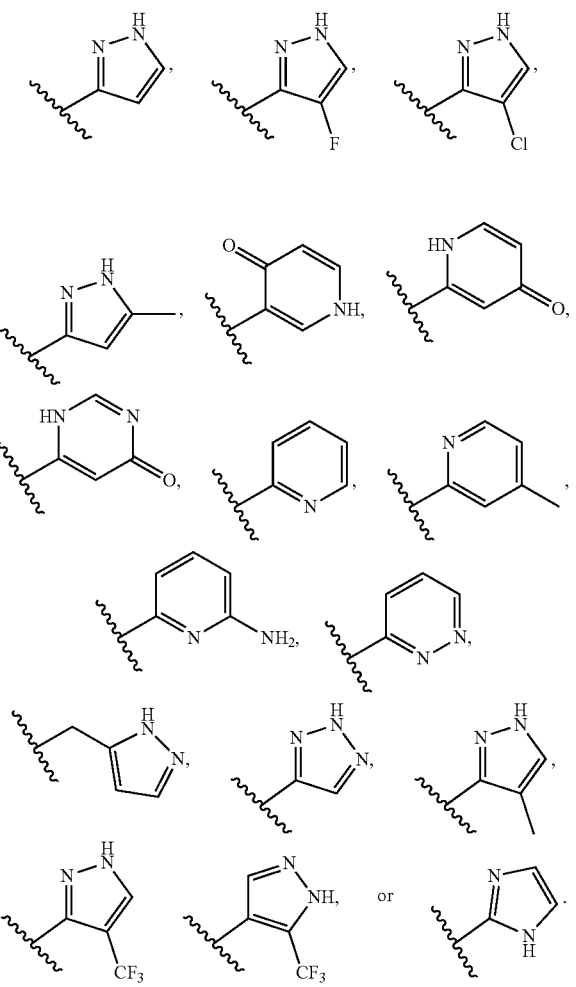

where A is optionally substituted, monocyclic $C_{1-9}$ heteroaryl ring.

In some compounds of the invention, A may be, e.g., a group of formula (C1):

where R⁸ is hydrogen, halogen, or optionally substituted $C_{1-6}$ alkyl.

In the compounds of the invention, R³ may be, e.g.:

In the compounds of the invention, R³ may be, e.g.:
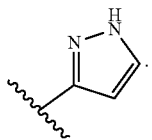 [SMILES: *c1cc[nH]n1]
In the compounds of the invention, R⁴ may be, e.g., hydrogen.
The compound of the invention may be, e.g., a compound listed in Table 1 below or a pharmaceutically acceptable salt thereof.
TABLE 1
| | |
|---|---|
| 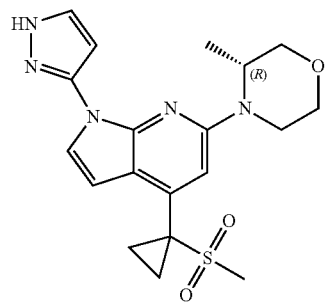 | 1 |
| 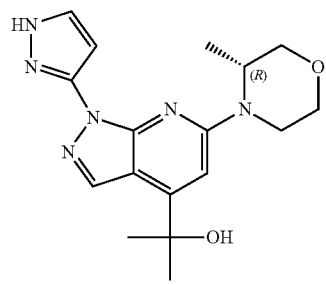 | 2 |
| 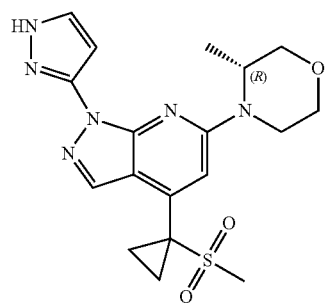 | 3 |
| 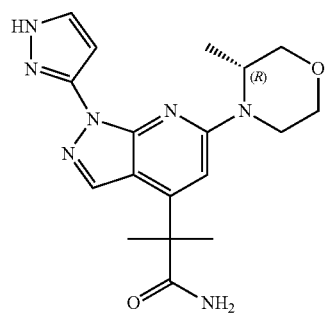 | 4 |
TABLE 1-continued
| | |
|---|---|
| 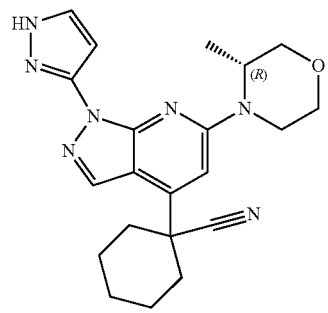 | 5 |
| 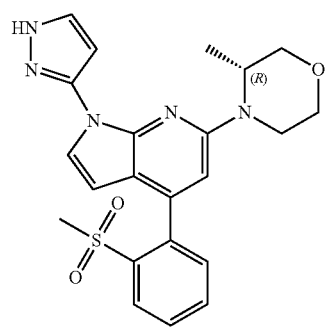 | 6 |
| 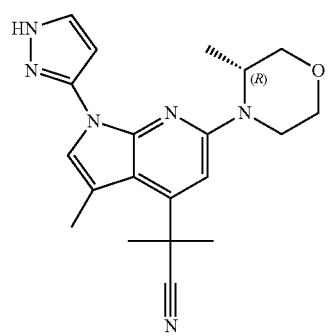 | 7 |
| 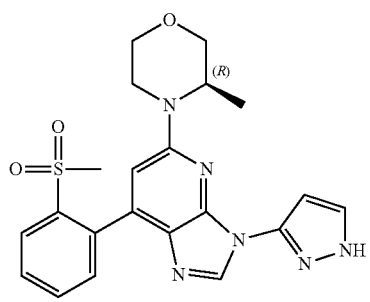 | 8 |
| 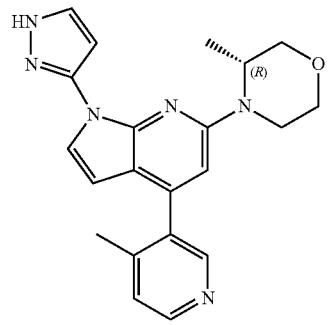 | 9 |

TABLE 1-continued
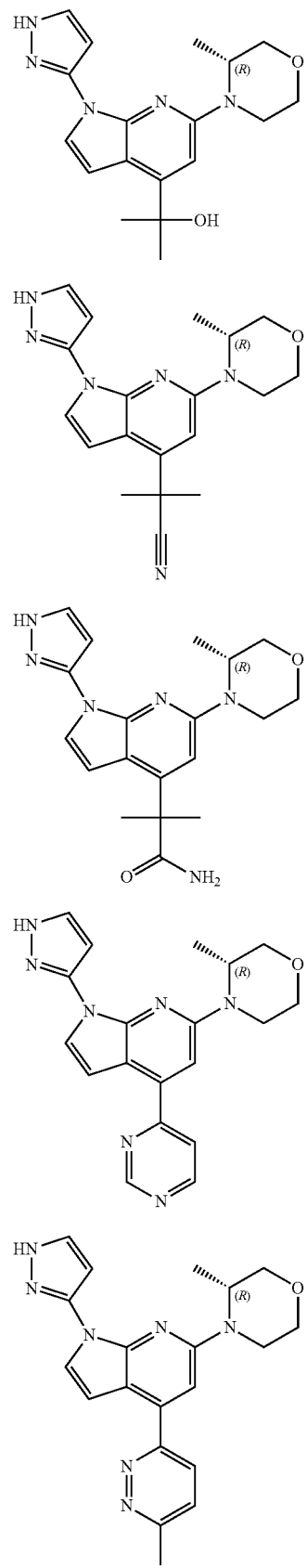
TABLE 1-continued
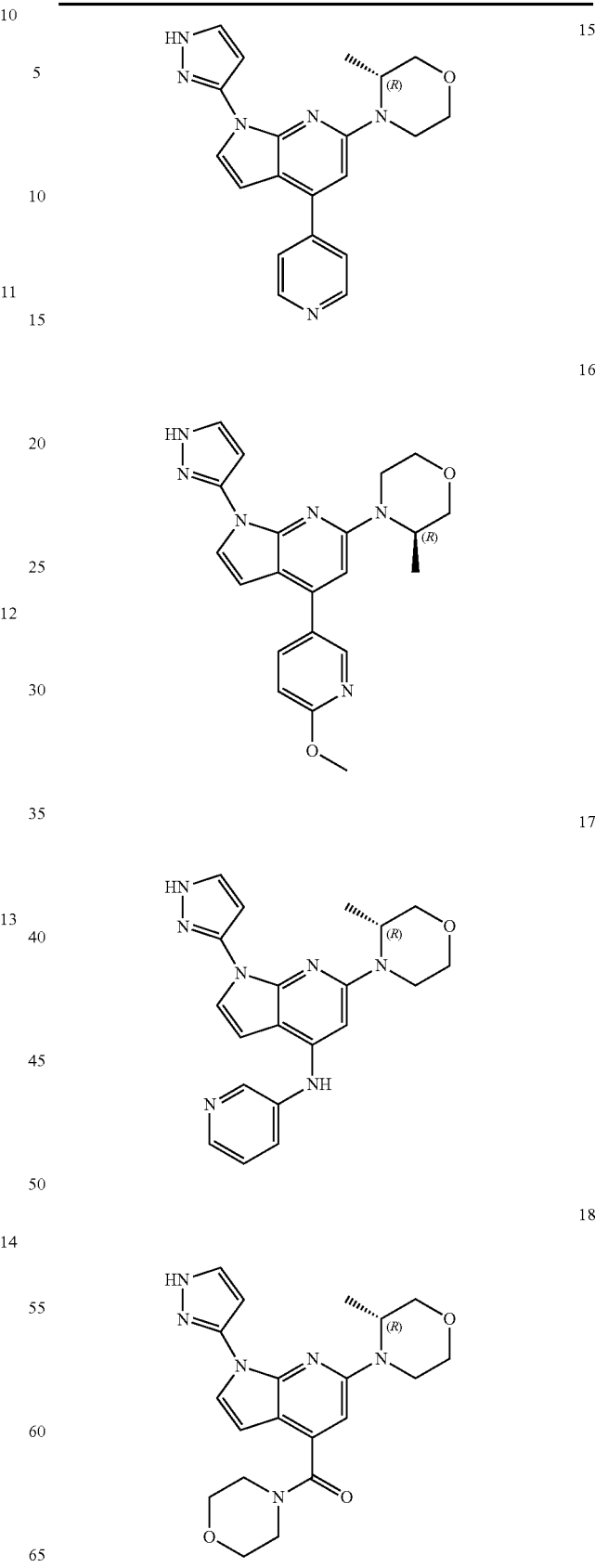

TABLE 1-continued
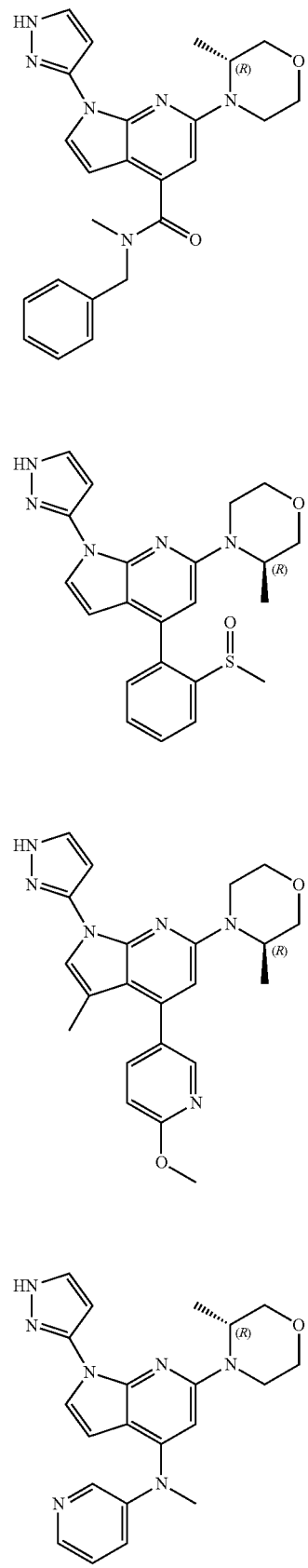
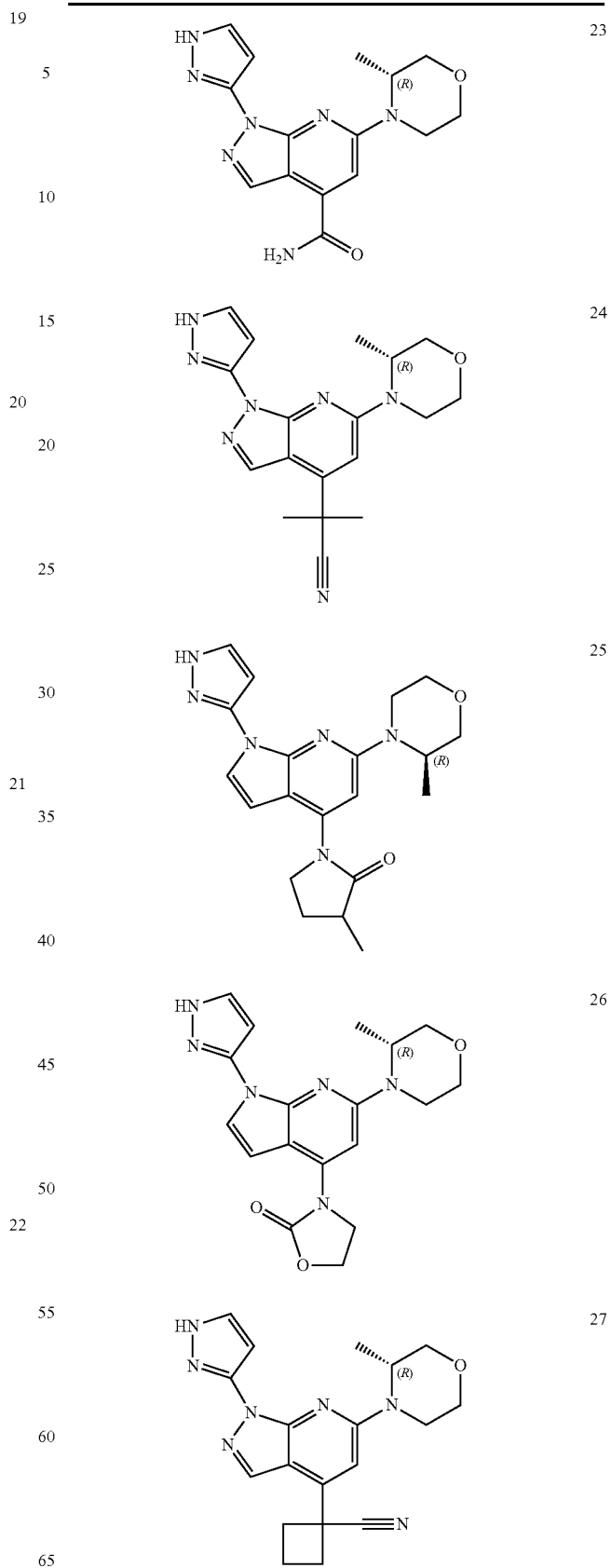

TABLE 1-continued
| | |
|---|---|
| 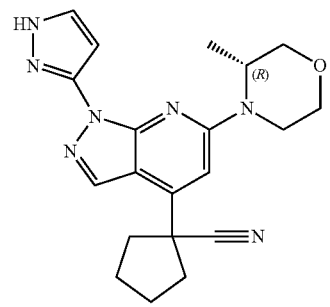 | 28 |
| 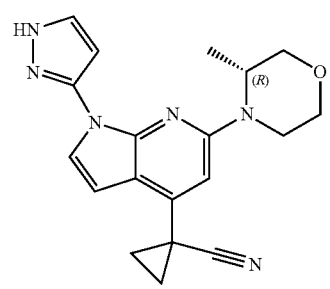 | 29 |
| 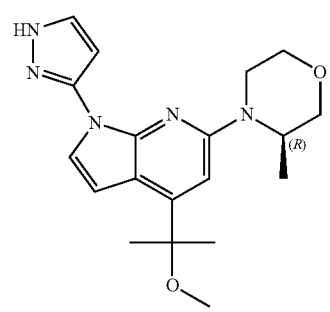 | 30 |
| 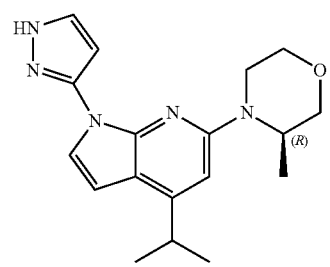 | 31 |
| 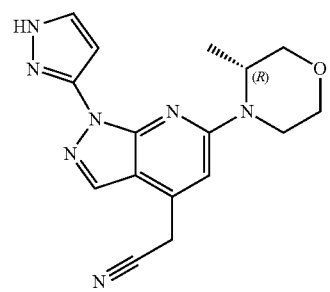 | 32 |
TABLE 1-continued
| | |
|---|---|
| 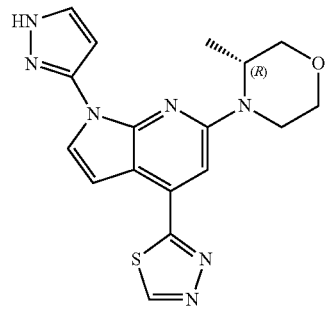 | 33 |
| 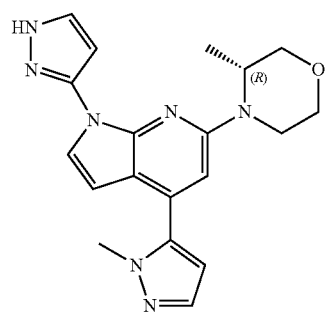 | 34 |
| 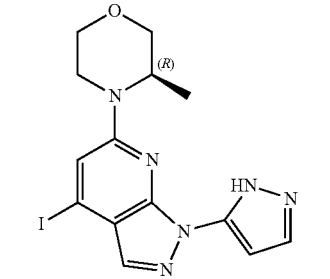 | 42 |
| 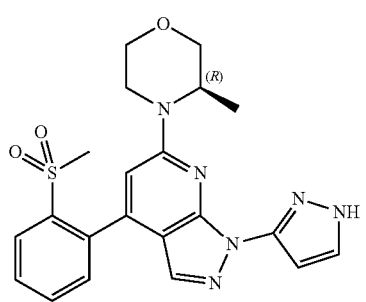 | 43 |
| 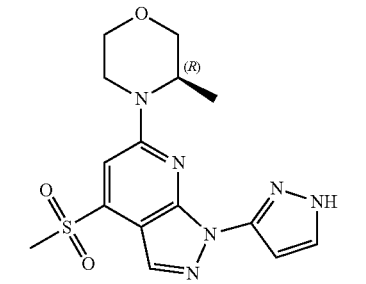 | 44 |

TABLE 1-continued
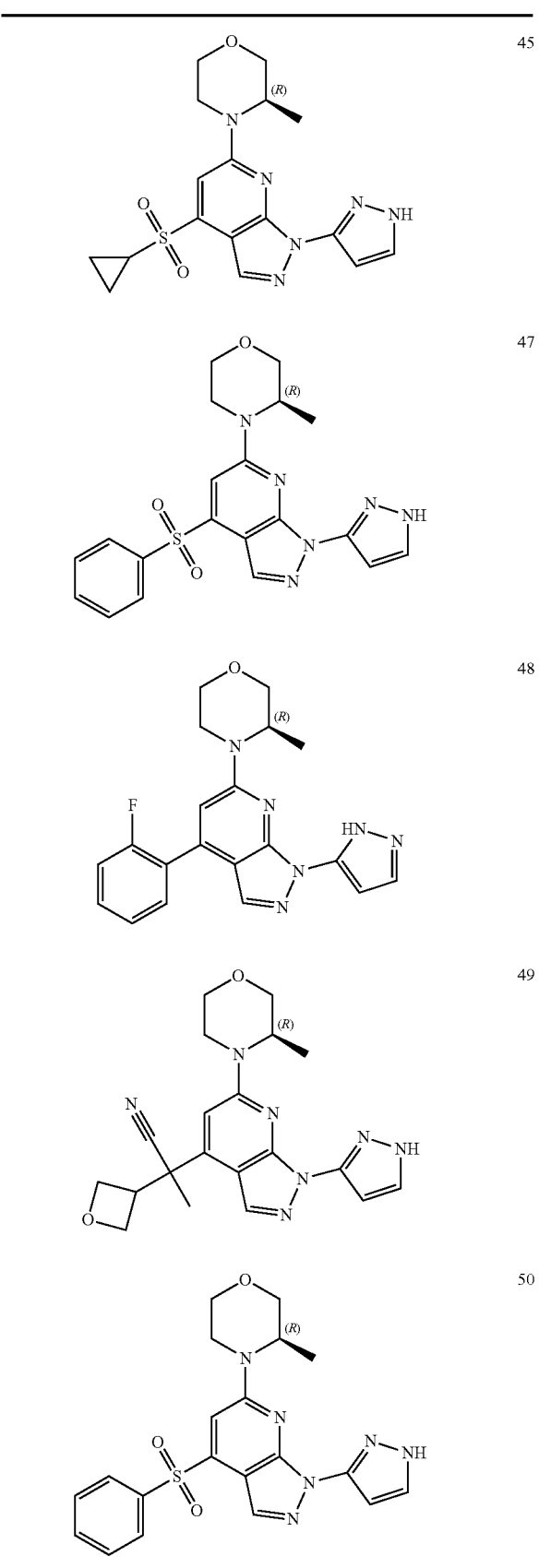
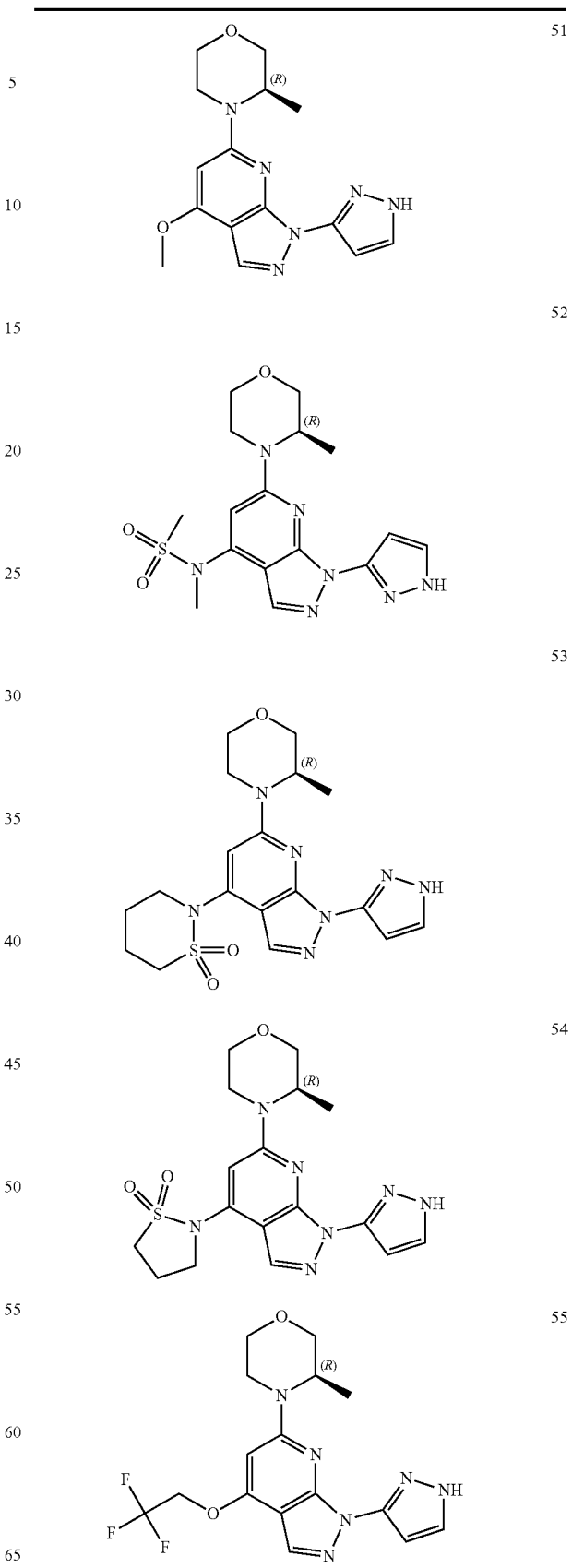

TABLE 1-continued
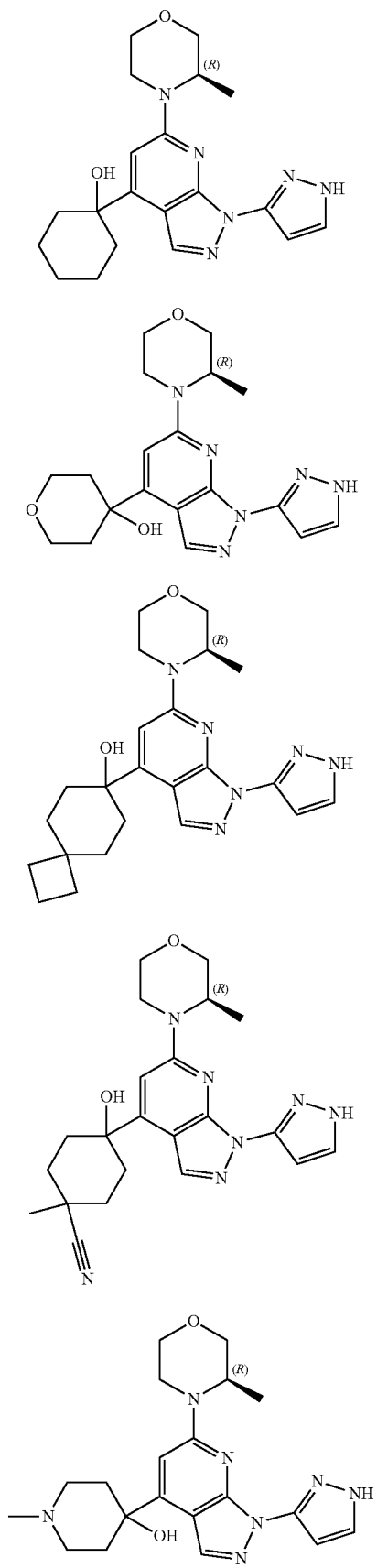
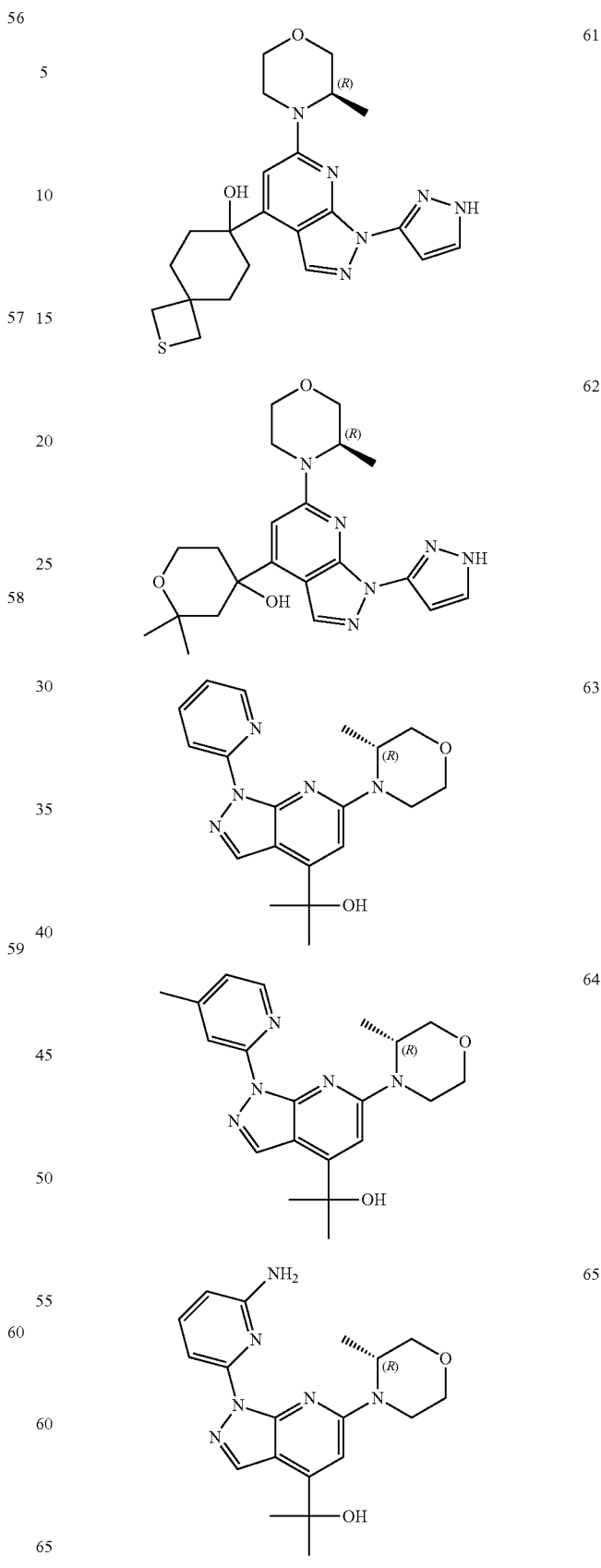

TABLE 1-continued
| | |
|---|---|
| 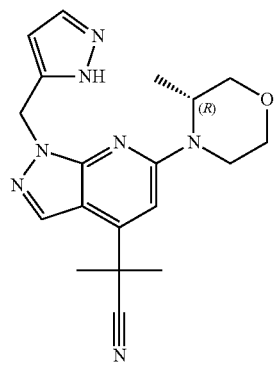 | 66 |
| 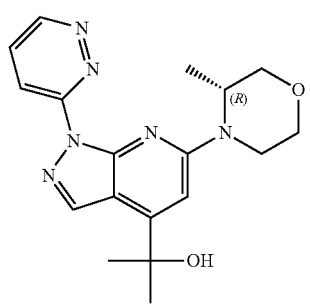 | 67 |
| 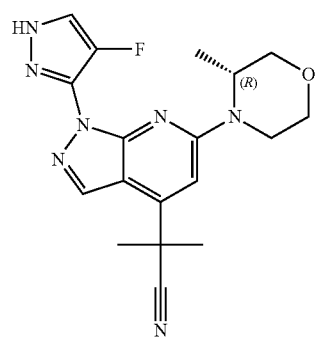 | 68 |
| 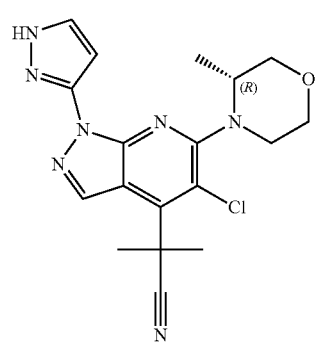 | 69 |
TABLE 1-continued
| | |
|---|---|
| 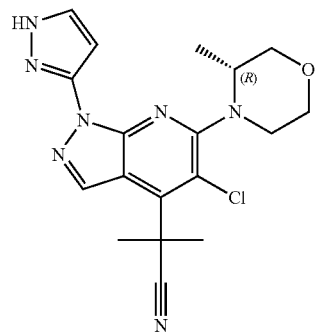 | 70 |
| 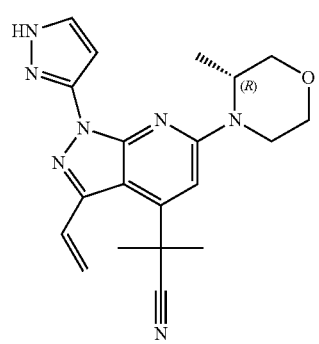 | 71 |
| 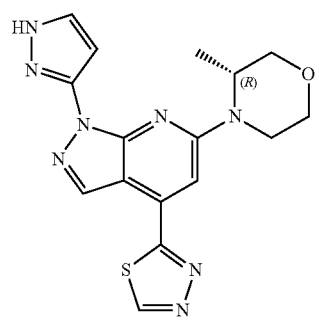 | 72 |
| 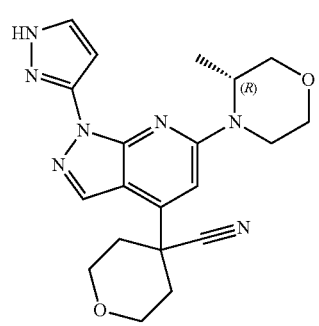 | 73 |
| 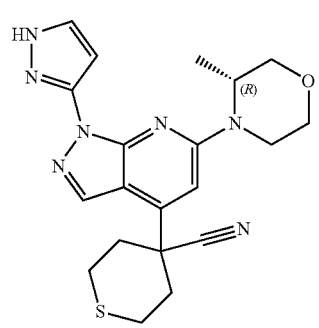 | 74 |

TABLE 1-continued
| | |
|---|---|
| 75 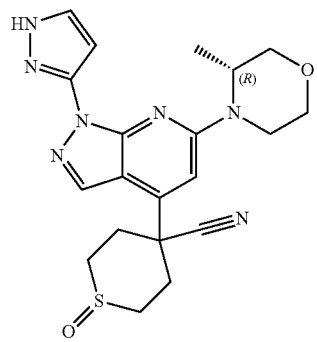 | 79 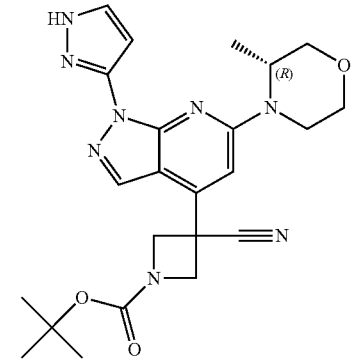 |
| 76 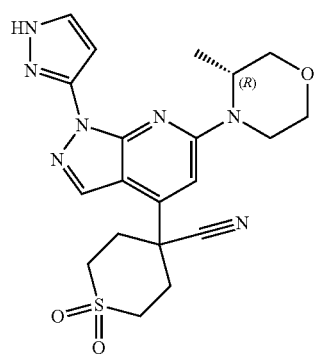 | 80 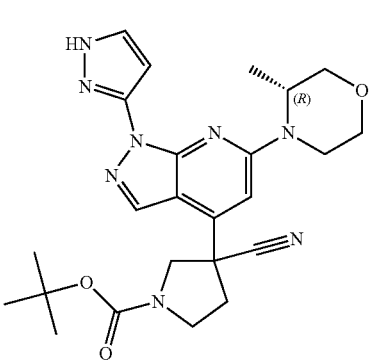 |
| 77 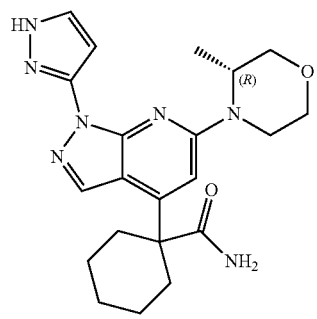 | 81 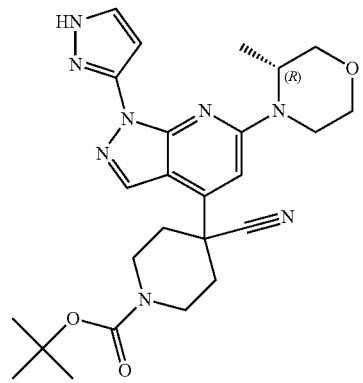 |
| 78 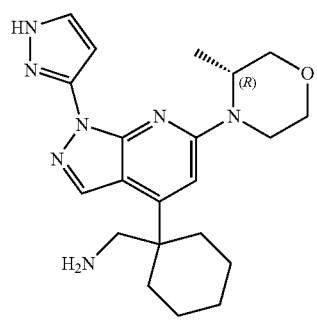 | 82 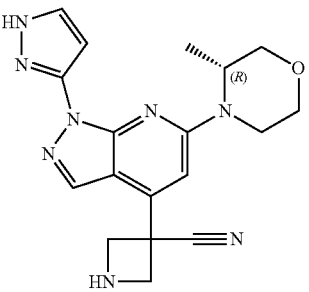 |

TABLE 1-continued
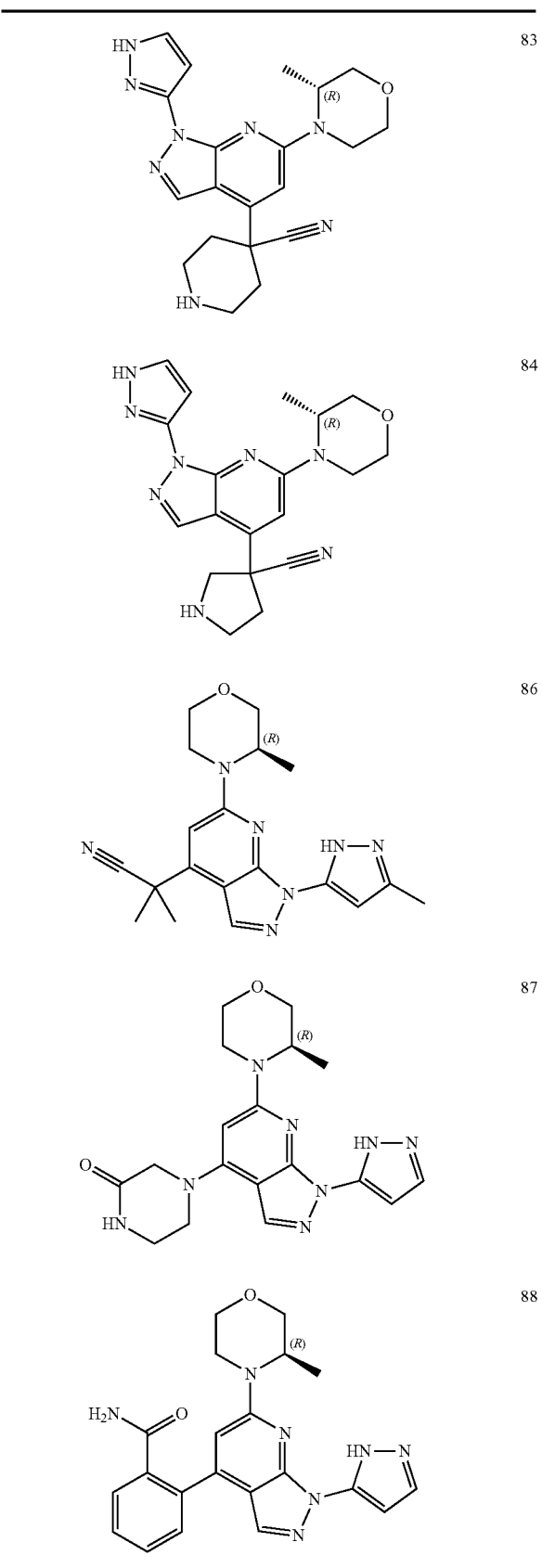
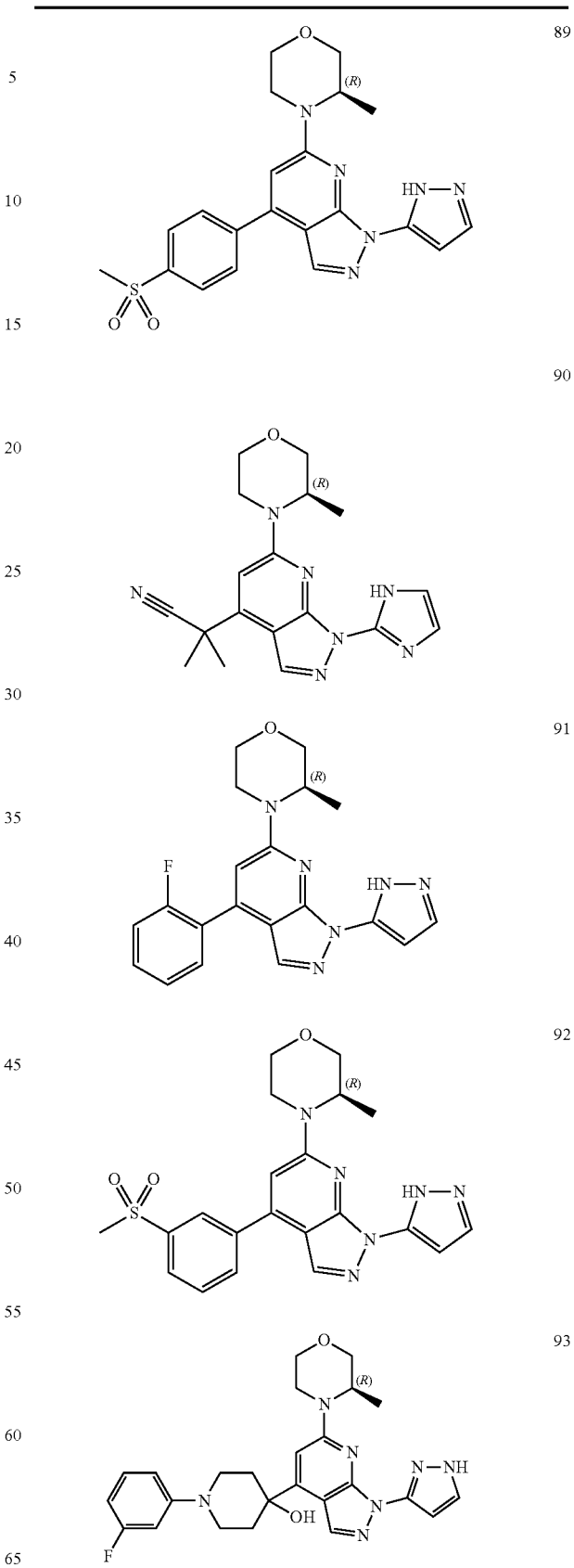

TABLE 1-continued
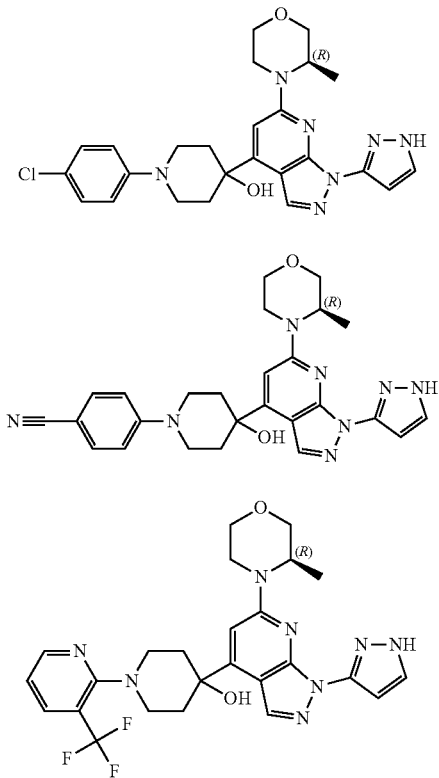
94
95
96
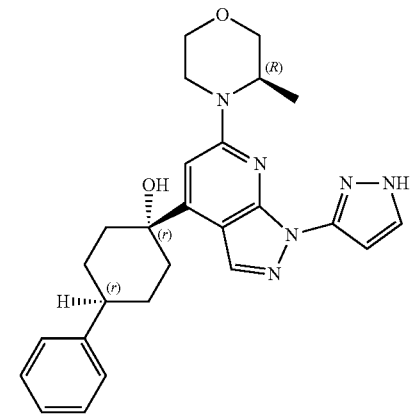
97
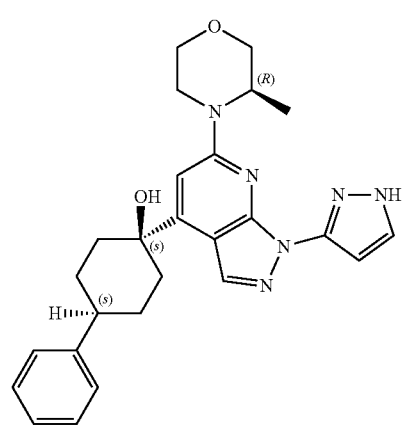
98
TABLE 1-continued
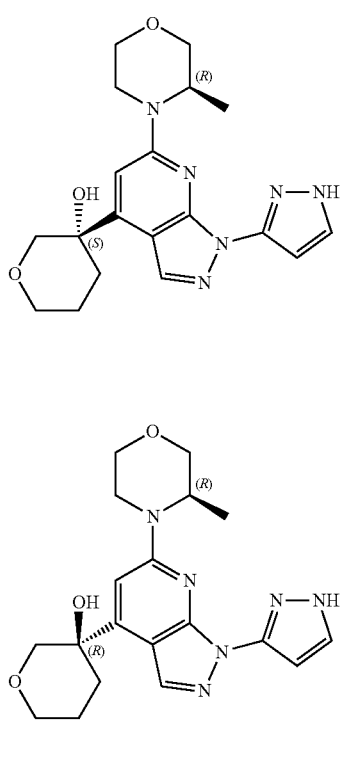
99
100
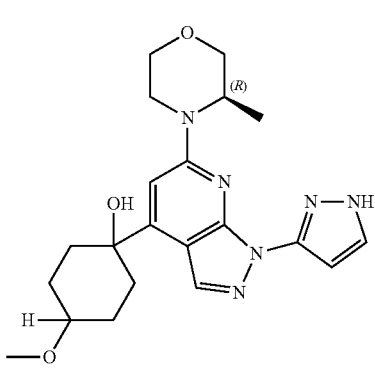
101
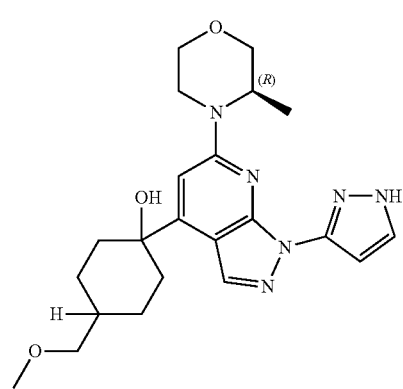
102

TABLE 1-continued
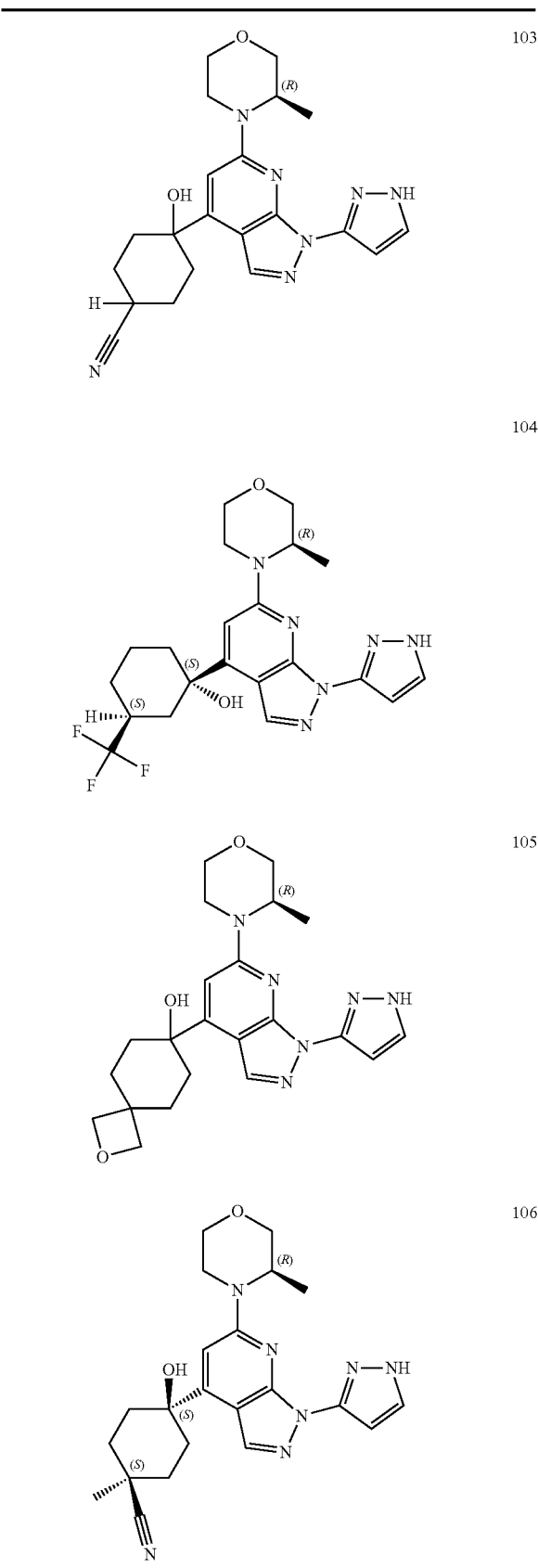
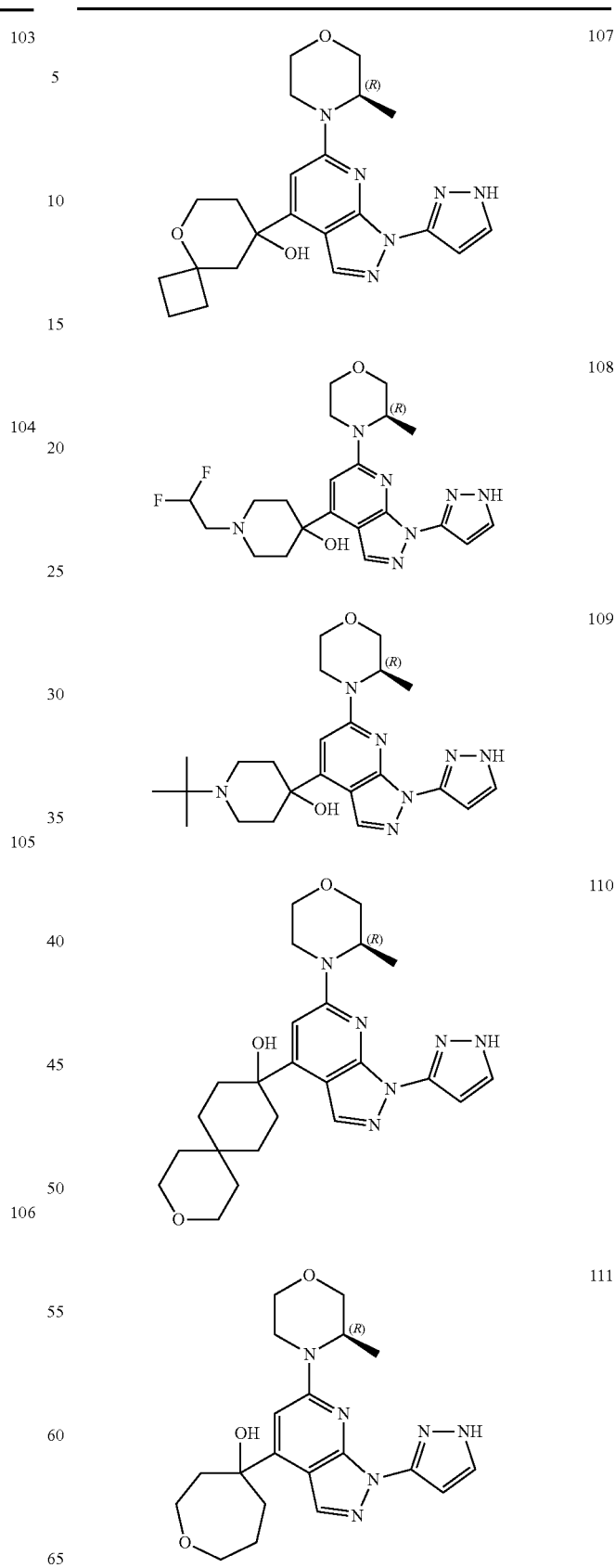

TABLE 1-continued
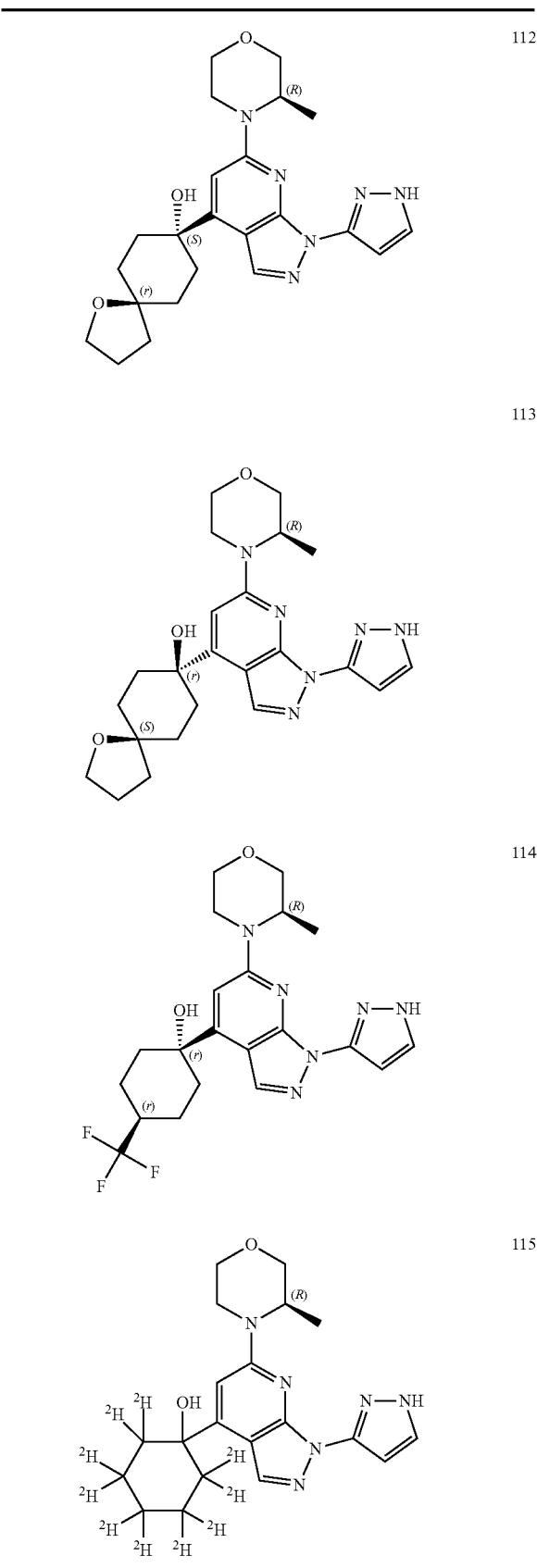
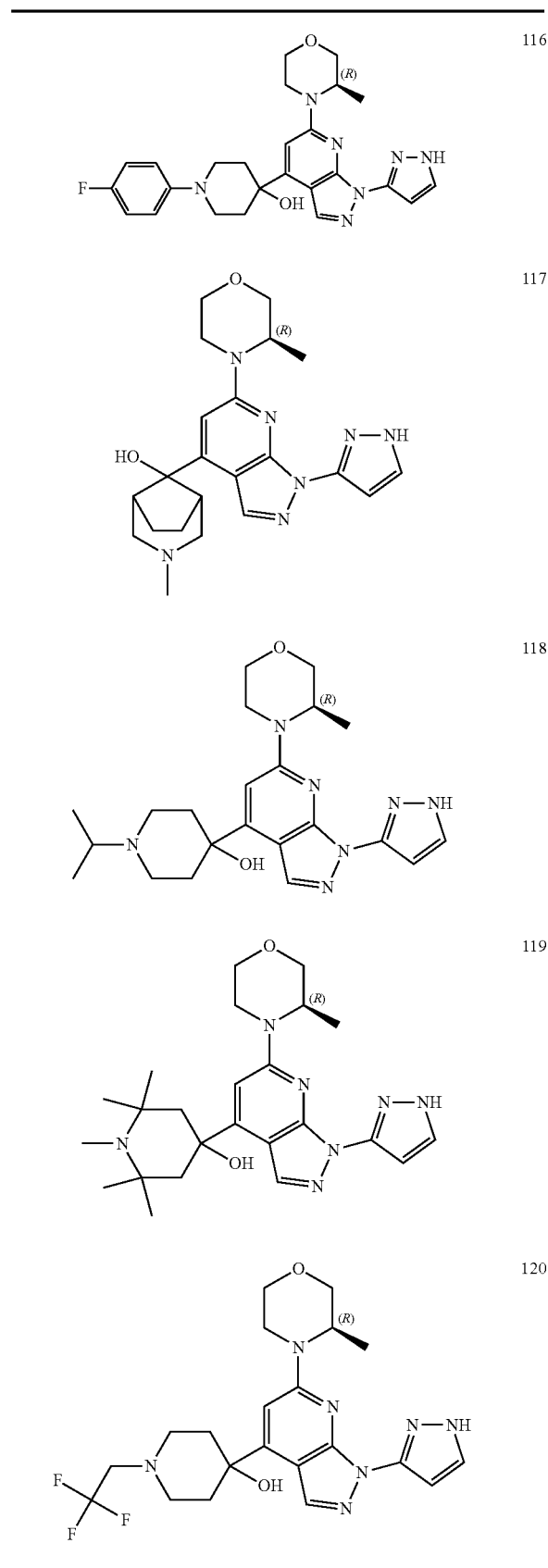

TABLE 1-continued
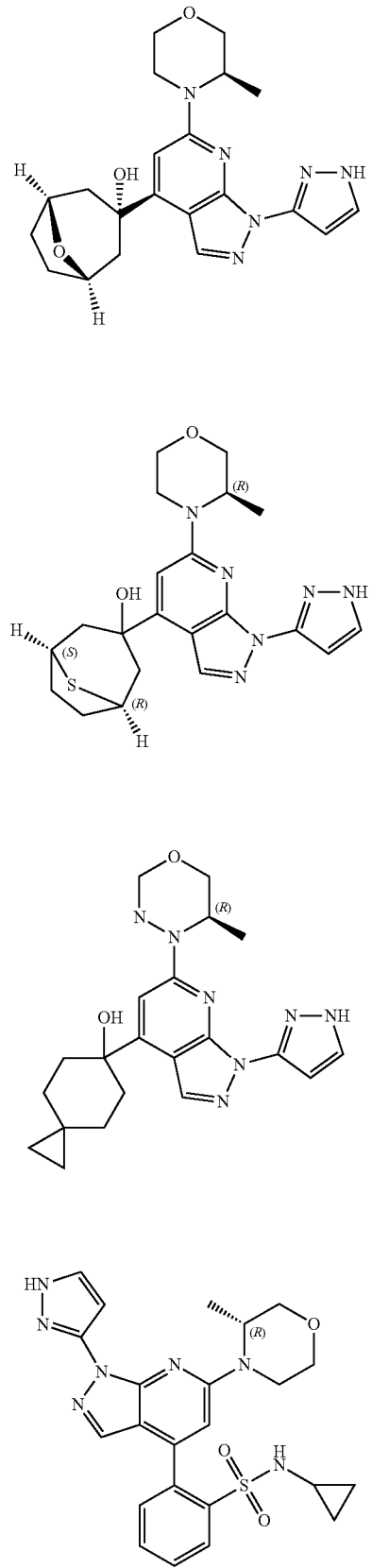
TABLE 1-continued
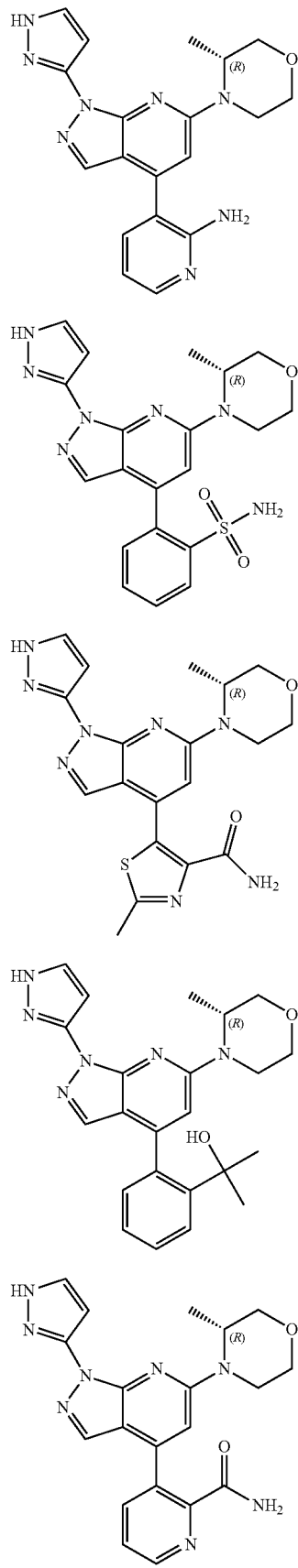

TABLE 1-continued
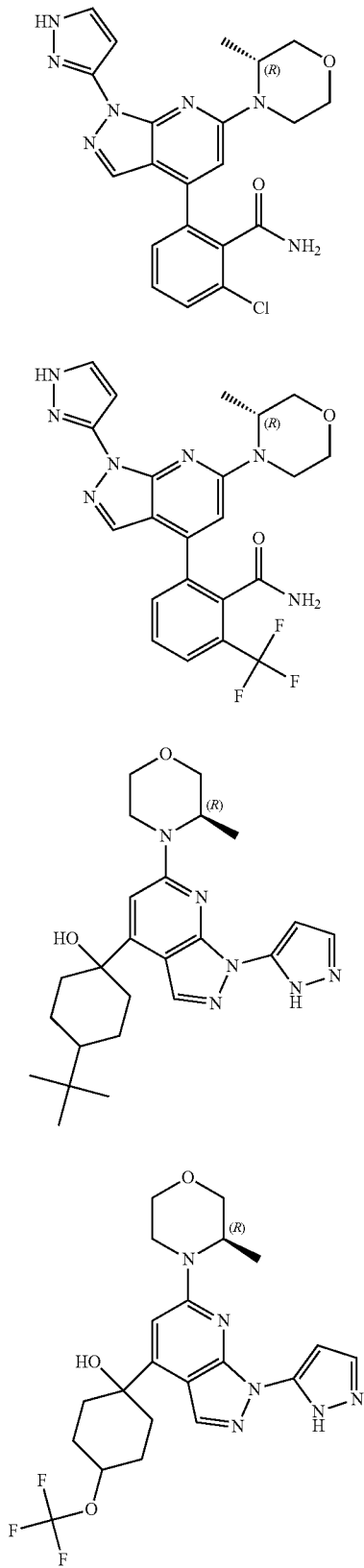
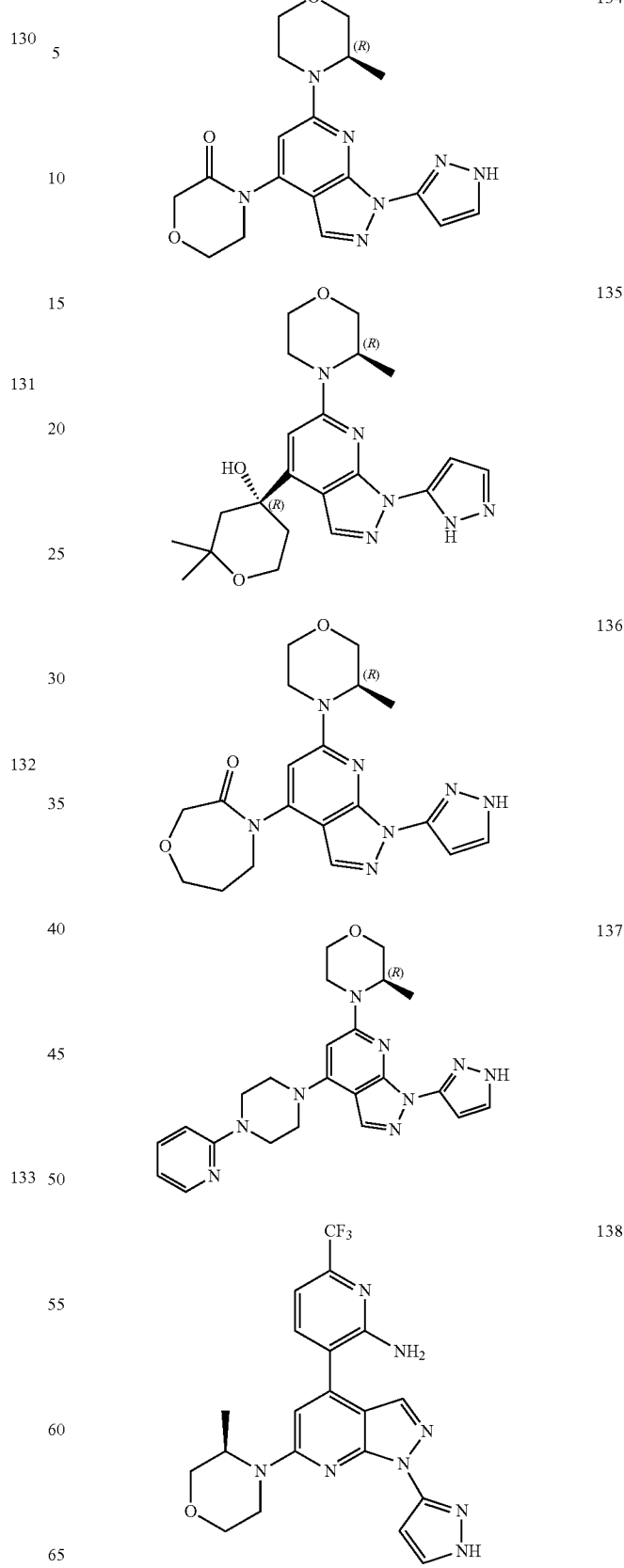

TABLE 1-continued
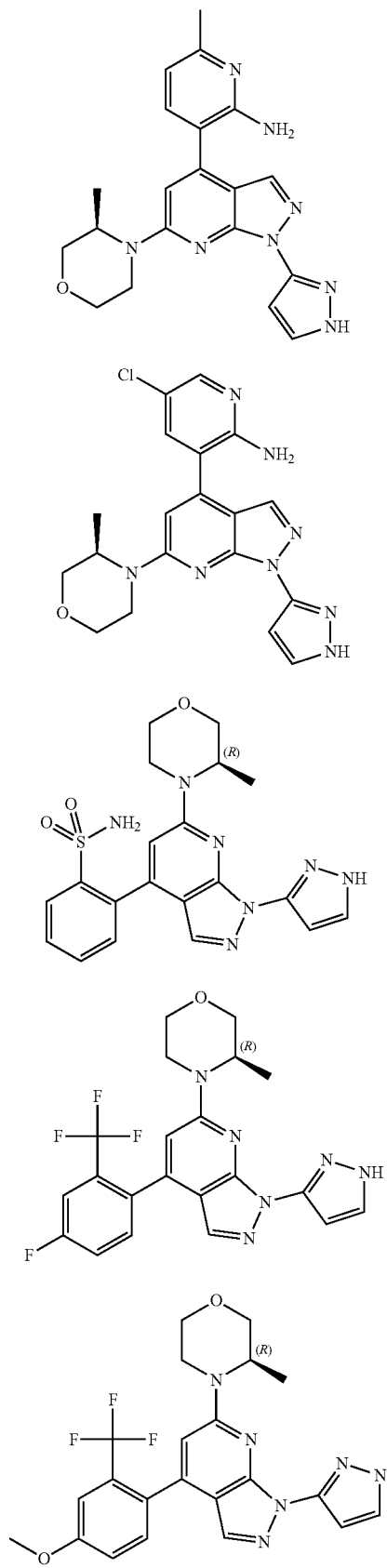
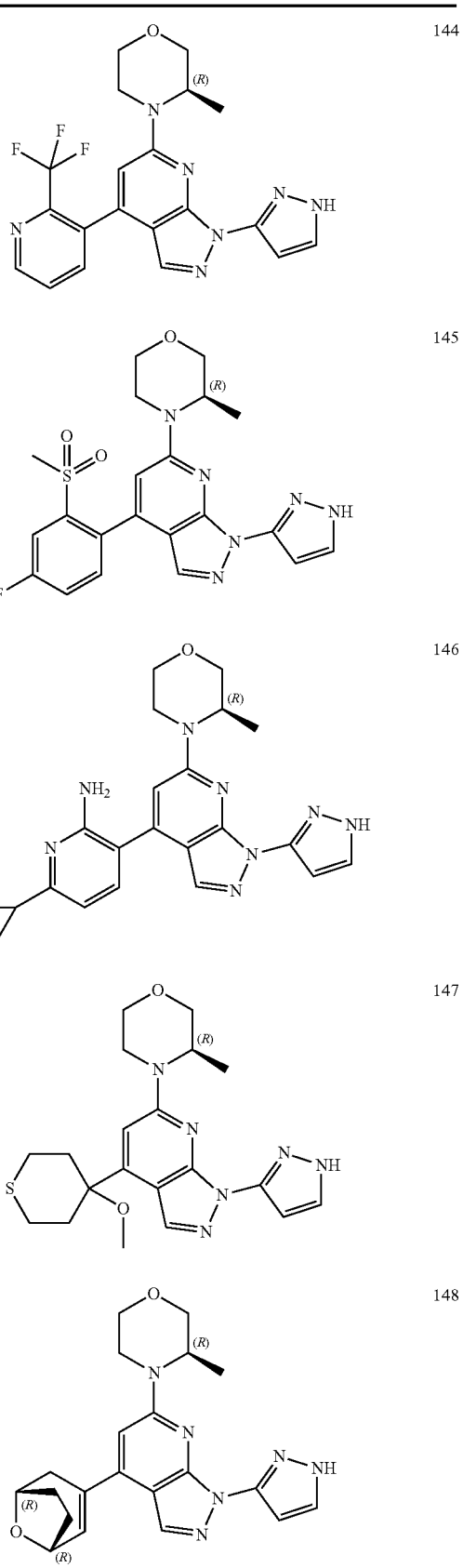

TABLE 1-continued

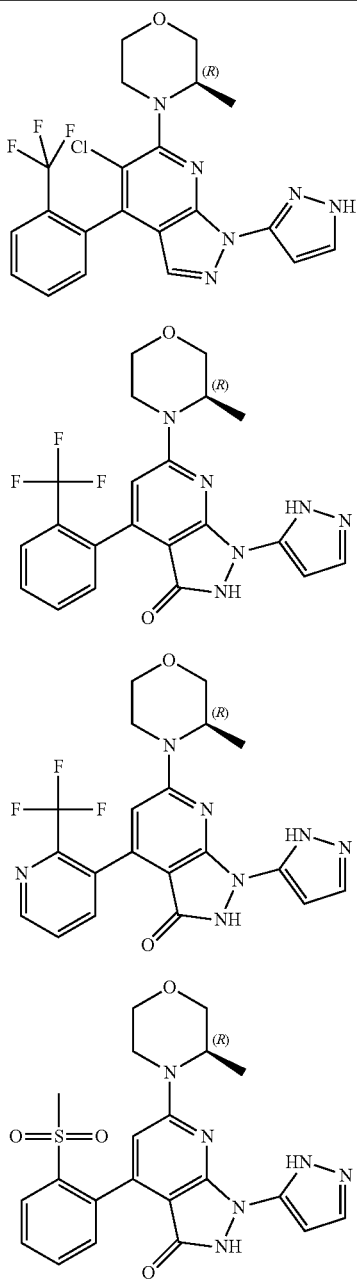

The invention includes (where possible) individual diastereomers, enantiomers, epimers, and atropisomers of the compounds disclosed herein, and mixtures of diastereomers and/or enantiomers thereof including racemic mixtures. Although the specific stereochemistries disclosed herein are preferred, other stereoisomers, including diastereomers, enantiomers, epimers, atropisomers, and mixtures of these may also have utility in treating ATR-mediated diseases. Inactive or less active diastereoisomers and enantiomers may be useful, e.g., for scientific studies relating to the receptor and the mechanism of activation.

It is understood that certain molecules can exist in multiple tautomeric forms. This invention includes all tautomers even though only one tautomer may be indicated in the examples.

The invention also includes pharmaceutically acceptable salts of the compounds, and pharmaceutical compositions including the compounds and a pharmaceutically acceptable carrier. The compounds are especially useful, e.g., in certain kinds of cancer and for slowing the progression of cancer once it has developed in a patient.

The compounds disclosed herein may be used in pharmaceutical compositions including (a) the compound(s) or pharmaceutically acceptable salts thereof, and (b) a pharmaceutically acceptable carrier. The compounds may be used in pharmaceutical compositions that include one or more other active pharmaceutical ingredients. The compounds may also be used in pharmaceutical compositions in which the compound disclosed herein or a pharmaceutically acceptable salt thereof is the only active ingredient.

Optical Isomers—Diastereomers—Geometric Isomers—Tautomers

Compounds disclosed herein may contain, e.g., one or more stereogenic centers and can occur as racemates, racemic mixtures, single enantiomers, individual diastereomers, and mixtures of diastereomers and/or enantiomers. The invention includes all such isomeric forms of the compounds disclosed herein. It is intended that all possible stereoisomers (e.g., enantiomers and/or diastereomers) in mixtures and as pure or partially purified compounds are included within the scope of this invention (i.e., all possible combinations of the stereogenic centers as pure compounds or in mixtures).

Some of the compounds described herein may contain bonds with hindered rotation such that two separate rotomers, or atropisomers, may be separated and found to have different biological activity which may be advantageous. It is intended that all of the possible atropisomers are included within the scope of this invention.

Some of the compounds described herein may contain olefinic double bonds, and unless specified otherwise, are meant to include both E and Z geometric isomers.

Some of the compounds described herein may exist with different points of attachment of hydrogen, referred to as tautomers. An example is a ketone and its enol form, known as keto-enol tautomers. The individual tautomers as well as mixtures thereof are encompassed by the invention.

Compounds disclosed herein having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Metabolites—Prodrugs

The invention includes therapeutically active metabolites, where the metabolites themselves fall within the scope of the claims. The invention also includes prodrugs, which are compounds that are converted to the claimed compounds as they are being administered to a patient or after they have been administered to a patient. The claimed chemical structures of this application in some cases may themselves be prodrugs.

Isotopically Enriched Derivatives

The invention includes molecules which have been isotopically enriched at one or more position within the molecule. Thus, compounds enriched for deuterium fall within the scope of the claims.

Methods of Preparing a Compound of the Invention

Compounds of the invention may be prepared using reactions and techniques known in the art and those described herein.

Method A

Compounds of the present invention may be prepared as shown in Scheme A and described herein. Commercially available 4-cyano-7-azaindole can be hydrolyzed to the acid and esterified under standard conditions. Regiospecific chlorination of the 6-position can be achieved by 7-aza oxidation with an oxidizing agent, e.g., mCPBA, followed by chlorination with mesyl chloride. The indole nitrogen may be protected with a suitable protecting group (PG), e.g., SEM or THP. The 6-chloro may be displaced with a suitably substituted morpholine under SNAr conditions that may optionally be catalyzed by palladium (0) or copper (I). The ester may then be derivatized by reduction to the alcohol with a suitable reducing agent, e.g., LiBH$_4$ or DIBAL-H, activated by forming a mesylate or iodo group and displaced with sodium methanesulfinate to form the methyl sulfone. Cyclopropanation at the benzylic position may be accomplished using dibromoethane in the presence of a base and a phase transfer catalyst. Deprotection of the azaindole then gives the key intermediate that can be derivatized by palladium- or copper-catalyzed couplings with an appropriate aryl iodide or heteroaryl iodide (R$^3$-I) to generate compounds of the present invention. In the case where R$^3$ bears a protecting group to facilitate the substitution reaction, a deprotection step may be require using acid, base and/or fluoride conditions to give compounds of the present invention.

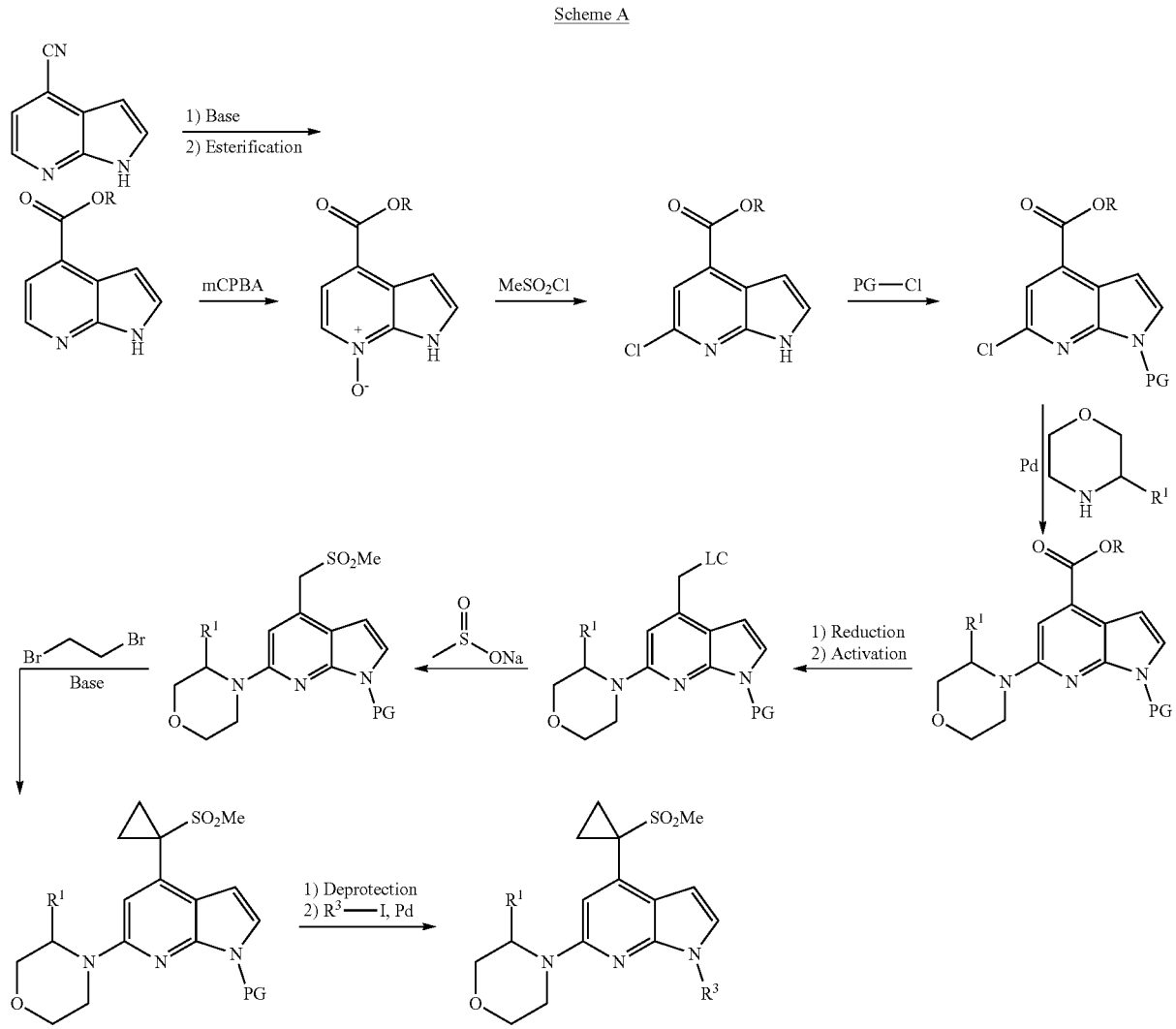

Scheme A

Method B

Compounds of the present invention may also be prepared as shown in Scheme B and described herein. Commercially available 4-chloro-7-azaindole can be activated to nucleophilic substitution by oxidation of the 7-aza group and methylation with dimethylsulfate. Addition of a suitably substituted morpholine followed by in situ elimination of methanol provides the 6-morpholino azaindole. An aryl group or heteroaryl group (R$^3$) can then be added by a copper-mediated arylation reaction. Depending on the nature of the heteroaryl group, a protecting group may be required to be in place prior to this coupling reaction. The 4-chloro group may be derivatized in a number of different ways to provide compounds of the present invention. For example, a palladium- or copper-mediated coupling may be used to install an aryl or heteroaryl group in the R$^2$ position. Alternatively, if R$^2$ is a substituted amine, a chloride displacement may occur under S$_N$Ar conditions, or under Buchwald-type coupling conditions. A sulfide could also be used to displace the 4-chloro group, which could optionally be oxidized to generate a sulfone. In the case where $R^3$ bears a protecting group, a deprotection step may be require using acid, base and/or fluoride conditions to give compounds of the present invention.

Scheme B

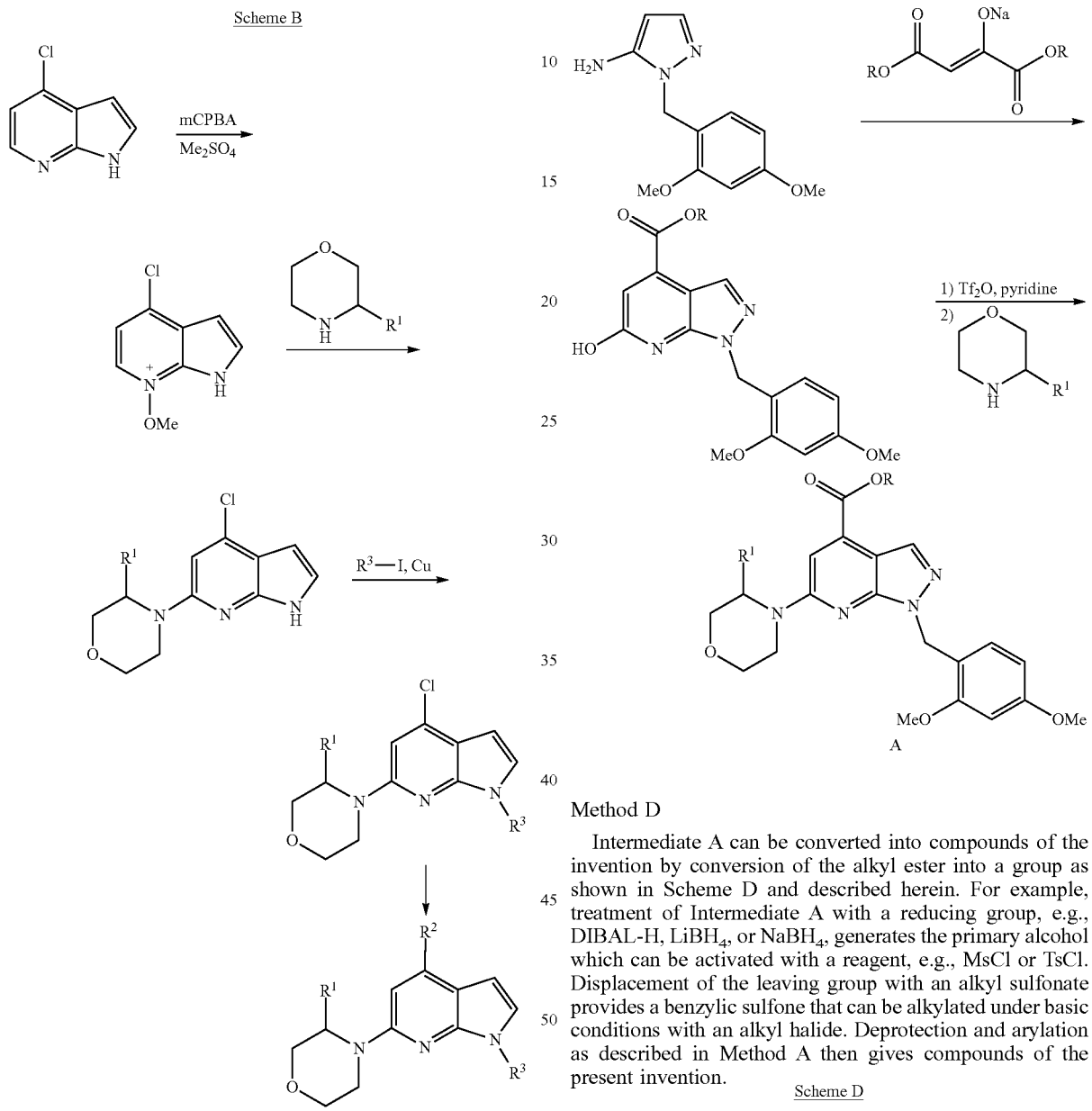

Method C

Compounds of the present invention can be prepared from key intermediate A, which can be prepared as shown in Scheme C and described herein. A protected 5-aminopyrazole can be prepared by condensing an appropriate aldehyde with hydrazine hydrate and acrylonitrile. Condensation with a dialkyl oxaloacetate salt in refluxing acetic acid then generates a substituted azaindazole. Activation of the hydroxyl group with triflic anhydride followed by nucleophilic displacement with a morpholine derivative generates key intermediate A.

Method D

Intermediate A can be converted into compounds of the invention by conversion of the alkyl ester into a group as shown in Scheme D and described herein. For example, treatment of Intermediate A with a reducing group, e.g., DIBAL-H, LiBH$_4$, or NaBH$_4$, generates the primary alcohol which can be activated with a reagent, e.g., MsCl or TsCl. Displacement of the leaving group with an alkyl sulfonate provides a benzylic sulfone that can be alkylated under basic conditions with an alkyl halide. Deprotection and arylation as described in Method A then gives compounds of the present invention.

Scheme D

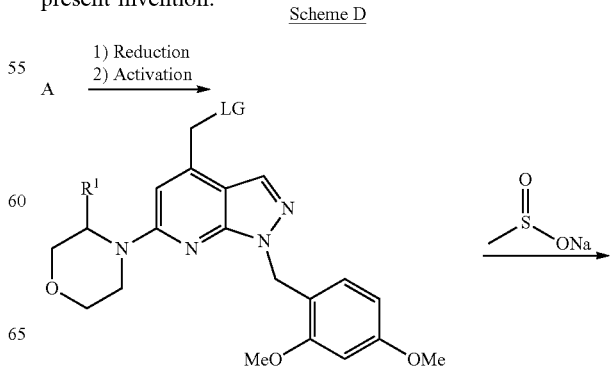

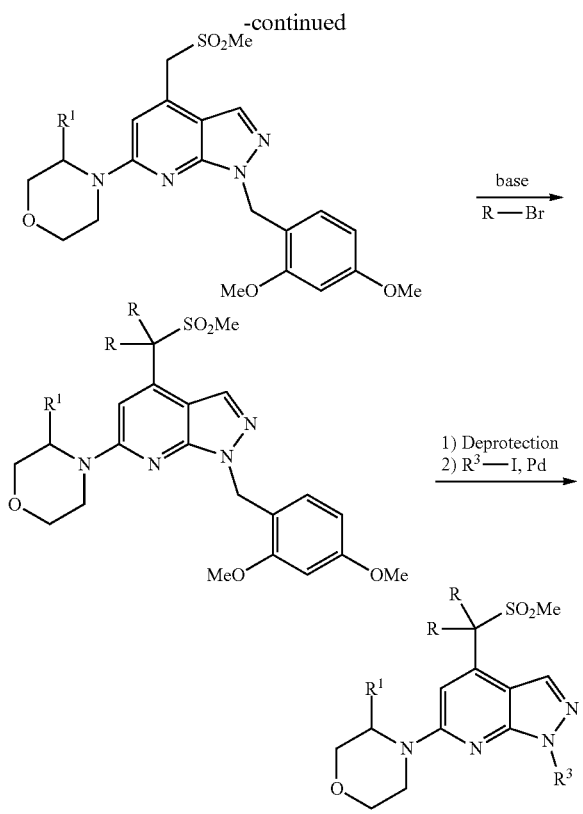

Method E

A compound of the invention may be prepared from Intermediate A as shown in Scheme E and described herein. Intermediate A may be treated with an alkylating agent like methyl magnesium bromide to convert the alkyl ester group into a tertiary alcohol. This material may be deprotected and arylated as described in Method A to give compounds of the present invention.

Scheme E

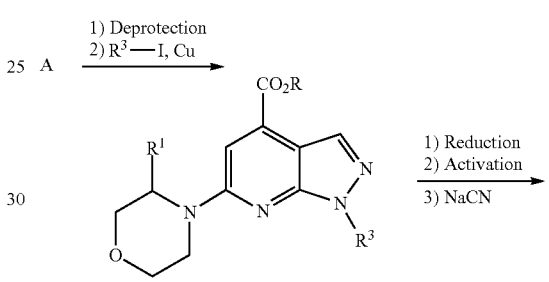

Method F

A compound of the invention may be prepared from Intermediate A as shown in Scheme F and described herein. Intermediate A may be deprotected under acidic conditions, then arylated under copper-catalyzed conditions. The ester group may then be reduced and activated with an agent, e.g., mesyl chloride ortosyl chloride, optionally with lithium iodide present. Displacement with sodium cyanide would then provide the aryl acetonitrile—an exemplary compound of the invention. Compounds of this type may be alkylated with an alkyl halide in the presence of base to provide the dialkylated aryl acetonitrile, which are compounds of the present invention. If R-X is a dihaloalkane, the corresponding cyclic derivative where the two R groups for a 3-7-member ring would be formed. Alternatively the primary alcohol can be coupled with a cyanohydrin under Mitsunobu conditions to give the nitrile derivatives directly. The nitrile may also be hydrolyzed to the primary amide under basic conditions or in the presence of a metal catalyst to provide compounds of the present invention.

Scheme F

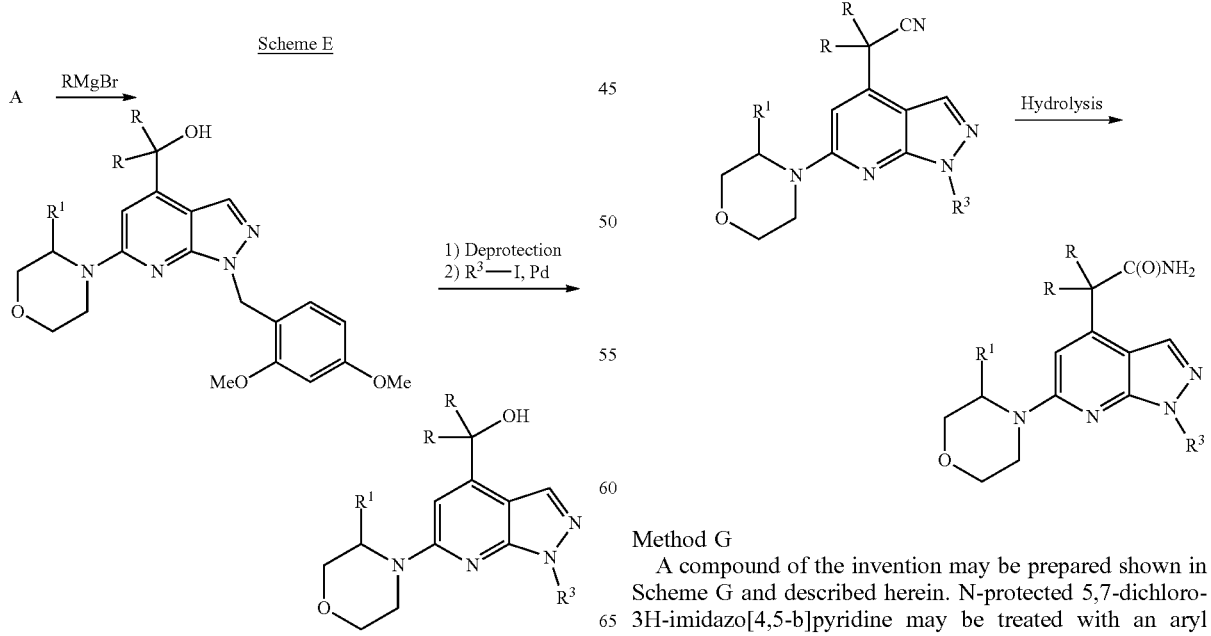

Method G

A compound of the invention may be prepared shown in Scheme G and described herein. N-protected 5,7-dichloro-3H-imidazo[4,5-b]pyridine may be treated with an aryl boronic acid under palladium catalysis to install an appropriate $R^2$ group. The second chloro substituent may be displaced with a suitably substituted morpholine under $S_NAr$ conditions that may optionally be catalyzed by palladium (0) or copper (I). Removal of the protecting group followed by arylation as described in Method A gives compounds of the present invention.

Scheme G

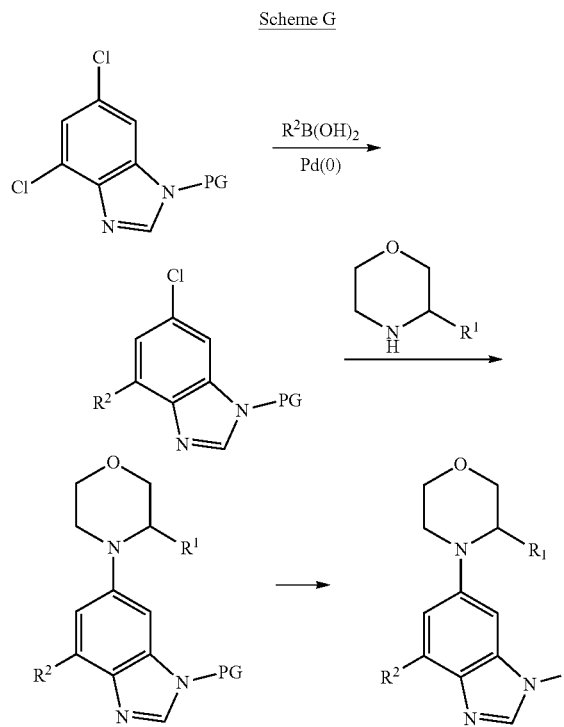

Method H

A compound of the invention may be prepared as shown in Scheme H and described herein. To the protected azaindole described in Method A is added an alkyl Grignard reagent to generate a tertiary alcohol. Removal of the protecting group on the azaindole followed by arylation as described in Method A gives compounds of the present invention.

Scheme H

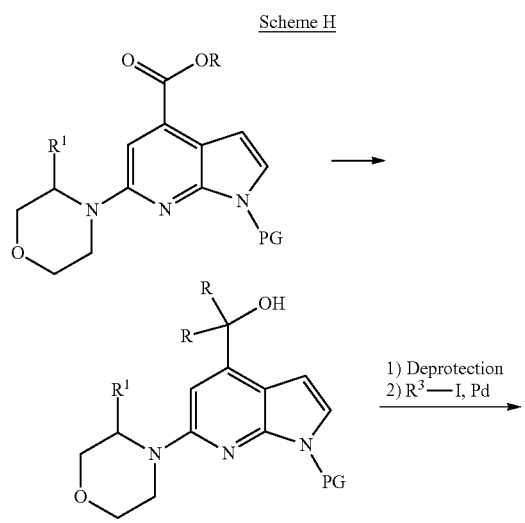

-continued

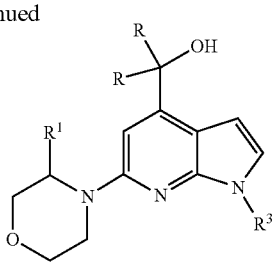

Method I

A compound of the invention may be prepared from Intermediate A as shown in Scheme I and described herein. The ester of Intermediate A may be hydrolyzed to the corresponding acid then treated with an amide under amide formation conditions using a suitable coupling reagent, e.g., EDC or HATU. Deprotection of the azaindole then gives the key intermediate that can be derivatized by palladium- or copper-catalyzed couplings with an appropriate aryl iodide or heteroaryl iodide ($R^3$-I) to generate compounds of the present invention. In the case where $R^3$ bears a protecting group to facilitate the substitution reaction, a deprotection step may be require using acid, base and/or fluoride conditions to give compounds of the present invention.

Scheme I

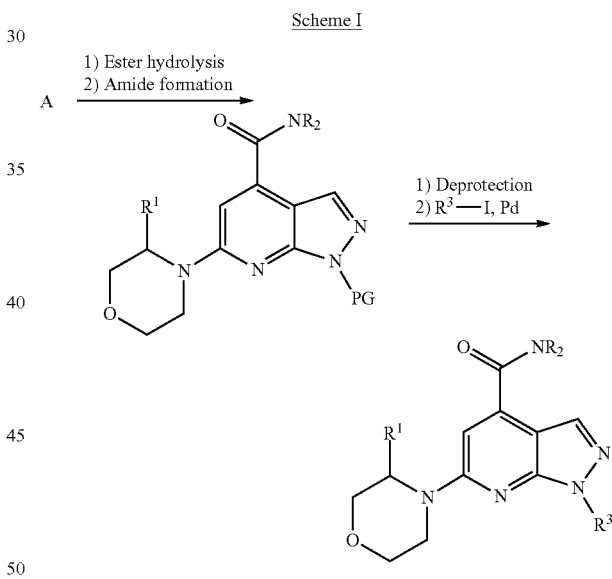

Method J

A compound of the invention may be prepared as shown in Scheme J and described herein. The ester intermediate from Method F may be hydrolyzed to the corresponding acid under standard conditions, e.g., aqueous LiOH or NaOH. This acid may be coupled with hydrazine using an activating agent, e.g., CDI or EDC, to generate the hydrazide. This may be formylated (R=H) or acylated (R=alkyl, aryl) to give the diacylhydrazine which can be cyclized to give compounds of the current invention. If the cyclization is carried out with $POCl_3$, an oxadiazole is produced. If the cyclization is carried out with Lawesson reagent, a thiadiazole is produced. In the case where $R^3$ bears a protecting group to facilitate these cyclizations, a deprotection step may be require using acid, base and/or fluoride conditions to give compounds of the present invention.

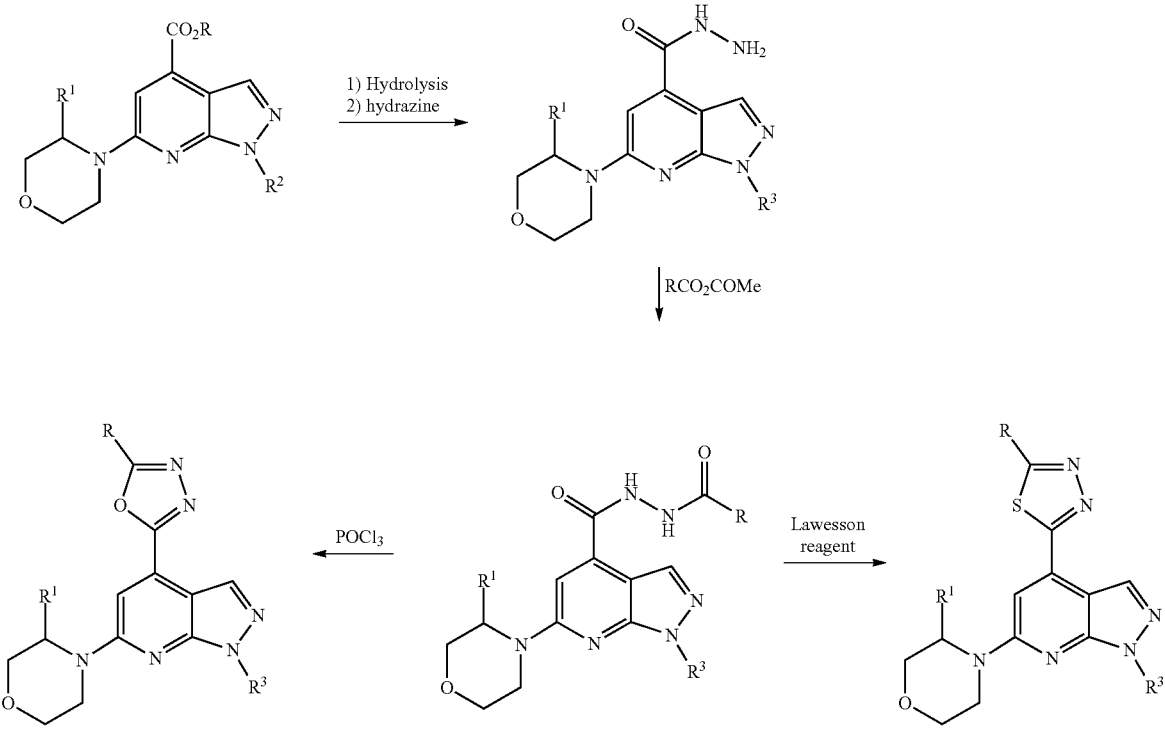

Scheme J

Method K

A compound of the invention may be prepared shown in Scheme K and described herein. 5-Chloro-3H-[1.2.3]triazolo[4,5-b]pyridine may be displaced with a suitably substituted morpholine under $S_NAr$ conditions that may optionally be catalyzed by palladium (0) or copper (I). The triazolyl nitrogen can be derivatized by palladium- or copper-catalyzed couplings with an appropriate aryl iodide or heteroaryl iodide ($R^3$-I) to install an appropriate $R^3$ group. Regiospecific chlorination of the 7-position can be achieved by 3-aza oxidation with an oxidizing agent, e.g., mCPBA, followed by chlorination with mesyl chloride. The 7-chloro group may be derivatized in a number of different ways to provide compounds of the present invention. For example, a palladium- or copper-mediated coupling may be used to install an aryl or heteroaryl group in the $R^2$ position. Alternatively, if $R^2$ is a substituted amine, a chloride displacement may occur under $S_NAr$ conditions, or under Buchwald-type coupling conditions. A sulfide could also be used to displace the 4-chloro group, which could optionally be oxidized to generate a sulfone. In the case where $R^3$ bears a protecting group to facilitate these cyclizations, a deprotection step may be require using acid, base and/or fluoride conditions to give compounds of the present invention.

Scheme K

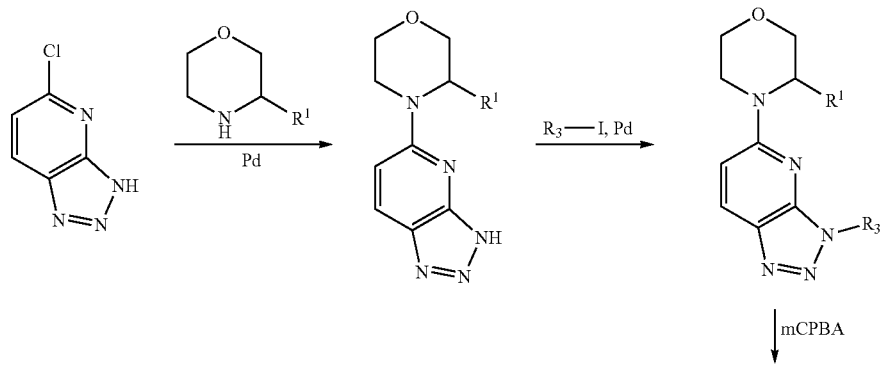

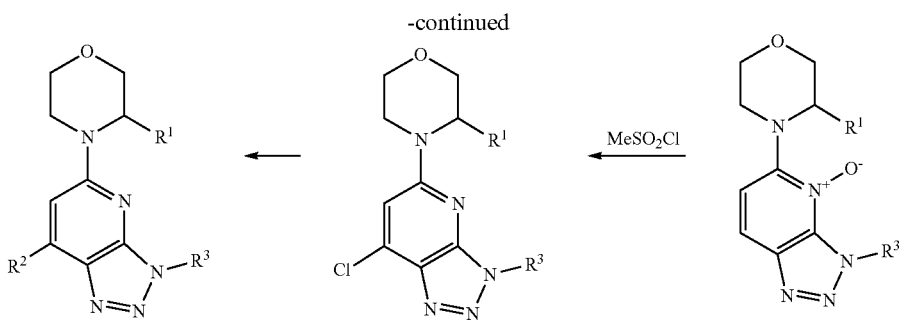

Method L 2,6-difluoro-4-iodo pyridine may be formylated by metalating with a strong base and trapping with a suitably formylating agent such as ethyl formate. The resulting aldehyde may be condensed with a suitably substituted pyrazole hydrazine to form the corresponding hydrazine which is cyclized to the azaindazole by heating to high temperature. The fluorine substituent on the azaindazole may be displaced by a suitably substituted morpholine under $S_NAr$ conditions to provide key intermediate B. Protection of the pyrazole NH with a suitable protecting group gives key intermediate C, typically as a mixture of N-protected regioisomers.

Scheme L

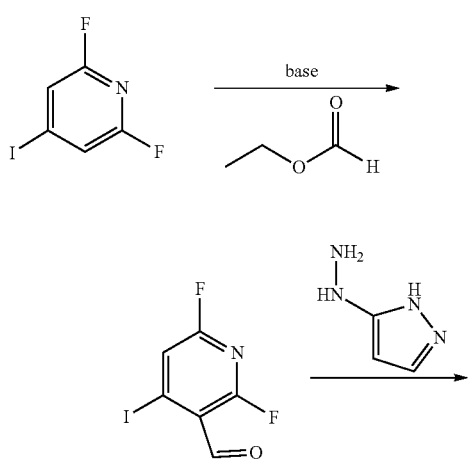

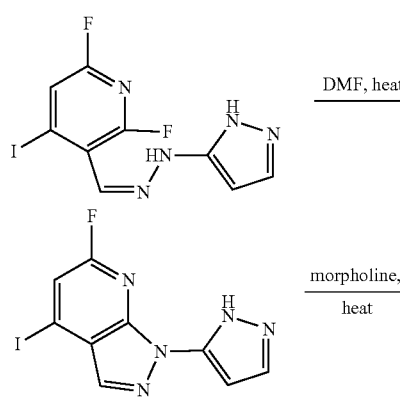

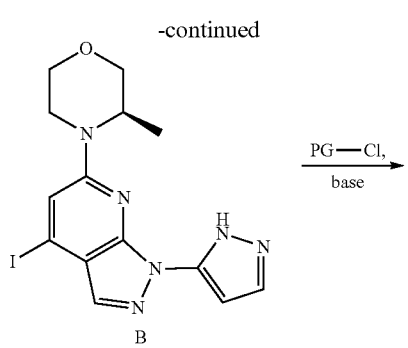

Method M

A compound of the invention may be prepared shown in Scheme M and described herein key intermediate C may be treated with an aryl boronic acid under palladium catalysis to install an appropriate $R^2$ group. Removal of the protecting group gives compounds of the present invention.

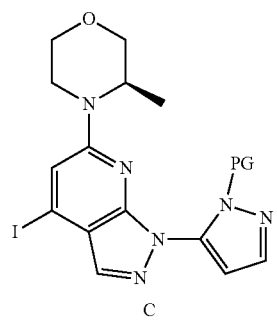

Scheme M

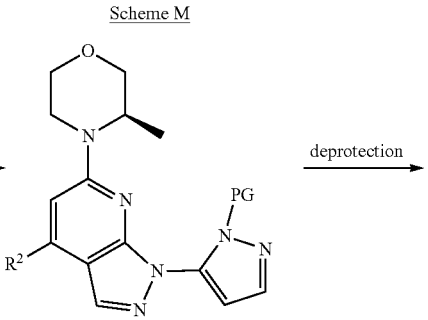

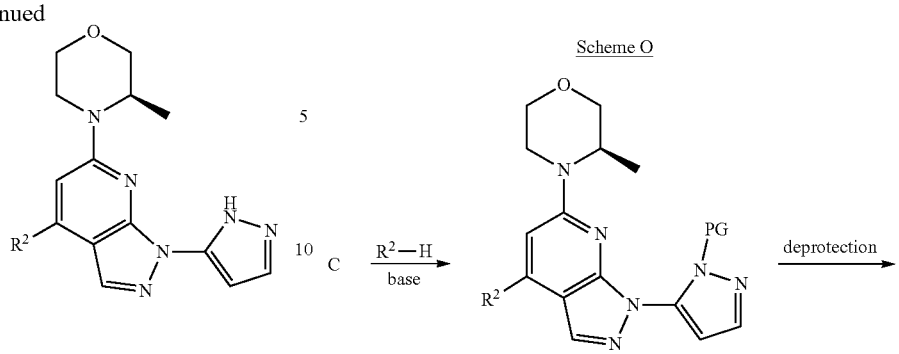

Method N

A compound of the invention may be prepared as shown in Scheme N and described herein. Key intermediate C may be metallated with an alkyl lithium or alkyl magnesium halide to generate an aryllithium or aryl magnesium bromide which can add to a suitable ketone to generate a tertiary alcohol derivative. In the case where the ketone contains one or more positions enriched for deuterium, the resulting product will also be isotopically enriched for deuterium. Removal of the protecting group gives compounds of the present invention. Alternatively, this chemistry may be carried out without a protecting group present using key intermediate B to directly provide compounds of the present invention.

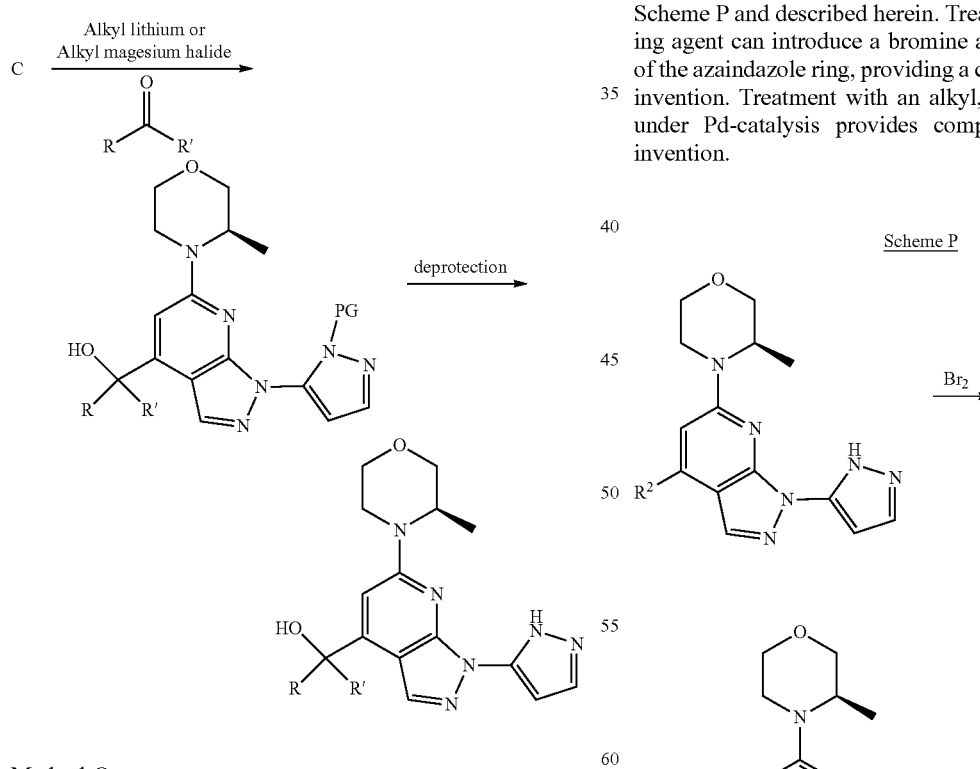

Method O

A compound of the invention may be prepared shown in Scheme O and described herein. Key intermediate C may be treated with a carbon, nitrogen or sulfur-based nucleophile to displace the iodo group and install a suitable $R^2$ group. Removal of the protecting group gives compounds of the present invention.

Method P

A compound of the invention may be prepared shown in Scheme P and described herein. Treatment with a brominating agent can introduce a bromine atom into the 3-position of the azaindazole ring, providing a compound of the present invention. Treatment with an alkyl, vinyl or aryl stannane under Pd-catalysis provides compounds of the present invention.

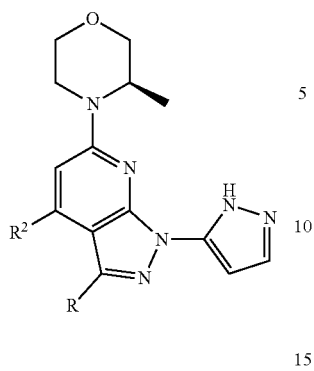

Method Q

A compound of the invention may be prepared shown in Scheme Q and described herein. 2,6-difluoro-4-iodonicotinaldehyde may be cyclized with hydrazine to form 6-fluoro-4-iodo-1H-pyrazolo[3,4-b]pyridine, which then may undergo a S$_N$Ar reaction with a substituted morpholine The resulting intermediate may undergo a second S$_N$Ar reaction with 2-cyanopropane under basic conditions to give the disubstituted azaindazole ring system. (An Ullman coupling on the NH of the azaindazole followed by deprotection provides compounds of the invention.

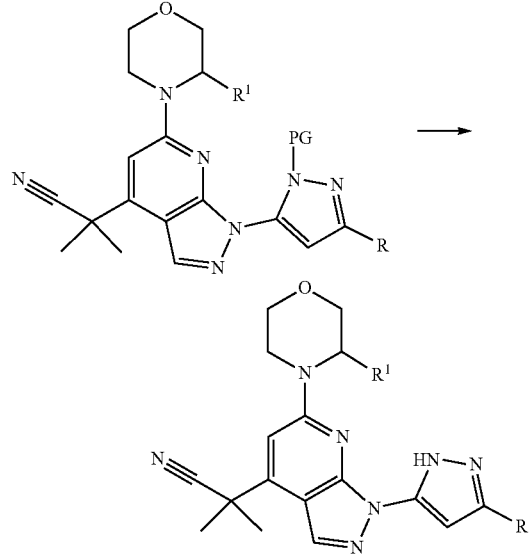

Method R

A compound of the invention may be prepared shown in Scheme R and described herein. Intermediate C may be converted to a boronate reagent by treatment of bis(pinacolato)diboron, a palladium catalyst and a base. This boronate may then be treated with an aryl halide or triflate under palladium catalysis to install an appropriate R$^2$ group. Removal of the protecting group gives compounds of the present invention.

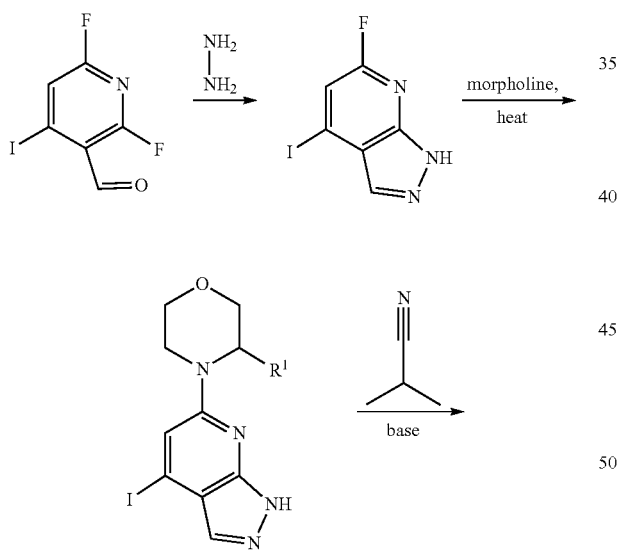

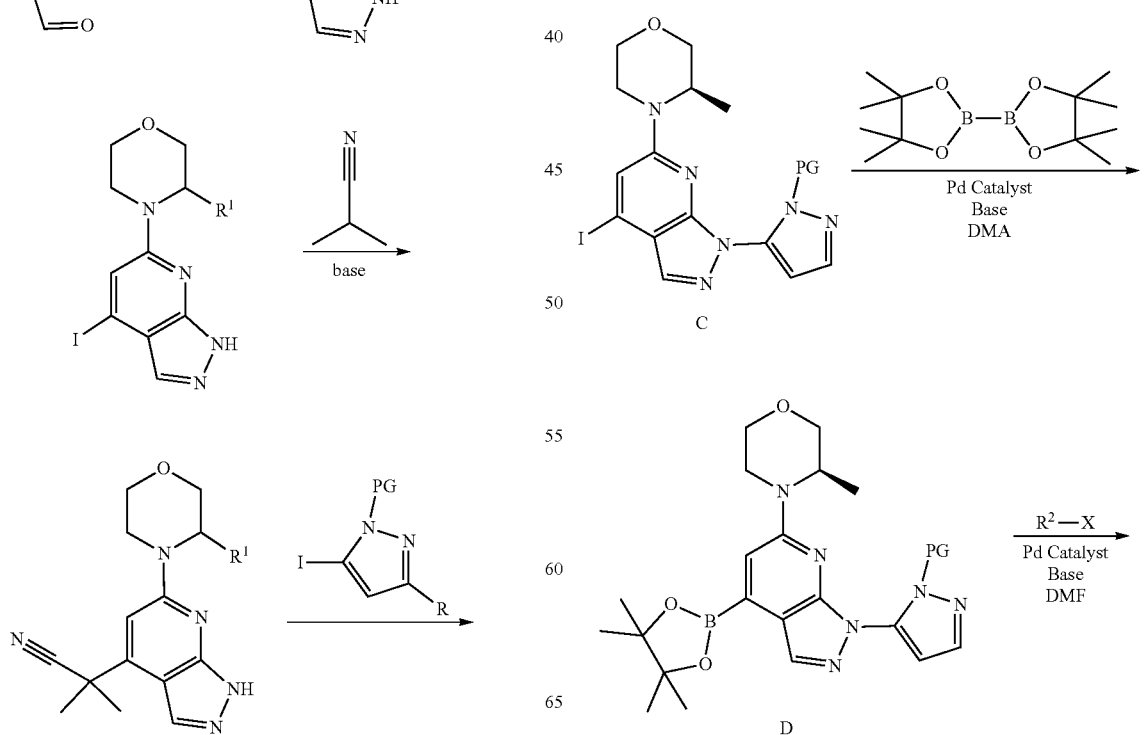

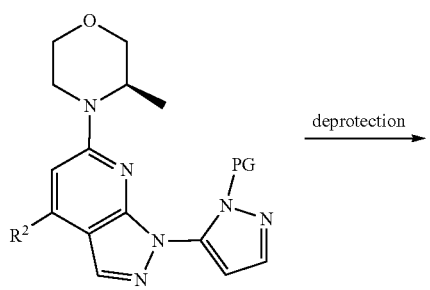

deprotection

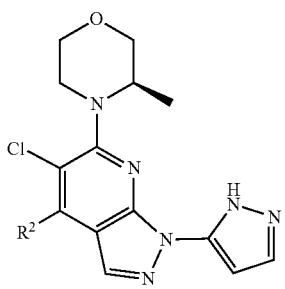

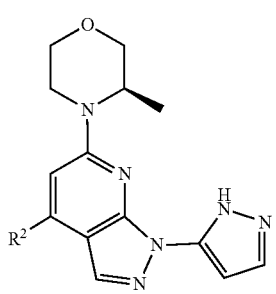

Method S

A compound of the invention may be prepared shown in Scheme R and described herein. Intermediate C may be chlorinated at the 5-position. The resulting intermediate may be treated with an aryl boronic acid or aryl boronic ester under palladium catalysis to install an appropriate $R^2$ group. Removal of the protecting group gives compounds of the present invention.

Method T

A compound of the invention may be prepared shown in Scheme T and described herein. 2,6-difluoro-4-iodo-pyridine-3-carboxaldehyde may be treated with a substituted morpholine to selectively displace the 6-fluoro substituent. Oxidation of the aldehyde is followed by hydrazide formation with an appropriately protected heterocyclic hydrazine. The hydrazide may be cyclized under basic conditions to form a iodopyrazolopyridinone ring system. This intermediate may undergo a subsequent $S_NAr$ reaction with a carbon, oxygen or sulfur nucleophile, or preferentially may be treated with an aryl boronic acid under palladium catalysis to install an appropriate $R^2$ group. Subsequent removal of the protecting group provides compounds of the present invention.

Scheme S

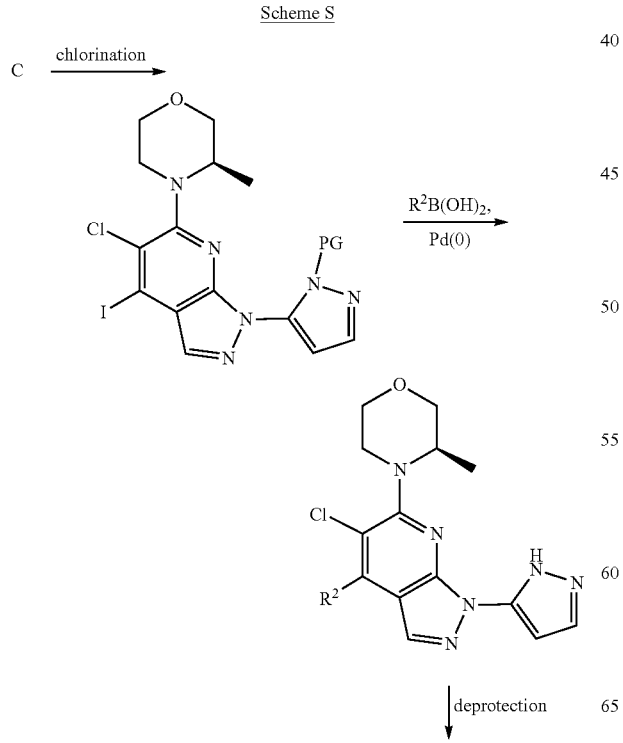

Scheme T

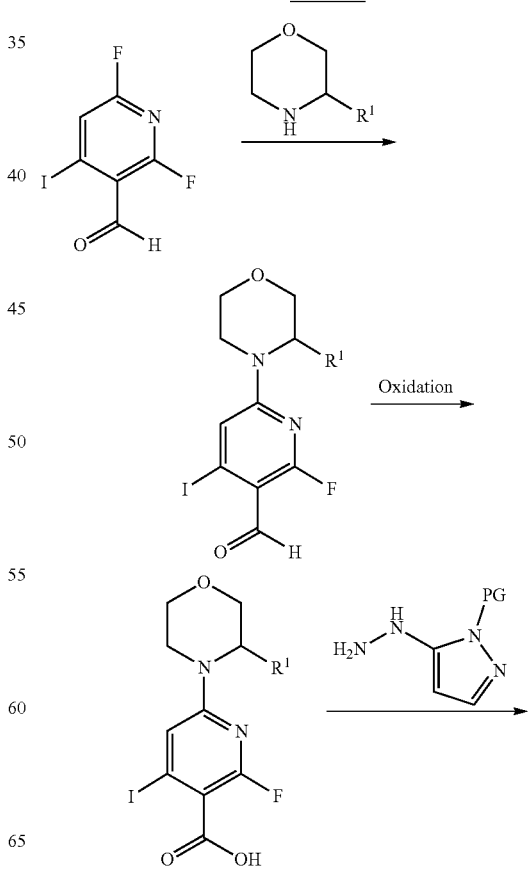

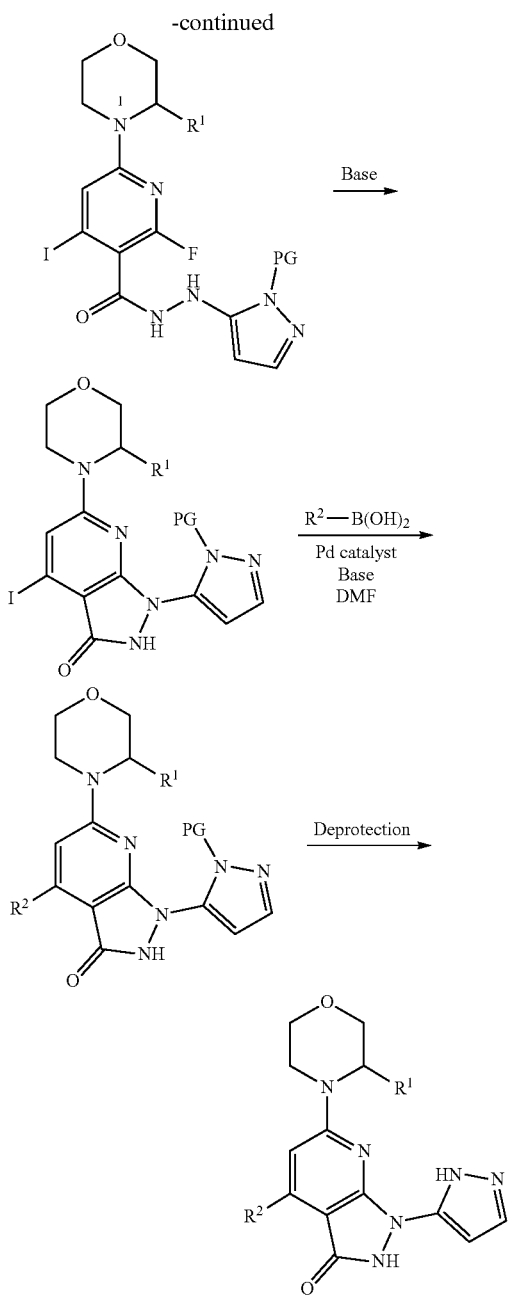

Methods of Treatment

Compounds of the invention may be used for the treatment of a disease or condition mediated by ATR kinase in a subject by administering to the subject an effective amount of the compound of the invention.

The disease or condition may have the symptom of cell hyperproliferation. For example, the disease or condition may be a cancer. The cancer may be, e.g., carcinoma, sarcoma, adenocarcinoma, lymphoma, leukemia, or melanoma. The cancer may be, e.g., a solid tumor.

Non-limiting examples of cancers include prostate cancer, breast cancer, ovarian cancer, multiple myeloma, brain cancer, glioma, lung cancer, salivary cancer, stomach cancer, thymic epithelial cancer, thyroid cancer, leukemia, melanoma, lymphoma, gastric cancer, pancreatic cancer, kidney cancer, bladder cancer, colon cancer, and liver cancer.

Non-limiting examples of carcinomas include medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, pre-invasive carcinoma, prickle cell carcinoma, pultaceous carcinoma, renal cell carcinoma of kidney, reserve cell carcinoma, carcinoma sarcomatodes, Schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Non-limiting examples of sarcomas include chondrosarcoma, fibrosarcoma, lymphosarcoma, melanosarcoma, myxosarcoma, osteosarcoma, Abernethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

Non-limiting examples of leukemias include acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, and undifferentiated cell leukemia.

Non-limiting examples of melanomas include acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungual melanoma, and superficial spreading melanoma.

A compound of the invention may be administered by a route selected from the group consisting of oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, intratumoral, and topical administration.

The methods of the invention may include a step of identifying a subject as being a candidate for an ATR inhibitor therapy. For example, the subject may be identified as being a candidate for an ATR inhibitor therapy by determining (i) whether the subject has cancer with defects in the ATM signaling cascade; (ii) whether the subject has cancer, cancer cells, or cells expressing genetic aberrations in cancer-driving genes or oncogenes; (iii) whether the subject has cancer, cancer cell, or cells with one or more defect(s) in a protein or gene involved in base excision repair; (iv) whether the subject has cancer with defects in a protein or gene involved in homologous recombination; (v) whether the subject has a cancer with defects in a protein or gene that have been implicated in sensitivity to ATR inhibitors or genetic perturbation of ATR; or (vi) whether the subject has a cancer with genetic or protein characteristics that have been implicated in sensitivity to ATR inhibitors.

The compounds, compositions, and methods described may be used to treat a subject having a cancer with an aberration in the ATM signaling cascade. For example, the aberration in the ATM signaling cascade may be, e.g., altered expression or activity of one or more of the following proteins/genes including but not limited to: ATM, p53, CHK2, MRE11, RAD50, NBS1, 53BP1, MDC1, H2AX, MCPH1/BRIT1, CTIP, and SMC1. Aberrations in ATM signaling may be identified as follows: a 20% or greater change in the phosphorylation of CHK2 may be indicative of an aberration in the ATM signaling cascade, or the inability of cells to arrest in G1 and S phase of the cell cycle in response to double strand DNA breaks may be indicative of an aberration in the ATM signaling cascade.

The compounds, compositions, and methods described may be used to treat a subject with a cancer, cancer cells, or cells having aberrant expression of cancer-driving proteins or oncogenes. For example, the cancer cell may have genetic aberrations that cause altered expression or activity of one or more of the following proteins/genes including but not limited to: KRAS, NRAS, HRAS, BRAF, MYC, MOS, E2F, CDC25A, CDC$_4$, CDK2, CCNE1, CCNA1, DNAPK, APOBEC3, CDC6 and RB1.

The compounds, compositions, and methods described may be used to treat a subject having a cancer, cancer cells, or cells with one or more aberration(s) in a protein or gene involved in base excision repair. For example, the aberration in base excision repair protein may be altered expression or activity of one or more of the following proteins/genes including but not limited to: UNG, SMUG1, MBD4, TDG, OGG1, MYH, NTH1, MPG, NEIL1, NEIL2, NEIL3 (DNA glycosylases); APE1, APEX2 (AP endonucleases); LIG1, LIG3 (DNA ligases I and III); XRCC1 (LIG3 accessory); PNK, PNKP (polynucleotide kinase and phosphatase); PARP1, PARP2 (Poly(ADP-Ribose) Polymerases); PolB, PolG (polymerases); FEN1 (endonuclease) or Aprataxin.

The compounds, compositions, and methods described may be used to treat a subject having a cancer, cancer cells or cells with one or more aberration(s) in a protein or gene involved in homologous recombination. For example, the aberration in homologous recombination may be altered expression or activity of one or more of the following proteins/genes including but not limited to: BRCA1, BRCA2, MRE11, RAD50, RAD51, RAD52, RAD54L, NBN, ATM, H2AX, PALB2, RPA, BRIP1, BARD1, ATR, ATRX, CHK1, CHK2, MDM2, MDM4, FANCA, FANCC, FANCD2, FANCE, FANCF, FANCG, and FANCL.

The compounds, compositions, and methods described may be used to treat a subject having a cancer, cancer cells or cells with one or more aberration(s) in a protein or gene implicated in sensitivity to ATR inhibitors or genetic perturbation of the ATR signaling pathway. For example, the aberration in genes that have been implicated in sensitivity to ATR inhibitors or genetic perturbation of ATR may be altered expression or activity of one or more of the following proteins/genes including but not limited to: ATR, CHK1, ERCC1, ERCC2, RAD17, RAD1, RAD9A, ERCC4, ATM, FANCE, GCP3, IDH1, PALB2, PMS2, ARID1A, SLX4, MSH4, RRM2, POLA, POLD1, RRM1, WEE1, CLSPN, PGBD5, XRCC1, XRCC3, XRCC5, KDM5D, CDC6, SLFN11, TLK1, and TLK2

There are many methods known in the art for determining whether a tumor has an aberration in a protein or gene. For example, sequencing of either the genomic DNA or mRNA products of each specified gene (e.g., UNG, PARP1, or LIG1) can be performed on a sample of the tumor to establish whether mutations expected to modulate the function or expression of the gene product are present. In addition to the mutational inactivation, tumor cells can modulate a gene by hypermethylating its promoter region, leading to reduced gene expression. This is most commonly assessed using methylation-specific polymerase chain reaction (PCR) to quantify methylation levels on the promoters of base excision repair genes of interest. Analysis of DNA repair gene promoter methylation is available commercially.

The expression levels of genes can be assessed by directly quantifying levels of the mRNA and protein products of each gene using standard techniques, e.g., quantitative reverse transcriptase-coupled polymerase chain reaction (RT-PCR), RNA-Seq for gene expression, and immunohistochemistry (IHC) for protein expression. Gene amplification or deletion leading to aberrantly over- or under-expressed proteins (respectively) can also be measured by FISH (fluorescent in situ hybridization) analysis using a probe specific for the gene of interest.

The methods described above (gene sequence, promoter methylation, and mRNA expression) may also be used to characterize the status (e.g., expression or mutation) of other genes or proteins of interest, e.g., DNA-damaging oncogenes expressed by a tumor or defects in the DNA repair pathways of a cell.

The compounds, compositions, and methods described may be used to treat a subject suffering from cancer with genetic characteristics have been implicated in sensitivity to ATR inhibitors. In some embodiments, the genetic characteristic is one or more of the following: cells with alternative lengthening of telomeres (ALT) characterized by cellular transformation in the absence of HTERT and/or ATRX mRNA or protein expression, the presence of C-circles or partially double stranded and circular extrachromosomal telomeric repeats (ECTR), the presence of telomeres of varying lengths and positive staining for the presence of ALT-associated promyelocytic leukemia (PML) nuclear bodies (APBs).

There are several methods to determine ALT characteristics in cells. Non-limiting examples of these methods include: HTERT and ATRX expression can be measured by Western blot, immunohistochemistry (IHC) or by mRNA expression (qRT-PCR) assays; the presence of C-circles can be measured in a PCR assay, the presence of telomeres of varying lengths can be measured by telomere restriction fragment analysis (TRF) which measures the heterogeneous range of telomere lengths in a cell population using the length distribution of the terminal restriction fragments; and staining for the presence of APBs can be accomplished using IHC by co-staining with a probe for telomeric DNA and PML protein.

Pharmaceutical Compositions

The compounds used in the methods described herein are preferably formulated into pharmaceutical compositions for administration to human subjects in a biologically compatible form suitable for administration in vivo. Pharmaceutical compositions typically include a compound as described herein and a pharmaceutically acceptable excipient. Certain pharmaceutical compositions may include one or more additional pharmaceutically active agents described herein.

The compounds described herein can also be used in the form of the free base, in the form of salts, zwitterions, solvates, or as prodrugs, or pharmaceutical compositions thereof. All forms are within the scope of the invention. The compounds, salts, zwitterions, solvates, prodrugs, or pharmaceutical compositions thereof, may be administered to a patient in a variety of forms depending on the selected route of administration, as will be understood by those skilled in the art. The compounds used in the methods described herein may be administered, for example, by oral, parenteral, buccal, sublingual, nasal, rectal, patch, pump, or transdermal administration, and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

For human use, a compound of the invention can be administered alone or in admixture with a pharmaceutical carrier selected with regard to the intended route of administration and standard pharmaceutical practice. Pharmaceutical compositions for use in accordance with the present invention thus can be formulated in a conventional manner using one or more physiologically acceptable carriers including excipients and auxiliaries that facilitate processing of a compound of the invention into preparations which can be used pharmaceutically.

This invention also includes pharmaceutical compositions which can contain one or more pharmaceutically acceptable carriers. In making the pharmaceutical compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semisolid, or liquid material (e.g., normal saline), which acts as a vehicle, carrier or medium for the active ingredient. Thus, the compositions can be in the form of tablets, powders, lozenges, sachets, cachets, elixirs, suspensions, emulsions, solutions, syrups, and soft and hard gelatin capsules. As is known in the art, the type of diluent can vary depending upon the intended route of administration. The resulting compositions can include additional agents, e.g., preservatives.

The excipient or carrier is selected on the basis of the mode and route of administration. Suitable pharmaceutical carriers, as well as pharmaceutical necessities for use in pharmaceutical formulations, are described in Remington: The Science and Practice of Pharmacy, 21st Ed., Gennaro, Ed., Lippincott Williams & Wilkins (2005), a well-known reference text in this field, and in the USP/NF (United States Pharmacopeia and the National Formulary). Examples of suitable excipients are lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents, e.g., talc, magnesium stearate, and mineral oil; wetting agents; emulsifying and suspending agents; preserving agents, e.g., methyl- and propylhydroxy-benzoates; sweetening agents; and flavoring agents. Other exemplary excipients are described in Handbook of Pharmaceutical Excipients, 6th Edition, Rowe et al., Eds., Pharmaceutical Press (2009).

These pharmaceutical compositions can be manufactured in a conventional manner, e.g., by conventional mixing, dissolving, granulating, dragee-making, levigating, emulsifying, encapsulating, entrapping, or lyophilizing processes. Methods well known in the art for making formulations are found, for example, in Remington: The Science and Practice of Pharmacy, 21st Ed., Gennaro, Ed., Lippincott Williams & Wilkins (2005), and Encyclopedia of Pharmaceutical Technology, eds. J. Swarbrick and J. C. Boylan, 1988-1999, Marcel Dekker, New York. Proper formulation is dependent upon the route of administration chosen. The formulation and preparation of such compositions is well-known to those skilled in the art of pharmaceutical formulation. In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

Dosages

The dosage of the compound used in the methods described herein, or pharmaceutically acceptable salts or prodrugs thereof, or pharmaceutical compositions thereof, can vary depending on many factors, e.g., the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds used in the methods described herein may be administered initially in a suitable dosage that may be adjusted as required, depending on the clinical response. In general, a suitable daily dose of a compound of the invention will be that amount of the compound that is the lowest dose effective to produce a therapeutic effect. Such an effective dose will generally depend upon the factors described above.

A compound of the invention may be administered to the patient in a single dose or in multiple doses. When multiple doses are administered, the doses may be separated from one another by, for example, 1-24 hours, 1-7 days, 1-4 weeks, or 1-12 months. The compound may be administered according to a schedule or the compound may be administered without a predetermined schedule. An active compound may be administered, for example, 1, 2, 3, 4, 5, 6, 7, 8, 9, 10, 11, or 12 times per day, every 2nd, 3rd, 4th, 5th, or 6th day, 1, 2, 3, 4, 5, 6, or 7 times per week, 1, 2, 3, 4, 5, or 6 times per month, or 1, 2, 3, 4, 5, 6, 7, 8, 9, 10, 11, or 12 times per year. It is to be understood that, for any particular subject, specific dosage regimes should be adjusted overtime according to the individual need and the professional judgment of the person administering or supervising the administration of the compositions.

While the attending physician ultimately will decide the appropriate amount and dosage regimen, an effective amount of a compound of the invention may be, for example, a total daily dosage of, e.g., between 0.05 mg and 3000 mg of any of the compounds described herein. Alternatively, the dosage amount can be calculated using the body weight of the patient. Such dose ranges may include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered.

In the methods of the invention, the time period during which multiple doses of a compound of the invention are administered to a patient can vary. For example, in some embodiments, doses of the compounds of the invention are administered to a patient over a time period that is 1-7 days; 1-12 weeks; or 1-3 months. In some embodiments, the compounds are administered to the patient over a time period that is, for example, 4-11 months or 1-30 years. In some embodiments, the compounds are administered to a patient at the onset of symptoms. In any of these embodiments, the amount of compound that is administered may vary during the time period of administration. When a compound is administered daily, administration may occur, for example, 1, 2, 3, 4, 5, 6, 7, 8, 9, 10, 11, or 12 times per day.

Formulations

A compound identified as capable of treating any of the conditions described herein, using any of the methods described herein, may be administered to patients or animals with a pharmaceutically-acceptable diluent, carrier, or excipient, in unit dosage form. The chemical compounds for use in such therapies may be produced and isolated by any standard technique known to those in the field of medicinal chemistry. Conventional pharmaceutical practice may be employed to provide suitable formulations or compositions to administer the identified compound to patients suffering from a disease or condition. Administration may begin before the patient is symptomatic.

Exemplary routes of administration of the compounds (e.g., a compound of the invention), or pharmaceutical compositions thereof, used in the present invention include oral, sublingual, buccal, transdermal, intradermal, intramuscular, parenteral, intravenous, intra-arterial, intracranial, subcutaneous, intraorbital, intraventricular, intraspinal, intraperitoneal, intranasal, inhalation, and topical administration. The compounds desirably are administered with a pharmaceutically acceptable carrier. Pharmaceutical formulations of the compounds described herein formulated for treatment of the disorders described herein are also part of the present invention.

Formulations for Oral Administration

The pharmaceutical compositions contemplated by the invention include those formulated for oral administration ("oral dosage forms"). Oral dosage forms can be, for example, in the form of tablets, capsules, a liquid solution or suspension, a powder, or liquid or solid crystals, which contain the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethyleneglycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

Formulations for oral administration may also be presented as chewable tablets, as hard gelatin capsules where the active ingredient is mixed with an inert solid diluent (e.g., potato starch, lactose, microcrystalline cellulose, calcium carbonate, calcium phosphate or kaolin), or as soft gelatin capsules where the active ingredient is mixed with water or an oil medium, for example, peanut oil, liquid paraffin, or olive oil. Powders, granulates, and pellets may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance. Any of a number of strategies can be pursued in order to obtain controlled release and the targeted plasma concentration versus time profile. In one example, controlled release is obtained by appropriate selection of various formulation parameters and ingredients, including, e.g., various types of controlled release compositions and coatings. Examples include single or multiple unit tablet or capsule compositions, oil solutions, suspensions, emulsions, microcapsules, microspheres, nanoparticles, patches, and liposomes. In some embodiments, compositions include biodegradable, pH, and/or temperature-sensitive polymer coatings.

Dissolution or diffusion-controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

The liquid forms in which the compounds and compositions of the present invention can be incorporated for administration orally include aqueous solutions, suitably flavored syrups, aqueous or oil suspensions, and flavored emulsions with edible oils, e.g., cottonseed oil, sesame oil, coconut oil, or peanut oil, as well as elixirs and similar pharmaceutical vehicles.

Formulations for Parenteral Administration

The compounds described herein for use in the methods of the invention can be administered in a pharmaceutically acceptable parenteral (e.g., intravenous or intramuscular) formulation as described herein. The pharmaceutical formulation may also be administered parenterally (intravenous, intramuscular, subcutaneous or the like) in dosage forms or formulations containing conventional, non-toxic pharmaceutically acceptable carriers and adjuvants. In particular, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. For example, to prepare such a composition, the compounds of the invention may be dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution and isotonic sodium chloride solution. The aqueous formulation may also contain one or more preservatives, for example, methyl, ethyl, or n-propyl p-hydroxybenzoate. Additional information regarding parenteral formulations can be found, for example, in the United States Pharmacopeia-National Formulary (USP-NF), herein incorporated by reference.

The parenteral formulation can be any of the five general types of preparations identified by the USP-NF as suitable for parenteral administration:

(1) "Drug Injection:" a liquid preparation that is a drug substance (e.g., a compound of the invention), or a solution thereof;

(2) "Drug for Injection:" the drug substance (e.g., a compound of the invention) as a dry solid that will be combined with the appropriate sterile vehicle for parenteral administration as a drug injection;

(3) "Drug Injectable Emulsion:" a liquid preparation of the drug substance (e.g., a compound of the invention) that is dissolved or dispersed in a suitable emulsion medium;

(4) "Drug Injectable Suspension:" a liquid preparation of the drug substance (e.g., a compound of the invention) suspended in a suitable liquid medium; and (5) "Drug for Injectable Suspension:" the drug substance (e.g., a compound of the invention) as a dry solid that will be combined with the appropriate sterile vehicle for parenteral administration as a drug injectable suspension.

Exemplary formulations for parenteral administration include solutions of the compound prepared in water suitably mixed with a surfactant, e.g., hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington: The Science and Practice of Pharmacy, 21st Ed., Gennaro, Ed., Lippincott Williams & Wilkins (2005) and in The United States Pharmacopeia: The National Formulary (USP 36 NF31), published in 2013.

Formulations for parenteral administration may, for example, contain excipients, sterile water, or saline, polyalkylene glycols, e.g., polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

The parenteral formulation can be formulated for prompt release or for sustained/extended release of the compound. Exemplary formulations for parenteral release of the compound include: aqueous solutions, powders for reconstitution, cosolvent solutions, oil/water emulsions, suspensions, oil-based solutions, liposomes, microspheres, and polymeric gels.

Combinations

Compounds of the present invention may be administered to a subject in combination with a one or more additional agents, e.g.:

(a) a cytotoxic agent;
(b) an antimetabolite;
(c) an alkylating agent;
(d) an anthracycline;
(e) an antibiotic;
(f) an anti-mitotic agent;
(g) a hormone therapy;
(h) a signal transduction inhibitor;
(i) a gene expression modulator;
(j) an apoptosis inducer;
(k) an angiogenesis inhibitor;
(l) an immunotherapy agent;
(m) a DNA damage repair inhibitor;
or
a combination thereof.

The cytotoxic agent may be, e.g., actinomycin-D, alemtuzumab, alitretinoin, allopurinol, altretamine, amifostine, amphotericin, amsacrine, arsenic trioxide, asparaginase, azacitidine, azathioprine, Bacille Calmette-Guerin (BCG), bendamustine, bexarotene, bevacuzimab, bleomycin, bortezomib, busulphan, capecitabine, carboplatin, carfilzomib, carmustine, cetuximab, cisplatin, chlorambucil, cladribine, clofarabine, colchicine, crisantaspase, cyclophosphamide, cyclosporine, cytarabine, cytochalasin B, dacarbazine, dactinomycin, darbepoetin alfa, dasatinib, daunorubicin, 1-dehydrotestosterone, denileukin, dexamethasone, dexrazoxane, dihydroxy anthracin dione, disulfiram, docetaxel, doxorubicin, emetine, epirubicin, erlotinib, epigallocatechin gallate, epoetin alfa, estramustine, ethidium bromide, etoposide, everolimus, filgrastim, finasunate, floxuridine, fludarabine, flurouracil (5-FU), fulvestrant, ganciclovir, geldanamycin, gemcitabine, glucocorticoids, gramicidin D, histrelin acetate, hydroxyurea, ibritumomab, idarubicin, ifosfamide, imatinib, irinotecan, interferons, interferon alfa-2a, interferon alfa-2b, ixabepilone, lactate dehydrogenase A (LDH-A), lenalidomide, letrozole, leucovorin, levamisole, lidocaine, lomustine, mechlorethamine, melphalan, 6-mercaptopurine, mesna, methotrexate, methoxsalen, metoprine, metronidazole, mithramycin, mitomycin-C, mitoxantrone, nandrolone, nelarabine, nilotinib, nofetumomab, oprelvekin, oxaliplatin, paclitaxel, pemetrexed, pentostatin, palifermin, pamidronate, pegademase, pegaspargase, pegfilgrastim, pemetrexed disodium, plicamycin, porfimer sodium, procaine, procarbazine, propranolol, puromycin, quinacrine, radicicol, radioactive isotopes, raltitrexed, rapamycin, rasburicase, salinosporamide A, sargramostim, sunitinib, temozolomide, teniposide, tetracaine, 6-thioguanine, thiotepa, topotecan, toremifene, trastuzumab, treosulfan, tretinoin, valrubicin, vinblastine, vincristine, vindesine, vinorelbine, zoledronate, or a combination thereof.

The antimetabolites may be, e.g., methotrexate, 6-mercaptopurine, 6-thioguanine, cytarabine, 5-fluorouracil decarbazine, cladribine, pemetrexed, gemcitabine, capecitabine, hydroxyurea, mercaptopurine, fludarabine, pralatrexate, clofarabine, cytarabine, decitabine, floxuridine, nelarabine, trimetrexate, thioguanine, pentostatin, or a combination thereof.

The alkylating agent may be, e.g., mechlorethamine, thiotepa, chlorambucil, melphalan, carmustine (BSNU), lomustine (CCNU), cyclothosphamide, busulfan, dibromomannitol, streptozotocin, mitomycin C, cis-dichlorodiamine platinum (II) (DDP) cisplatin, altretamine, cyclophosphamide, ifosfamide, hexamethylmelamine, altretamine, procarbazine, dacarbazine, temozolomide, streptozocin, carboplatin, cisplatin, oxaliplatin, uramustine, bendamustine, trabectedin, semustine, or a combination thereof.

The anthracycline may be, e.g., daunorubicin, doxorubicin, aclarubicin, aldoxorubicin, amrubicin, annamycin, carubicin, epirubicin, idarubicin, mitoxantrone, valrubicin, or a combination thereof.

The antibiotic may be, e.g., dactinomycin, bleomycin, mithramycin, anthramycin (AMC), ampicillin, bacampicillin, carbenicillin, cloxacillin, dicloxacillin, flucloxacillin, mezlocillin, nafcillin, oxacillin, piperacillin, pivampicillin, pivmecillinam, ticarcillin, aztreonam, imipenem, doripenem, ertapenem, meropenem, cephalosporins, clarithromycin, dirithromycin, roxithromycin, telithromycin, lincomycin, pristinamycin, quinupristin, amikacin, gentamicin, kanamycin, neomycin, netilmicin, paromomycin, tobramycin, streptomycin, sulfamethizole, sulfamethoxazole, sulfisoxazole, demeclocycline, minocycline, oxytetracycline, tetracycline, penicillin, amoxicillin, cephalexin, erythromycin, clarithromycin, azithromycin, ciprofloxacin, levofloxacin, ofloxacin, doxycycline, clindamycin, metronidazole, tigecycline, chloramphenicol, metronidazole, tinidazole, nitrofurantoin, vancomycin, teicoplanin, telavancin, linezolid, cycloserine, rifamycins, polymyxin B, bacitracin, viomycin, capreomycin, quinolones, daunorubicin, doxorubicin, 4'-deoxydoxorubicin, epirubicin, idarubicin, plicamycin, mitomycin-c, mitoxantrone, or a combination thereof.

The anti-mitotic agent may be, e.g., vincristine, vinblastine, vinorelbine, docetaxel, estramustine, ixabepilone, paclitaxel, maytansinoid, a dolastatin, a cryptophycin, or a combination thereof.

The signal transduction inhibitor may be, e.g., imatinib, trastuzumab, erlotinib, sorafenib, sunitinib, temsirolimus, vemurafenib, lapatinib, bortezomib, cetuximab panitumumab, matuzumab, gefitinib, STI 571, rapamycin, flavopiridol, imatinib mesylate, vatalanib, semaxinib, motesanib, axitinib, afatinib, bosutinib, crizotinib, cabozantinib, dasatinib, entrectinib, pazopanib, lapatinib, vandetanib, or a combination thereof.

The gene expression modulator may be, e.g., a siRNA, a shRNA, an antisense oligonucleotide, an HDAC inhibitor, or a combination thereof. An HDAC inhibitor may be, e.g., trichostatin A, trapoxin B, valproic acid, vorinostat, belinostat, LAQ824, panobinostat, entinostat, tacedinaline, mocetionstat, givinostat, resminostat, abexinostat, quisinostat, rocilinostat, practinostat, CHR-3996, butyric acid, phenylbutyric acid, 4SC202, romidepsin, sirtinol, cambinol, EX-527, nicotinamide, or a combination thereof. An antisense oligonucleotide may be, e.g., custirsen, apatorsen, AZD9150, trabadersen, EZN-2968, LErafAON-ETU, or a combination thereof. An siRNA may be, e.g., ALN-VSP, CALAA-01, Atu-027, SPC2996, or a combination thereof.

The hormone therapy may be, e.g., a luteinizing hormone-releasing hormone (LHRH) antagonist. The hormone therapy may be, e.g., firmagon, leuproline, goserelin, buserelin, flutamide, bicalutadmide, ketoconazole, aminoglutethimide, prednisone, hydroxyl-progesterone caproate, medroxy-progesterone acetate, megestrol acetate, diethylstil-bestrol, ethinyl estradiol, tamoxifen, testosterone propionate, fluoxymesterone, flutamide, raloxifene, droloxifene, iodoxyfene, 4-hydroxytamoxifen, trioxifene, keoxifene, LY117018, onapristone, toremifine citrate, megestrol acetate, exemestane, fadrozole, vorozole, letrozole, anastrozole, nilutamide, tripterelin, histerelin, arbiraterone, medroxyprogesterone acetate, diethylstilbestrol, premarin, fluoxymesterone, tretinoin, fenretinide, troxacitabine, or a combination thereof.

The apoptosis inducers may be, e.g., a recombinant human TNF-related apoptosis-inducing ligand (TRAIL), camptothecin, bortezomib, etoposide, tamoxifen, or a combination thereof.

The angiogenesis inhibitors may be, e.g., sorafenib, sunitinib, pazopanib, everolimus or a combination thereof.

The immunotherapy agent may be, e.g., a monoclonal antibody, cancer vaccine (e.g., a dendritic cell (DC) vaccine), oncolytic virus, cytokine, adoptive T cell therapy, Bacille Calmette-Guerin (BCG), GM-CSF, thalidomide, lenalidomide, pomalidomide, imiquimod, or a combination thereof. The monoclonal antibody may be, e.g., anti-CTLA4, anti-PD1, anti-PD-L1, anti-LAG3, anti-KIR, or a combination thereof. The monoclonal antibody may be, e.g., alemtuzumab, trastuzumab, ibritumomab tiuxetan, brentuximab vedotin, trastuzumab, ado-trastuzumab emtansine, blinatumomab, bevacizumab, cetuximab, pertuzumab, panitumumab, ramucirumab, obinutuzumab, ofatumumab, rituximab, pertuzumab, tositumomab, gemtuzumab ozogamicin, tositumomab, or a combination thereof. The cancer vaccine may be, e.g., Sipuleucel-T, BioVaxID, NeuVax, DCVax, SuVaxM, CIMAvax®, Provenge,®, hsp110 chaperone complex vaccine, CDX-1401, MIS416, CDX-110, GVAX Pancreas, HyperAcute™ Pancreas, GTOP-99 (My- Vax®), or Imprime PGG®. The oncolytic virus may be, e.g., talimogene laherparepvec. The cytokine may be, e.g., IL-2, IFNα, or a combination thereof. The adoptive T cell therapy may be, e.g., tisagenlecleucel, axicabtagene ciloleucel, or a combination thereof.

The DNA damage repair inhibitor may be, e.g., a PARP inhibitor, a cell checkpoint kinase inhibitor, or a combination thereof. The PARP inhibitor may be, e.g., olaparib, rucaparib, veliparib (ABT-888), niraparib (ZL-2306), iniparib (BSI-201), talazoparib (BMN 673), 2X-121, CEP-9722, KU-0059436 (AZD2281), PF-01367338 or a combination thereof. The cell checkpoint kinase inhibitor may be, e.g., MK-1775 or AZD1775, AZD7762, LY2606368, PF-0477736, AZD0156, GDC-0575, ARRY-575, CCT245737, PNT-737 or a combination thereof.

EXAMPLES

The following examples are meant to illustrate the invention. They are not meant to limit the invention in any way.

Example 1. Preparation of Compounds

Compound 1

Step 1. A suspension of 4-chloro-7-azaindole (25 g) in DMA (140 mL) was purged with vacuum/$N_2$ gas (3 cycles). Zinc powder (1.07 g), zinc cyanide (11.26 g), dppf (2.72 g) and $Pd_2(dba)_3$ (2.39 g) were then added. The mixture was purged again with vacuum/$N_2$ gas (3 cycles) and heated to 120° C. for 4 h. The reaction mixture was allowed to cool down to 100° C. and water (428 mL) was added over 30 min. The mixture was then cooled to rt over 2 h. The crude product was filtered and washed with water (2×95 mL), then added to 3 N HCl (150 mL) and the mixture was stirred at rt for 2 h. The insolubles were removed by filtration. To the filtrate was added 50% aq. NaOH until pH 12 was reached. Filtration and drying afforded 1H-pyrrolo[2,3-b]pyridine-4-carbonitrile (11.6 g) as a tan solid.

Step 2. A mixture of 1H-pyrrolo[2,3-b]pyridine-4-carbonitrile (10.4 g) and NaOH (29 g) in water (100 mL) and EtOH (100 mL) was heated to reflux for 18 h. Upon cooling to rt, the mixture was treated with concentrated HCl to pH 2. The solids were collected by filtration and dried under high vacuum to afford 1H-pyrrolo[2,3-b]pyridine-4-carboxylic acid (11.8 g) as a tan solid.

Step 3. To EtOH (120 mL) at 0° C. was added dropwise thionyl chloride (12.4 mL). and the mixture was allowed to stir at rt for 30 min, 1H-pyrrolo[2,3-b]pyridine-4-carboxylic acid (12.0 g) was then added and the reaction mixture was heated to reflux for 8 h. Upon cooling to rt, solvents were removed under reduced pressure. The residue thus obtained was suspended in water (150 mL), pH was adjusted to pH 9 with aq. sat. $K_2CO_3$. The mixture was extracted with EtOAc (2×150 mL). The combined extracts were washed with brine, dried over $MgSO_4$, filtered and concentrated to dryness to afford ethyl 1H-pyrrolo[2,3-b]pyridine-4-carboxylate (10.5 g) as a tan solid.

Step 4. To a mixture of ethyl 1H-pyrrolo[2,3-b]pyridine-4-carboxylate (9.5 g) in EtOAc (95 mL) at 0° C. was added mCPBA (15.5 g) portionwise. The reaction mixture was allowed to warm to rt and stirred for 3 h. The precipitate was filtered, washed with EtOAc (3×30 mL) and the residue was dried under high vacuum to afford 4-(ethoxycarbonyl)-1H-pyrrolo[2,3-b]pyridine 7-oxide (8.8 g) as a light yellow solid.

Step 5. To a solution of 4-(ethoxycarbonyl)-1H-pyrrolo[2,3-b]pyridine 7-oxide (25.5 g) in DMF (250 mL) was added dropwise methanesulfonyl chloride (11.5 mL). The mixture was then heated to 80° C. for 1 h, then was cooled to rt and additional methanesulfonyl chloride (11.5 mL) was added. The mixture was heated again at 80° C. for 1 h. Upon cooling to 0° C., the reaction mixture was poured into ice-water (480 mL) with vigorous stirring. Then the mixture was allowed to stir at 0° C. for 2 h. The precipitate was filtered and washed with water (3×200 mL). The residue was dried under high vacuum to afford ethyl 6-chloro-1H-pyrrolo[2,3-b]pyridine-4-carboxylate (25.0 g) as a beige solid which was used in the subsequent step without further purification.

Step 6. To a solution of ethyl 6-chloro-1H-pyrrolo[2,3-b]pyridine-4-carboxylate (25 g) in DMF (250 mL) at 0° C. was added NaH (6.68 g) over 45 min followed by stirring at 0° C. for 1 h. SEM-CI (23.6 mL) was added over 20 min and the mixture was allowed to stir at 0° C. for 1 h. Water (300 mL) was slowly added and the mixture was extracted with EtOAc (2×200 mL) then washed with brine, dried over $MgSO_4$, filtered and concentrated to dryness. The residue was purified by flash chromatography on silica gel (15-30% EtOAc/hexanes) to afford ethyl 6-chloro-1-((2-(trimethylsilyl)ethoxy)methyl)-1H-pyrrolo[2,3-b]pyridine-4-carboxylate (32.4 g) as an orange oil.

Step 7. To a solution of ethyl 6-chloro-1-((2-(trimethylsilyl)ethoxy)methyl)-1H-pyrrolo[2,3-b]pyridine-4-carboxylate (32.3 g) in toluene (150 mL) were added (R)-3-methylmorpholine (12.4 mL), BINAP (3.4 g) and cesium carbonate (89 g). The mixture was degassed (3 cycles of vacuum/argon) and palladium acetate (1.0 g) was added and the reaction mixture was degassed again, then heated to 120° C. for 4 h. Upon cooling to rt, the mixture was diluted with EtOAc (500 mL), filtered through a pad of diatomaceous earth and washed with EtOAc (2×250 mL). The filtrate was concentrated to dryness under reduced pressure and purified by silica gel chromatography (0-40% EtOAc/hexanes) to afford ethyl (R)-6-(3-methylmorpholino)-1-((2-(trimethylsilyl)ethoxy)methyl)-1H-pyrrolo[2,3-b]pyridine-4-carboxylate (26 g) as a yellow oil.

Step 8. To a solution of ethyl (R)-6-(3-methylmorpholino)-1-((2-(trimethylsilyl)ethoxy)methyl)-1H-pyrrolo[2,3-b]pyridine-4-carboxylate (4.9 g) in THF (80 mL) was added MeOH (0.048 mL). The reaction mixture was heated to 65° C. then a solution of 2 M $LiBH_4$ in THF (9 mL) was added dropwise over 1 h. The reaction mixture was stirred at 65° C. for 18 h. Upon cooling to rt, acetone (2 mL) was added and stirred at rt for 30 min. The mixture was diluted with 1:1 aq. sat. $NH_4Cl$/water (100 mL) and extracted with EtOAc (2×100 mL). The combined organic extracts were washed with brine, dried over $MgSO_4$, filtered and concentrated to dryness. The residue was purified by silica gel chromatography (5-50% EtOAc/hexanes) to afford (R)-(6-(3-methylmorpholino)-1-((2-(trimethylsilyl)ethoxy)methyl)-1H-pyrrolo[2,3-b] pyridin-4-yl)methanol (3.9 g) as a yellow gum.

Step 9. To a solution of (R)-(6-(3-methylmorpholino)-1-((2-(trimethylsilyl)ethoxy)methyl)-1H-pyrrolo[2,3-b]pyridin-4-yl)methanol (7.5 g) in dichloromethane (70 mL) at 0° C. was added triethylamine (2.8 mL), followed by methanesulfonyl chloride (1.55 mL). The reaction mixture was stirred at rt for 90 min then diluted with dichloromethane (100 mL) and water (100 mL). The layers were partitioned, the aqueous layer was extracted with dichloromethane (100 mL). The combined organic extracts were washed with brine, dried over $MgSO_4$, filtered and concentrated to dryness to afford (R)-(6-(3-methylmorpholino)-1-((2-(trimethylsilyl)ethoxy)methyl)-1H-pyrrolo[2,3-b]pyridin-4-yl)

methyl methanesulfonate (9 g) as a yellow gum which was used in the subsequent step without further purification.

Step 10. To a solution of (R)-(6-(3-methylmorpholino)-1-((2-(trimethylsilyl)ethoxy)methyl)-1H-pyrrolo[2,3-b]pyridin-4-yl)methyl methanesulfonate (9 g) in dioxane (80 mL) was added LiI (5.3 g). The mixture was heated to 100° C. for 2.5 h under argon. Upon cooling to rt, the mixture was diluted with EtOAc (100 mL) and water (100 mL). The layers were partitioned and the aqueous layer was extracted with EtOAc (80 mL). The combined organic extracts were washed with 2M sodium hydrogen sulfite (80 mL), water (80 mL), brine (80 mL), dried over $MgSO_4$, filtered and concentrated to afford (R)-4-(4-(iodomethyl)-1-((2-(trimethylsilyl)ethoxy)methyl)-1H-pyrrolo[2,3-b]pyridin-6-yl)-3-methylmorpholine (9.6 g) as a dark oil which was used as such in the subsequent step without further purification.

Step 11. To a solution of (R)-4-(4-(iodomethyl)-1-((2-(trimethylsilyl)ethoxy)methyl)-1H-pyrrolo[2,3-b]pyridin-6-yl)-3-methylmorpholine (9.6 g) in DMF (80 mL) was added sodium methanesulfinate (2.4 g). The reaction mixture was stirred at rt for 18 h. The reaction mixture was EtOAc (100 mL) and water (100 mL), the layers were partitioned and the aqueous layer was extracted with EtOAc (80 mL). The combined organic extracts were washed with aqueous sodium thiosulfate (80 mL), water (80 mL) and brine, dried over $MgSO_4$, filtered and concentrated. The residue was purified by silica gel chromatography (10-90% EtOAc/hexanes) to afford (R)-3-methyl-4-(4-((methylsulfonyl)methyl)-1-((2-(trimethylsilyl)ethoxy)methyl)-1H-pyrrolo[2,3-b]pyridin-6-yl)morpholine (7.5 g) as a grey green gum.

Step 12. To a solution of (R)-3-methyl-4-(4-((methylsulfonyl)methyl)-1-((2-(trimethylsilyl)ethoxy)methyl)-1H-pyrrolo[2,3-b]pyridin-6-yl)morpholine (7.5 g) in toluene (80 mL) were added TBAB (1 g) and 50% NaOH (36 mL), followed by 1,2-dibromoethane (2 mL). The mixture was heated to 65° C. for 18 h. Additional 1,2-dibromoethane (16 mL) was then added by syringe pump over 18 h while the mixture was stirred at 65° C. The reaction mixture was aged at 65° C. for an additional 18 h then cooled to rt. The mixture was diluted with EtOAc (200 mL) and water (150 mL), the layers were partitioned and the aqueous layer was extracted with EtOAc (100 mL). The combined organic extracts were washed with brine, dried over $MgSO_4$, filtered and concentrated to dryness under reduced pressure. The residue was purified by silica gel chromatography (10-80% EtOAc/hexanes) to afford (R)-3-methyl-4-(4-(1-(methylsulfonyl)cyclopropyl)-1-((2-(trimethylsilyl)ethoxy)methyl)-1H-pyrrolo[2,3-b]pyridin-6-yl)morpholine (5.4 g) as a yellow foam.

Step 13. To a solution of (R)-3-methyl-4-(4-(1-(methylsulfonyl)cyclopropyl)-1-((2-(trimethylsilyl)ethoxy)methyl)-1H-pyrrolo[2,3-b]pyridin-6-yl)morpholine (5.4 g) in dichloromethane (50 mL) at 0° C. was added TFA (18 mL). The reaction mixture was warmed to rt and stirred for 18 h. Toluene (40 mL) was added and the mixture was concentrated. The residue was diluted with dioxane (40 mL) and the pH of the mixture was adjusted to pH 10 by addition of 3N NaOH. The mixture was heated to 80° C. for 3 h then cooled to rt. The mixture was diluted with EtOAc (150 mL) and water (150 mL). The layers were partitioned and the aqueous layer was extracted with EtOAc (100 mL). The combined organic extracts were washed with brine, dried over $MgSO_4$, filtered and concentrated to dryness. The residue was purified by silica gel chromatography (30-100% EtOAc/hexanes) to afford (R)-3-methyl-4-(4-(1-(methylsulfonyl)cyclopropyl)-1H-pyrrolo[2,3-b]pyridin-6-yl)morpholine (1.65 g) as a light yellow foam.

Step 14. To a solution of 3-iodo-1H-pyrazole (2.5 g) in DMF (25 mL) at 0° C. was added cesium carbonate (9.43 g). Then SEM-Cl (2.8 mL) was added over 15 min. The mixture was allowed to stir at rt for 18 h. Water (60 mL) was slowly added and the mixture was partitioned with $Et_2O$ (60 mL). The aqueous layer was extracted with $Et_2O$ (30 mL) and the combined organic extracts were washed with water (3×50 mL), brine, dried over $MgSO_4$, filtered and concentrated to dryness. The residue was purified by silica gel chromatography (0-30% EtOAc/hexanes) to afford 3-iodo-1-((2-(trimethylsilyl)ethoxy)methyl)-1H-pyrazole (3.3 g) as a colorless liquid. 1H-NMR showed 1:1 ratio of two regioisomers.

Step 15. To (R)-3-methyl-4-(4-(1-(methylsulfonyl)cyclopropyl)-1H-pyrrolo[2,3-b]pyridin-6-yl)morpholine (100 mg), 3-iodo-1-((2-(trimethylsilyl)ethoxy)methyl)-1H-pyrazole (145 mg), cesium carbonate (244 mg) and L-proline (21 mg) in a microwave vessel was added NMP (1 mL) followed by CuBr (20 mg). The vessel was capped and degassed (3 cycles vacuum/argon), then heated to 150° C. for 4 h. Upon cooling to rt, the reaction mixture was quenched with 20 mL of $NH_4Cl:H_2O:NH_4OH$ (4:3:1) and EtOAc (15 mL), filtered through diatomaceous earth and extracted with ethyl acetate (2×150 mL). The combined organic extracts were washed with brine, dried over $MgSO_4$, filtered and concentrated to dryness. The residue was purified by silica gel chromatography (20-100% EtOAc/hexanes) to afford (R)-3-methyl-4-(4-(1-(methylsulfonyl)cyclopropyl)-1-(1-((2-(trimethylsilyl)ethoxy)methyl)-1H-pyrazol-3-yl)-1H-pyrrolo[2,3-b]pyridin-6-yl)morpholine (25 mg) as a mixture of regioisomers.

Step 16. To a solution of (R)-3-methyl-4-(4-(1-(methylsulfonyl)cyclopropyl)-1-(1-((2-(trimethylsilyl)ethoxy)methyl)-1H-pyrazol-3-yl)-1H-pyrrolo[2,3-b]pyridin-6-yl)morpholine (25 mg) in dichloromethane (1 mL) was added TFA (0.2 mL). The reaction mixture was stirred at rt for 18 h. Toluene (10 mL) was added and the volatiles were removed under reduced pressure. The residue was dissolved in dioxane (3 mL) and aqueous saturated $NaHCO_3$ (3 mL), the mixture was heated to 65° C. for 18 h, then 80° C. for 18 h. Upon cooling to rt, the mixture was extracted with dichloromethane (2×15 mL). The combined organic extracts were washed with brine, dried over $MgSO_4$, filtered and concentrated to dryness. The residue was purified by silica gel chromatography (20-100% EtOAc/hexanes) to provide the desired product. The residue was suspended in $CH_3CN$ (1 mL) and water (1 mL) and lyophilized to afford (R)-3-methyl-4-(4-(1-(methylsulfonyl)cyclopropyl)-1-(1H-pyrazol-3-yl)-1H-pyrrolo[2,3-b]pyridin-6-yl)morpholine (15 mg) as a light yellow foam. $^1$H NMR (400 MHz, $CDCl_3$): δ 7.66 (d; J=3.74 Hz; 1H); 7.62 (d; J=2.36 Hz; 1H); 6.98 (s; 1H); 6.78 (s; 1H); 6.59 (d; J=3.76 Hz; 1H); 4.32-4.37 (m; 1H); 4.05-4.09 (m; 1H); 3.87-3.91 (m; 1H); 3.83-3.84 (m; 2H); 3.64-3.71 (m; 1H); 3.28-3.35 (m; 1H); 2.83 (s; 3H); 1.93-1.96 (m; 2H); 1.39-1.42 (m; 2H); 1.29 (d; J=6.71 Hz; 3H). MS: [M+1]: 402.2.

Intermediate A

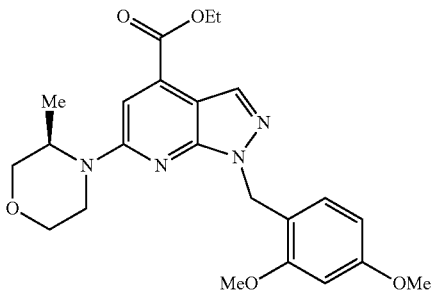 [SMILES: CCOC(=O)c1cc(N2CCOC[C@H]2C)nc2c1cnn2Cc1ccc(OC)cc1OC]

Step 1. To a cold (0° C.) solution of acrylonitrile (12.4 mL) in THF (75 mL) was added hydrazine monohydrate (8.7 mL) dropwise over 30 min to keep the internal temperature below 10° C. The resulting mixture was stirred for 30 min in an ice bath, then warmed to rt for 3 h. The mixture was cooled again in an ice bath and 2,4-dimethoxybenzaldehyde (31 g) was added over 10 mins. The resulting mixture was stirred for 25 min in an ice bath, warmed to rt for 1 h, then concentrated in vacuo and placed under high vacuum overnight with stirring to remove water.

The resulting residue was dissolved in n-BuOH (70 mL) and treated with NaOMe (20.4 g) giving dark coloration and an exotherm. The mixture was heated to reflux for 1 h, cooled to room temperature and poured into brine. EtOAc was added and the organic layer was separated, washed with brine, dried over $MgSO_4$, filtered through a diatomaceous earth pad and concentrated in vacuo. The material was placed under high vacuum to remove residual n-BuOH. The procedure was repeated on the same scale and the combined materials were purified on silica gel eluting with 1:1 EtOAc/hexanes to provide 35 g of 1-(2,4-dimethoxybenzyl)-1H-pyrazol-5-amine.

Step 2. To a solution of 1-(2,4-dimethoxybenzyl)-1H-pyrazol-5-amine (14 g) in AcOH (140 mL) was added diethyl oxalacetate sodium salt (16.1 g). The resulting suspension was a placed in an oil bath and heated to reflux for 2 hrs. The reaction was cooled in an ice bath, then was added slowly via dropping funnel to 440 mL of cold water with rapid stirring. The resulting suspension was stirred for 2 hours, filtered, rinsed with water and air-dried overnight to give 19.2 g of ethyl 1-(2,4-dimethoxybenzyl)-6-hydroxy-1H-pyrazolo[3,4-b]pyridine-4-carboxylate as a yellow solid.

Step 3. To a suspension of ethyl 1-(2,4-dimethoxybenzyl)-6-hydroxy-1H-pyrazolo[3,4-b]pyridine-4-carboxylate (11.0 g) in acetonitrile (100 mL) at 0° C. was added pyridine (1.8 mL) followed by addition of triflic anhydride (3.8 mL) at such rate that the internal temperature was maintained below 5° C. The reaction mixture was allowed to warm to room temperature over 1 h, was quenched with water (100 mL) and extracted with dichloromethane (2×100 mL). The combined organic extracts were washed with brine, dried over $MgSO_4$, filtered and concentrated to dryness under reduced pressure to afford 10 g of ethyl 1-(2,4-dimethoxybenzyl)-6-(((trifluoromethyl)sulfonyl)oxy)-1H-pyrazolo[3,4-b]pyridine-4-carboxylate as a yellow solid which was used in the subsequent step without further purification.

Step 4. To a solution of crude ethyl 1-(2,4-dimethoxybenzyl)-6-(((trifluoromethyl)sulfonyl)oxy)-1H-pyrazolo[3,4-b]pyridine-4-carboxylate (10 g) in DMF (100 mL) at 0° C. was added (R)-3-methylmorpholine (6.8 g) and pyridine (2.0 mL). The reaction mixture was stirred at room temperature for 5 days, then diluted with water (100 mL) and EtOAc (120 mL). The layers were partitioned and the aq. layer was extracted with EtOAc (100 mL). The combined organic extracts were washed with brine, dried over $MgSO_4$, filtered, and concentrated to dryness in vacuo. The residue was purified by ISCO CombiFlash (120 g column) eluting with 10-100% EtOAc/hexanes to afford 5.8 g of ethyl (R)-6-(3-methylmorpholino)-1H-pyrazolo[3,4-b]pyridine-4-carboxylate (Intermediate A) as a yellow gum. LCMS (+ESI): m/z=441.1 [M+H]+.

Compound 2

Step 1. To a solution of Intermediate A (400 mg) in THF (4 mL) at −78° C. was added MeMgBr (3M/$Et_2O$, 1 mL) and the reaction mixture was allowed to warm to room temperature. The reaction mixture was quenched with cooled aq. saturated $NH_4Cl$ and extracted with EtOAc (2×30 mL). The combined organic layers were washed with brine, dried over $MgSO_4$, filtered and concentrated to dryness under reduced pressure. The residue was purified by ISCO CombiFlash (40 g column) eluting with 10-100% EtOAc/hexanes to afford 380 mg of (R)-2-(1-(2,4-dimethoxybenzyl)-6-(3-methylmorpholino)-1H-pyrazolo[3,4-b]pyridin-4-yl)propan-2-ol as a yellow oil.

Step 2. To a solution of (R)-2-(1-(2,4-dimethoxybenzyl)-6-(3-methylmorpholino)-1H-pyrazolo[3,4-b]pyridin-4-yl)propan-2-ol (380 mg) in dichloromethane (4 mL) at room temperature was added TFA (1.36 mL) and the solution was stirred at for 18 h. The volatiles were removed under reduced pressure and the residue was suspended in EtOAc (30 mL) and washed with sat. aq. $NaHCO_3$. The aqueous layer was extracted with EtOAc (20 mL) and the combined organic layers were washed with brine, dried over $MgSO_4$, filtered and concentrated to dryness under reduced pressure to afford 160 mg of (R)-2-(6-(3-methylmorpholino)-1H-pyrazolo[3,4-b]pyridin-4-yl)propan-2-ol.

Step 3. A microwave tube was charged with (R)-2-(6-(3-methylmorpholino)-1H-pyrazolo[3,4-b]pyridin-4-yl)propan-2-ol (160 mg), SEM-protected 3-iodopyrazole (376 mg), $Cs_2CO_3$ (475 mg), L-proline (13 mg), CuBr (13 mg) and NMP (3 mL). Then the vessel was capped and degassed (3 cycles vacuum/argon), heated to 150° C. for 18 h. Upon cooling to room temperature, the reaction mixture was diluted with EtOAc (50 mL) then purified by ISCO CombiFlash (24 g column) eluting with 10-100% EtOAc/hexanes to afford 100 mg of (R)-2-(6-(3-methylmorpholino)-1-(1-((2-(trimethylsilyl)ethoxy)methyl)-1H-pyrazol-3-yl)-1H-pyrazolo[3,4-b]pyridin-4-yl)propan-2-ol as yellow gum. 1H-NMR and LCMS showed two regioisomers of SEM N-protected pyrazole.

Step 4. To a solution of (R)-2-(6-(3-methylmorpholino)-1-(1-((2-(trimethylsilyl)ethoxy)methyl)-1H-pyrazol-3-yl)-1H-pyrazolo[3,4-b]pyridin-4-yl)propan-2-ol (100 mg) in dichloromethane (1 mL) at room temperature was added TFA (0.211 mL) and the reaction mixture was stirred for 18 h. Toluene (10 mL) was added and the volatiles were removed under reduced pressure. The flask was put under high vacuum to remove residual TFA. The residue was diluted in dioxane (3 mL) and 1N NaOH (1 mL) was added. The reaction mixture was heated to reflux for 3 h, cooled to room temperature, then diluted with EtOAc (20 mL) and water (20 mL). The layers were partitioned and the aqueous layer was extracted with EtOAc (10 mL). The combined organic layers were washed with brine, dried over $MgSO_4$, filtered and concentrated to dryness under reduced pressure. The residue was adsorbed in silica gel for purification by ISCO CombiFlash (12 g column) eluting with 40-100% EtOAc/hexanes. The desired product fractions were combined and concentrated to dryness. The residue was diluted in $CH_3CN$ (1 mL) and water (1 mL) for lyophilization to afford 22 mg of (R)-2-(6-(3-methylmorpholino)-1-(1H-pyrazol-3-yl)-1H-pyrazolo[3,4-b]pyridin-4-yl)propan-2-ol the desired product as a colorless foam. Purity by HPLC at 254 nm: 93.0%, $^1$H NMR (400 MHz, CDCl$_3$): δ 8.12 (s; 1H); 7.63 (d; J=2.10 Hz; 1H); 6.83 (s; 1H); 6.72 (s; 1H); 4.45-4.49 (m; 1H); 4.02-4.09 (m; 2H); 3.77-3.86 (m; 3H); 3.66 (td; J=11.90; 3.16 Hz; 1H); 3.39 (td; J=12.73; 3.87 Hz; 1H); 1.73 (s; 6H); 1.35 (d; J=6.74 Hz; 3H).

Compound 3

Step 1. To a solution of Intermediate A (3.4 g) in THF (35 mL) was added MeOH (0.062 mL). The reaction mixture was heated to 65° C. then a solution of 2 M LiBH$_4$ in THF (5.8 mL) was added dropwise over 1 h. The reaction mixture was stirred at 65° C. for 4 h then cooled to room temperature. Acetone (1 mL) was added and stirred at room temperature for 30 min. The mixture was diluted with 1:1 aq. sat. NH$_4$Cl/water (80 mL) and EtOAc (80 mL). The layers were partitioned and the aq. layer was extracted with EtOAc (40 mL). The combined organic extracts were washed with brine, dried over MgSO$_4$, filtered and concentrated to dryness under reduced pressure. The residue was purified by ISCO CombiFlash (80 g column) eluting with 30-100% EtOAc/hexanes to afford (R)-(1-(2,4-dimethoxybenzyl)-6-(3-methylmorpholino)-1H-pyrazolo[3,4-b]pyridin-4-yl)methanol and (R)-(1-(2,4-dimethoxybenzyl)-6-(3-methylmorpholino)-2H-pyrazolo[3,4-b]pyridin-4-yl)methanol as colourless foams (separable mixture of positional isomers).

Step 2. To a solution of (R)-(1-(2,4-dimethoxybenzyl)-6-(3-methylmorpholino)-2H-pyrazolo[3,4-b]pyridin-4-yl)methanol (600 mg) in dichloromethane (7 mL) at 0° C. was added triethylamine (0.141 mL), followed by methanesulfonyl chloride (0.254 mL). The reaction mixture was stirred at room temperature for 90 min then diluted with dichloromethane (40 mL) and water (40 mL). The layers were partitioned, the aq. layer was extracted with dichloromethane (30 mL) and the combined organic extracts were washed with brine, dried over MgSO$_4$, filtered and concentrated to dryness to afford 700 mg of (R)-(1-(2,4-dimethoxybenzyl)-6-(3-methylmorpholino)-2H-pyrazolo[3,4-b]pyridin-4-yl)methyl methanesulfonate which was used in the subsequent step without further purification.

Step 3. To a solution of (R)-(1-(2,4-dimethoxybenzyl)-6-(3-methylmorpholino)-2H-pyrazolo[3,4-b]pyridin-4-yl)methyl methanesulfonate (700 mg) in dioxane (7 mL) was added LiI (393 mg). The mixture was heated to 50° C. for 2.5 h under argon. Upon cooling to room temperature, the mixture was diluted with EtOAc (50 mL) and water (50 mL). The layers were partitioned and the aq. layer was extracted with EtOAc (30 mL). The combined organic extracts were washed with 2M sodium hydrogen sulfite (50 mL), water (50 mL) and brine (50 mL) then dried over MgSO$_4$, filtered and concentrated to dryness under reduced pressure to afford 760 mg of (R)-4-(2-(2,4-dimethoxybenzyl)-4-(iodomethyl)-2H-pyrazolo[3,4-b]pyridin-6-yl)-3-methylmorpholine which was used as such in the subsequent step without further purification.

Step 4. To a solution of (R)-4-(2-(2,4-dimethoxybenzyl)-4-(iodomethyl)-2H-pyrazolo[3,4-b]pyridin-6-yl)-3-methylmorpholine (790 mg) in DMF (8 mL) was added sodium methanesulfinate (190 mg). The reaction mixture was stirred at room temperature for 2 h then diluted with EtOAc (40 mL) and water (40 mL). The layers were partitioned and the aq. layer was extracted with EtOAc (30 mL). The combined organic extracts were washed with aq. sodium thiosulfate (50 mL), water (50 mL) and brine, then dried over MgSO$_4$, filtered and concentrated to dryness under reduced pressure. The residue was adsorbed on silica gel for purification by Isco CombiFlash (40 g column) eluting with 30-100% EtOAc/hexanes to afford 640 mg of (R)-4-(2-(2,4-dimethoxybenzyl)-4-((methylsulfonyl)methyl)-2H-pyrazolo[3,4-b]pyridin-6-yl)-3-methylmorpholine as a colorless foam.

Step 5: To a solution of (R)-4-(1-(2,4-dimethoxybenzyl)-4-((methylsulfonyl)methyl)-2H-pyrazolo[3,4-b]pyridin-6-yl)-3-methylmorpholine (640 mg) in toluene (3 mL) was added TBAB (45 mg) and 1,2-dibromoethane (0.156 mL) followed by 50% NaOH (2.9 mL). The reaction mixture was heated to 60° C. for 2 h. Additional 1,2-dibromoethane (0.5 mL) was added, the mixture was heated again at 60° C. for 18 h. Upon cooling to rt, the mixture was diluted with EtOAc (30 mL) and water (25 mL), the layers were partitioned and the aq. layer was extracted with EtOAc (20 mL). The combined organic extracts were washed with brine, dried over MgSO$_4$, filtered and concentrated to dryness under reduced pressure. The residue was adsorbed in silica gel for purification by ISCO CombiFlash (24 g column) eluting with 30-100% EtOAc/hexanes to afford 510 mg of (R)-4-(1-(2,4-dimethoxybenzyl)-4-(1-methylsulfonyl)cyclopropyl)-2H-pyrazolo[3,4-b]pyridin-6-yl)-3-methylmorpholine as a light yellow foam.

Step 6. (R)-3-methyl-4-(4-(1-(methylsulfonyl)cyclopropyl)-1H-pyrazolo[3,4-b]pyridin-6-yl)morpholine: To a solution of (R)-4-(1-(2,4-dimethoxybenzyl)-4-(1-(methylsulfonyl)cyclopropyl)-2H-pyrazolo[3,4-b]pyridin-6-yl)-3-methylmorpholine (510 mg) in dichloromethane (5 mL) at 0° C. was added TFA (1.6 mL). The reaction mixture was allowed to warm to room temperature and stirred at for 5 h. Toluene (10 mL) was added to the reaction mixture and the volatiles were removed in vacuo then co-evaporated with toluene (10 mL). The residue was dissolved in EtOAc (50 mL) and aqueous saturated NaHCO$_3$ (40 mL) with vigorous stirring. The layers were partitioned and the aqueous layer was extracted with EtOAc (30 mL). The combined extracts were washed with brine, dried over MgSO$_4$, filtered and concentrated to dryness in vacuo to afford 350 mg of (R)-3-methyl-4-(4-(1-(methylsulfonyl)cyclopropyl)-1H-pyrazolo[3,4-b]pyridin-6-yl)morpholine as a light yellow foam which was used in the next step without further purification.

Step 7. A microwave tube was charged with (R)-3-methyl-4-(4-(1-(methylsulfonyl)cyclopropyl)-1H-pyrazolo[3,4-b]pyridin-6-yl)morpholine (160 mg), pyrazole (310 mg), Cs$_2$CO$_3$ (390 mg), L-proline (11 mg), CuBr (11 mg) and NMP (2 mL). The vessel was capped and degassed (3 cycles vacuum/argon), then heated to 150° C. for 18 h. Upon cooling to room temperature, the reaction mixture was diluted with EtOAc (20 mL) and NH$_4$Cl:H$_2$O:NH$_4$OH (4:3:1, 20 mL), then filtered through diatomaceous earth. The layers were separated and the aqueous layer was extracted with EtOAc (20 mL). The combined organic layers were washed with brine, dried over MgSO$_4$, filtered and concentrated to dryness in vacuo. The residue was adsorbed on silica gel for purification by ISCO CombiFlash (24 g column) eluting with 20-100% EtOAc/Hexanes to provide (R)-3-methyl-4-(4-(1-(methylsulfonyl)cyclopropyl)-1-(1-((2-(trimethylsilyl)ethoxy)methyl)-1H-pyrazol-5-yl)-1H-pyrazolo[3,4-b]pyridin-6-yl)morpholine and the corresponding SEM-pyrazole regioisomer.

Step 8. To a solution of (R)-3-methyl-4-(4-(1-(methylsulfonyl)cyclopropyl)-1-(1-((2-(trimethylsilyl)ethoxy)methyl)-1H-pyrazol-5-yl)-1H-pyrazolo[3,4-b]pyridin-6-yl)morpholine (37 mg) in dichloromethane (1 mL) was added TFA (0.319 mL) and the reaction mixture was stirred for 18 h. Toluene (10 mL) was added and the volatiles were removed under reduced pressure. The residue was dissolved in dioxane (3 mL) and aqueous saturated NaHCO$_3$ (3 mL), and the mixture was heated to 65° C. for 4 h then 80° C. for 18 h. Upon cooling to room temperature, the mixture was extracted with dichloromethane (2×15 mL) and the combined organic extracts were washed with brine, dried over MgSO$_4$, filtered and concentrated to dryness. The residue was purified by flash chromatography on silica gel eluting with EtOAc and 5% MeOH/EtOAc. The resulting residue was suspended in CH$_3$CN (2 mL) and water (2 mL) and lyophilized to afford 23 mg of (R)-3-methyl-4-(4-(1-(methylsulfonyl)cyclopropyl)-1-(1H-pyrazol-3-yl)-1H-pyrazolo[3,4-b]pyridin-6-yl)morpholine: as a light yellow foam. $^1$H NMR (400 MHz, CDCl$_3$): δ 8.11 (s; 1H); 7.70 (d; J=2.26 Hz; 1H); 6.93 (d; J=2.26 Hz; 1H); 6.84 (s; 1H); 4.41-4.43 (m; 1H); 4.06-4.09 (m; 2H); 3.77-3.87 (m; 2H); 3.61-3.68 (m; 1H); 3.33-3.40 (m; 1H); 2.85 (s; 3H); 1.97-2.00 (m; 2H); 1.41-1.44 (m; 2H); 1.35 (d; J=6.78 Hz; 3H). [M+1]: m/z 403.1.

Compound 4

Step 1. To a solution of Intermediate A (5.8 g, 13.167 mmol) in dichloromethane (60 mL) at 0° C. was added TFA (20 mL). The reaction mixture was warmed to room temperature and stirred for 18 h. Toluene (60 mL) was added, the volatiles were removed in vacuo and co-evaporated with toluene (20 mL). The residue was dissolved in dichloromethane (300 mL) then treated with aqueous saturated NaHCO$_3$ (200 mL) with vigorous stirring. The layers were separated and the aqueous layer was extracted with dichloromethane (150 mL). The combined extracts were washed with brine, dried over MgSO$_4$, filtered and concentrated to dryness in vacuo to afford 3.8 g of ethyl (R)-6-(3-methylmorpholino)-1H-pyrazolo[3,4-b]pyridine-4-carboxylate as a yellow solid which was used in the next step without further purification.

Step 2. A mixture of ethyl (R)-6-(3-methylmorpholino)-1H-pyrazolo[3,4-b]pyridine-4-carboxylate (3.8 g), pyrazole (6.37 g), Cs$_2$CO$_3$ (10.7 g), L-proline (300 mg), CuBr (292 mg) and NMP (40 mL) was degassed (3 cycles vacuum/argon), heated to 150° C. for 18 h. Upon cooling to room temperature, the reaction mixture was diluted 10% citric acid to adjust pH to 6-7 and EtOAc was added (350 mL). The mixture was filtered through diatomaceous earth and washed with EtOAc. The layers were partitioned and the aqueous layer was extracted with EtOAc (150 mL). The combined organic layers were washed with brine, dried over MgSO$_4$, filtered and concentrated to dryness in vacuo. The residue was purified by flash chromatography on silica gel eluting with 0-10% MeOH/dichloromethane to afford 3.6 g of (R)-6-(3-methylmorpholino)-1-(1-((2-(trimethylsilyl)ethoxy)methyl)-1H-pyrazol-3-yl)-1H-pyrazolo[3,4-b]pyridine-4-carboxylic acid and its SEM regioisomer as a yellow oil.

Step 3. To a solution of (R)-6-(3-methylmorpholino)-1-(1-((2-(trimethylsilyl)ethoxy)methyl)-1H-pyrazol-3-yl)-1H-pyrazolo[3,4-b]pyridine-4-carboxylicacid (3.6 g) in DMF (36 mL) was added potassium carbonate (2.7 g) followed by iodomethane (0.6 mL). The reaction mixture was stirred at room temperature for 18 h. EtOAc (50 mL) and water (50 mL) were added, the layers were separated and the aq. layer was extracted with EtOAc (40 mL). The combined organic layers were washed with brine, dried over MgSO$_4$, filtered and concentrated to dryness in vacuo. The residue was purified by ISCO CombiFlash (80 g column) eluting with 0-70% EtOAc/hexanes to afford 2.2 g of methyl (R)-6-(3-methylmorpholino)-1-(1-((2-(trimethylsilyl)ethoxy)methyl)-1H-pyrazol-3-yl)-1H-pyrazolo[3,4-b]pyridine-4-carboxylate as a yellow solid.

Step 4. To a solution of methyl (R)-6-(3-methylmorpholino)-1-(1-((2-(trimethylsilyl)ethoxy)methyl)-1H-pyrazol-3-yl)-1H-pyrazolo[3,4-b]pyridine-4-carboxylate (2.2 g) in THF (20 mL) and MeOH (0.038 mL) at room temperature was added lithium borohydride (3.4 mL). The mixture was heated to 65° C. for 4 h then cooled to room temperature. Acetone (1 mL) was added and stirred for 30 min. The mixture was diluted with (1:1) NH$_4$Cl/water (50 mL) then extracted with EtOAc (2×40 mL). The combined organic layers were washed with brine, dried over MgSO$_4$, filtered and concentrated to dryness in vacuo to afford 2 g of (R)-(6-(3-methylmorpholino)-1-(1-((2-(trimethylsilyl)ethoxy)methyl)-1H-pyrazol-3-yl)-1H-pyrazolo[3,4-b]pyridin-4-yl)methanol which was used without further purification.

Step 5. To a solution of (R)-(6-(3-methylmorpholino)-1-(1-((2-(trimethylsilyl)ethoxy)methyl)-1H-pyrazol-3-yl)-1H-pyrazolo[3,4-b]pyridin-4-yl)methanol (2 g) in dichloromethane (20 mL) at 0° C. was added Et$_3$N (0.69 mL) followed by MsCl (0.38 mL). The reaction was then stirred at room temperature for 2 h. The mixture was diluted with dichloromethane (60 mL) and water (60 mL). The layers were partitioned and the aq. layer was extracted with dichloromethane (30 mL). The combined organic layers were washed with brine, dried over MgSO$_4$, filtered and concentrated in vacuo to afford 2.3 g of (R)-(6-(3-methylmorpholino)-1-(1-((2-(trimethylsilyl)ethoxy)methyl)-1H-pyrazol-3-yl)-1H-pyrazolo[3,4-b]pyridin-4-yl)methyl methanesulfonate which was used in the subsequent step without further purification.

Step 6. To a solution of (R)-(6-(3-methylmorpholino)-1-(1-((2-(trimethylsilyl)ethoxy)methyl)-1H-pyrazol-3-yl)-1H-pyrazolo[3,4-b]pyridin-4-yl)methyl methanesulfonate (2.3 g) in DMF (18 mL) at room temperature was added NaCN (325 mg). The reaction mixture was stirred for 18 h then diluted with EtOAc (40 mL) and water (40 mL). The layers were partitioned and the aq. layer was extracted with EtOAc (35 mL). The combined organic layers were washed with brine, dried over MgSO$_4$, filtered and concentrated in vacuo. The residue was purified by ISCO CombiFlash (24 g column) eluting with 20-100% EtOAc/hexanes to afford 440 mg of (R)-2-(6-(3-methylmorpholino)-1-(1-((2-(trimethylsilyl)ethoxy)methyl)-1H-pyrazol-3-yl)-1H-pyrazolo[3,4-b]pyridin-4-yl)acetonitrile.

Step 7. To a solution of (R)-2-(6-(3-methylmorpholino)-1-(1-((2-(trimethylsilyl)ethoxy)methyl)-1H-pyrazol-3-yl)-1H-pyrazolo[3,4-b]pyridin-4-yl)acetonitrile (430 mg) in THF (5 mL) at 0° C. was added iodomethane (0.148 mL) followed by a dropwise addition of potassium tert-butoxide (2.37 mL) over 10 min. The reaction mixture was stirred at 0° C. for 1 h then poured into aq. sat. NH$_4$Cl and extracted with EtOAc (2×35 mL). The combined organic layers were washed with brine, dried over MgSO$_4$, filtered and concentrated to dryness in vacuo. The residue was adsorbed in silica gel for purification by ISCO CombiFlash (24 g Gold SiO$_2$ column) eluting with 10-90% EtOAc/hexanes to afford 140 mg of (R)-2-methyl-2-(6-(3-methylmorpholino)-1-(1-((2-(trimethylsilyl)ethoxy)methyl)-1H-pyrazol-3-yl)-1H-pyrazolo[3,4-b]pyridin-4-yl)propanenitrile.

Step 8. To a solution of (R)-2-methyl-2-(6-(3-methylmorpholino)-1-(1-((2-(trimethylsilyl)ethoxy)methyl)-1H-pyrazol-3-yl)-1H-pyrazolo[3,4-b]pyridin-4-yl)propanenitrile (90 mg) in EtOH/H$_2$O (2 mL/0.4 mL) was added hydrido (dimethylphosphinous acid-kP)[hydrogen bis(dimethylphosphinito-kP)]platinum(II) (4 mg). The mixture was heated to 80° C. then cooled and concentrated to dryness. The residue was adsorbed in silica for purification by ISCO CombiFlash (12 g Gold SiO$_2$ column) eluting with 30-100% EtOAc/hexanes to afford 82 mg of (R)-2-methyl-2-(6-(3-methylmorpholino)-1-(1-((2-(trimethylsilyl)ethoxy)methyl)-1H-pyrazol-3-yl)-1H-pyrazolo[3,4-b]pyridin-4-yl)propanamide as a colorless solid.

Step 9. To a solution of (R)-2-methyl-2-(6-(3-methylmorpholino)-1-(1-((2-(trimethylsilyl)ethoxy)methyl)-1H-pyrazol-3-yl)-1H-pyrazolo[3,4-b]pyridin-4-yl)propanamide (81 mg) in dichloromethane (2 mL) was added TFA (0.30 mL) and the reaction mixture was stirred at room temperature for 18 h. Additional TFA (0.5 mL) was added and the mixture was stirred for 6 h. Toluene (10 mL) was added and the volatiles were removed under reduced pressure. The residue was diluted in 5 mL of MeOH/water (85:15) and the stirred at room temperature for 18 h. The volatiles were removed under reduced pressure and the residue was dissolved in EtOAc (25 mL) and treated with aq. sat. NaHCO$_3$ (20 mL). The layers were partitioned and the aq. layer was extracted with EtOAc (20 mL). The combined organic layers were washed with brine, dried over MgSO$_4$, filtered and concentrated to dryness in vacuo. The residue was adsorbed in silica gel for purification by ISCO CombiFlash (12 g Gold SiO$_2$ column) eluting with 80-100% EtOAc/hexanes to afford 23 mg of (R)-2-methyl-2-(6-(3-methylmorpholino)-1-(1H-pyrazol-3-yl)-1H-pyrazolo[3,4-b]pyridin-4-yl)propanamide as a colorless foam. $^1$H NMR (400 MHz, DMSO): δ 12.80 (s; 1H); 7.90 (s; 1H); 7.83 (s; 1H); 7.06 (s; 1H); 7.02 (s; 1H); 6.76-6.77 (m; 1H); 6.65 (s; 1H); 4.47-4.50 (m; 1H); 4.06 (d; J=13.56 Hz; 1H); 3.99 (d; J=11.46 Hz; 1H); 3.78 (d; J=11.34 Hz; 1H); 3.63-3.66 (m; 1H); 3.47-3.53 (m; 1H); 3.17-3.23 (m; 1H); 1.54 (s; 6H); 1.22 (d; J=6.68 Hz; 3H). MS (+ESI): m/z 370.2.

Compound 5

Step 1. To a solution of (R)-(6-(3-methylmorpholino)-1-(1-((2-(trimethylsilyl)ethoxy)methyl)-1H-pyrazol-3-yl)-1H-pyrazolo[3,4-b]pyridin-4-yl)methanol from Example 4 Step 5 (115 mg) and 2-hydroxyisobutyronitrile (0.07 mL) in dry toluene (10 mL) was added tributylphosphine (0.2 mL) and TMAD (133.6 mg) and the resulting mixture was stirred at room temperature for 1 h then diluted with water and extracted with EtOAc. The organic extracts were dried and was concentrated to dryness, then purified by Combi-Flash (12 g column) eluting with 10-80% EtOAc/hexanes to afford 110 mg of (R)-2-(6-(3-methylmorpholino)-1-(1-((2-(trimethylsilyl)ethoxy)methyl)-1H-pyrazol-3-yl)-1H-pyrazolo[3,4-b]pyridin-4-yl)acetonitrile as a light yellow oil.

Step 2: To a solution of (R)-2-(6-(3-methylmorpholino)-1-(1-((2-(trimethylsilyl)ethoxy)methyl)-1H-pyrazol-3-yl)-1H-pyrazolo[3,4-b]pyridin-4-yl)acetonitrile (68 mg) in toluene (2 mL) was added tetrabutylammonium bromide (9.66 mg) and 50% NaOH (0.5 mL), followed by 1,5-dibromopentane (0.027 mL). The mixture was heated to 65° C. for 2 h then diluted with water and extracted with EtOAc. The combined organic extracts were dried over NaSO$_4$, concentrated to dryness and purified by Combi-Flash (4 g column) eluting with 20-80% EtOAc/hexanes to afford 54 mg of (R)-1-(6-(3-methylmorpholino)-1-(1-((2-(trimethylsilyl)ethoxy)methyl)-1H-pyrazol-3-yl)-1H-pyrazolo[3,4-b]pyridin-4-yl)cyclohexane-1-carbonitrile as a light yellow oil.

Step 3. To a solution of (R)-1-(6-(3-methylmorpholino)-1-(1-((2-(trimethylsilyl)ethoxy)methyl)-1H-pyrazol-3-yl)-1H-pyrazolo[3,4-b]pyridin-4-yl)cyclohexane-1-carbonitrile (54 mg) in dichloromethane (2 mL) was added TFA (0.27 mL). The reaction mixture was stirred at room temperature for 18 h then concentrated under reduced pressure. The residue was dissolved in 5 mL of MeOH/H$_2$O (85:15) and stirred at room temperature for 18 h and concentrated. The residue was dissolved in EtOAc (25 mL) and aq. sat. NaHCO$_3$ (25 mL) was added. The layers were partitioned and the aqueous layer was extracted with EtOAc (10 mL). The combined organic layers were washed with brine, dried over MgSO$_4$, filtered and concentrated. The residue was adsorbed on silica gel for purification by ISCO CombiFlash (4 g column) eluting with 30-100% EtOAc/Hexane to afford 11 mg of (R)-1-(6-(3-methylmorpholino)-1-(1H-pyrazol-3-yl)-1H-pyrazolo[3,4-b]pyridin-4-yl)cyclohexane-1-carbonitrile as an off-white foam. $^1$H NMR (400 MHz, CDCl$_3$): δ 1.37 (d; 3H); 1.96 (d; 5H); 2.09 (t; 2H); 2.29 (d; 2H); 3.39 (td; 1H); 3.65 (td; 1H); 3.87-3.77 (m; 2H); 4.08 (d; 3H); 4.49 (d; 1H); 6.82 (s; 1H); 6.99 (d; 1H); 7.80 (d; 1H); 8.22 (s; 1H).

Compound 6

Step 1. To a mechanically stirred suspension of 4-chloro-1H-pyrrolo[2,3-b]pyridine (35 g) in EtOAc (600 mL) at 0° C. was added mCPBA (51.41 g) in portions over 30 min. The reaction mixture was then stirred at rt for 18 h, and the solids were collected by filtration and washed with n-heptane (350 mL). The residue was dried under high vacuum afford 62 g of 4-chloro-1H-pyrrolo[2,3-b]pyridine 7-oxide 3-chlorobenzoate as a grey solid.

Step 2. To a mixture of 4-chloro-1H-pyrrolo[2,3-b]pyridine 7-oxide 3-chlorobenzoate (30 g) in acetonitrile (300 mL) was added dimethyl sulfate (9.6 mL) and the reaction mixture was heated to 60° C. for 18 h. Upon cooling to rt, (R)-3-methylpholine (14 g) was added followed by diisopropylethylamine (48.2 mL) and the reaction mixture was heated to 60° C. for 18 h. Upon cooling to rt, the volatiles were removed in vacuo and the residue was purified by column chromatography on silica gel eluting with 10-40% EtOAc/hexanes to afford 12 g of (R)-4-(4-chloro-1H-pyrrolo[2,3-b]pyridin-6-yl)-3-methylmorpholine as a light grey solid.

Step 3. A mixture of (R)-4-(4-chloro-1Hpyrrolo[2,3-b]pyridin-6-yl)-3-methylmorpholine (11.64 g), iodopyrazole (15.11 g), CuI (81 mg), trans-N,N-dimethylcyclohexane-1,2-diamine (0.66 mL) and K$_3$PO$_4$ (17.23 g) in dioxane (110 mL) was purged 3× with argon and heated to 110° C. for 18 h. The mixture was cooled and filtered through a pad of silica gel, eluting with EtOAc (700 mL). The filtrate was concentrated to dryness in vacuo then purified by flash chromatography on silica gel eluting with 10-25% EtOAc/hexanes. The pure fractions were combined and concentrated to afford 19.3 g of (R)-4-(4-chloro-1-(1-((2-(trimethylsilyl)ethoxy)methyl)-1H-pyrazol-3-yl)-1H-pyrrolo[2,3-b]pyridin-6-yl)-3-methylmorpholine as a mixture of SEM regioisomers.

Step 4. To a solution of (R)-4-(4-chloro-1-(1-((2-(trimethylsilyl)ethoxy)methyl)-1H-pyrazol-3-yl)-1H-pyrrolo[2,3-b]pyridin-6-yl)-3-methylmorpholine (5.0 g), bis(pinacolato)diboron (4.25 g), Pd$_2$(dba)$_3$ (510 mg) and tricyclohexyl phosphine (780 mg) in dioxane (70 mL) was added potassium acetate (3.32 g). The mixture was purged with argon and heated to 100° C. overnight then cooled, diluted with ethyl acetate and filtered through a pad of diatomaceous earth. The filtrate was concentrated to dryness and resubmitted to the reaction conditions. After overnight, the reaction mixture was diluted with ethyl acetate, filtered through a pad of diatomaceous earth and concentrated to dryness. Purification by column chromatography, eluting with 0-50% ethyl acetate/hexanes provided 4.38 g of (R)-3-methyl-4-(4-(4,4,5,5-tetramethyl-1,3,2-dioxaborolan-2-yl)-1-(1-((2-(trimethylsilyl)ethoxy)methyl)-1H-pyrazol-3-yl)-1H-pyrrolo[2,3-b]pyridin-6-yl)morpholine as a yellow powder.

Step 5. To a one dram vial containing (R)-3-methyl-4-(4-(4,4,5,5-tetramethyl-1,3,2-dioxaborolan-2-yl)-1-(1-((2-(trimethylsilyl)ethoxy)methyl)-1H-pyrazol-3-yl)-1H-pyrrolo[2,3-b]pyridin-6-yl)morpholine (106 mg), 2-bromophenyl methyl sulfone (93 mg), [1,1-bis(diphenylphosphino)ferrocene]dichloropalladium(II) (10 mg) was added dioxane (1 mL) and 2N Na$_2$CO$_3$ (250 µL), The mixture was evacuated, purged with argon (3×) and heated at 120° C. for 24 h then cooled and partitioned between water and ethyl acetate. The organic phase was separated and the aqueous phase was extracted three times with ethyl acetate. The combined organic layers were washed with brine, dried over Na$_2$SO$_4$, filtered and concentrated. The crude material was purified on a Redisep Gold Column (12 g) using 0 to 100%. ethyl acetate/hexanes to give 76 mg of (R)-3-methyl-4-(4-(2-(methylsulfonyl)phenyl)-1-(1-((2-(trimethylsilyl)ethoxy)methyl)-1H-pyrazol-3-yl)-1H-pyrrolo[2,3-b]pyridin-6-yl) morpholine.

Step 6. To a solution of (R)-3-methyl-4-(4-(2-(methylsulfonyl)phenyl)-1-(1-((2-(trimethylsilyl)ethoxy)methyl)-1H-pyrazol-3-yl)-1H-pyrrolo[2,3-b]pyridin-6-yl)morpholine (76 mg) in dichloromethane (2 mL) was added TFA (0.45 mL). The reaction was stirred at room temperature overnight, then concentrated and redissolved in 85/15 MeOH/H$_2$O and stirred an additional 4 h. The reaction mixture was concentrated and partitioned between ethyl acetate and water. The organic layer was separated, and the aqueous layer was extracted with ethyl acetate (3×). The combined organic layers were washed with brine, dried over Na$_2$SO$_4$, filtered and concentrated. The crude material was purified on a Redisep column (24 g) eluting with 40 to 60% ethyl acetate/hexanes to provide 58 mg of (R)-3-methyl-4-(4-(2-(methylsulfonyl)phenyl)-1-(1H-pyrazol-3-yl)-1H-pyrrolo[2,3-b]pyridin-6-yl)morpholine. $^1$H NMR (d$_6$-DMSO) δ 12.7 (s, 1H), 8.2 (d 1H), 7.8 (m, 1H), 7.7 (m, 2H), 7.6 (m 1H), 7.5 (m 1H), 7.0 (s, 1H), 6.7 (s, 1H), 4.3 (m, 1H), 4.0 (m, 1H), 3.7 (m, 2H), 3.5 (m, 1H), 3.2 (m, 1H), 2.9 (s, 3H), 1.2 (d 3H).

Compound 7

Step 1. To a solution of 4-chloro-3-methyl-1H-pyrrolo[2,3-b]pyridine 7-oxide 3-chlorobenzoate (508 mg) in acetonitrile (10 mL) was added 3-chlorobenzoic acid (275 mg) and dimethyl sulfate (0.29 mL) and the reaction was heated at 60° C. for 36 h. Upon cooling, (R)-3-methylmorpholine (423 mg) and DIPEA (1.45 mL) were added and the reaction was heated at 60° C. for 26 h. The reaction mixture was concentrated and purified by silica gel chromatography using 40 to 100% ethyl acetate/hexanes to give 243 mg of (R)-4-(4-chloro-3-methyl-1H-pyrrolo[2,3-b]pyridin-6-yl)-3-methylmorpholine.

Step 2. To a 100 mL flask containing (R)-4-(4-chloro-3-methyl-1H-pyrrolo[2,3-b]pyridin-6-yl)-3-methylmorpholine (2.08 g) was added 3-iodo-1-((2-(trimethylsilyl)ethoxy)methyl)-1H-pyrazole (2.79 g) in dioxane (20 mL). Argon was bubbled into the mixture and ground K$_3$PO$_4$ (2.9 g) was added followed by trans-N,N'-dimethylcyclohexane-1,2-diamine (111 mg) and CuI (15 mg). The reaction was heated at 100° C. for 44 h then filtered through diatomaceous earth and rinsed with ethyl acetate. The filtrate was washed with water and the organic layer was dried over Na$_2$SO$_4$, filtered and concentrated. Purification on a Redisep Gold column (80 g) eluting with 0-100% ethyl acetate/hexanes provided 2.53 g of (R)-3-methyl-4-(6-(1-(methylsulfonyl)cyclopropyl)-2-((1-((2-(trimethylsilyl)ethoxy)methyl)-1H-pyrazol-3-yl)thio)pyrimidin-4-yl)morpholine as a mixture of regioisomers.

Step 3. To a solution of (R)-4-(4-chloro-3-methyl-1-(1-((2-(trimethylsilyl)ethoxy)methyl)-1H-pyrazol-3-yl)-1H-pyrrolo[2,3-b]pyridin-6-yl)-3-methylmorpholine (138 mg) in THF (1 mL) was added isobutyronitrile (350 µL) followed by LiHMDS (1M in THF, 2.7 mL). The mixture was heated in a microwave at 100° C. for 15 mins then cooled and partitioned between saturated aq. NH$_4$Cl and ethyl acetate. The aqueous layer was extracted 3× with ethyl acetate and the combined organic layers were washed with brine, dried over Na$_2$SO$_4$, filtered and concentrated. Purification on a Redisep Gold column (24 g) using 0-100% ethyl acetate/hexanes provided 136 mg of (R)-2-methyl-2-(3-methyl-6-(3-methylmorpholino)-1-(1-((2-(trimethylsilyl)ethoxy)methyl)-1H-pyrazol-3-yl)-1H-pyrrolo[2,3-b]pyridin-4-yl)propanenitrile as an oil.

Step 4. To a solution of (R)-2-methyl-2-(3-methyl-6-(3-methylmorpholino)-1-(1-((2-(trimethylsilyl)ethoxy)methyl)-1H-pyrazol-3-yl)-1H-pyrrolo[2,3-b]pyridin-4-yl)propanenitrile (135 mg) in dichloromethane (1 mL) was added TFA (250 µL). The reaction was stirred at room temperature for 3 days, then concentrated and partitioned between ethyl acetate and saturated aq. NaHCO$_3$. The organic layer was separated, and the aqueous layer extracted with ethyl acetate (3×). The combined organic layers were dried over Na$_2$SO$_4$, filtered and concentrated. Purification on a Redisep Gold column (12 g) using 30-100% ethyl acetate/hexanes provided 15 mg of (R)-2-methyl-2-(3-methyl-6-(3-methylmorpholino)-1-(1H-pyrazol-3-yl)-1H-pyrrolo[2,3-b]pyridin-4-yl)propanenitrile. $^1$H NMR (d$_6$-DMSO) δ 12.7 (s, 1H), 7.8 (s, 1H), 7.6 (s, 1H), 6.9 (s, 1H), 6.6 (s, 1H), 5.7 (s, 1H), 4.4 (m, 1H), 4.0 (m, 1H), 3.9 (m, 1H), 3.8 (m, 1H), 3.7 (m, 1H), 3.5 (m, 1H), 3.2 (m, 1H), 2.6 (s, 3H), 1.2 (d 3H).

Compound 8

Step 1. To a solution of 5,7-dichloro-3H-imidazo[4,5-b]pyridine (457 mg) and 2-(chloromethoxy)ethyl-trimethyl-silane (516 µL) in DMF (8 mL) was added diisopropylethylamine (509 µL) and the mixture was stirred at room temperature for 1 h. Water and Et$_2$O were added and the phases were separated. The aqueous phase was extracted with Et$_2$O (2×), and the combined organic extracts were washed with brine and dried over Na$_2$SO$_4$, filtered and evaporated under reduced pressure. The crude mixture was purified using silica gel chromatography eluting with 0 to 70% EtOAc/hexanes to afford 473 mg of 2-[(5,7-dichloroimidazo[4,5-b]pyridin-3-yl)methoxy]ethyltrimethylsilane (tentative assignment) and 120 mg of 2-[(5,7-dichloroimidazo[4,5-b]pyridin-1-yl)methoxy]ethyltrimethylsilane (tentative assignment). Major isomer: $^1$H NMR (400 MHz, CDCl$_3$) δ 8.22 (s, 1H), 7.35 (s, 1H), 5.64 (s, 2H), 3.69-3.48 (m, 2H), 0.99-0.85 (m, 2H), −0.04 (s, 9H). LCMS: 318.12 (M+H). Minor isomer: $^1$H NMR (400 MHz, CDCl$_3$) δ 8.21 (s, 1H), 7.30 (s, 1H), 5.74 (s, 2H), 3.68-3.42 (m, 2H), 1.05-0.84 (m, 2H), -0.07 (s, 9H). LCMS: 319.97 (M+H). LCMS: 318.25 (M+H).

Step 2. To a solution of 2-[(5,7-dichloroimidazo[4,5-b]pyridin-3-yl)methoxy]ethyl-trimethyl-silane (90 mg), K$_3$PO$_4$ (2 M, 424 µL) and (2-methylsulfonylphenyl)boronic acid (68 mg) in dioxane (1 mL) under nitrogen was added Pd(dppf)Cl$_2$·CH$_2$Cl$_2$ (31 mg) then stirred overnight at 80° C. Water was added along with EtOAc and the phases were separated. The aqueous phase was extracted EtOAc (2×), and the combined organic extracts were washed with brine, dried over Na$_2$SO$_4$, filtered and evaporated under reduced pressure. The crude mixture was purified using silica gel chromatography eluting with 0 to 100% EtOAc/hexanes to afford 2-[[7-chloro-5-(2-methylsulfonylphenyl)imidazo[4,5-b]pyridin-3-yl]methoxy]ethyl-trimethyl-silane as a 1:1 mixture of regioisomers. ¹H NMR (400 MHz, CDCl₃) δ 8.22 (dd, J=7.7, 1.6 Hz, 1H), 8.14 (s, 1H), 7.79-7.64 (m, 2H), 7.41 (dd, J=7.3, 1.6 Hz, 1H), 7.33 (s, 1H), 5.67 (s, 2H), 3.77-3.63 (m, 2H), 3.03 (s, 3H), 1.04-0.91 (m, 2H), -0.03 (s, 9H). LCMS: 437.94 (M+H).

Step 3. To a solution of 2-[[7-chloro-5-(2-methylsulfonylphenyl)imidazo[4,5-b]pyridin-3-yl]methoxy]ethyl-trimethyl-silane (640 mg) in dry dioxane (1 mL) was added cesium carbonate (952 mg), RuPhos Pd G1 methyl t-butyl ether adduct (119 mg) and (3R)-3-methylmorpholine (332 µL). The mixture was purged with nitrogen then heated to 100° C. in a sealed vial for 16 hr. Water and EtOAc were added and the phases were separated. The aqueous phase was extracted with EtOAc (2×), and the combined organic extracts were washed with brine then dried over Na₂SO₄, filtered and evaporated under reduced pressure. The residue was taken up in DMSO and purified using reverse phase chromatography to afford 490 mg of trimethyl-[2-[[5-[(3R)-3-methylmorpholin-4-yl]-7-(2-methylsulfonylphenyl)imidazo[4,5-b]pyridin-3-yl]methoxy]ethyl]silane. ¹H NMR (400 MHz, CDCl₃) δ 8.21 (dd, J=7.9, 1.4 Hz, 1H), 7.95 (s, 1H), 7.68 (td, J=7.5, 1.4 Hz, 1H), 7.59 (td, J=7.7, 1.5 Hz, 1H), 7.52 (dd, J=7.5, 1.4 Hz, 1H), 6.62 (s, 1H), 5.56 (d, J=2.3 Hz, 1H), 5.06 (s, 1H), 4.33 (d, J=13.2 Hz, 1H), 4.03 (dd, J=11.4, 3.6 Hz, 1H), 3.93 (dd, J=11.4, 3.1 Hz, 1H), 3.84-3.71 (m, 2H), 3.63-3.53 (m, 2H), 3.49 (td, J=6.5, 5.5, 3.8 Hz, 1H), 3.32 (s, 3H), 1.34 (d, J=6.7 Hz, 3H), 0.97-0.83 (m, 2H), -0.06 (s, 9H). LCMS: 505.19 (M+H).

Step 4. To a solution of trimethyl-[2-[[5-[(3R)-3-methylmorpholin-4-yl]-7-(2-methylsulfonylphenyl) imidazo[4,5-b]pyridin-3-yl]methoxy]ethyl]silane (55 mg) in dichloromethane (1 mL) was slowly added TFA (250 µL) and the mixture was stirred overnight at room temperature. Additional TFA (250 µL) was added and the mixture was stirred over the weekend. The volatiles were removed under reduced pressure and the crude residue was dissolved in EtOAc and treated with a saturated solution of NaHCO₃, then the layers were separated. The aqueous layer was extracted with EtOAc (2×) and the combined organic extracts were dried over sodium sulfate, filtered, and concentrated. The residue was purified using reverse phase chromatography to afford 31 mg of (3R)-3-methyl-4-[7-(2-methylsulfonylphenyl)-3H-imidazo[4,5-b]pyridin-5-yl]morpholine. ¹H NMR (400 MHz, CDCl₃) δ 8.23 (dd, J=7.9, 1.4 Hz, 1H), 7.74 (s, 1H), 7.70 (td, J=7.5, 1.4 Hz, 1H), 7.63 (td, J=7.7, 1.5 Hz, 1H), 7.48 (dd, J=7.5, 1.4 Hz, 1H), 6.73 (s, 1H), 4.25 (q, J=7.0 Hz, 1H), 4.02 (dd, J=11.4, 3.6 Hz, 1H), 3.92-3.84 (m, 1H), 3.80 (d, J=2.1 Hz, 2H), 3.64 (td, J=11.7, 3.0 Hz, 1H), 3.27 (td, J=12.5, 3.8 Hz, 1H), 2.97 (s, 3H), 1.27 (d, J=6.7 Hz, 3H). LCMS: 374.08 (M+H).

Step 5. To a solution of (3R)-3-methyl-4-[5-(2-methylsulfonylphenyl)-3H-imidazo[4,5-b]pyridin-7-yl]morpholine (290 mg), 2-[(3-iodopyrazol-1-yl)methoxy]ethyl-trimethylsilane (510 mg), 3-(1,1-difluoroethyl)benzenesulfinic acid (54 mg) and cesium carbonate (634 mg) in NMP (3.5 mL) under nitrogen was added copper bromide (45 mg), and the mixture was heated at 120° C. overnight. The mixture was cooled, treated with saturated aqueous NH₄Cl, water, and ammonium hydroxide (4:1:3), and extracted with EtOAc. The aqueous phase was extracted with EtOAc (2×) and the combined organic phases were washed with brine, dried over Na₂SO₄, filtered and concentrated. The crude product was purified using reverse phase chromatography to afford 220 mg of trimethyl-[2-[[3-[5-[(3R)-3-methylmorpholin-4-yl]-7-(2-methylsulfonylphenyl)imidazo[4,5-b]pyridin-3-yl] pyrazol-1-yl]methoxy]ethyl]silane as a mixture of regioisomers. LCMS: 569.38 (M+H).

Step 6. To a solution of trimethyl-[2-[[3-[5-[(3R)-3-methylmorpholin-4-yl]-7-(2-methylsulfonylphenyl) imidazo[4,5-b]pyridin-3-yl]pyrazol-1-yl]methoxy]ethyl]silane (14 mg) in dichloromethane (1 mL) was added TFA (56 µL) and the mixture was stirred overnight at room temperature. The volatiles were removed under reduced pressure and the mixture was dissolved in dioxane (1 mL) and basified to pH 10 using 3N NaOH, and heated at 80° C. for 3 h. The mixture was partitioned between EtOAc and water. The aqueous phase was extracted with EtOAc (2×), and the combined organic extracts were washed with brine, dried over Na₂SO₄, filtered and concentrated. The residue was taken up in DMSO and purified using reverse phase chromatography to afford 3.7 mg of (3R)-3-methyl-4-[7-(2-methylsulfonylphenyl)-3-(1H-pyrazol-3-yl)imidazo[4,5-b]pyridin-5-yl] morpholine. ¹H NMR (400 MHz, DMSO-d₆) δ 13.03 (s, 1H), 8.47 (s, 1H), 8.14 (dd, J=7.8, 1.5 Hz, 1H), 7.96 (d, J=2.3 Hz, 1H), 7.80 (dtd, J=21.7, 7.5, 1.5 Hz, 2H), 7.52 (dd, J=7.4, 1.5 Hz, 1H), 6.97 (d, J=2.2 Hz, 1H), 6.79 (s, 1H), 4.42-4.32 (m, 1H), 3.99 (d, J=11.8 Hz, 2H), 3.82-3.65 (m, 2H), 3.54 (td, J=11.7, 3.0 Hz, 1H), 3.19 (s, 3H), 3.18-3.07 (m, 1H), 1.19 (d, J=6.6 Hz, 3H). LCMS: 438.94 (M+H).

Intermediate C

Step 1. To a -5° C. solution of 3-aminopyrazole (24.7 g, 297 mmol) in 6N HCl (181 mL) was added a 1M aqueous solution of NaNO₂ (300 mL, 297 mmol). A solution of SnCl₂ (113 g, 595 mmol) in conc. HCl (510 mL) was then added dropwise and the resulting mixture was stirred at r.t. for 2 hr. The solvents were evaporated under reduced pressure to provide 3-hydrazineylidene-3H-pyrazole as a light brown solid which was used as is without further purification. ¹H NMR (400 MHz, DMSO-d₆, δ ppm): 9.90 (s, 3H), 7.65 (d, J=2.4 Hz, 1H), 5.81 (d, J=2.3 Hz, 1H).

Step 2. A 500 mL frame dried RBF was loaded with 2,6-difluoro-4-iodopyridine (17 g, 70.5 mmol) and anhydrous THF (255 mL). The yellow reaction mixture was cooled to -78° C. and commercial LDA (1.0M in THF/hexanes, 84.7 mL, 84.7 mmol) was added dropwise at such rate that the internal temperature remained below -68° C. The light brown solution was allowed to stir at -78° C. for 1 h and then ethyl formate (8.5 mL, 105.678 mmol) was added over 10 min. The reaction was monitored by TLC and was complete after 30 min. Formic acid (5.3 mL, 140.5 mmol) was added dropwise and the mixture was stirred at -78° C. for 10 min then diluted with EtOAc (150 mL). The mixture was allowed to warm to 0° C. and water (100 mL) was added. The layers were separated and the aq. layer was extracted with EtOAc (150 mL). The combined organic layers were washed with brine, dried over Na₂SO₄, filtered and concentrated in vacuo to afford 19 g of 2,6-difluoro-4-iodo-pyridine-3-carbaldehyde as a light brown solid. ¹H NMR: (400 MHz, CDCl₃), δ 10.11 (s, 1H), 7.54 (d; J=2.87 Hz; 1H).

Step 3. To a suspension of 3-hydrazineylidene-3H-pyrazole (12.5 g, 94.3 mmol) in 95% EtOH (70 mL) was added 2,6-difluoro-4-iodo-pyridine-3-carbaldehyde (4.4 g, 16.3 mmol) and the mixture was stirred at rt for 15 min. The bulk of the volatiles was then removed under reduced pressure. The orange mixture was dissolved in EtOAc and NaHCO₃ and stirred at rt 15 minutes, resulting in vigorous gas evolution. The phases were separated and the aqueous phase was extracted 3× with EtOAc. The combined organic extracts were washed with water and brine then dried over MgSO₄, filtered and evaporated under reduced pressure to afford (E)-3-((2-(1H-pyrazol-3-yl)hydrazineylidene) methyl)-2,6-difluoro-4-iodopyridine (5.5 g, 15.9 mmol) as a yellow/orange solid. $^1$H NMR (400 MHz, DMSO-d$_6$) 12.02 (s, 1H), 10.89 (s, 1H), 7.92 (s, 1H), 7.82 (d, 1H), 7.54 (s, 1H), 5.97 (s, 1H).

Step 4. A solution of (E)-3-((2-(1H-pyrazol-3-yl)hydrazineylidene)methyl)-2,6-difluoro-4-iodopyridine (8.6 g, 24.7 mmol) in NMP (115 mL) was split in 20 mL batches that were heated at 200° C. in a microwave reactor for 20 min. The combined mixtures were then added dropwise to water with vigorous stirring to give a cloudy mixture which was stirred 5 min at rt, then cooled to 0° C. The precipitate was filtered, washed with water and dried on a Buchner funnel for 1 h and under reduced pressure for 1 h to afford 6-fluoro-4-iodo-1-(1H-pyrazol-3-yl)-1H-pyrazolo[3,4-b] pyridine (6.8 g, 20.7 mmol) as a light brown powder. $^1$H NMR (400 MHz, DMSO-d$_6$) δ 13.13 (s, 1H), 8.29 (s, 1H), 7.95 (t, 1H), 7.71 (d, 1H), 6.67 (t, 1H).

Step 5. A solution of 6-fluoro-4-iodo-1-(1H-pyrazol-3-yl)-1H-pyrazolo[3,4-b]pyridine (6.8 g, 20.7 mmol) and (R)-3-methylmorpholine (1.24 mL, 7.23 mmol) in DMSO (35 mL) was sealed in a thick-walled tube and heated to 120° C. for 45 min. The mixture was then added dropwise to an Erlenmeyer flask filled with water with vigorous stirring. The cloudy mixture was stirred at rt 5 min, then 20 min at 0° C. The precipitate was filtered on a Buchner funnel and the precipitate was washed with water and dried on the Buchner funnel overnight to afford (R)-4-(4-iodo-1-(1H-pyrazol-3-yl)-1H-pyrazolo[3,4-b]pyridin-6-yl)-3-methylmorpholine (6.9 g, 16.8 mmol)—Intermediate B.

Step 6. To a solution of Intermediate B (2.00 g, 4.88 mmol) in DMF (20 mL) was added 2-(chloromethoxy) ethyltrimethylsilane (1.04 mL, 5.8 mmol) followed by diisopropylethylamine (1.28 mL, 7.3 mmol) and the resulting mixture was stirred for 40 min. The mixture was partitioned between EtOAc and water and the aqueous phase was extracted with EtOAc (2×). The combined organic layers were washed with water (2×) and brine, then dried over Na$_2$SO$_4$, filtered and evaporated. Purification by silica gel chromatography (gradient 0 to 80% EtOAc/hexanes) provided 2-[[3-[4-iodo-6-[(3R)-3-methylmorpholin-4-yl]pyrazolo[3,4-b]pyridin-1-yl]pyrazol-1-yl]methoxy]ethyltrimethylsilane (0.67 g, 1.25 mmol) and 2-[[5-[4-iodo-6-[(3R)-3-methylmorpholin-4-yl]pyrazolo[3,4-b]pyridin-1-yl]pyrazol-1-yl]methoxy]ethyltrimethylsilane (0.17 g, 0.31 mmol).

Compound 86

Step 1. In a round bottom flask was dissolved 2,6-difluoro-4-iodo-pyridine-3-carbaldehyde (1.76 g, 6.54 mmol) in DME (15 mL) and hydrazine hydrate (535 µL, 65% purity, 7.1 mmol) was added. The reaction mixture was stirred at rt for 4 h. Water was added to the heterogeneous yellow solution and it was stirred for 30 minutes at rt. The resulting solid was then collected by filtration, rinsed with water and dried under vacuum overnight to afford 6-fluoro-4-iodo-1H-pyrazolo[3,4-b]pyridine.

Step 2. In a RBF was dissolved 6-fluoro-4-iodo-1H-pyrazolo[3,4-b]pyridine (2.18 g, 8.29 mmol) in DMSO (30 mL). To this solution was added (3R)-3-methylmorpholine (3.43 g, 33.94 mmol, 3.85 mL) and the reaction mixture was stirred at 120° C. overnight before slowly cooling down the reaction down to rt. Water was added slowly over 5-10 minutes and the flask was put in an ice bath were the solution was stirred for 1 h. The resulting solid was then collected by filtration, washed with water and air dried with suction for 1 h and then under vacuum overnight to give (3R)-4-(4-iodo-1H-pyrazolo[3,4-b]pyridin-6-yl)-3-methyl-morpholine (2.12 g, 6.16 mmol).

Step 3. In a RBF was dissolved 6-fluoro-4-iodo-1H-pyrazolo[3,4-b]pyridine (1.54 g, 5.86 mmol) in DMF (40 mL) and cooled to 0° C. To this solution was added Sodium hydride; 60 wt % (281.0 mg, 7.03 mmol, 60% purity) and the reaction mixture was stirred at 0° C. for 30 minutes. SEM-Cl (1.46 g, 8.78 mmol, 1.55 mL) was then added and the solution was stirred at 0° C. for 5 minutes before coming back to r.t. and stirred 1 more hour. Saturated NH$_4$Cl followed by water were added and the mixture stirred 30 minutes and the resulting solid was collected by filtration and dried overnight under vacuum to give 2-[(6-fluoro-4-iodo-pyrazolo[3,4-b]pyridin-2-yl)methoxy]ethyl-trimethyl-silane as a mixture of SEM regioisomers.

Step 4. In a RBF was dissolved 2-[[4-iodo-6-[(3R)-3-methylmorpholin-4-yl]pyrazolo[3,4-b]pyridin-1-yl] methoxy]ethyl-trimethyl-silane (103 mg, 217.11 µmol) in THF (1 mL). To this solution was added 2-methylpropanenitrile (150.15 mg, 2.17 mmol, 195 µL) followed by LiHMDS (1 M, 1.09 mL). The reaction mixture was stirred at 20° C. for 15 min and then heated to 100° C. for 12 min under microwave irradiation. Water was added along with EtOAc and the phases were separated. Aqueous phase was extracted a second time with EtOAc. The combined organic phases were washed with a saturated solution of brine before being dried over MgSO$_4$, filtered and evaporated under reduced pressure. The crude product was purified using a 15.5 g Gold C18 Isco column and an elution of 10 to 100% water/MeCN to afford 2-methyl-2-[6-[(3R)-3-methylmorpholin-4-yl]-1-(2-trimethylsilylethoxymethyl)pyrazolo[3,4-b]pyridin-4-yl]propanenitrile.

Step 5. In a RBF was dissolved 2-methyl-2-[6-[(3R)-3-methylmorpholin-4-yl]-1-(2-trimethylsilylethoxymethyl) pyrazolo[3,4-b]pyridin-4-yl]propanenitrile (690 mg, 1.66 mmol) in DCM (30 mL) and TFA (3.80 mL, 50 mmol) was added. The reaction mixture was stirred at rt overnight and then the volatiles were removed in vacuo. The crude was dissolved in 1 mL of DMSO and purified using a 15.5 g Gold C18 Isco column and an elution of 5 to 100% water/MeCN to afford 2-methyl-2-[6-[(3R)-3-methylmorpholin-4-yl]-1H-pyrazolo[3,4-b]pyridin-4-yl]propanenitrile.

Step 6. A solution of 2-methyl-2-[6-[(3R)-3-methylmorpholin-4-yl]-1H-pyrazolo[3,4-b]pyridin-4-yl]propanenitrile (100 mg, 0.35 mmol), 5-iodo-3-methyl-1-tetrahydropyran-2-yl-pyrazole (205 mg, 0.7 mmol), Cesium carbonate (285 mg, 0.87 mmol), (1S,2S)—N$_1$,N$_2$-dimethylcyclohexane-1,2-diamine (100 mg, 0.70 mmol) in NMP (1.2 mL) was flushed with nitrogen for 5 minutes before adding Copper Iodide (67 mg, 0.35 mmol). The mixture was heated to 120° C. for 16 h. Water was added, the mixture stirred for 30 minutes and the resulting solid was collected by filtration and dried under vacuum 1 h. This solid was then dissolved in 1 mL of DMSO and purified by reverse phase Combiflash (5 to 100% water/MeCN in 20 CV to afford 2-methyl-2-[6-[(3R)-3-methylmorpholin-4-yl]-1-(5-methyl-2-tetrahydropyran-2-yl-pyrazol-3-yl)pyrazolo[3,4-b] pyridin-4-yl]propanenitrile.

Step 7. In a round bottom flask 2-methyl-2-[6-[(3R)-3-methylmorpholin-4-yl]-1-(5-methyl-2-tetrahydropyran-2-yl-pyrazol-3-yl)pyrazolo[3,4-b]pyridin-4-yl]propanenitrile (42 mg, 93 µmol) was dissolved in MeOH (0.5 mL). To this solution was added HCl in MeOH (1.25 M, 112 µL) and the reaction mixture was stirred at 60° C. for 1 h. The volatiles were evaporated under reduced pressure and crude was purified using a 15.5 g Gold C18 Isco column and an elution of 5 to 100% water/MeCN to afford Compound 86. $^1$H NMR (400 MHz, DMSO-d$_6$) δ 12.51 (s, 1H), 8.27 (s, 1H), 6.73 (s, 1H), 6.49 (d, J=2.0 Hz, 1H), 4.46 (s, 1H), 4.09-4.00 (m, 1H), 3.97 (dd, J=11.4, 3.5 Hz, 1H), 3.76 (d, J=11.4 Hz, 1H), 3.64

(dd, J=11.5, 3.1 Hz, 1H), 3.49 (td, J=11.9, 3.1 Hz, 1H), 3.19 (td, J=12.6, 3.8 Hz, 1H), 2.30 (s, 3H), 1.85 (s, 6H), 1.20 (d, J=6.7 Hz, 3H).

Compound 99

Step 1. A solution of 2-[[5-[4-iodo-6-[(3R)-3-methylmorpholin-4-yl]pyrazolo[3,4-b]pyridin-1-yl]pyrazol-1-yl]methoxy]ethyl-trimethyl-silane (500 mg, 0.92 mmol) in THF (8 mL) was cooled to -78° C. and slowly treated with nBuLi (2.5 M, 0.48 mL). The mixture was stirred as such for 40 min. A solution of tetrahydropyran-3-one (27 μL, 2.78 mmol) in 1.5 mL THF was then added to the mixture. The flask was removed from the dry ice bath and stirring was continued for 1 h. The mixture was then quenched with a saturated $NH_4Cl$ solution and added EtOAc and the phases were separated. The aqueous phase was extracted twice more with EtOAc, and the combined organic extracts were washed with a saturated solution of brine before being dried over $Na_2SO_4$, filtered and evaporated under reduced pressure to provide 3-[6-[(3R)-3-methylmorpholin-4-yl]-1-[2-(2-trimethylsilylethoxymethyl)pyrazol-3-yl]pyrazolo[3,4-b]pyridin-4-yl]tetrahydropyran-3-ol.

Step 2. A solution of 3-[6-[(3R)-3-methylmorpholin-4-yl]-1-[2-(2-trimethylsilylethoxymethyl)pyrazol-3-yl]pyrazolo[3,4-b]pyridin-4-yl]tetrahydropyran-3-ol (168 mg, 0.325 mmol), triethylsilane (291 mg, 2.50 mmol, 0.4 mL), DCM (1 mL), TFA (5.96 g, 52.3 mmol, 4 mL) at rt and stirred for 10 min. The volatiles were removed under reduced pressure and the residue was purified using reverse phase chromatography, affording a mixture of compound 99 and compound 100, which were separated by SFC.

Compound 121

Step 1. A solution of Intermediate C (200 mg, 0.37 mmol) in THF (4 mL) was cooled to −78° C. and slowly treated with nBuLi (2.5 M, 0.19 mL). The mixture was stirred for 40 min then a solution of 8-oxabicyclo[3.2.1]octan-3-one (27 μL, 1.2 mmol) in 0.4 mL THF was added. The flask was then removed from the dry ice bath and allowed to warm to rt over 1.5 h. The mixture was then quenched with a saturated $NH_4Cl$ solution and extracted with EtOAc. The aqueous phase was extracted twice more with EtOAc, and the combined organic extracts were washed with a saturated solution of brine before being dried over $Na_2SO_4$, filtered and evaporated under reduced pressure. The residue was used in the next step without further purification.

Step 2. A solution of 3-[6-[(3R)-3-methylmorpholin-4-yl]-1-[2-(2-trimethylsilylethoxymethyl)pyrazol-3-yl]pyrazolo[3,4-b]pyridin-4-yl]-8-oxabicyclo[3.2.1]octan-3-ol (100 mg, 0.18 mmol) and triethylsilane (0.23 mL, 1.42 mmol) in DCM (1 mL) was treated with TFA (2.3 mL, 30 mmol) at rt and stirred for 10 min. The volatiles were removed under reduced pressure and the residue was purified using silica gel chromatography eluting with 0-10% MeOH, then reverse phase chromatography elution with 0-100% MeCN/$H_2O$ to provide compound 121. $^1$H NMR (400 MHz, DMSO-$d_6$) δ 12.79 (s, 1H), 8.04 (s, 1H), 7.83 (s, 1H), 6.80 (s, 1H), 6.78 (s, 1H), 5.33 (s, 1H), 4.49-4.40 (m, 3H), 4.05-3.91 (m, 2H), 3.77 (d, J=11.4 Hz, 1H), 3.64 (dd, J=11.5, 3.1 Hz, 1H), 3.49 (td, J=11.7, 2.9 Hz, 1H), 3.23-3.11 (m, 1H), 2.43-2.31 (m, 4H), 1.81 (dd, J=20.9, 11.5 Hz, 4H), 1.20 (d, J=6.6 Hz, 3H).

Compound 125

Step 1. To a solution of 2-amino-3-bromopyridine (1.0 g, 5.8 mmol) in DCM (10 mL) at rt were added di-tert-butyldicarbamate (2.65 g, 12.1 mmol) and DMAP (35 mg, 0.29 mmol) followed by slow addition of $Et_3N$ (1.8 mL, 12.9 mmol). The reaction mixture was stirred at rt for 18 h then partitioned between water (50 mL) and DCM (40 mL). The aq. layer was extracted with DCM (40 mL) and the combined organic layers were washed with brine, dried over $MgSO_4$, filtered and concentrated in vacuo. The residue was adsorbed on silica gel for purification by Combi-Flash (80 g Gold $SiO_2$), eluting from 100% hexanes to 35% EtOAc/hexanes over 25 min to afford 1.8 g of di-tert-butyl (3-bromopyridin-2-yl)dicarbamate as a colorless solid. MS (+ESI) m/z 395.1/397.1 (M+Na)

Step 2. Di-tert-butyl (3-bromopyridin-2-yl)dicarbamate (150 mg, 0.40 mmol), bis(pinacolato)diboron (204 mg, 0.80 mmol) and potassium acetate (120 mg, 1.21 mmol) were dissolved in dry DMF (1 mL), followed by Pd(dppf)$Cl_2$·$CH_2Cl_2$ (33 mg, 0.04 mmol). The reaction was purged with argon and then heated to 85° C. for 16 h. The mixture was diluted with EtOAc and filtered through a pad of celite. The volatiles were evaporated to provide tert-butyl (tert-butoxycarbonyl)(3-(4,4,5,5-tetramethyl-1,3,2-dioxaborolan-2-yl)pyridin-2-yl)carbamate, which was used without further purification.

Step 3. 2-[[3-[4-iodo-6-[(3R)-3-methylmorpholin-4-yl]pyrazolo[3,4-b]pyridin-1-yl]pyrazol-1-yl]methoxy]ethyltrimethylsilane (120 mg, 0.22 mmol), $K_3PO_4$ (142 mg, 0.66 mmol), Pd(dppf$Cl_2$).$CH_2Cl_2$ (9 mg, 0.011 mmol) and tert-butyl (tert-butoxycarbonyl)(3-(4,4,5,5-tetramethyl-1,3,2-dioxaborolan-2-yl)pyridin-2-yl)carbamate (186 mg, 0.44 mmol) were dissolved in dry DMF (2 mL). The reaction was purged with argon and heated to 85° C. for 16 h. The product was purified by combiflash (C18, 26 g) using 5-100% MeCN in H2O (0.1% formic acid) for 20 min to give tert-butyl (R)-(tert-butoxycarbonyl)(3-(6-(3-methylmorpholino)-1-(1-((2-(trimethylsilyl)ethoxy)methyl)-1H-pyrazol-3-yl)-1H-pyrazolo[3,4-b]pyridin-4-yl)pyridin-2-yl)carbamate (35 mg).

Step 4. To a solution of tert-butyl (R)-(tert-butoxycarbonyl)(3-(6-(3-methylmorpholino)-1-(1-((2-(trimethylsilyl)ethoxy)methyl)-1H-pyrazol-3-yl)-1H-pyrazolo[3,4-b]pyridin-4-yl)pyridin-2-yl)carbamate (35 mg, 0.05 mmol) in DCM (1.5 mL) was added TFA (0.40 mL, 5.2 mmol) and $Et_3SiH$ (0.03 mL, 0.17 mmol) and the reaction was stirred for 1.5 h. The volatiles were evaporated and the residue was purified by combi-flash ($SiO_2$, 4 g) using 0-100% hexanes in EtOAc for 15 min to provide (R)-3-(6-(3-methylmorpholino)-1-(1H-pyrazol-3-yl)-1H-pyrazolo[3,4-b]pyridin-4-yl)pyridin-2-amine (18 mg).

Compound 126

Step 1. A microwave tube was loaded with (R)-4-(4-iodo-1-(1-((2-(trimethylsilyl)ethoxy)methyl)-1H-pyrazol-3-yl)-1H-pyrazolo[3,4-b]pyridin-6-yl)-3-methylmorpholine (Intermediate C, 700 mg, 1.30 mmol), (2-(N-(tert-butyl)sulfamoyl)phenyl)boronic acid (492 mg, 1.68 mmol), 2M $K_2CO_3$ (2 mL, 4 mmol), Pd(PPh$_3$)$_4$ (75 mg, 0.065 mmol) and dioxane (7 mL). The tube was sealed and flushed with $N_2$ (3 cycles of vacuum/$N_2$). The mixture was heated to 100° C. for 5 h. LCMS showed complete reaction. Upon cooling to rt, the mixture was diluted with EtOAc (40 mL) and water (40 mL). The layers were separated and the aq. layer was extracted with EtOAc (70 mL). The combined organic layers were washed with brine, dried over $MgSO_4$, filtered and concentrated to dryness. The residue was adsorbed on silica gel for purification by ISCO CombiFlash (40 g column, $SiO_2$ Gold) eluting with 20-100% EtOAc/hexanes to afford 700 mg of (R)—N-(tert-butyl)-2-(6-(3-methylmorpholino)-1-(1-((2-(trimethylsilyl)ethoxy)methyl)-1H-pyrazol-3-yl)-1H-pyrazolo[3,4-b]pyridin-4-yl)benzenesulfonamide.

Step 2. To a solution of (R)—N-(tert-butyl)-2-(6-(3-methylmorpholino)-1-(1-((2-(trimethylsilyl)ethoxy)methyl)-1H-pyrazol-3-yl)-1H-pyrazolo[3,4-b]pyridin-4-yl)benzenesulfonamide (700 mg, 1.12 mmol) and triethylsilane (0.68 mL, 4.26 mmol) in DCM (10 mL) at rt was added TFA (9 mL, 118 mmol). The reaction mixture was stirred at rt for 4 h. The volatiles were removed under vacuo and the residue was dissolved in TFA (10 mL). The mixture was stirred at rt for 18 h, then heated to 40° C. for 1 h and 50° C. for 1 h. The volatiles were removed under reduced pressure and co-evaporated with DCM (3×). The residue was adsorbed on silica gel for purification by ISCO CombiFlash (24 g column Gold $SiO_2$) eluting with 30-100% EtOAc/hexanes. The desired product fractions were combined and concentrated to dryness under reduced pressure. The residue was dissolved in $CH_3CN$ (3 mL) and water (5 mL) for lyophilization to afford 350 mg of (R)-2-(6-(3-methylmorpholino)-1-(1H-pyrazol-3-yl)-1H-pyrazolo[3,4-b]pyridin-4-yl) benzenesulfonamide as a light yellow foam. +ESI [M+1]: 440.2. Purity by HPLC at 254 nm: >99%, 10-90% $CH_3CN$/$H_2O$ (+0.1% formic acid) over 20 min. $^1$H NMR (400 MHz, DMSO): δ 12.83 (s; 1H); 8.11-8.13 (m; 1H); 7.86 (s; 1H); 7.68-7.72 (m; 2H); 7.61 (s; 1H); 7.50-7.52 (m; 1H); 7.42 (s; 2H); 6.83 (s; 1H); 6.80 (s; 1H); 4.33-4.38 (m; 1H); 4.08 (d; J=13.32 Hz; 1H); 3.97-4.00 (m; 1H); 3.73-3.76 (m; 1H); 3.64-3.68 (m; 1H); 3.49-3.55 (m; 1H); 3.15-3.21 (m; 1H); 1.22 (d; J=6.61 Hz; 3H).

Compound 138

Step 1. (3R)-4-[4-iodo-1-[2-[(4-methoxyphenyl)methyl]pyrazol-3-yl]pyrazolo[3,4-b]pyridin-6-yl]-3-methyl-morpholine (500 mg, 0.943 mmol), bis(pinacolato)diboron (359 mg, 1.41 mmol) and potassium acetate (324 mg, 3.30 mmol) were combined in DMF (5 mL) and this solution was degassed by bubbling $N_2$ through the mixture with sonication for 10 minutes. Pd(dppf)$Cl_2$.DCM (69 mg, 0.0943 mmol) was then added and the mixture degassed again for 5 minutes. The reaction was then heated to 95° C. for 2 h. The mixture was cooled to rt and partitioned between EtOAc and water (3 volumes each). The organic layer was washed with water (2×3 volumes), dried over $Na_2SO_4$ and concentrated to dryness. The product was then purified by combiflash (0-100% EtOAc/hex).

Step 2. A solution of (3R)-4-[1-[2-[(4-methoxyphenyl)methyl]pyrazol-3-yl]-4-(4,4,5,5-tetramethyl-1,3,2-dioxaborolan-2-yl)pyrazolo[3,4-b]pyridin-6-yl]-3-methyl-morpholine (220 mg, 0.415 mmol) and 3-bromo-6-(trifluoromethyl)pyridin-2-amine (200 mg, 0.830 mmol) in DMF (9 mL) was added aq. $K_2CO_3$ (1.1 mL, 1.24 mmol) and then Pd(dppf)$Cl_2$-DCM complex (68 mg, 0.083 mmol) was added. The reaction was heated to 110° C. in the microwave for 10 minutes. The mixture was cooled to rt and partitioned between EtOAc and water (3 volumes each). The organic layer was washed with water (2×3 volumes), dried over $Na_2SO_4$ and concentrated to dryness. The product was then purified by combiflash (0-100% EtOAc/hex).

Step 3. 3-[1-[2-[(4-methoxyphenyl)methyl]pyrazol-3-yl]-6-[(3R)-3-methylmorpholin-4-yl]pyrazolo[3,4-b]pyridin-4-yl]-6-(trifluoromethyl)pyridin-2-amine (120 mg, 0.213 mmol) was dissolved in trifluoroacetic acid (3.0 mL, 0.21 mmol) and the reaction was stirred for 2 h. The reaction was evaporated to dryness, the residue taken up in DMSO (1 mL) and the product purified by reverse-phase combiflash (5-95% MeCN/water). +ESI [M+1]: 445.0. Purity by HPLC at 254 nm: >99%, 10-90% $CH_3CN$/$H_2O$ (+0.1% formic acid) over 20 min. $^1$H NMR (400 MHz, DMSO-d6) δ 12.81 (s, 1H), 7.84 (brm, 2H), 7.72 (d, J=7.5 Hz, 1H), 7.09 (d, J=7.5 Hz, 1H), 6.86-6.77 (m, 2H), 6.45 (s, 2H), 4.48 (s, 1H), 4.11 (d, J=13.4 Hz, 1H), 4.07-3.93 (m, 1H), 3.75 (d, J=11.3 Hz, 1H), 3.64 (d, J=9.8 Hz, 1H), 3.49 (t, J=11.1 Hz, 1H), 3.20 (t, J=12.6 Hz, 1H), 1.20 (d, J=6.9 Hz, 3H).

Compound 139

Step 1. A solution of [1-[2-[(4-methoxyphenyl)methyl]pyrazol-3-yl]-6-[(3R)-3-methylmorpholin-4-yl]pyrazolo[3,4-b]pyridin-4-yl]boronic acid (250 mg, 0.558 mmol) and 3-bromo-6-methyl-pyridin-2-amine (0.33 mL, 1.12 mmol) in DMF (9 mL) was added $K_2CO_3$ (1.1 mL, 1.67 mmol) and flushed with nitrogen, then added Pd(dppf)$Cl_2$-DCM complex (91 mg, 0.11 mmol). The reaction was heated in the microwave at 100° C. for 10 minutes and then the mixture was cooled to rt and partitioned between EtOAc and water (3 volumes each). The org layer was washed with water (2×3 volumes), dried over $Na_2SO_4$ and concentrated to dryness. The product was then purified by combiflash (0-100% EtOAc/hex).

Step 2. 3-[1-[2-[(4-methoxyphenyl)methyl]pyrazol-3-yl]-6-[(3R)-3-methylmorpholin-4-yl]pyrazolo[3,4-b]pyridin-4-yl]-6-methyl-pyridin-2-amine (250 mg, 0.490 mmol) was dissolved in trifluoroacetic acid (4.0 mL, 0.49 mmol) and the reaction heated to 60° C. and monitored by UPLC-MS. After 1 h, the reaction was cooled to rt and the next day evaporated to dryness. The product was purified by reverse phase chromatography (5-95% MeCN/water). +ESI [M+1]: 391.0 Purity by HPLC at 254 nm: >99%, 10-90% $CH_3CN$/$H_2O$ (+0.1% formic acid) over 20 min. $^1$H NMR (400 MHz, DMSO-d6) δ 12.81 (s, 1H), 7.84 (br, 2H), 7.59 (br, 1H), 6.82-6.76 (m, 2H), 6.68 (s, 1H), 4.46 (s, 1H), 4.09 (d, J=13.3 Hz, 1H), 3.97 (d, J=10.2 Hz, 1H), 3.75 (d, J=11.3 Hz, 1H), 3.64 (d, J=11.8 Hz, 1H), 3.49 (t, J=10.6 Hz, 1H), 3.19 (t, J=13.0 Hz, 1H), 2.55-2.50 (m, 3H), 2.38 (s, 3H), 1.22 (d, J=6.6 Hz, 3H).

Compound 149

Step 1. To a solution of Intermediate C (690 mg, 1.28 mmol) in chloroform (10 mL) was added N-chlorosuccinimide (170 mg, 1.27 mmol) and stirred at rt overnight. The solution was heated up to 65° C. for 1 h, then added an extra 138 mg of added N-chlorosuccinimide and stirred at 65° C. for 2 h. The solvent was removed under reduced pressure and the residue was purified by silica gel chromatography eluting with 0-100% EtOAc/hexanes to afford of 2-[[5-[5-chloro-4-iodo-6-[(3R)-3-methylmorpholin-4-yl]pyrazolo[3,4-b]pyridin-1-yl]pyrazol-1-yl]methoxy]ethyl-trimethyl-silane (240 mg).

Step 2. To a solution of 2-[[5-[5-chloro-4-iodo-6-[(3R)-3-methylmorpholin-4-yl]pyrazolo[3,4-b]pyridin-1-yl]pyrazol-1-yl]methoxy]ethyl-trimethyl-silane (107 mg, 0.187 mmol) and 4,4,5,5-tetramethyl-2-[2-(trifluoromethyl)phenyl]-1,3,2-dioxaborolane (0.33 mL, 0.382 mmol) in 1,4-dioxane (1 mL) was added $K_3PO_4$ (0.50 mL, 0.560 mmol). The vial was flushed with nitrogen, then added Pd(dppf)$Cl_2$ (30 mg, 0.0373 mmol) and heated up to 110° C. for 3 h under microwave. The solution was diluted with water and DCM and filtered on a phase separator. The aqueous phase was washed twice with DCM and the combined organic extracts were evaporated under reduced pressure. The product was used in the next reaction without further purification.

Step 3. To a solution of unpurified 2-[[5-[5-chloro-6-[(3R)-3-methylmorpholin-4-yl]-4-[2-(trifluoromethyl)phenyl]pyrazolo[3,4-b]pyridin-1-yl]pyrazol-1-yl]methoxy]ethyl-trimethylsilane (110 mg, 0.186 mmol) in DCM (1 mL) was added 0.2 mL of triethylsilane and 1 mL of TFA. The resulting solution was stirred at rt for 1 h and the solvent was removed under reduced pressure. The residue was purified using reverse phase chromatography eluting with 0-100% MeCN/$H_2O$ followed by additional purification using normal phase chromatography eluting with 0-10% MeOH/DCM to afford the desired product as a 1:1 mixture of atropisomers which was used for biological testing. Further purification using chiral SFC affording the two separated atropisomers (respectively 4.0 mg, 6.8% and 4.7 mg, 8.0%). Mass spec: m/z: 463.2.

Compound 150

Step 1. 2,6-difluoro-4-iodo-pyridine-3-carboxaldehyde (9.00 g, 33.5 mmol) was dissolved in DMSO (330 mL) and (3R)-3-methylmorpholine (3.8 mL, 33.3 mmol) was added. The solution was heated at 120° C. for 2 h. The solution was cooled and added dropwise to water (1.5 L) with vigorous stirring. Ice was then added and the suspension was stirred for another 2 h. The solids were filtered and dried under house vacuum for 15 h. The resulting beige solid (10.9 g) was dissolved in a minimum of DCM and purified by silica gel chromatography (0 to 100% EtOAc/Hexanes gradient) to afford 2-fluoro-4-iodo-6-[(3R)-3-methylmorpholin-4-yl] pyridine-3-carbaldehyde (6.36 g, 18.16 mmol) as a beige solid.

Step 2. To a solution of 2-fluoro-4-iodo-6-[(3R)-3-methylmorpholin-4-yl]pyridine-3-carbaldehyde (5.86 g, 16.7 mmol) in tert-butanol (20 mL) and water (6.5 mL) at rt was added 2-methyl-2-butene (82 mL, 164 mmol), sodium chlorite (7.56 g, 83.6 mmol) and sodium phosphate monobasic-dihydrate (2.64 g, 16.9 mmol). The resulting mixture was stirred at rt for 15 h. A saturated aq. solution of sodium sulfite was slowly added followed by addition of formic acid until acidic pH was reached. EtOAc was added and the phases were separated. The aqueous phase was extracted 3 times with EtOAc, and the combined organic extracts were dried over $MgSO_4$, filtered and evaporated under reduced pressure to give a beige solid. This material was triturated in $Et_2O$ for 30 minutes before being filtered to provide 2.06 g of an off-white solid. The filtrate was concentrated and purified on a 100 g C18 column using a 0 to 100% MeCN/water gradient to afford an additional 2.83 g of beige solid for a total of 4.89 g of 2-fluoro-4-iodo-6-[(3R)-3-methylmorpholin-4-yl]pyridine-3-carboxylic acid.

Step 3. To 2-fluoro-4-iodo-6-[(3R)-3-methylmorpholin-4-yl]pyridine-3-carboxylic acid (4.89 g, 13.4 mmol) in DMF (67 mL) was added azaniumyl-[2-[(4-methoxyphenyl) methyl]pyrazol-3-yl]ammonium dichloride (4.65 g, 16.0 mmol) followed by 2,6-lutidine (12 mL, 100 mmol). HATU (6.17 g, 16.2 mmol) was then added and the reaction mixture was stirred at rt for 1 h. The solution was then added dropwise into water (400 mL) with vigorous stirring to provide a suspension which was stirred for 1 h prior to filtration. The resulting solid was dried under vacuum for 15 h to afford 2-fluoro-4-iodo-N'-[2-[(4-methoxyphenyl) methyl]pyrazol-3-yl]-6-[(3R)-3-methylmorpholin-4-yl] pyridine-3-carbohydrazide (7.48 g, 13.2 mmol) as a beige solid.

Step 4. 2-fluoro-4-iodo-N'-[2-[(4-methoxyphenyl) methyl]pyrazol-3-yl]-6-[(3R)-3-methylmorpholin-4-yl] pyridine-3-carbohydrazide (2.00 g, 3.53 mmol) was dissolved in DMF (70 mL) and NaH (285 mg, 7.13 mmol) was added. The mixture was stirred at rt for 10 minutes then heated slowly to 60° C. over 30 min. Water, brine and EtOAc were added and the phases were separated. The aqueous phase was extracted 3 times with EtOAc and the combined organics were dried over $MgSO_4$, filtered and evaporated under reduced pressure. The resulting material was purified by silica gel chromatography (0 to 10% MeOH/DCM gradient) afford 4-iodo-1-[2-[(4-methoxyphenyl)methyl]pyrazol-3-yl]-6-[(3R)-3-methylmorpholin-4-yl]-2H-pyrazolo[3,4-b]pyridin-3-one (1.19 g, 2.18 mmol) as a brown solid.

Step 5. To a solution of 4-iodo-1-[2-[(4-methoxyphenyl) methyl]pyrazol-3-yl]-6-[(3R)-3-methylmorpholin-4-yl]-2H-pyrazolo[3,4-b]pyridin-3-one (100 mg, 0.183 mmol) and 2-trifluoromethylphenylboronic acid (87 mg, 0.43 mmol) in 1,4-dioxane (1.8 mL) was added $K_2CO_3$ (0.28 mL, 0.55 mmol). The mixture was flushed with nitrogen for 5 minutes before Pd(dppf)Cl$_2$ (30 mg, 0.037 mmol) was added then heated to 110° C. for 15 minutes under microwave irradiation. Water was added along with DCM and the phases were separated. The aqueous phase was extracted 3× with DCM and the organic extracts were combined, dried over $MgSO_4$, filtered and evaporated under reduced pressure to afford 1-[2-[(4-methoxyphenyl)methyl]pyrazol-3-yl]-6-[(3R)-3-methylmorpholin-4-yl]-4-[2-(trifluoromethyl)phenyl]-2H-pyrazolo[3,4-b]pyridin-3-one (103 mg, 0.182 mmol) as a black solid. The material was used in the next step without purification.

Step 6. The unpurified material from Step 5 was dissolved in trifluoroacetic acid (2.0 mL) and stirred at 60° C. for 1.5 h then concentrated in vacuo. The resulting material was dissolved in DMSO (1 mL) and purified by silica gel chromatography (0 to 100% MeCN/water gradient) to afford 6-[(3R)-3-methylmorpholin-4-yl]-1-(1H-pyrazol-5-yl)-4-[2-(trifluoromethyl)phenyl]-2H-pyrazolo[3,4-b]pyridin-3-one (35 mg, 0.079 mmol) as a beige solid. $^1$H NMR (400 MHz, DMSO-d$_6$) δ12.60 (s, 1H), 10.86 (s, 1H), 7.84 (d, J=7.8 Hz, 1H), 7.79-7.75 (m, 1H), 7.73 (t, J=7.5 Hz, 1H), 7.65 (t, J=7.6 Hz, 1H), 7.47 (d, J=7.0 Hz, 1H), 6.76 (s, 1H), 6.48 (d, J=5.5 Hz, 1H), 4.44-4.33 (m, 1H), 4.12-4.03 (m, 1H), 4.01-3.91 (m, 1H), 3.73 (d, J=11.4 Hz, 1H), 3.65 (dd, J=11.4, 2.7 Hz, 1H), 3.57-3.46 (m, 1H), 3.17 (td, J=12.7, 12.2, 3.5 Hz, 1H), 1.20 (dd, J=10.9, 6.6 Hz, 3H).

Example 2. ATR/ATRIP Enzymatic Assay

Detection of ATR kinase activity utilized the AlphaScreen system to measure the phosphorylation of the substrate protein p53. Recombinant purified ATR/ATRIP (Eurofins cat #14-953) at a final concentration of 0.63 nM in assay buffer (50 mM Hepes pH 7.4, 0.1 mM vanadate, 0.5 mM DTT, 0.1 mM EGTA, 5 mM MnCl$_2$, 0.01% Brij-30, 1% glycerol, 0.05% BSA) was mixed with compound serially diluted in 10% DMSO. The final DMSO concentration was 1.25%. A pre-mix of GST-tagged p53 (full length, Enzo Life Sciences cat # BML-FW9370) and adenosine 5'-triphosphate, ATP (Sigma-Aldrich cat #10519979001, Roche Diagnostic) in assay buffer was added to the enzyme:compound mix for a final concentration of 25 nM GST-p53 and 3 μM ATP. The reaction was allowed to proceed at room temperature for 1 hour then stopped by the addition of a pre-mix of phospho-p53 (Ser 15) antibody (New England Biolabs cat #9284S) at 1:3000 final dilution, 14.3 pg/mL glutathione donor beads (PerkinElmer Life Sciences cat #6765301) and 14.3 pg/mL protein A acceptor beads (PerkinElmer Life Sciences cat #670137) final bead concentration in buffer (60 mM EDTA in 50 mM Tris, pH 7.4 and 0.1% BSA). Plates were incubated at room temperature in the dark for 4 hours and read on a BMG Polarstar using AlphaScreen dedicated filters. The assay was run in a 96-well format using white polypropylene half-area plates (Costar cat #3693). IC$_{50}$ values were determined using a 4-parameter fit algorithm.

Example 3. ATR Assay in Hela Cells

HeLa S3 cells were plated in 384-plate format at a density of 16K cells per 25 μL well in regular media F-12K 10% FBS and incubated overnight at 37° C. 1-5% CO$_2$. Media was then replaced by 20 μL per well Opti-MEM no phenol red and 5 μL of serial diluted compounds were added to the assay plate for a final DMSO concentration of 0.5%. Cells and compounds were incubated at room temperature for 20 minutes before addition of 5 μL of gemcitabine at a final concentration of 1.5 μM. The plate was incubated at 37° C., 1-5% $CO_2$ for 3.5 to 4 hours. The media was removed and the cells were lysed in 15 μL of PerkinElmer lysis buffer for 10-20 min; 4 μL of lysates were then transferred to proxi white plate 384-format ((PerkinElmer Life Sciences cat #6008280). Quantification of CHK1 phosphorylation at Ser345 was done using Alphascreen SureFire CHK1 p-Ser345 (PerkinElmer Life Sciences cat # TGRCHK1S1 OK) and Alphascreen protein A. (PerkinElmer Life Sciences cat #67060617C). The plate was read on an Envision using AlphaScreen dedicated filters. $IC_{50}$ values were determined using a 4-parameter fit algorithm.

Exemplary prepared compounds and their activities in the ATR/ATRIP enzymatic assays are shown in Table 2 below.

TABLE 2

| Compound | Method | Structure | ATR IC50 (nM) | MS (+ESI) [M + 1] |
|---|---|---|---|---|
| 1 | A | 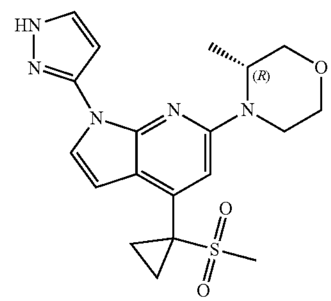 | 57 | m/z 441.1 |
| 2 | E | 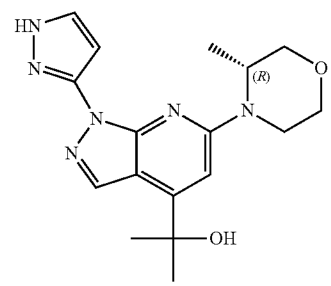 | 40 | m/z 343.2 |
| 3 | D | 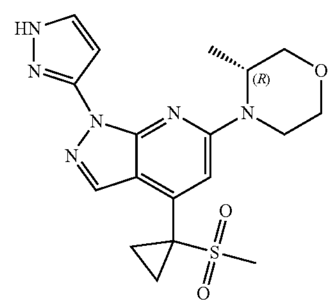 | 9 | m/z 403.1 |
| 4 | F | 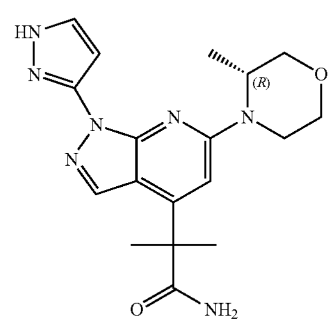 | 56 | m/z 370.2 |

TABLE 2-continued

| Compound | Method | Structure | ATR IC50 (nM) | MS (+ESI) [M + 1] |
|---|---|---|---|---|
| 5 | F | 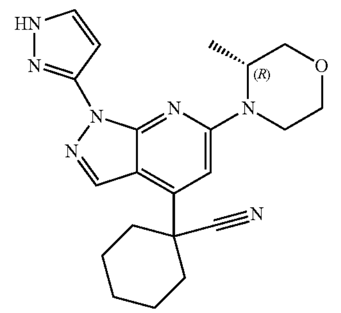 | 3 | m/z 392.2 |
| 6 | B | 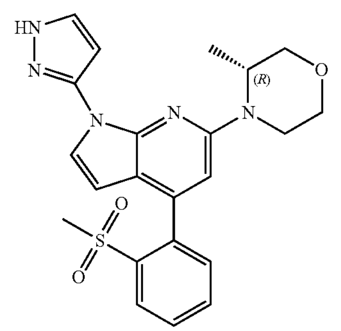 | 425 | m/z 438.2 |
| 7 | B | 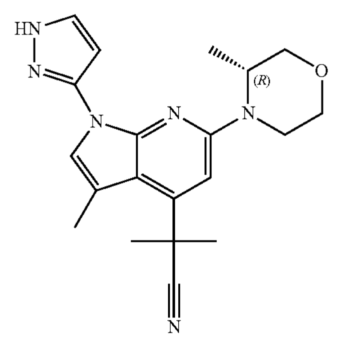 | 403 | m/z 365.2 |
| 8 | G | 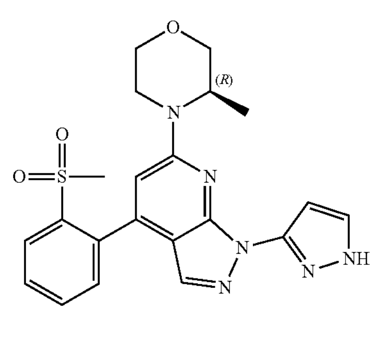 | 316 | m/z 438.9 |

TABLE 2-continued

| Compound | Method | Structure | ATR IC50 (nM) | MS (+ESI) [M + 1] |
|---|---|---|---|---|
| 9 | B | 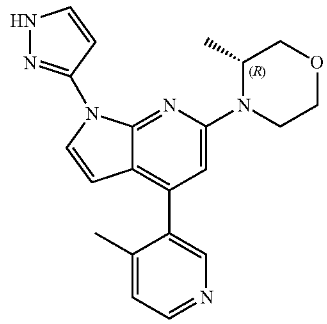 | 37 | m/z 375.1 |
| 10 | H | 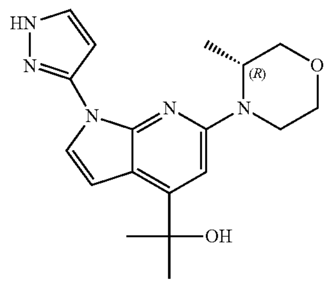 | 1600 | m/z 342.1 |
| 11 | B | 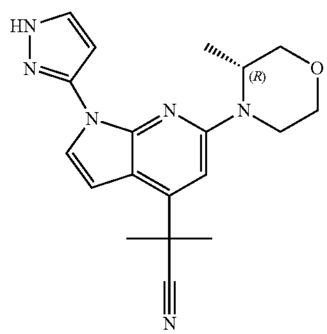 | 101 | m/z 351.2 |
| 12 | B | 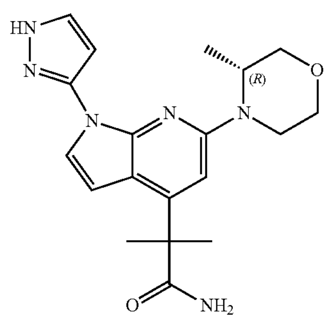 | 379 | m/z 369.2 |
| 13 | B | 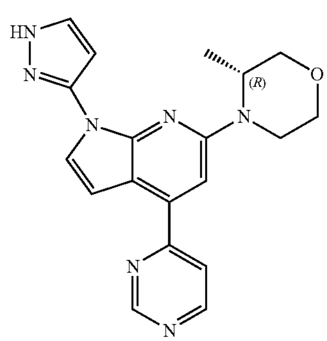 | 1650 | m/z 362.2 |

TABLE 2-continued

| Compound | Method | Structure | ATR IC50 (nM) | MS (+ESI) [M + 1] |
|---|---|---|---|---|
| 14 | B | 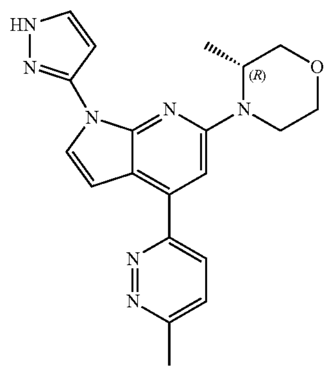 | 1150 | m/z 376.2 |
| 15 | B | 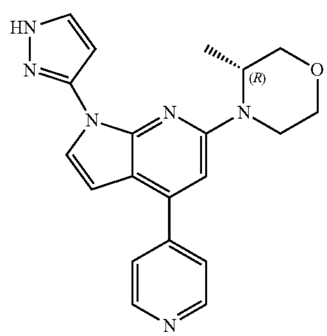 | 1870 | m/z 361.2 |
| 16 | B | 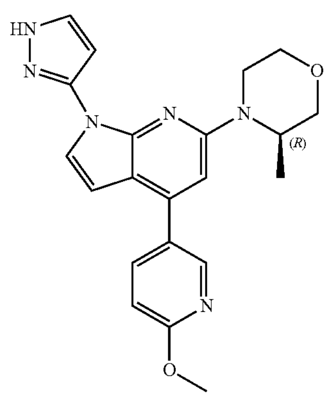 | 1520 | m/z 391.2 |
| 17 | B | 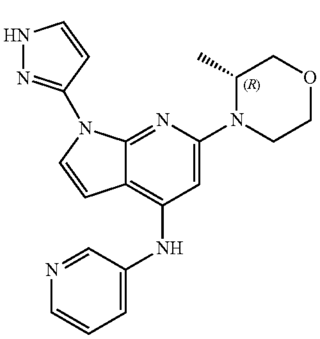 | 1210 | m/z 376.2 |

TABLE 2-continued

| Compound | Method | Structure | ATR IC50 (nM) | MS (+ESI) [M + 1] |
|---|---|---|---|---|
| 18 | I | 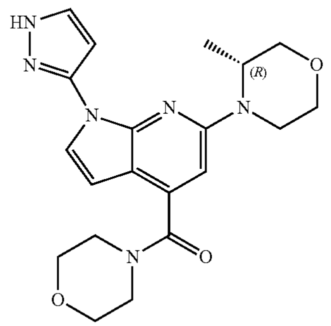 | 1940 | m/z 397.2 |
| 19 | I | 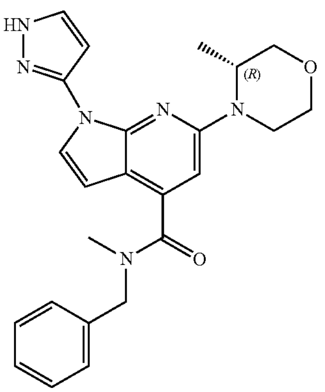 | 540 | m/z 431.2 |
| 20 | B | 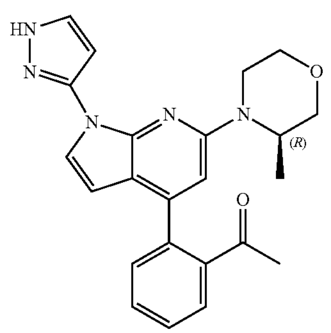 | 229 | m/z 422.2 |
| 21 | B | 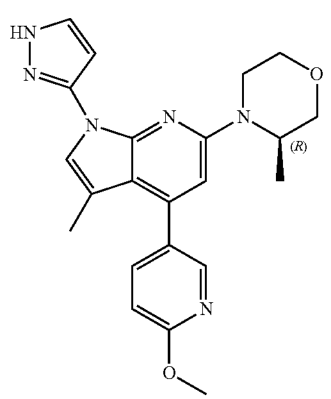 | 828 | m/z 405.2 |

TABLE 2-continued

| Compound | Method | Structure | ATR IC50 (nM) | MS (+ESI) [M + 1] |
|---|---|---|---|---|
| 22 | B | 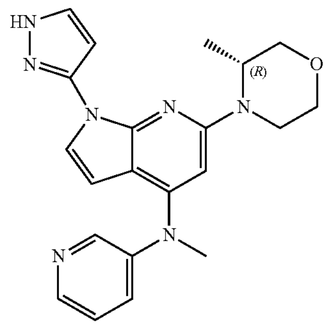 | 876 | m/z 390.2 |
| 23 | I | 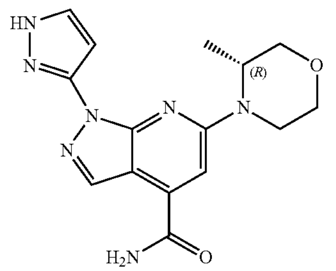 | 264 | m/z 328.2 |
| 24 | F | 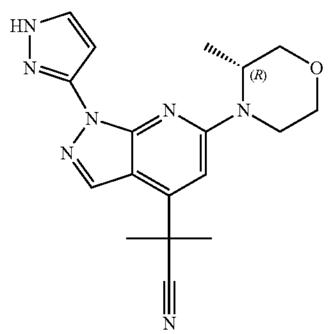 | 6 | m/z 352.2 |
| 25 | B | 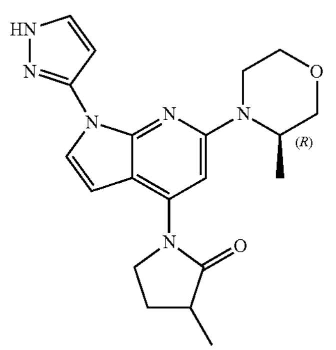 | 1500 | m/z 382.2 |
| 26 | B | 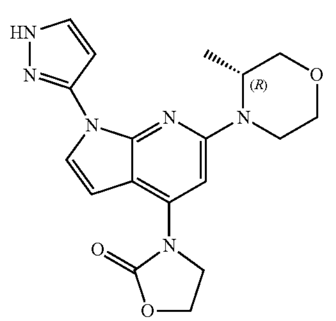 | 860 | m/z 370.2 |

TABLE 2-continued

| Compound | Method | Structure | ATR IC50 (nM) | MS (+ESI) [M + 1] |
|---|---|---|---|---|
| 27 | F | 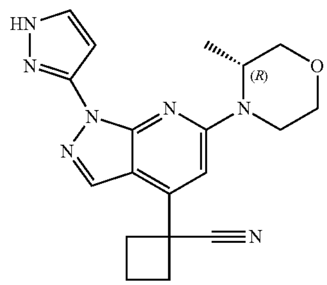 | 135 | m/z 364.2 |
| 28 | F | 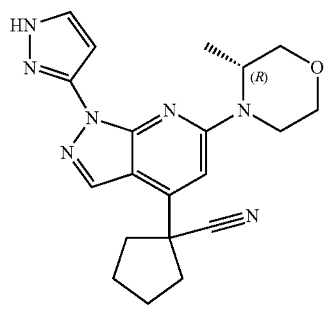 | 4 | m/z 378.2 |
| 29 | B | 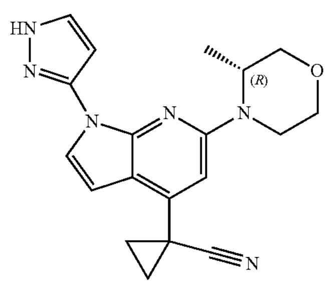 | 580 | m/z 349.2 |
| 30 | E | 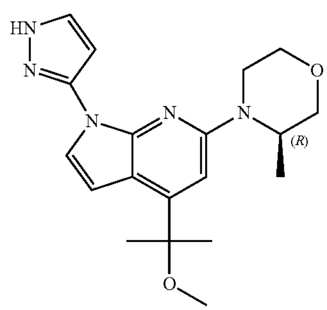 | 284 | m/z 356.2 |
| 31 | F | 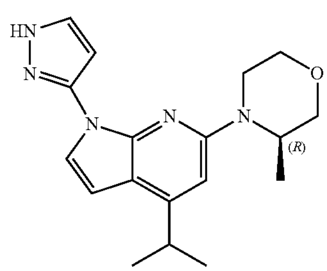 | 1420 | m/z 326.2 |

TABLE 2-continued
| Compound | Method | Structure | ATR IC50 (nM) | MS (+ESI) [M + 1] |
|---|---|---|---|---|
| 32 | F | 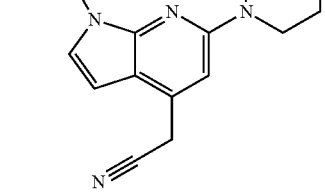 | 54 | m/z 324.2 |
| 33 | J | 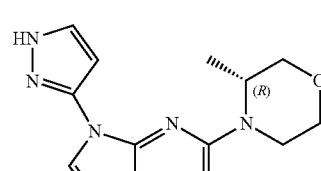 | 154 | m/z 369.1 |
| 34 | B | 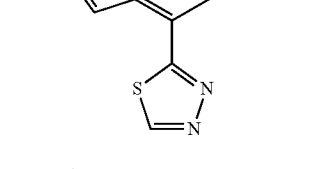 | 451 | m/z 364.1 |
| 35 | A | 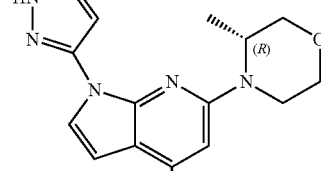 | >1000 | |
| 36 | A | 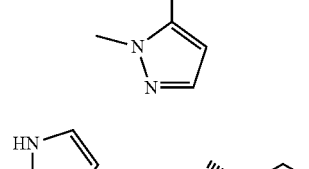 | >1000 | |

TABLE 2-continued

| Compound | Method | Structure | ATR IC50 (nM) | MS (+ESI) [M + 1] |
|---|---|---|---|---|
| 37 | A | 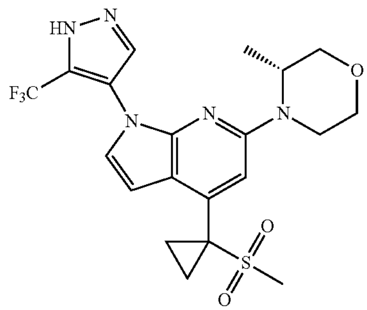 [SMILES: C[C@@H]1COCCN1c1cc(C2(S(C)(=O)=O)CC2)c2ccn(-c3cn[nH]c3C(F)(F)F)c2n1] | >1000 | |
| 38 | A | 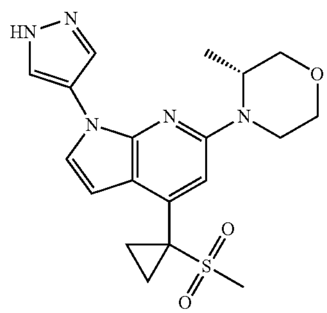 [SMILES: C[C@@H]1COCCN1c1cc(C2(S(C)(=O)=O)CC2)c2ccn(-c3cn[nH]c3)c2n1] | >1000 | |
| 39 | B | 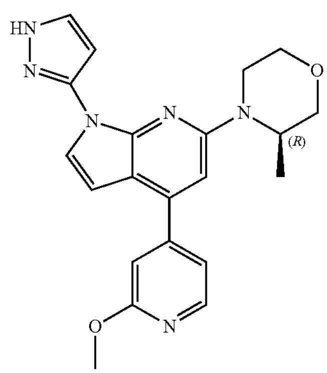 | >10000 | |
| 40 | B | 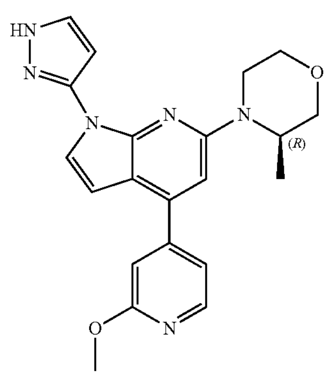 | >10000 | |

TABLE 2-continued

| Compound | Method | Structure | ATR IC50 (nM) | MS (+ESI) [M + 1] |
|---|---|---|---|---|
| 41 | B | 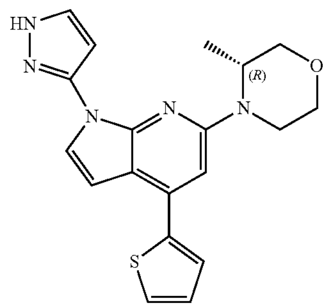 | >10000 | |
| 42 | L | 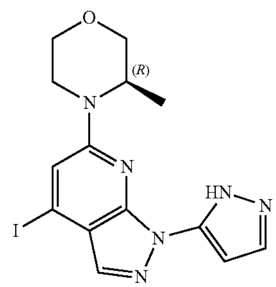 | 32 | 410.72 |
| 43 | M | 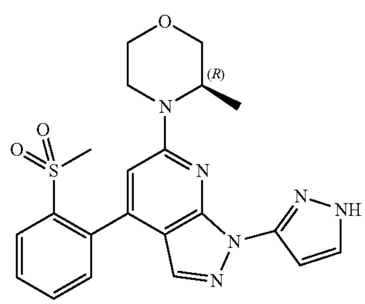 | 10 | 438.87 |
| 44 | O | 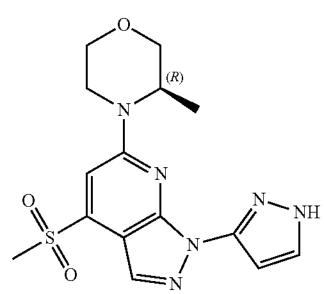 | 27 | 362.86 |
| 45 | O | 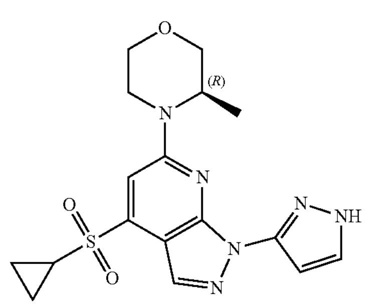 | 5 | 388.82 |

TABLE 2-continued
| Compound | Method | Structure | ATR IC50 (nM) | MS (+ESI) [M + 1] |
|---|---|---|---|---|
| 47 | O | 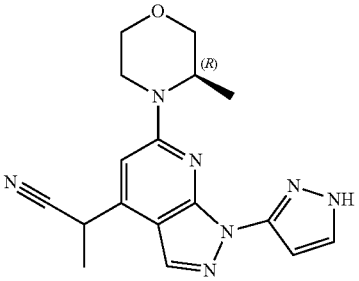 | 12 | 338.16 |
| 48 | M | 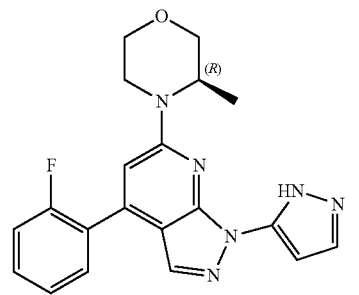 | 5 | 379,13 |
| 49 | M | 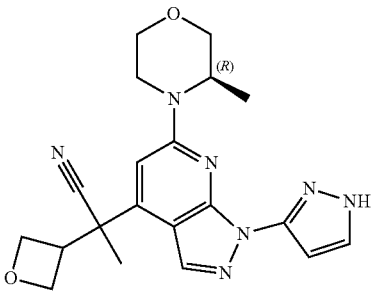 | 11 | 393.86 |
| 50 | O | 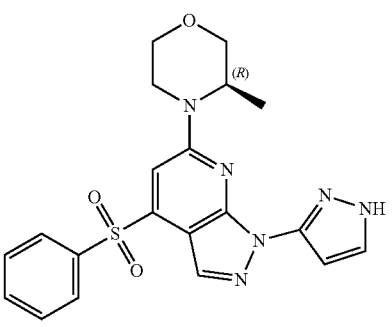 | 116 | 425.13 |
| 51 | O | 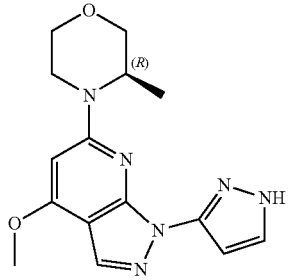 | 141 | 314.93 |

TABLE 2-continued

| Compound | Method | Structure | ATR IC50 (nM) | MS (+ESI) [M + 1] |
|---|---|---|---|---|
| 52 | O | 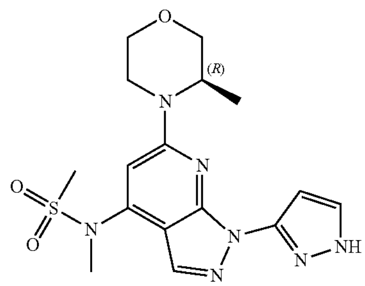 | 8 | 391.87 |
| 53 | O | 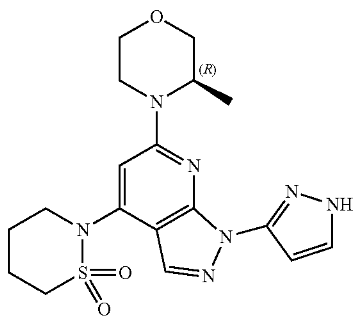 | 9 | 417.89 |
| 54 | O | 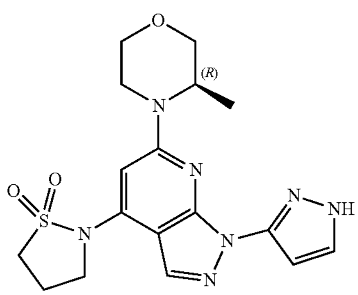 | 23 | 403.89 |
| 55 | O | 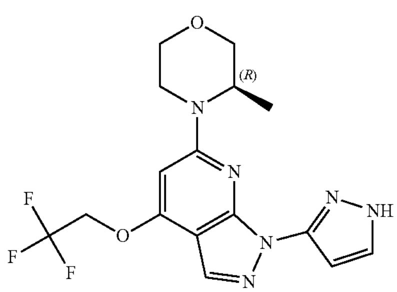 | 13 | 384.1 |
| 56 | N | 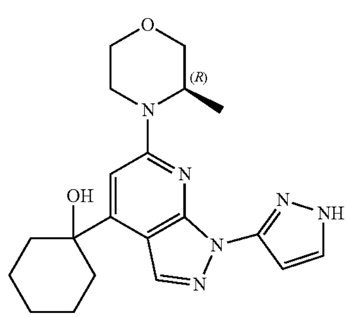 | <5 | 383.97 |

TABLE 2-continued

| Compound | Method | Structure | ATR IC50 (nM) | MS (+ESI) [M + 1] |
|---|---|---|---|---|
| 57 | N | 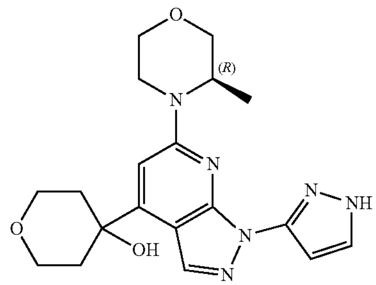 | 11 | 384.97 |
| 58 | N | 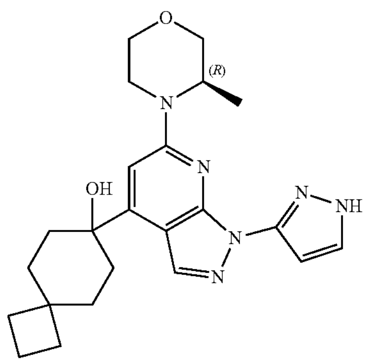 | 6 | 424.0 |
| 59 | N | 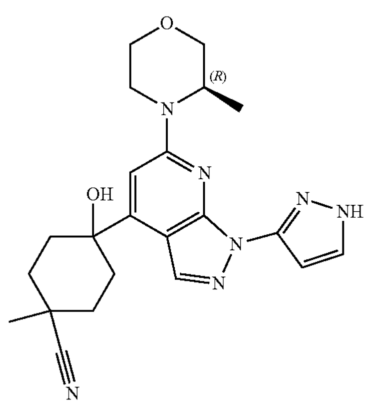 | 10 | 422.08 |
| 60 | N | 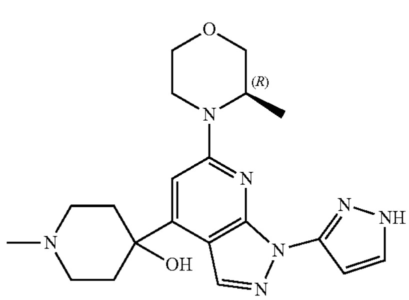 | 37 | 398.18 |

TABLE 2-continued

| Compound | Method | Structure | ATR IC50 (nM) | MS (+ESI) [M + 1] |
|---|---|---|---|---|
| 61 | N | 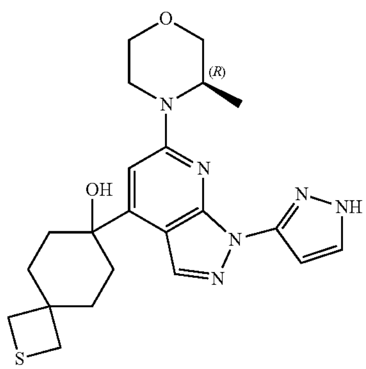 | 2 | 441.19 |
| 62 | N | 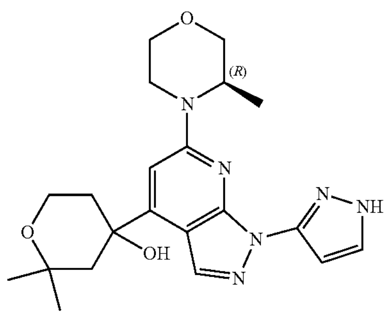 | 19 | 413.25 |
| 63 | E | 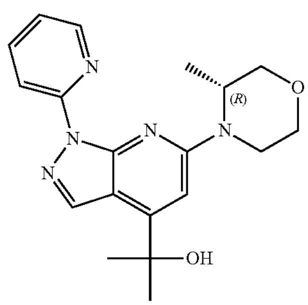 | 11 | 354.2 |
| 64 | E | 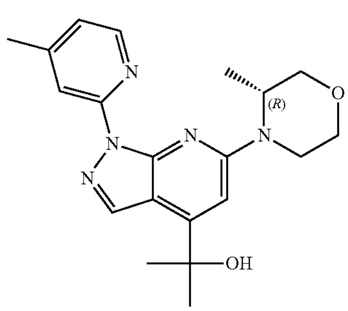 | 92 | 368.2 |

TABLE 2-continued
| Compound | Method | Structure | ATR IC50 (nM) | MS (+ESI) [M + 1] |
|---|---|---|---|---|
| 65 | E | 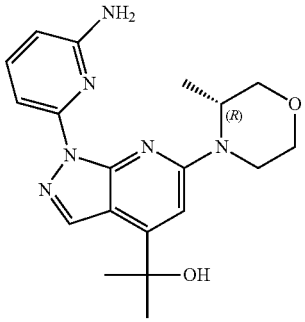 | 104 | 369.2 |
| 66 | F | 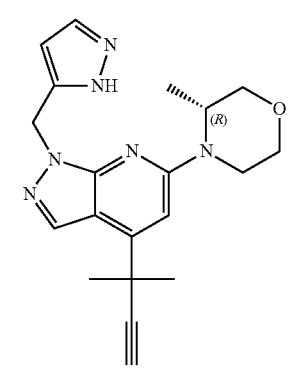 | 448 | 366.2 |
| 67 | E | 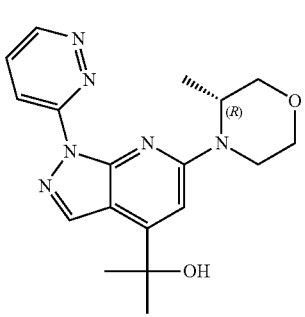 | 198 | 355.2 |
| 68 | F | 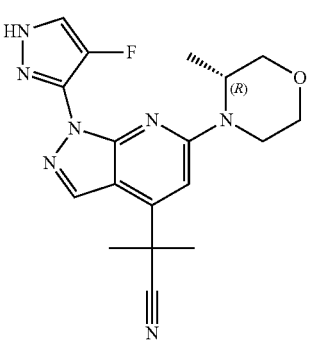 | 1340 | 370.2 |

TABLE 2-continued

| Compound | Method | Structure | ATR IC50 (nM) | MS (+ESI) [M + 1] |
|---|---|---|---|---|
| 69 | F | 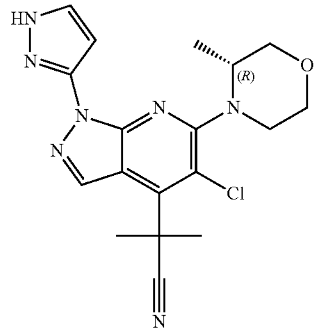 | 554 | 386.1 |
| 70 | P | 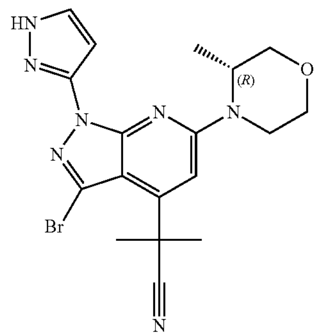 | <5 | 430.2 |
| 71 | P | 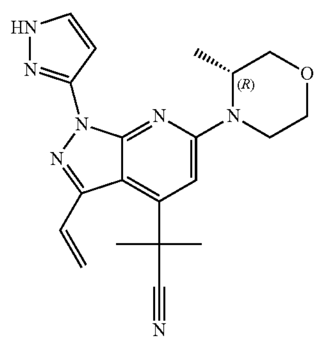 | <5 | 378.2 |
| 72 | J | 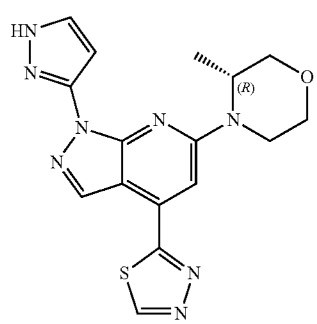 | 94 | 369.1 |

TABLE 2-continued

| Compound | Method | Structure | ATR IC50 (nM) | MS (+ESI) [M + 1] |
|---|---|---|---|---|
| 73 | O | 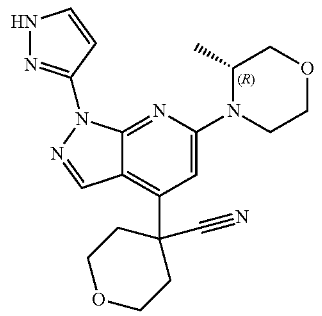 | 3 | 394.2 |
| 74 | O | 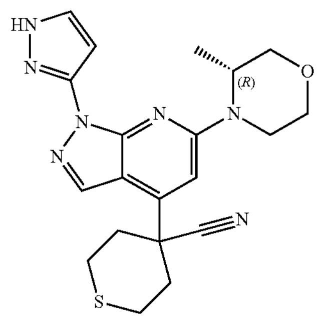 | 8 | 410.2 |
| 75 | O | 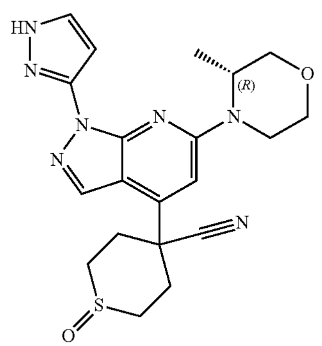 | 29 | 426.2 |
| 76 | O | 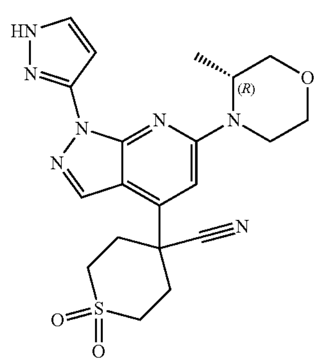 | 36 | 442.1 |

TABLE 2-continued

| Compound | Method | Structure | ATR IC50 (nM) | MS (+ESI) [M + 1] |
|---|---|---|---|---|
| 77 | O | 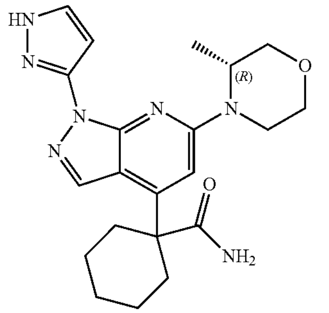 | 5 | 410.3 |
| 78 | O | 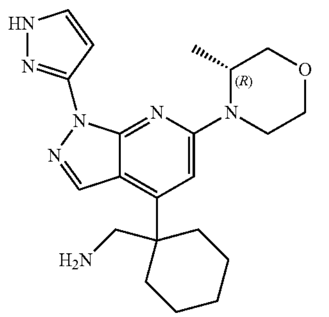 | 24 | 396.3 |
| 79 | O | 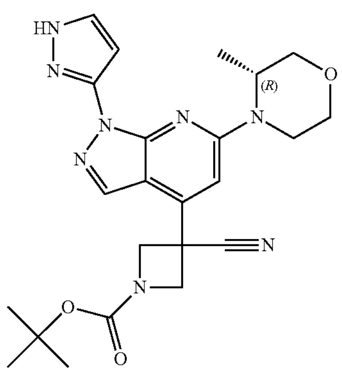 | 30 | 465.3 |
| 80 | O | 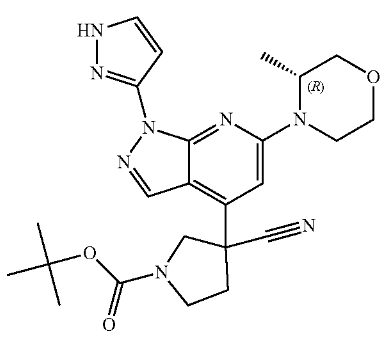 | 6 | 479.3 |

TABLE 2-continued

| Compound | Method | Structure | ATR IC50 (nM) | MS (+ESI) [M + 1] |
|---|---|---|---|---|
| 81 | O | 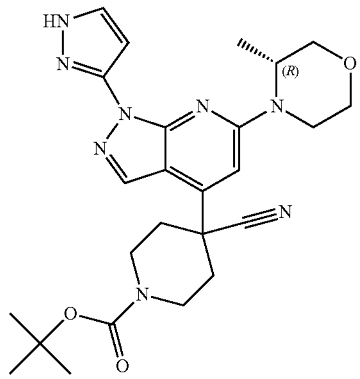 | 8 | 493.25 |
| 82 | O | 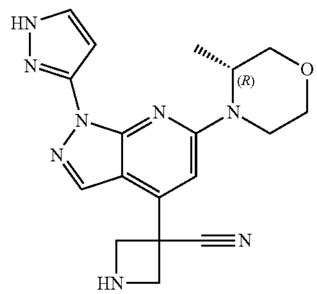 | 17 | 365.2 |
| 83 | O | 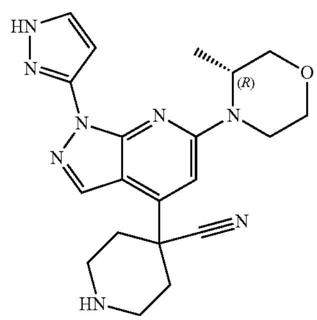 | 22 | 393.2 |
| 84 | O | 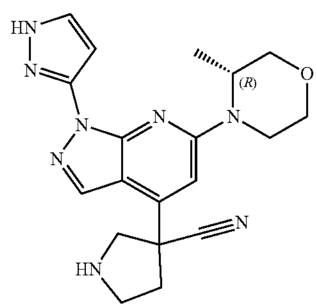 | 9 | 379.2 |
| 86 | Q | 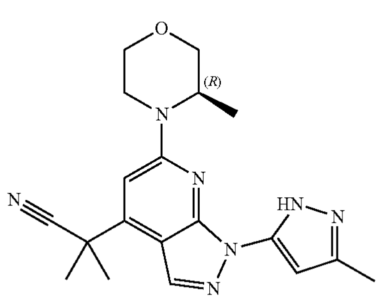 | <5 | 365.85 |

TABLE 2-continued

| Compound | Method | Structure | ATR IC50 (nM) | MS (+ESI) [M + 1] |
|---|---|---|---|---|
| 87 | O | 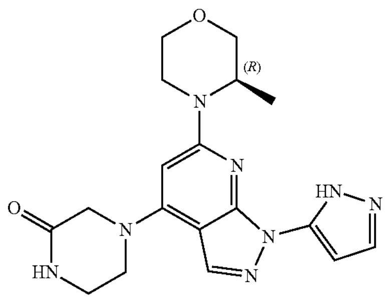 | 10 | 383.24 |
| 88 | M | 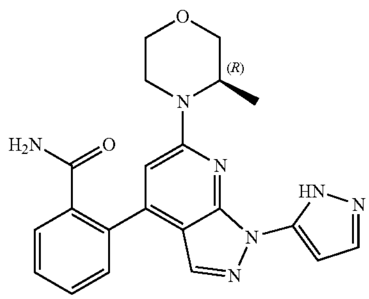 | 30 | 404.15 |
| 89 | M | 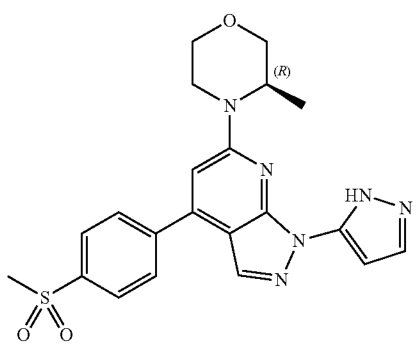 | 31 | 439.2 |
| 90 | F | 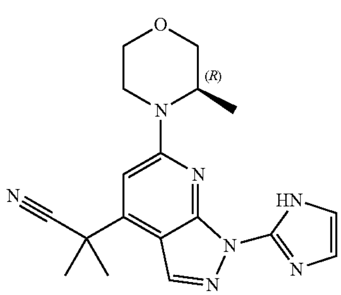 | 165 | 351.91 |
| 91 | M | 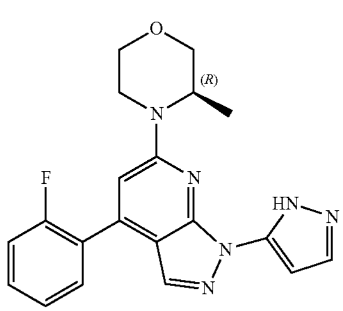 | <5 | 379.13 |

TABLE 2-continued

| Compound | Method | Structure | ATR IC50 (nM) | MS (+ESI) [M + 1] |
|---|---|---|---|---|
| 92 | M | 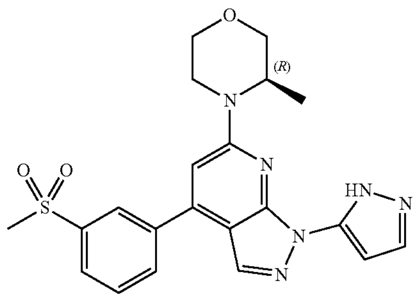 | 8 | 439.07 |

In Table 2, the Method column indicates a preparatory method described above used in the preparation of the compounds.

Exemplary prepared compounds and their ATR inhibitory activities in the HeLa S3 whole cell assay are shown in Table 3 below.

TABLE 3

| Compound | Method | Structure | HeLa S3 ATR IC50 (nM) | MS (+ESI) [M + 1] |
|---|---|---|---|---|
| 93 | N | 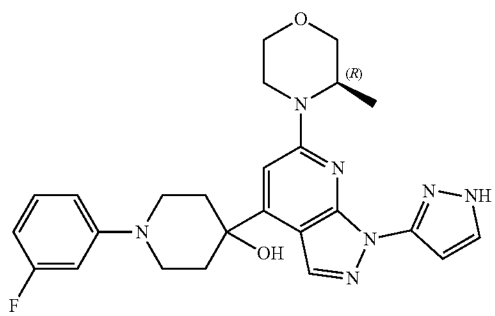 | 0.5 | 478.1 |
| 94 | N | 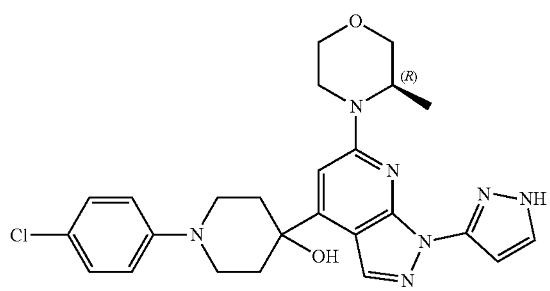 | 1.9 | 494.1 |
| 95 | N | 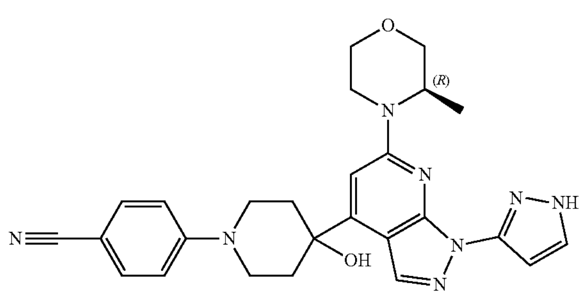 | 2.0 | 485.14 |

TABLE 3-continued

| Compound | Method | Structure | HeLa S3 ATR IC50 (nM) | MS (+ESI) [M + 1] |
|---|---|---|---|---|
| 96 | N | 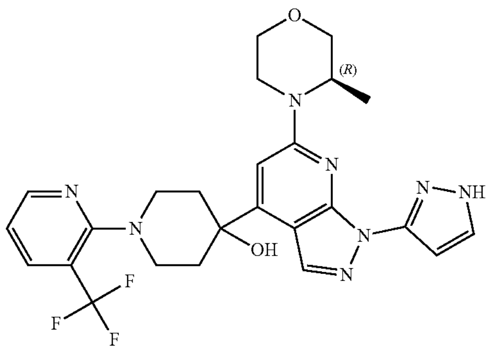 | 20 | 529.28 |
| 97 | N | 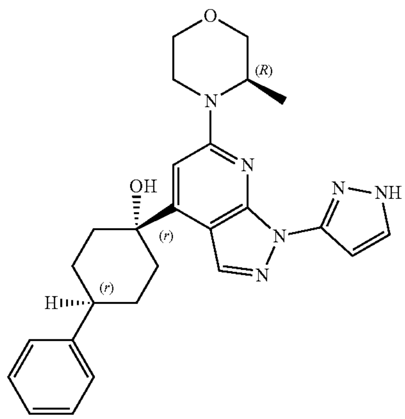 | 0.9 | 459.18 |
| 98 | N | 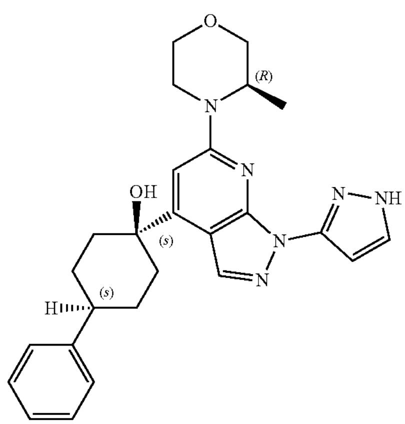 | 1.2 | 458.92 |
| 99 | N | 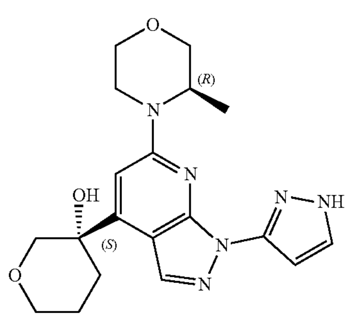 | 3.0 | 385.17 |

TABLE 3-continued

| Compound | Method | Structure | HeLa S3 ATR IC50 (nM) | MS (+ESI) [M + 1] |
|---|---|---|---|---|
| 100 | N | 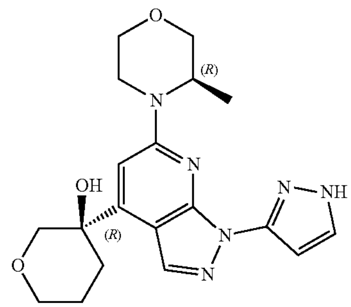 | 2.0 | 385.03 |
| 101 | N | 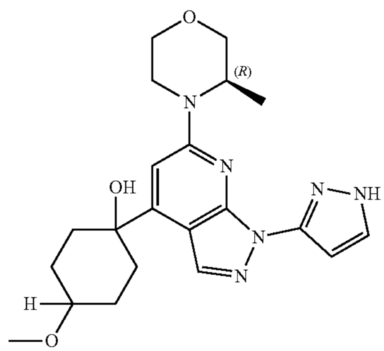 | 1.0 | 412.92 |
| 102 | N | 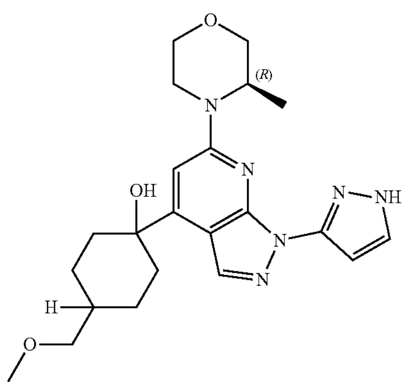 | 0.9 | 427.19 |
| 103 | N | 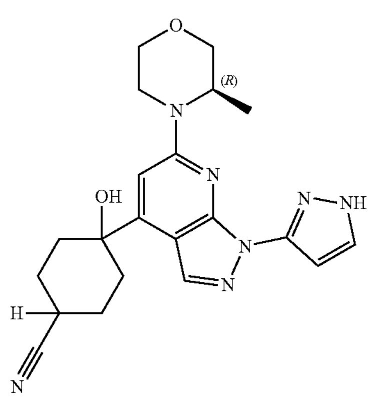 | 1.7 | 407.87 |

TABLE 3-continued

| Compound | Method | Structure | HeLa S3 ATR IC50 (nM) | MS (+ESI) [M + 1] |
|---|---|---|---|---|
| 104 | N | 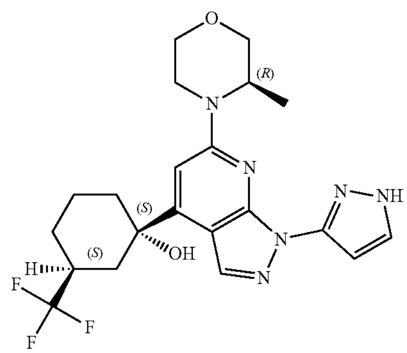 | 2.4 | 451.22 |
| 105 | N | 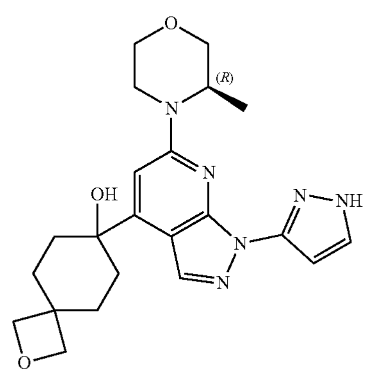 | 1.1 | 426.06 |
| 106 | N | 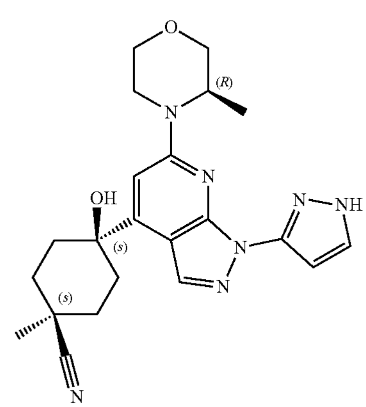 | 3.3 | 422.08 |
| 107 | N | 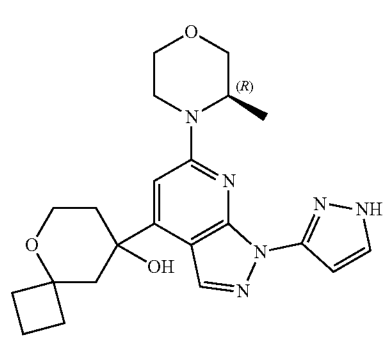 | 2.0 | 425.13 |

TABLE 3-continued

| Compound | Method | Structure | HeLa S3 ATR IC50 (nM) | MS (+ESI) [M + 1] |
|---|---|---|---|---|
| 108 | N | 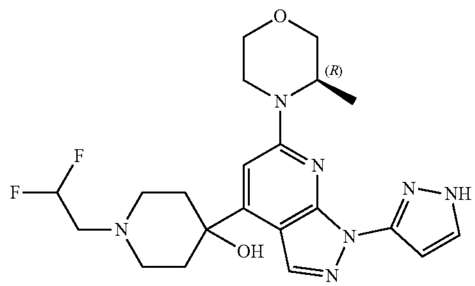 | 1.3 | 448.9 |
| 109 | N | 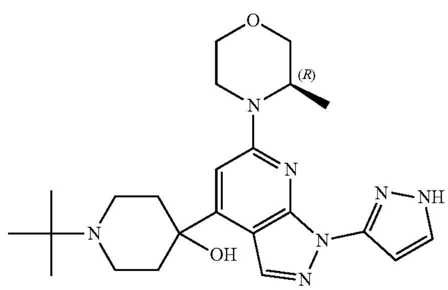 | 17 | 440.13 |
| 110 | N | 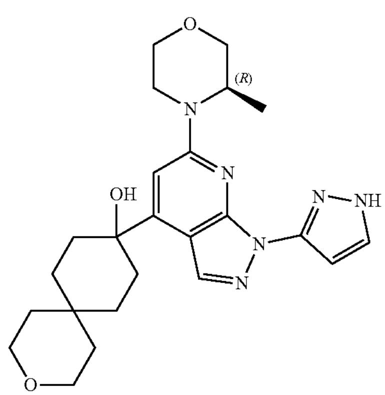 | 0.7 | 453.28 |
| 111 | N | 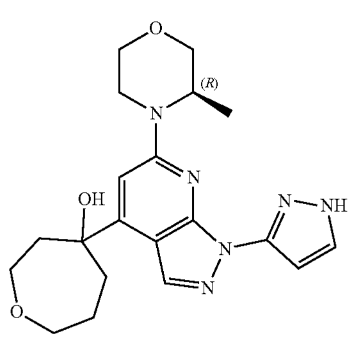 | 2.4 | 399.97 |

TABLE 3-continued

| Compound | Method | Structure | HeLa S3 ATR IC50 (nM) | MS (+ESI) [M + 1] |
|---|---|---|---|---|
| 112 | N | 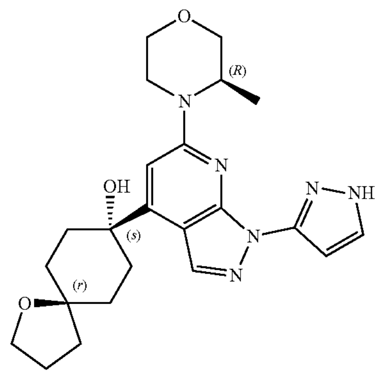 | 0.8 | 438.94 |
| 113 | N | 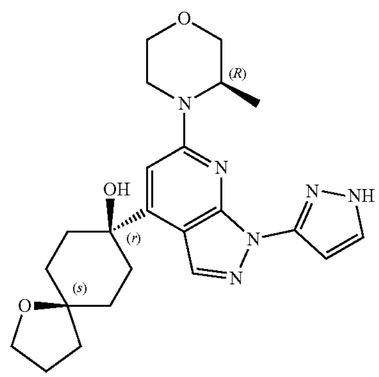 | 2.1 | 439.34 |
| 114 | N | 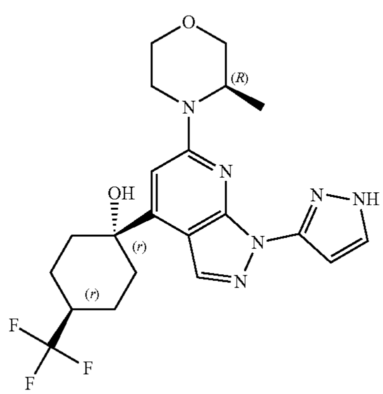 | 0.8 | 451.09 |
| 115 | N | 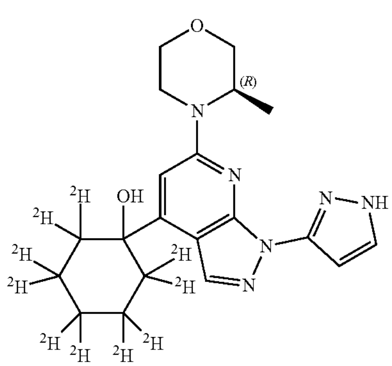 | 1.5 | 393.27 |

TABLE 3-continued

| Compound | Method | Structure | HeLa S3 ATR IC50 (nM) | MS (+ESI) [M + 1] |
|---|---|---|---|---|
| 116 | N | 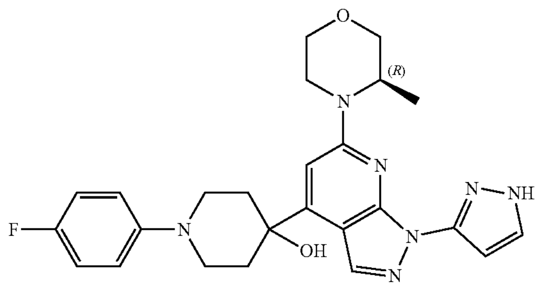 | 1.2 | 479.03 |
| 117 | N | 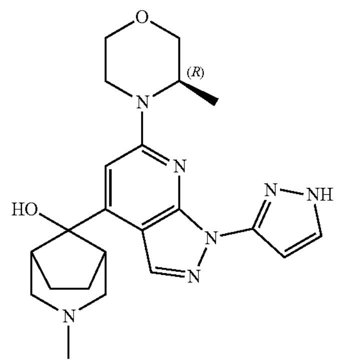 | 38 | 424.93 |
| 118 | N | 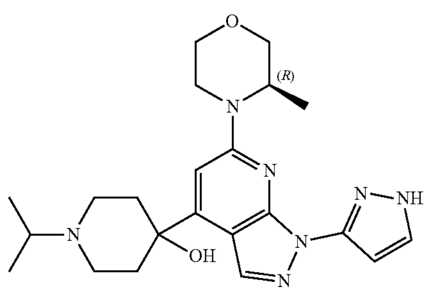 | 6.4 | 426.26 |
| 119 | N | 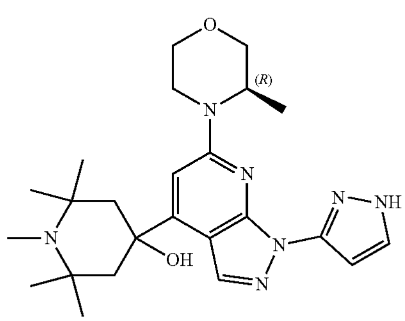 | 14 | 454.27 |
| 120 | N | 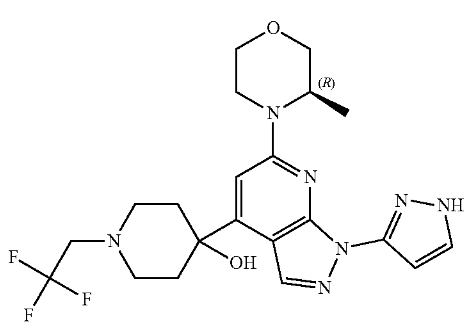 | 1.2 | 466.16 |

TABLE 3-continued

| Compound | Method | Structure | HeLa S3 ATR IC50 (nM) | MS (+ESI) [M + 1] |
|---|---|---|---|---|
| 121 | N | 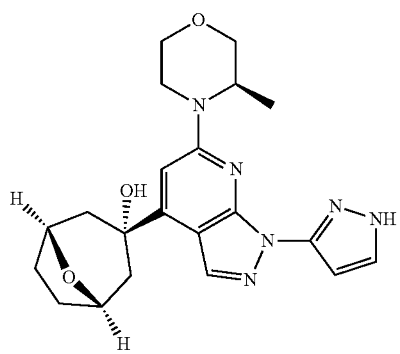 [SMILES: C[C@@H]1COCCN1c1cc([C@]2(O)C[C@H]3CC[C@@H](C2)O3)c2cnn(-c3cc[nH]n3)c2n1] | 0.9 | 411.32 |
| 122 | N | 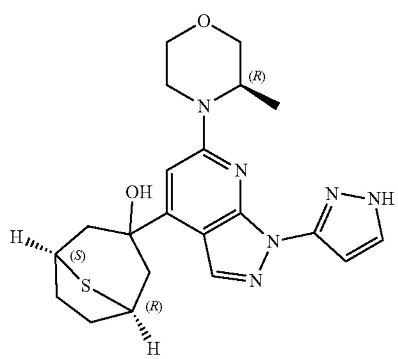 | 1.1 | 427.12 |
| 123 | N | 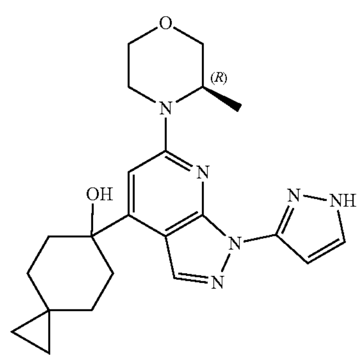 | 0.9 | 409.13 |
| 124 | M | 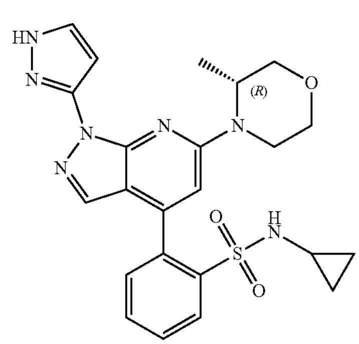 | 63 | 480.2 |

TABLE 3-continued

| Compound | Method | Structure | HeLa S3 ATR IC50 (nM) | MS (+ESI) [M + 1] |
|---|---|---|---|---|
| 125 | M | 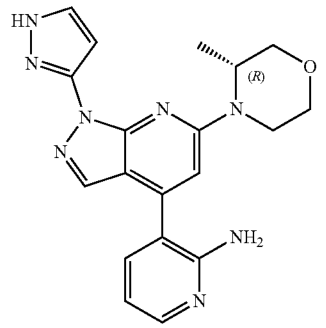 | 11 | 377.1 |
| 126 | M | 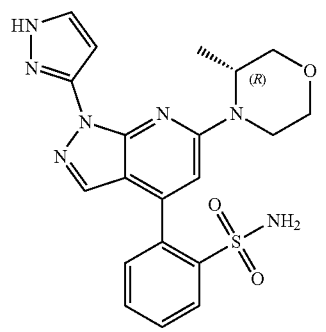 | 17 | 440.2 |
| 127 | M | 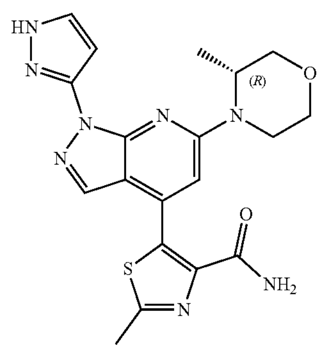 | 7.0 | 425.2 |
| 128 | M | 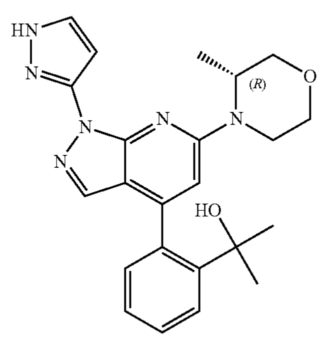 | 2.4 | 419.3 |

TABLE 3-continued

| Compound | Method | Structure | HeLa S3 ATR IC50 (nM) | MS (+ESI) [M + 1] |
|---|---|---|---|---|
| 129 | M | 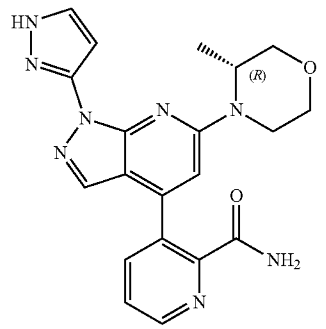 | 11 | 405.20 |
| 130 | M | 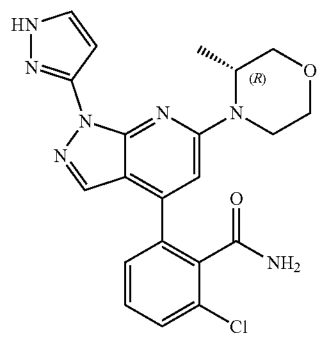 | 13 | 438.20 |
| 131 | M | 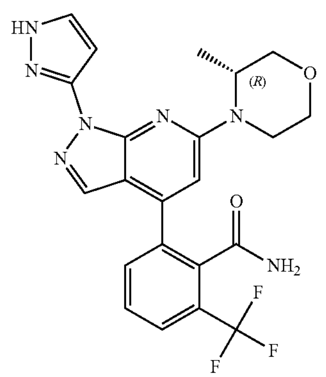 | 1.8 | 472.20 |
| 132 | N | 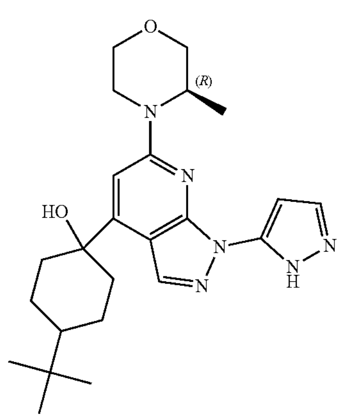 | 1.9 | 439.20 |

TABLE 3-continued

| Compound | Method | Structure | HeLa S3 ATR IC50 (nM) | MS (+ESI) [M + 1] |
|---|---|---|---|---|
| 133 | N | 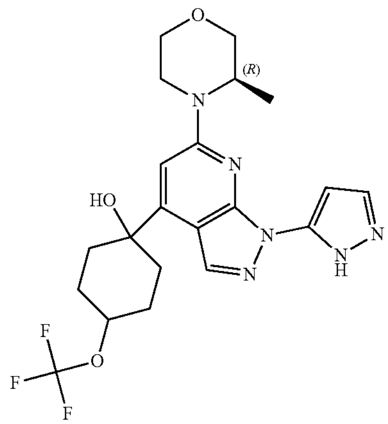 | 1.5 | 466.89 |
| 134 | O | 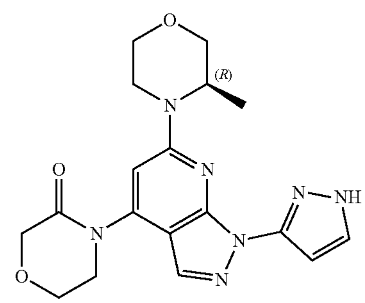 | 41 | 385.1 |
| 135 | N | 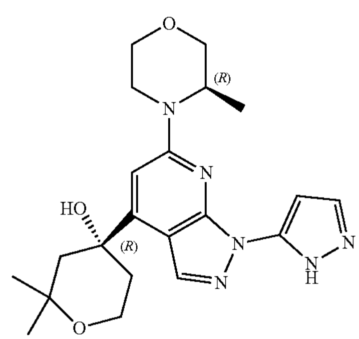 | 3.4 | 413.18 |
| 136 | O | 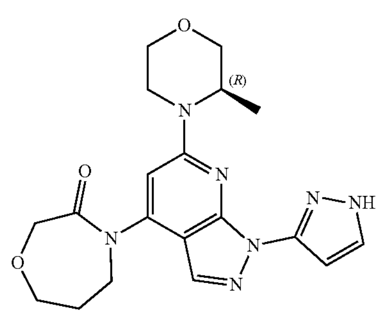 | 46 | 398.18 |

TABLE 3-continued

| Compound | Method | Structure | HeLa S3 ATR IC50 (nM) | MS (+ESI) [M + 1] |
|---|---|---|---|---|
| 137 | O | 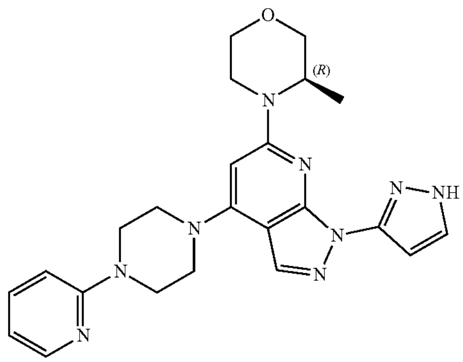 | 2.1 | 446.37 |
| 138 | R | 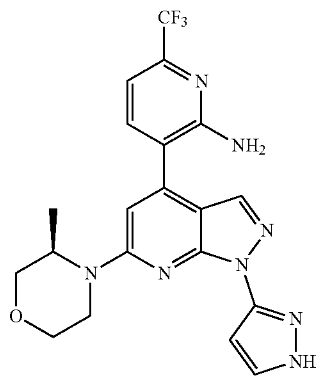 [SMILES: C[C@@H]1COCCN1c1cc(-c2ccc(C(F)(F)F)nc2N)c2cnn(-c3cc[nH]n3)c2n1] | 9.4 | 445.0 |
| 139 | M | 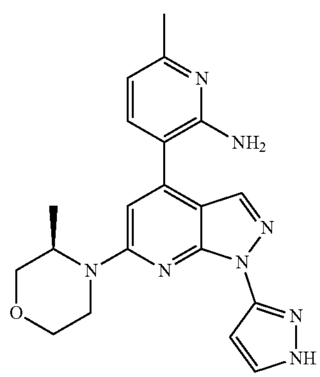 [SMILES: Cc1ccc(-c2cc(N3CCOC[C@H]3C)nc3c2cnn3-c2cc[nH]n2)c(N)n1] | 4.2 | 391.0 |
| 140 | M | 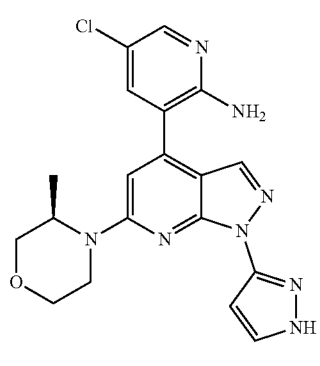 [SMILES: C[C@@H]1COCCN1c1cc(-c2cc(Cl)cnc2N)c2cnn(-c3cc[nH]n3)c2n1] | 7.2 | 411.1/413.1 |

TABLE 3-continued

| Compound | Method | Structure | HeLa S3 ATR IC50 (nM) | MS (+ESI) [M + 1] |
|---|---|---|---|---|
| 141 | B | 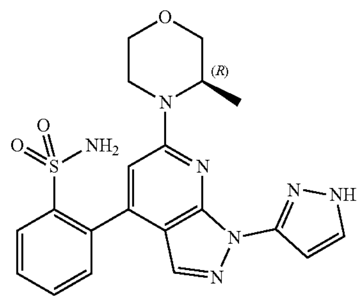 | 9.3 | 439.9 |
| 142 | M | 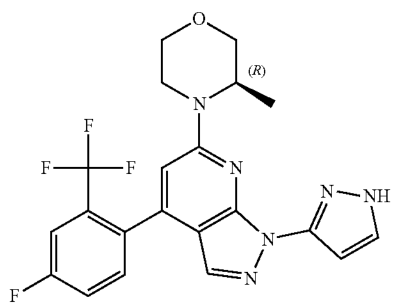 | 3.6 | 447.0 |
| 143 | M | 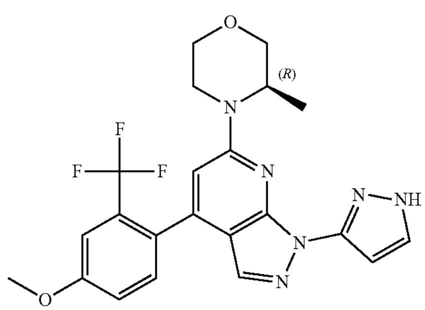 | 7.2 | 459.2 |
| 144 | M | 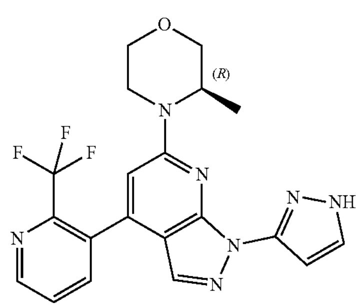 | 1.3 | 430.2 |
| 145 | M | 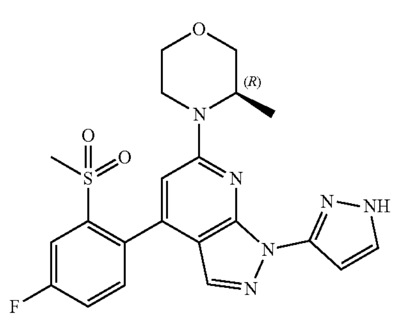 | 3.8 | 457.1 |

TABLE 3-continued

| Compound | Method | Structure | HeLa S3 ATR IC50 (nM) | MS (+ESI) [M + 1] |
|---|---|---|---|---|
| 146 | M | 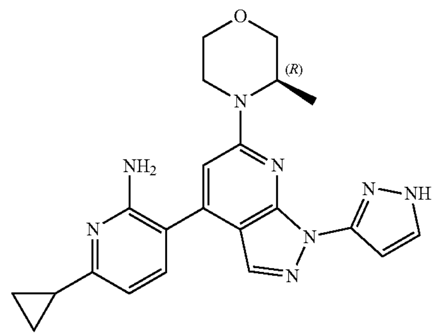 | 3.1 | 417.3 |
| 147 | N | 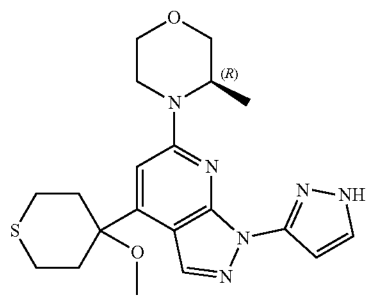 | 0.8 | 416.2 |
| 148 | M | 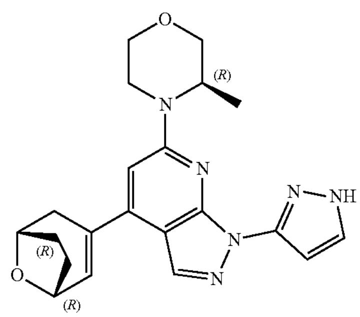 | 2.5 | 393.1 |
| 149 | S | 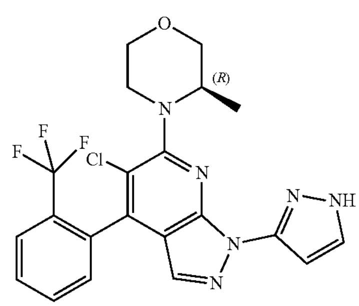 | 27 | 463.2, 465.2 |
| 150 | T | 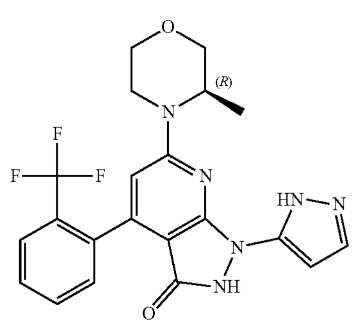 | 7.8 | 445.3 |

TABLE 3-continued

| Compound | Method | Structure | HeLa S3 ATR IC50 (nM) | MS (+ESI) [M + 1] |
|---|---|---|---|---|
| 151 | T | 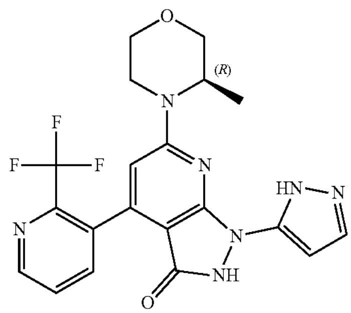 | 9.1 | 446.1 |
| 152 | T | 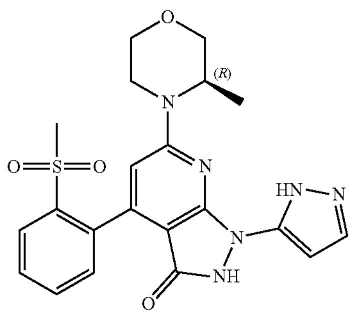 | 22 | 455.1 |

In Table 3, the Method column indicates a preparatory method described above used in the preparation of the compounds.

Other Embodiments

Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

What is claimed is:
1. A compound of formula (I):

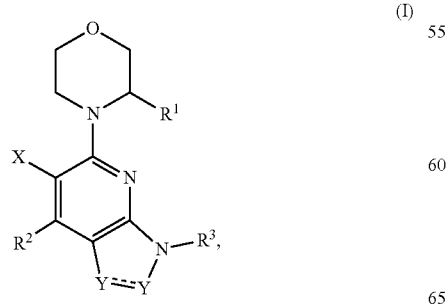

or a pharmaceutically acceptable salt thereof, wherein

===== is a double bond, and each Y is independently N or CR⁴; ===== or is a single bond, and each Y is independently NR^Y, carbonyl, or C (R^Y)₂; wherein each R^Y is independently H or optionally substituted C₁₋₆ alkyl;

R¹ is optionally substituted C₁₋₆ alkyl or H;

R² is optionally substituted C₂₋₉ heterocyclyl, optionally substituted C₁₋₆ alkyl, optionally substituted C₃₋₈ cycloalkyl, optionally substituted C₂₋₉ heterocyclyl C₁₋₆ alkyl, optionally substituted C₆₋₁₀ aryl, optionally substituted C₁₋₉ heteroaryl, optionally substituted C₁₋₉ heteroaryl C₁₋₆ alkyl, halogen, —N(R⁵)₂, —OR⁵, —CON(R⁶)₂, —SO₂N(R⁶)₂, —SO₂R^5A, or -Q-R^5B;

R³ is optionally substituted C₁₋₉ heteroaryl;

each R⁴ is independently hydrogen, halogen, optionally substituted C₁₋₆ alkyl, optionally substituted C₂₋₆ alkenyl, or optionally substituted C₂₋₆ alkynyl;

each R⁵ is independently hydrogen, optionally substituted C₁₋₆ alkyl, optionally substituted C₆₋₁₀ aryl C₁₋₆ alkyl, optionally substituted C₆₋₁₀ aryl, optionally substituted C₁₋₉ heteroaryl, or —SO₂R^5A; or both R⁵, together with the atom to which they are attached, combine to form an optionally substituted C₂₋₉ heterocyclyl;

each R^5A is independently optionally substituted C₁₋₆ alkyl, optionally substituted C₃₋₈ cycloalkyl, or optionally substituted C₆₋₁₀ aryl;

R^5B is hydroxyl, optionally substituted C₁₋₆ alkyl, optionally substituted C₆₋₁₀ aryl, optionally substituted C₁₋₉ heteroaryl, —N(R⁵)₂, —CON(R⁶)₂, —SO₂N(R⁶)₂, —SO₂R^5A, or optionally substituted alkoxy;

each R⁶ is independently hydrogen, optionally substituted C₁₋₆ alkyl, optionally substituted C₂₋₆ alkoxyalkyl, optionally substituted C$_{6-10}$ aryl C$_{1-6}$ alkyl, optionally substituted C$_{6-10}$ aryl, optionally substituted C$_{3-8}$ cycloalkyl, or optionally substituted C$_{1-9}$ heteroaryl; or both R$^6$, together with the atom to which they are attached, combine to form an optionally substituted C$_{2-9}$ heterocyclyl;

Q is optionally substituted C$_{2-9}$ heterocyclylene, optionally substituted C$_{3-8}$ cycloalkylene, optionally substituted C$_{1-9}$ heteroarylene, or optionally substituted C$_{6-10}$ arylene; and X is hydrogen or halogen.

2. The compound of claim 1, wherein the compound is a compound of formula (II):

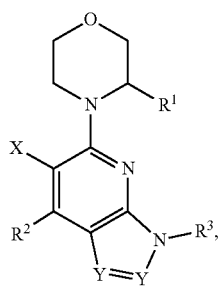

(II)

or a pharmaceutically acceptable salt thereof, wherein
each Y is independently N or CR$^4$;
R$^1$ is optionally substituted C$_{1-6}$ alkyl or H;
R$^2$ is optionally substituted C$_{2-9}$ heterocyclyl, optionally substituted C$_{1-6}$ alkyl, optionally substituted C$_{3-8}$ cycloalkyl, optionally substituted C$_{2-9}$ heterocyclyl C$_{1-6}$ alkyl, optionally substituted C$_{6-10}$ aryl, optionally substituted C$_{1-9}$ heteroaryl, optionally substituted C$_{1-9}$ heteroaryl C$_{1-6}$ alkyl, halogen, —N(R$^5$)$_2$, —OR$^5$, —CON(R$^6$)$_2$, —SO$_2$N(R$^6$)$_2$, —SO$_2$R$^{5A}$, or -Q-R$^{5B}$;
R$^3$ is optionally substituted C$_{1-9}$ heteroaryl;
each R$^4$ is independently hydrogen, halogen, optionally substituted C$_{1-6}$ alkyl, optionally substituted C$_{2-6}$ alkenyl, or optionally substituted C$_{2-6}$ alkynyl;
each R$^5$ is independently hydrogen, optionally substituted C$_{1-6}$ alkyl, optionally substituted C$_{6-10}$ aryl C$_{1-6}$ alkyl, optionally substituted C$_{6-10}$ aryl, optionally substituted C$_{1-9}$ heteroaryl, or —SO$_2$R$^{5A}$; or both R$^5$, together with the atom to which they are attached, combine to form an optionally substituted C$_{2-9}$ heterocyclyl;
each R$^{5A}$ is independently optionally substituted C$_{1-6}$ alkyl, optionally substituted C$_{3-8}$ cycloalkyl, or optionally substituted C$_{6-10}$ aryl;
R$^{5B}$ is hydroxyl, optionally substituted C$_{1-6}$ alkyl, optionally substituted C$_{6-10}$ aryl, optionally substituted C$_{1-9}$ heteroaryl, —N(R$^5$)$_2$, —CON(R$^6$)$_2$, —SO$_2$N(R$^6$)$_2$, —SO$_2$R$^{5A}$, or optionally substituted alkoxy;
each R$^6$ is independently hydrogen, optionally substituted C$_{1-6}$ alkyl, optionally substituted C$_{2-6}$ alkoxyalkyl, optionally substituted C$_{6-10}$ aryl C$_{1-6}$ alkyl, optionally substituted C$_{6-10}$ aryl, optionally substituted C$_{3-8}$ cycloalkyl, or optionally substituted C$_{1-9}$ heteroaryl; or both R$^6$, together with the atom to which they are attached, combine to form an optionally substituted C$_{2-9}$ heterocyclyl;

Q is optionally substituted C$_{2-9}$ heterocyclylene, optionally substituted C$_{3-8}$ cycloalkylene, optionally substituted C$_{1-9}$ heteroarylene, or optionally substituted C$_{6-10}$ arylene; and X is hydrogen or halogen.

3. The compound of claim 1, wherein the compound is a compound of formula (IB):

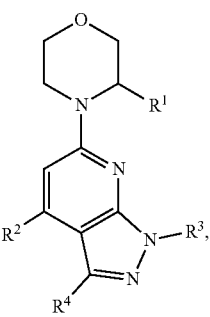

(IB)

or a pharmaceutically acceptable salt thereof.

4. The compound of claim 1, wherein the compound is a compound of formula (IB-a):

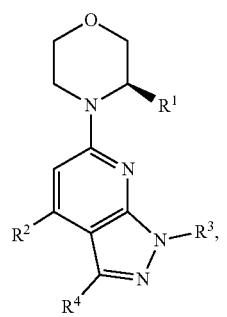

(IB-a)

or a pharmaceutically acceptable salt thereof.

5. The compound of claim 1, wherein the compound is a compound of formula (I-a):

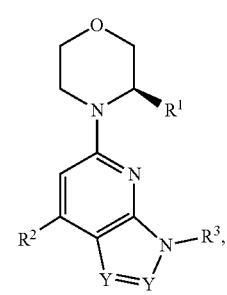

(I-a)

or a pharmaceutically acceptable salt thereof.

6. The compound of claim 1, wherein the compound is a compound of formula (IA):

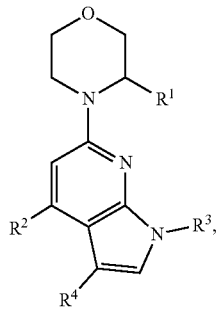

(IA)

or a pharmaceutically acceptable salt thereof.

7. The compound of claim 1, wherein the compound is a compound of formula (IA-a):

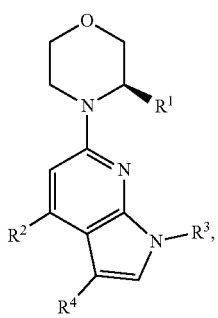

(IA-a)

or a pharmaceutically acceptable salt thereof.

8. The compound of claim 1, wherein the compound is a compound of formula (IC):

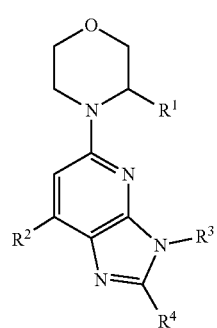

(IC)

or a pharmaceutically acceptable salt thereof.

9. The compound of claim 1, wherein the compound is a compound of formula (IC-a):

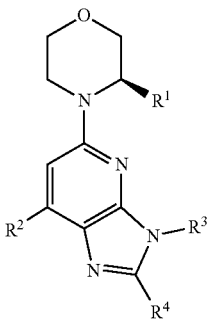

(IC-a)

or a pharmaceutically acceptable salt thereof.

10. The compound of claim 1, wherein $R^1$ is methyl.

11. The compound of claim 1, wherein $R^2$ is optionally substituted $C_{2-9}$ heterocyclyl, optionally substituted $C_{1-6}$ alkyl, optionally substituted $C_{3-8}$ cycloalkyl, optionally substituted $C_{6-10}$ aryl, optionally substituted $C_{1-9}$ heteroaryl, optionally substituted $C_{1-9}$ heteroaryl $C_{1-6}$ alkyl, $-N(R^5)_2$, $-CON(R^6)_2$, $-SO_2N(R^6)_2$, or $-SO_2R^{5A}$.

12. The compound of claim 1, wherein each $R^{5A}$ is independently optionally substituted $C_{1-6}$ alkyl or optionally substituted $C_{3-8}$ cycloalkyl.

13. The compound of claim 1, wherein each $R^6$ is independently hydrogen, optionally substituted $C_{1-6}$ alkyl, optionally substituted $C_{6-10}$ aryl $C_{1-6}$ alkyl, optionally substituted $C_{6-10}$ aryl, or optionally substituted $C_{1-9}$ heteroaryl; or both $R^6$, together with the atom to which they are attached, combine to form an optionally substituted $C_{2-9}$ heterocyclyl.

14. The compound of claim 1, wherein $R^2$ is:

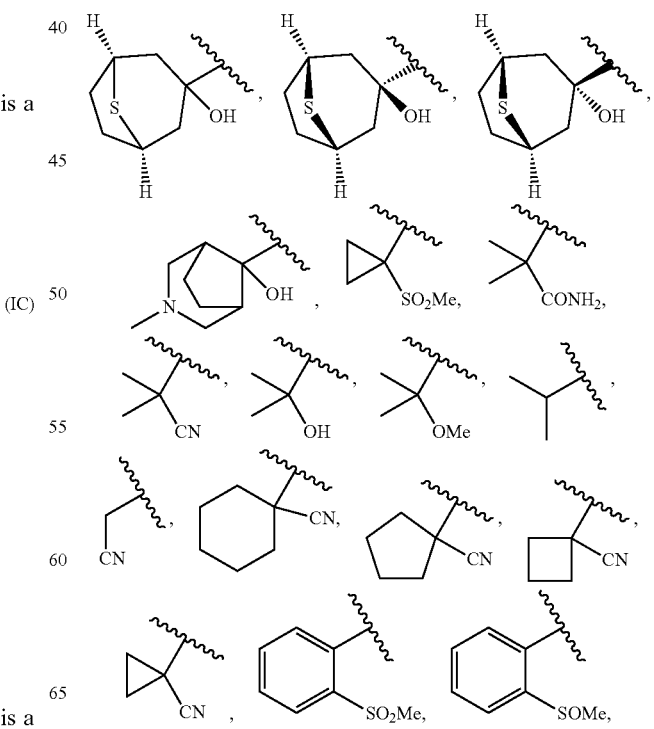

233
-continued
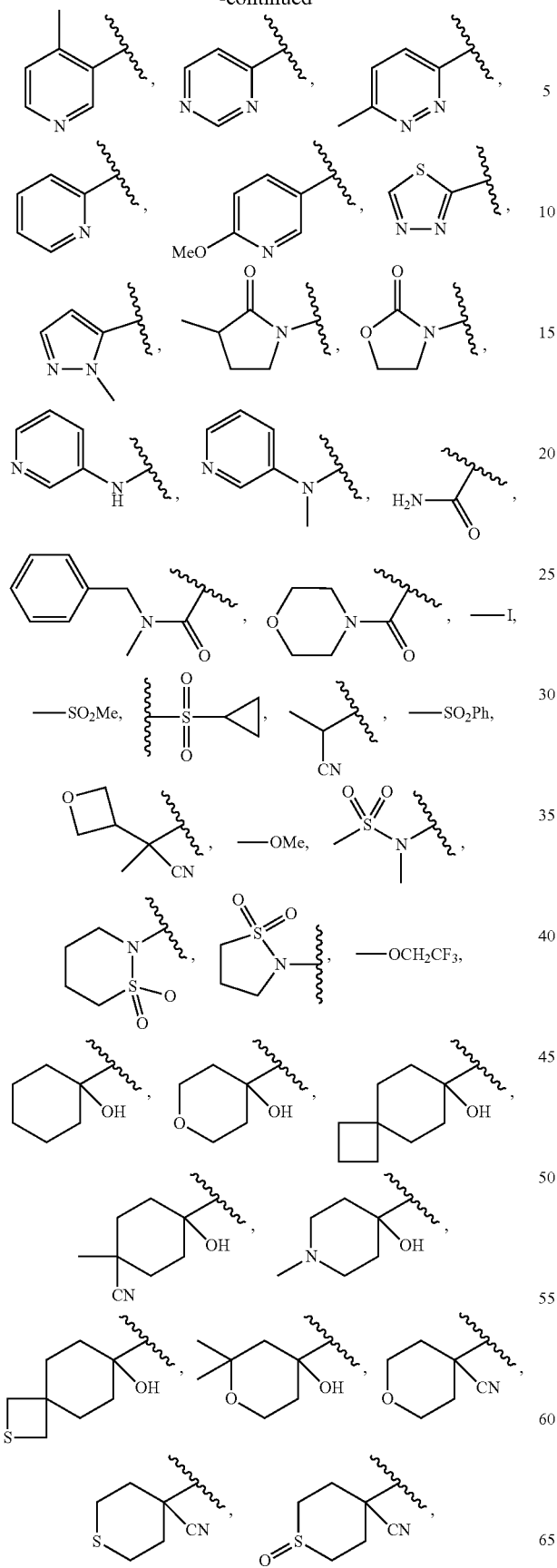
234
-continued
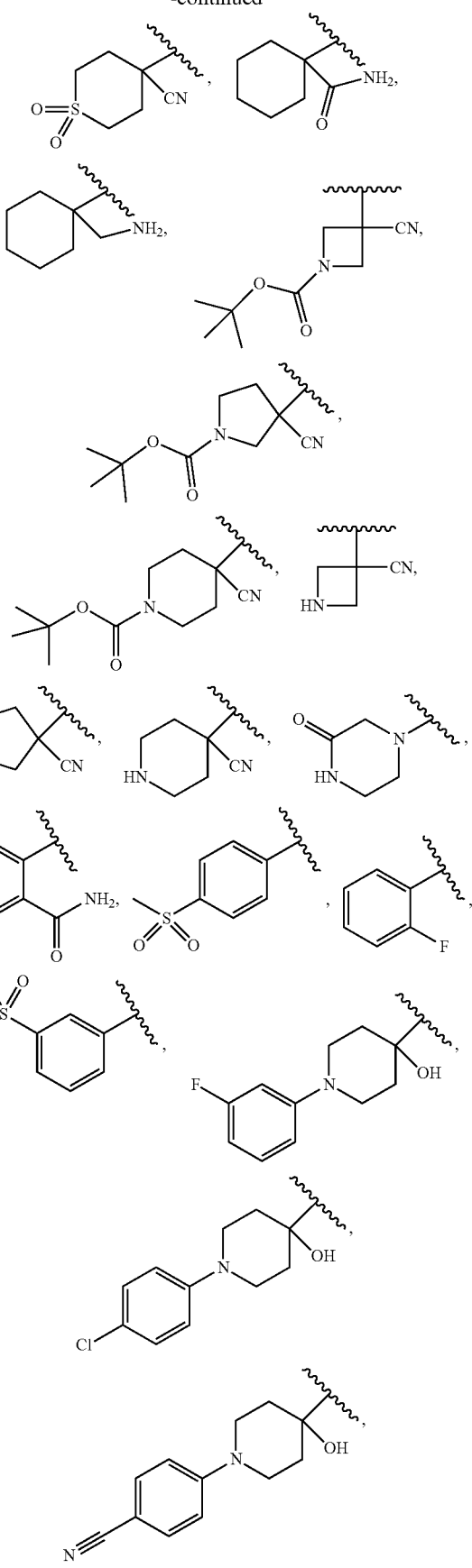

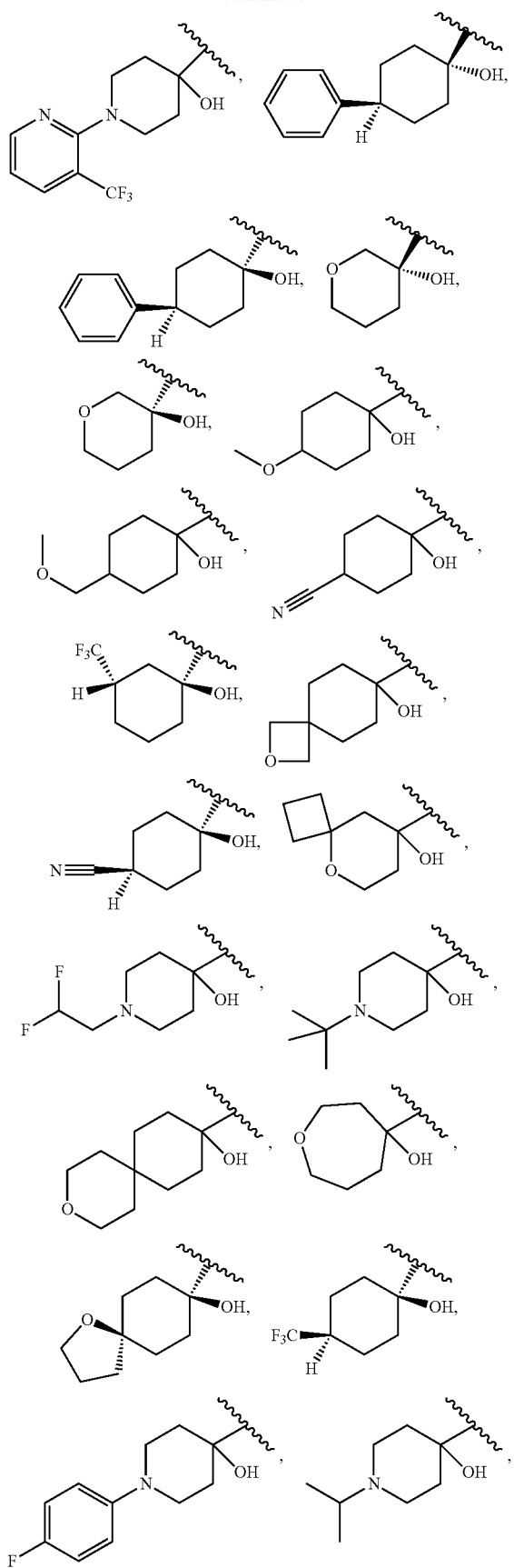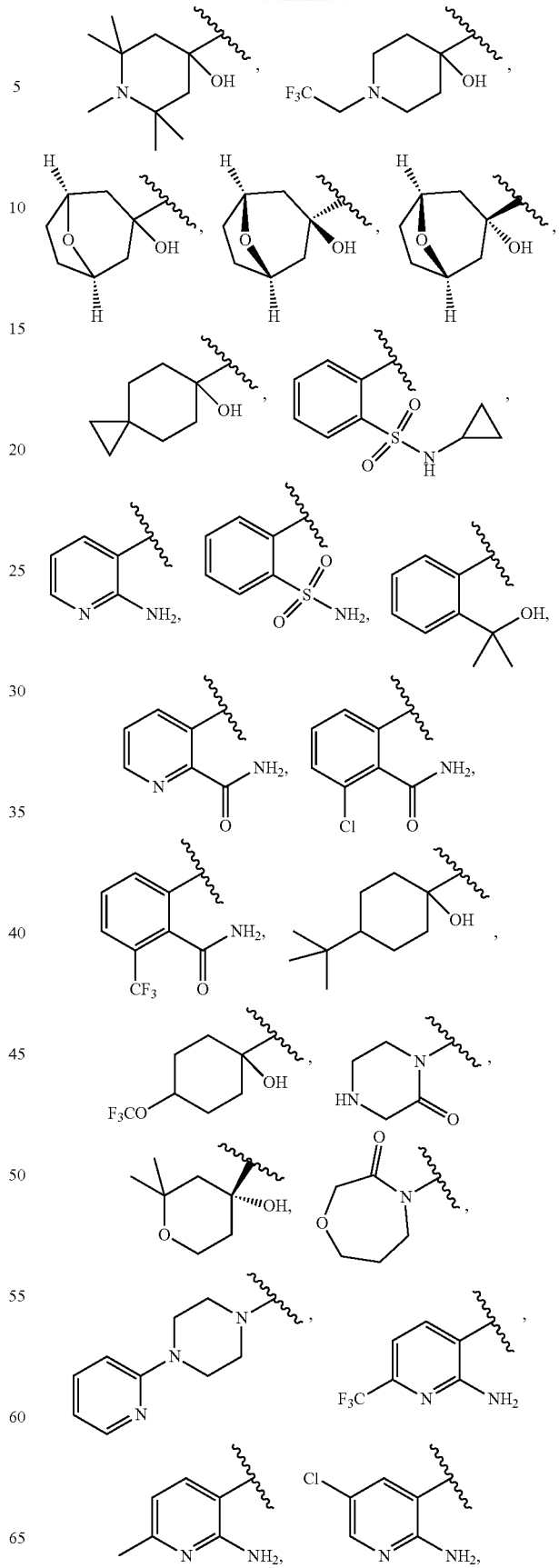

15. The compound of claim 1, wherein $R^3$ is optionally substituted, monocyclic $C_{1-9}$ heteroaryl comprising at least one nitrogen atom.

16. The compound of claim 1, wherein $R^3$ is:

17. The compound of claim 1, wherein $R^4$ is hydrogen.
18. The compound of claim 1, wherein X is hydrogen.
19. A compound selected from the group consisting of -continued
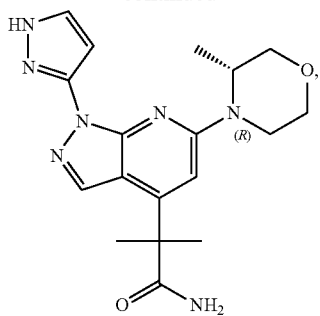
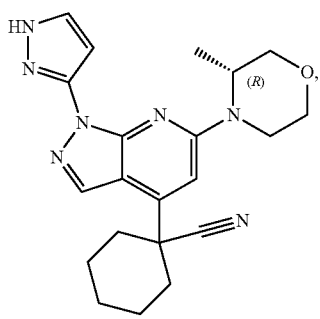
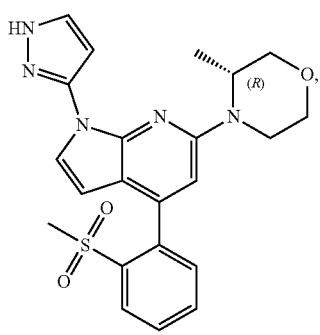
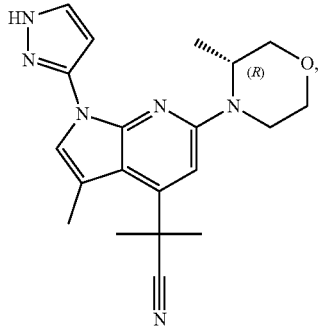
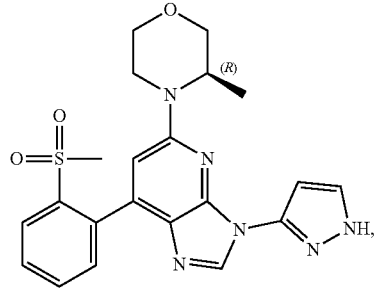
-continued
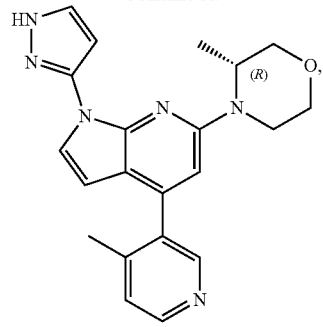
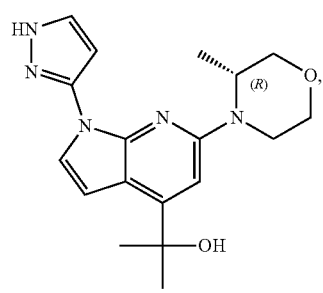
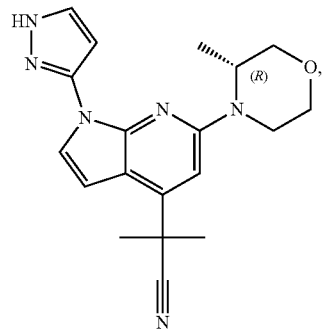
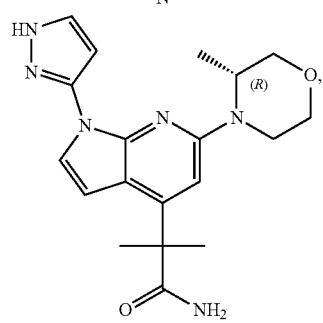
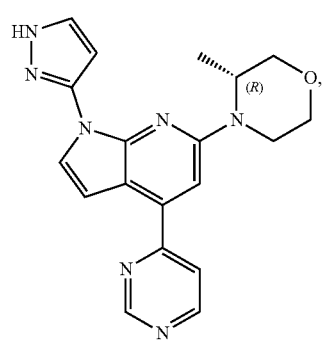

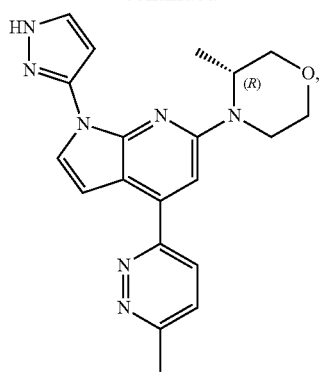
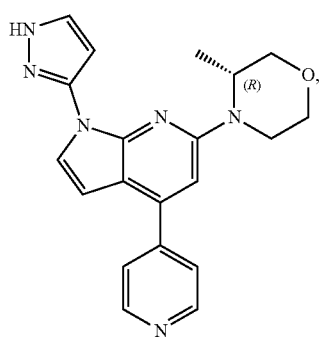
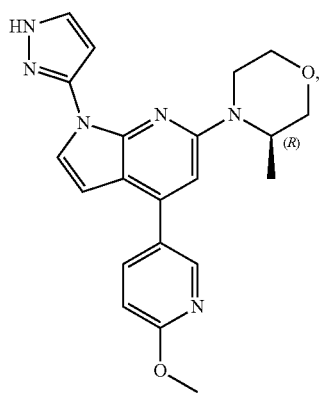
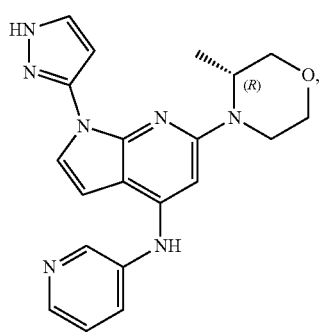
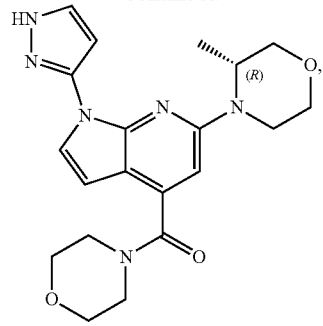
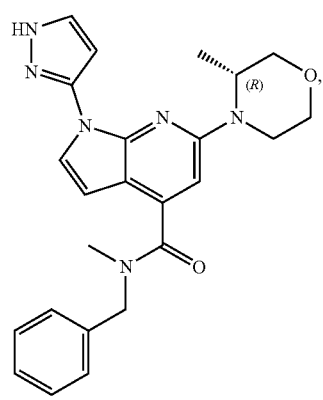
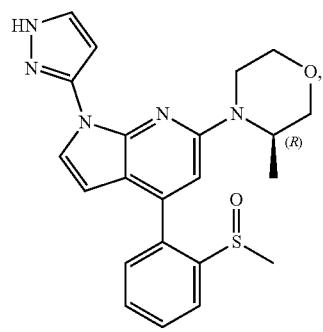
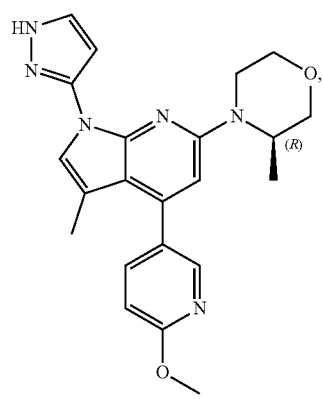

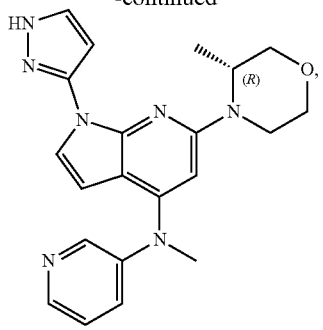
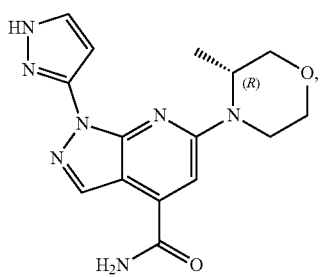
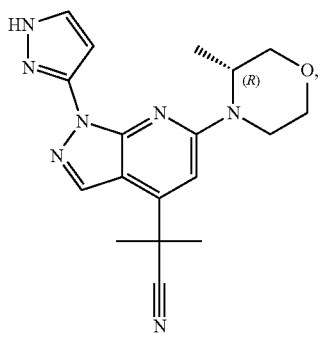
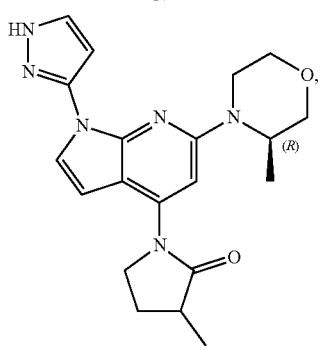
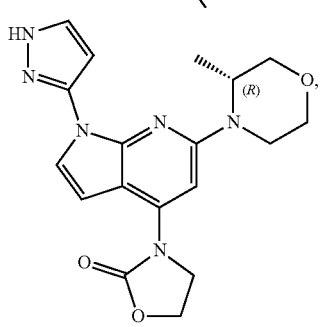
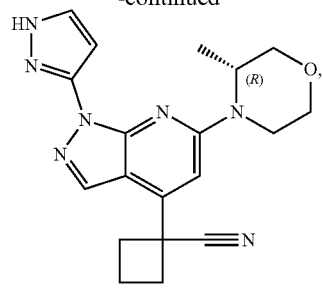
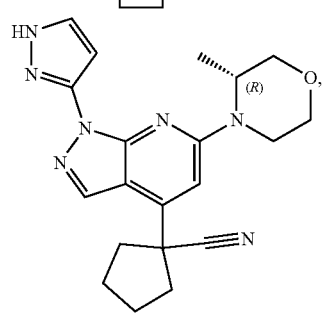
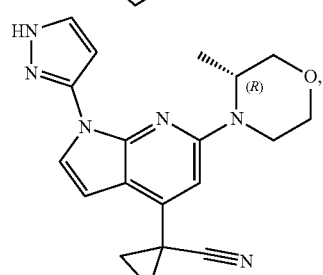
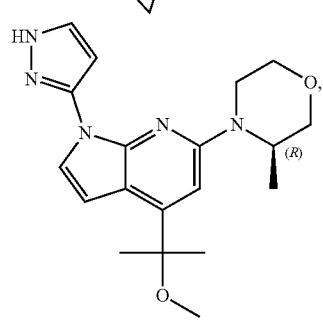
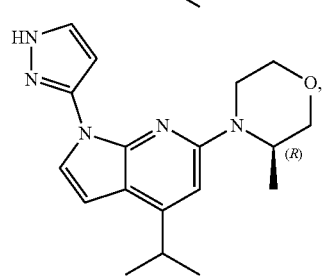
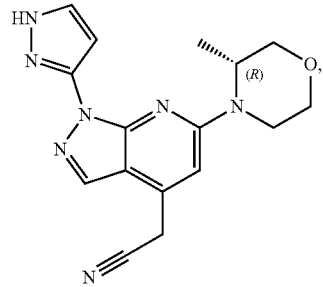

-continued

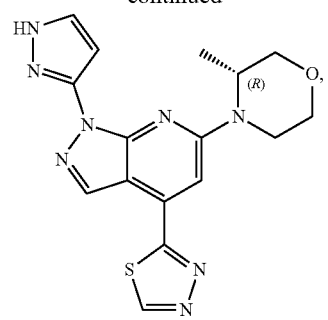

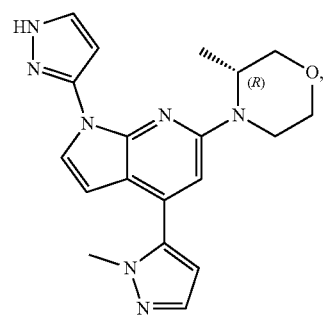

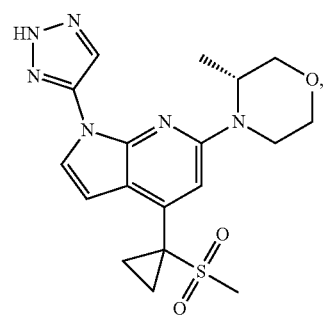

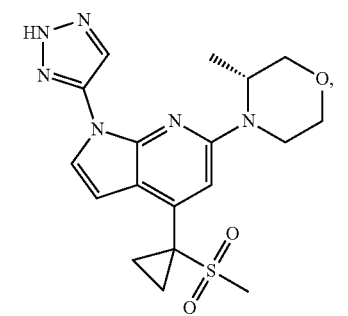

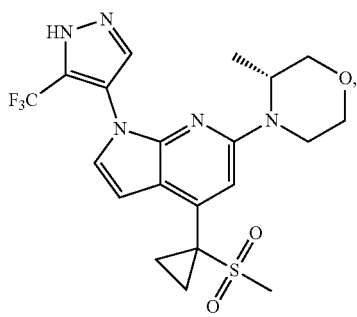

-continued

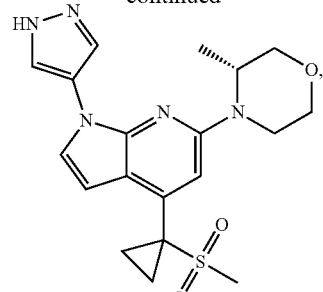

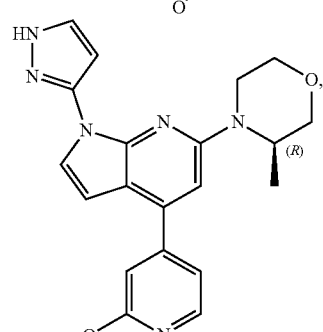

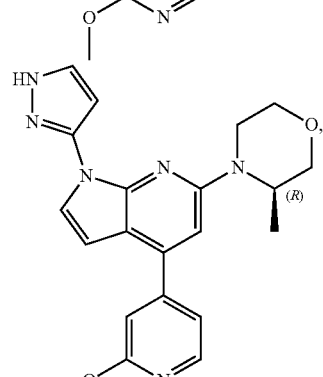

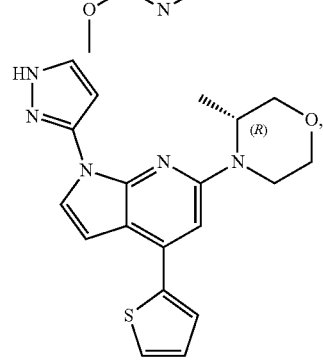

and pharmaceutically acceptable salts thereof.

20. A pharmaceutical composition comprising the compound of claim 1 and a pharmaceutically acceptable excipient.

21. A method of inhibiting ATR kinase in a cell expressing ATR kinase, the method comprising contacting the cell with the compound of claim 1.

22. The method of claim 21, wherein the cell is in a subject.

23. A method of treating a subject in need of a treatment for cancer comprising administering to the subject the compound of claim 1.

* * * * *

UNITED STATES PATENT AND TRADEMARK OFFICE
CERTIFICATE OF CORRECTION

PATENT NO. : 12,264,155 B2
APPLICATION NO. : 17/245574
DATED : April 1, 2025
INVENTOR(S) : Sheldon N. Crane et al.

Page 1 of 2

It is certified that error appears in the above-identified patent and that said Letters Patent is hereby corrected as shown below:

In the Claims

Column 228, Claim 1, Line 35, replace "====== or is a single bond," with --or ====== is a single bond,--;

Column 233, Claim 14, Line 10, replace " 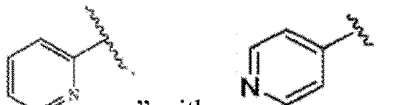 " with -- ' --;

Column 233, Claim 14, Line 40, replace " 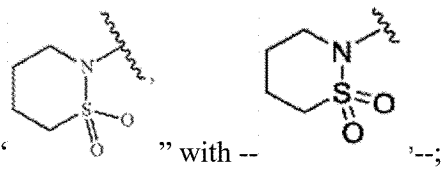 " with -- ' --;

Column 237, Claim 14, Line 25, replace " 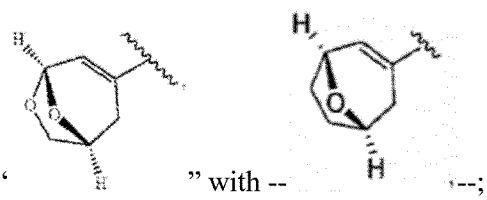 " with -- ' --;

Signed and Sealed this
Fifth Day of August, 2025

Coke Morgan Stewart
*Acting Director of the United States Patent and Trademark Office*

CERTIFICATE OF CORRECTION (continued)
U.S. Pat. No. 12,264,155 B2

Column 239, Claim 19, Lines 1-13, replace " 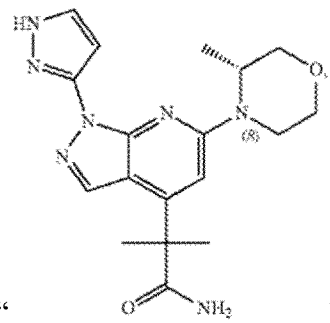 " with

-- 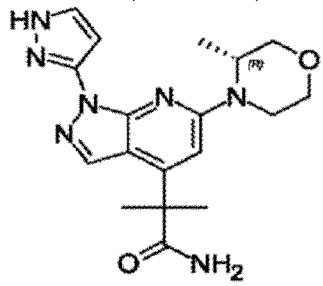 --.